(12) United States Patent
Luthringer et al.

(10) Patent No.: US 12,006,300 B2
(45) Date of Patent: Jun. 11, 2024

(54) SIGMA LIGAND COMPOUNDS AND USES THEREOF

(71) Applicant: Minerva Neurosciences, Inc., Waltham, MA (US)

(72) Inventors: Remy Luthringer, Geneva (CH); Nadine Noel, Gildwiller (FR); Florent Schmitt, Uttenheim (FR); Sandra Werner, Ostwald (FR); Hans Maag, Oberammergau (DE); Jay Saoud, Groton, MA (US)

(73) Assignee: Minerva Neurosciences, Inc., Burlington, MA (US)

( * ) Notice: Subject to any disclaimer, the term of this patent is extended or adjusted under 35 U.S.C. 154(b) by 0 days.

(21) Appl. No.: 17/400,207

(22) Filed: Aug. 12, 2021

(65) Prior Publication Data

US 2023/0054070 A1    Feb. 23, 2023

Related U.S. Application Data

(60) Provisional application No. 63/066,064, filed on Aug. 14, 2020.

(51) Int. Cl.
| | | |
|---|---|---|
| *C07D 401/04* | (2006.01) | |
| *C07D 217/06* | (2006.01) | |
| *C07D 217/08* | (2006.01) | |
| *C07D 223/16* | (2006.01) | |
| *C07D 401/06* | (2006.01) | |
| *C07D 401/12* | (2006.01) | |
| *C07D 401/14* | (2006.01) | |
| *C07D 403/04* | (2006.01) | |
| *C07D 403/10* | (2006.01) | |
| *C07D 405/06* | (2006.01) | |
| *C07D 405/12* | (2006.01) | |
| *C07D 405/14* | (2006.01) | |
| *C07D 417/06* | (2006.01) | |

(52) U.S. Cl.
CPC ......... *C07D 401/04* (2013.01); *C07D 217/06* (2013.01); *C07D 217/08* (2013.01); *C07D 223/16* (2013.01); *C07D 401/06* (2013.01); *C07D 401/12* (2013.01); *C07D 401/14* (2013.01); *C07D 403/04* (2013.01); *C07D 403/10* (2013.01); *C07D 405/06* (2013.01); *C07D 405/12* (2013.01); *C07D 405/14* (2013.01); *C07D 417/06* (2013.01)

(58) Field of Classification Search
CPC .. C07D 223/16; C07D 217/06; C07D 217/08; C07D 401/06; A61K 31/55; A61K 31/472; A61K 31/4725
See application file for complete search history.

(56) References Cited

U.S. PATENT DOCUMENTS

| | | | |
|---|---|---|---|
| 7,166,617 B2 | 1/2007 | Yamabe et al. | |
| 7,446,103 B2 | 11/2008 | Best et al. | |
| 8,962,612 B2* | 2/2015 | Hamaguchi | .......... C07D 209/44 |
| | | | 514/217 |
| 9,365,498 B2 | 6/2016 | Holson et al. | |
| 9,447,030 B2 | 9/2016 | Holson et al. | |
| 9,890,172 B2 | 2/2018 | Holson et al. | |
| 10,450,301 B2 | 10/2019 | Granger et al. | |
| 2005/0234096 A1* | 10/2005 | Bischoff | ................... A61P 3/10 |
| | | | 546/141 |

FOREIGN PATENT DOCUMENTS

| | | | |
|---|---|---|---|
| EP | 1260512 A1 | 11/2002 | |
| WO | WO 2014/053568 A1 | 4/2014 | |
| WO | WO 2017/190109 A1 | 11/2017 | |
| WO | WO 2019/222238 A2 | 11/2019 | |
| WO | WO 2022/013136 A1 * | 1/2022 | |
| WO | WO-2022169961 A1 | 8/2022 | |

OTHER PUBLICATIONS

Banker et al., Prodrugs, Modern Pharmaceutics, Third Edition, Revised and Expanded, pp. 451 and 596 (1996).*
Bundgaard, Design of Prodrugs, p. 1, 1985.*
Silverman, Prodrugs and Drug Delivery Systems, The Organic Chemistry of Drug Design and Drug Action, pp. 352-399, 1992.*
Wolff, Some consideration for prodrug design, Burger's Medicinal Chemistry and Drug Discovery, 5th Edition, vol. 1: Principles and Practice, pp. 975-977, 1995.*
Fujimura et al., CAPLUS Abstract No. 1973:546429 (1973).*
Lu et al., Palladium-Catalyzed Domino Heck/C—H Activation/ Intermolecular Direct Arylation Reactions, Synthesis, No. 16, pp. 2595-2599 (2011).*

(Continued)

*Primary Examiner* — Deepak R Rao
(74) *Attorney, Agent, or Firm* — COOLEY LLP

(57) ABSTRACT

The present disclosure relates to compounds of Formula (I):

and their prodrugs, solvates, pharmaceutically acceptable salts, pharmaceutical compositions, methods of use, and methods of their preparation. The compounds disclosed herein are useful for modulating Sigma receptors and have antiviral activity, and may also be useful in the treatment and/or prevention of pain disorders, neurological disorders (e.g., Parkinson's disease and Alzheimer's disease), and cancer.

41 Claims, 5 Drawing Sheets

(56) References Cited

OTHER PUBLICATIONS

Wang et al., "σ$_2$R/TMEM97 in retinal ganglion cell degeneration," Scientific Reports (2022) 12:20753, 11 pages.

Bender et al., ""Bayes Affinity Fingerprints" Improve Retrieval Rates in Virtual Screening and Define Orthogonal Bioactivity Space: When Are Multitarget Drugs a Feasible Concept?", J. Chem. Inf. Model. 2006, 46, 2445-2456.

Cushing et al., "Discovery and in Vivo Evaluation of (S)-N-(1-(7-Fluoro-2-(pyridin-2-yl)quinolin-3-yl)ethyl)-9H-purin-6-amine (AMG319) and Related PI3Kδ Inhibitors for Inflammation and Autoimmune Disease," J. Med. Chem. 2015, 58, 480-511.

Takamatsu et al., "Synthesis of Indolines by Copper-Mediated Intramolecular Aromatic C—H Amination," J. Org. Chem. 2015, 80, 3242-3249.

Bonhaus, D.W. et al., "The pharmacology and distribution of human 5-hydroxytryptamine$_{2B}$ (5-HT$_{2b}$) receptor gene products: comparison with 5-HT$_{2a}$ and 5-HT$_{2c}$ receptors," Brit. J. Pharmacol., (1995), 115: 622-628.

Bylund, D. B. et al., "International Union of Pharmacology nomenclature of adrenoceptors," Pharmacol. Rev. (1994), 46: 121-136.

Keefe et al., "Cognitive Effects of MIN-101 in Patients With Schizophrenia and Negative Symptoms Results From a Randomized Controlled Trial," J Clin Psychiatry, May/Jun. 2018, 79:3, e1-e6.

Schwinn, D. A. et al., "Cloning and pharmacological characterization of human alpha-1 adrenergic receptors: sequence corrections and direct comparison with other species homologues," J Pharmacol. Exp. Ther., (1995), 272: 134-142.

Vicentic, A. et al., "Biochemistry and Pharmacology of Epitope-Tagged α1-Adrenergic Receptor Subtypes," J. Pharmacol. Exp. Ther., (2002), 302: 58-65.

Lizama, B. N., et al., "Sigma-2 Receptors—From Basic Biology to Therapeutic Target: A Focus on Age-Related Degenerative Diseases", International Journal of Molecular Sciences (2023); 24(7): 6251; 27 pages.

\* cited by examiner

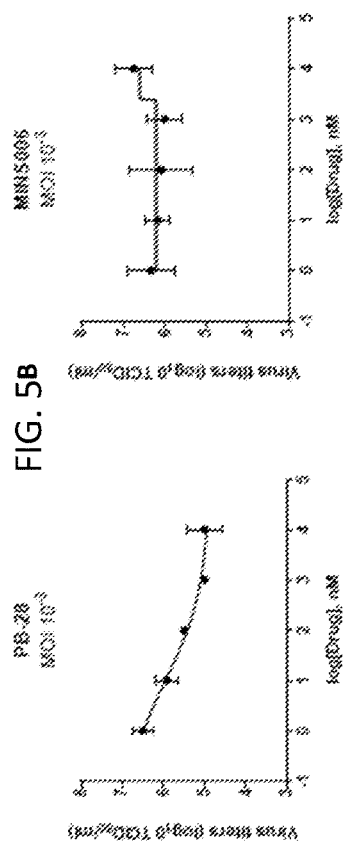
FIG. 5A
FIG. 5B
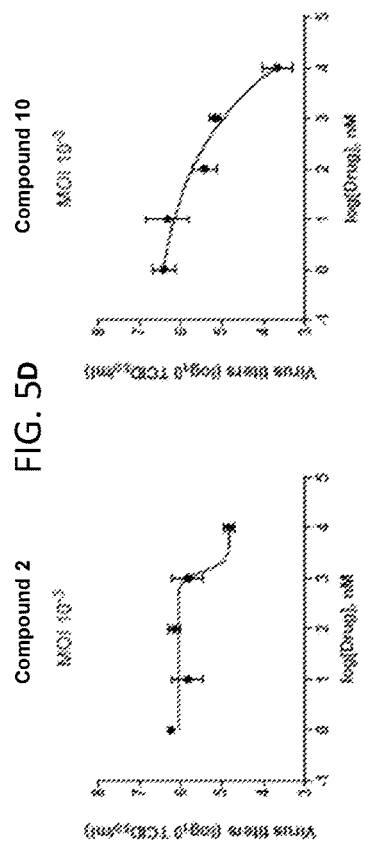
FIG. 5C
FIG. 5D
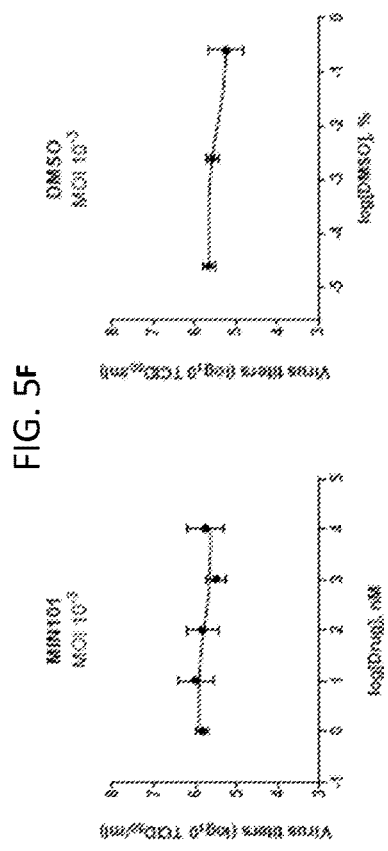
FIG. 5E
FIG. 5F

SIGMA LIGAND COMPOUNDS AND USES THEREOF

RELATED APPLICATIONS

This application claims the priority to, and the benefit of, U.S. Provisional Patent Application No. 63/066,064, filed Aug. 14, 2020. The contents of which are incorporated herein by reference in their entirety

BACKGROUND

Sigma receptors are implicated in a variety of diseases and disorders, including, for example, pain disorders, neurological disorders (e.g., Parkinson's disease and Alzheimer's disease), and cancer. More recently, Sigma receptor modulating compounds have been shown to have antiviral activity.

Coronaviruses are a group of related viruses that cause diseases in humans and animals. In humans, coronaviruses cause respiratory tract infections that are typically mild, though some forms can be lethal, such as SARS, MERS, and COVID-19. Coronavirus disease 2019 (COVID-19) is an infectious disease caused by the severe acute respiratory syndrome coronavirus 2 (SARS-CoV-2). As of August, 2020, there have been over 20 million confirmed case of COVID-19 worldwide, which have been responsible for more than 700,000 deaths. (Johns Hopkins Coronavirus Resource Center). The economic impact of COVID-19 has also been staggering. For instance, as of the week ending Jul. 25, 2020, the advanced unadjusted insured unemployment rate in the U.S. was 10.7%, whereas a year earlier the rate was only 1.2%. (U.S. Dept. of Labor Press Release, Aug. 6, 2020.) While vaccines have proven to be effective in reducing the occurrence of COVID-19 and the severity of COVID-19 symptoms in breakthrough cases, there are emerging variants that are more transmissible that may be more problematic even in subjects with a vaccine. For this reason, among others (e.g., mistrust in vaccines, subjects who are ineligible for administration of the vaccine, and limited supplies to meet global demand), further treatments in addition to access to vaccines are desperately needed.

Thus, improved Sigma receptor modulating compounds may be able to address a unmet need in the treatment of viruses, as well as pain disorders, neurological disorders (e.g., Parkinson's disease and Alzheimer's disease), and cancer.

SUMMARY

In some aspects, the present disclosure provides, inter alia, a compound of Formula (I):

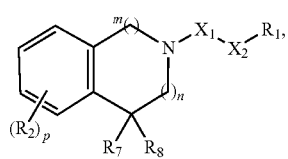

(I)

or a prodrug, solvate, or pharmaceutically acceptable salt thereof, wherein $X_1$ is absent, $-(CR_3R_4)_q-$, $-O-$, $-S(O)_2-$, $-C(O)-$, $-C(S)-$, $-S(O)-$, $-NR_3C(O)-$, $-C(O)NR_3-$, $-C(O)O-$, or $-OC(O)-$;

$X_2$ is absent, $-(CR_3R_4)_q-$, $-O-$, $-S(O)_2-$, $-C(O)-$, $-C(S)-$, $-S(O)-$, $-NR_3C(O)-$, $-C(O)NR_3-$, $-C(O)O-$, or $-OC(O)-$;

$R_1$ is H, OH, halogen, $NH_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, $C_6$-$C_{10}$ aryl, 5- to 12-membered heteroaryl comprising 1-6 heteroatoms selected from N, O, and S, 5- to 14-membered saturated or unsaturated heterocycloalkyl comprising 1-5 heteroatoms selected from N, O, and S; wherein the alkyl, alkenyl, alkynyl, haloalkyl, alkoxyl, haloalkoxyl, cycloalkyl, aryl, heteroaryl, or heterocycloalkyl of any of the foregoing is optionally substituted with one or more $R_5$;

each $R_2$ independently is H, OH, halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, $-C(O)$ $C_1$-$C_6$alkyl, $-C(O)OC_1$-$C_6$alkyl, $-C(O)NH_2$, $-C(O)NHC_1$-$C_6$alkyl, $-C(O)N(C_1$-$C_6$alkyl$)_2$, $C_6$-$C_{10}$ aryl, 5- to 12-membered heteroaryl comprising 1-6 heteroatoms selected from N, O, and S, or 5- to 14-membered saturated or unsaturated heterocycloalkyl comprising 1-5 heteroatoms selected from N, O, and S; wherein the alkyl, alkenyl, alkynyl, haloalkyl, alkoxyl, haloalkoxyl, cycloalkyl, aryl, heteroaryl, or heterocycloalkyl of any of the foregoing is optionally substituted with one or more $R_6$;

each $R_3$ independently is H, halogen, or $C_1$-$C_6$ alkyl;

each $R_4$ independently is H, halogen, or $C_1$-$C_6$ alkyl;

each $R_5$ independently is OH, halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, $C_6$-$C_{10}$ aryl, or 5- to 14-membered saturated or unsaturated heterocycloalkyl comprising 1-5 heteroatoms selected from N, O, and S; wherein the alkyl, alkenyl, alkynyl, cycloalkyl, or aryl of any of the foregoing is optionally substituted with one or more $-C(O)C_1$-$C_6$alkyl, $-C(O)OC_1$-$C_6$alkyl, $-C(O)NH_2$, $-C(O)NHC_1$-$C_6$alkyl, or $-C(O)N(C_1$-$C_6$alkyl$)_2$;

each $R_6$ independently is OH, halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, $C_6$-$C_{10}$ aryl, or 5- to 14-membered saturated or unsaturated heterocycloalkyl comprising 1-5 heteroatoms selected from N, O, and S; wherein the alkyl, alkenyl, alkynyl, cycloalkyl, or aryl of any of the foregoing is optionally substituted with one or more $-C(O)C_1$-$C_6$ alkyl, $-C(O)OC_1$-$C_6$ alkyl, $-C(O)NH_2$, $-C(O)NHC_1$-$C_6$ alkyl, or $-C(O)N(C_1$-$C_6$alkyl$)_2$;

$R_7$ is $C_1$-$C_6$ alkyl optionally substituted with one or more OH, halogen, or $C_1$-$C_6$ alkoxyl;

$R_8$ is $C_1$-$C_6$ alkyl optionally substituted with one or more OH, halogen, or $C_1$-$C_6$ alkoxyl; or $R_7$ and $R_8$, together with the carbon atom they are attached, form a $C_3$-$C_6$ cycloalkyl optionally substituted with one or more OH, halogen, or $C_1$-$C_6$ alkoxyl;

m is 0, 1, 2, or 3;

n is 0, 1, 2, or 3;

p is 0, 1, 2, 3, or 4; and each q independently is 1, 2, 3, or 4.

In one aspect, the present disclosure provides, inter alia, a compound of Formula (Ia):

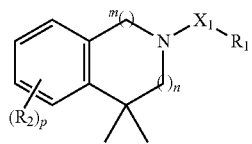

or a prodrug, solvate, or pharmaceutically acceptable salt thereof, wherein $X_1$ is a absent, $(CR_3R_4)_q$, —C(O)—, —C(S)—, —S(O)—, —NR$_3$C(O)—, or —C(O)O—;

$R_1$ is H, OH, halogen, NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl, wherein the alkyl, alkenyl, alkynyl, haloalkyl, alkoxyl, haloalkoxyl, or cycloalkyl is optionally substituted with one or more $R_5$;

each $R_2$ is independently H, OH, halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, —C(O)$C_1$-$C_6$alkyl, —C(O)O$C_1$-$C_6$alkyl, —C(O)NH$_2$, —C(O)NHC$_1$-$C_6$alkyl, —C(O)N(C$_1$-$C_6$alkyl)$_2$, $C_6$-$C_{10}$ aryl, 5- to 12-membered heteroaryl comprising 1-6 heteroatoms selected from N, O, and S, or 5- to 14-membered saturated or unsaturated heterocycloalkyl comprising 1-5 heteroatoms selected from N, O, and S wherein the alkyl, alkenyl, alkynyl, haloalkyl, alkoxyl, haloalkoxyl, cycloalkyl, aryl, heteroaryl, or heterocycloalkyl of any of the foregoing is optionally substituted with one or more $R_6$;

each $R_3$ is independently H or halogen;
each $R_4$ is independently H or halogen;
each $R_5$ independently is OH, halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, or $C_6$-$C_{10}$ aryl, wherein the alkyl, alkenyl, alkynyl, cycloalkyl, or aryl of any of the foregoing is optionally substituted with one or more —C(O)$C_1$-$C_6$alkyl, —C(O)O$C_1$-$C_6$alkyl, —C(O)NH$_2$, —C(O)NHC$_1$-$C_6$alkyl, or —C(O)N(C$_1$-$C_6$alkyl)$_2$;

each $R_6$ independently is OH, halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, $C_6$-$C_{10}$ aryl, or 5- to 14-membered saturated or unsaturated heterocycloalkyl comprising 1-5 heteroatoms selected from N, O, and S wherein the alkyl, alkenyl, alkynyl, cycloalkyl, or aryl of any of the foregoing is optionally substituted with one or more —C(O)$C_1$-$C_6$alkyl, —C(O)O$C_1$-$C_6$alkyl, —C(O)NH$_2$, —C(O)NHC$_1$-$C_6$alkyl, or —C(O)N(C$_1$-$C_6$alkyl)$_2$;

m is 0, 1, 2, or 3;
n is 0, 1, 2, or 3;
p is 0, 1, 2, 3, or 4; and
q is 1, 2, 3, or 4.

In one aspect, the present disclosure provides a pharmaceutical composition comprising a compound of the present disclosure, or a pharmaceutically acceptable salt thereof, and a pharmaceutically acceptable diluent or carrier.

In some embodiments, the present disclosure provides a method of modulating a Sigma receptor (e.g., Sigma-1 or Sigma-2) with a compound of Formula (I), MIN-101, MIN-101-B, MIN-5006, or a pharmaceutically acceptable salt, prodrug, or solvate thereof.

In some embodiments, the present disclosure provides a method of treating a disease, disorder or symptom of a disease or disorder, comprising administering to an individual in need thereof a therapeutically effective amount of a compound of Formula (I), MIN-101, MIN-101-B, MIN-5006, or a pharmaceutically acceptable salt, prodrug, or solvate thereof, wherein Sigma receptor activity is involved or implicated in the disease or disorder.

In one aspect, the present disclosure provides a method of treating or preventing an infectious disease or disorder, wherein the infectious disease or disorder is caused by a bacterium, a fungus, or a virus.

In one aspect, the present disclosure provides a method of treating or preventing a viral infection in a subject, or an illness resulting from the viral infection, comprising administering to an individual in need thereof a therapeutically effective amount of a compound of Formula (I), or a pharmaceutically acceptable salt, prodrug, or solvate thereof.

In one embodiment, the viral infection is caused by a coronavirus, herpes simplex virus, human immunodeficiency virus, influenza, or human papillomavirus.

In one embodiment, the coronavirus is SARS-CoV-2 (severe acute respiratory syndrome coronavirus 2).

In one embodiment, the illness resulting from the viral infection is COVID-19.

In one embodiment, the illness resulting from the viral infection is severe acute respiratory syndrome.

In some embodiments, the present disclosure provides a method of treating a disease, or symptom of a disease, comprising administering to an individual in need thereof a therapeutically effective amount of a compound of Formula (I), MIN-101, MIN-101-B, MIN-S006, or a pharmaceutically acceptable salt, prodrug, or solvate thereof, wherein the disease, or symptom of a disease, is anxiety, depression, emotional abnormality, schizophrenia, narcotic intoxication, narcotic addiction, sharp pain, dyskinesia, cerebrovascular disease, epilepsy, dementia, Parkinson's syndrome, attention deficit disorder, irritable bowel syndrome, irritable colon, spastic colon, colitis mucosus, enterocolitis, diverticulitis, dysentery, hypertension, arrhythmia, angina pectoris, amyotrophic lateral sclerosis (ALS), Huntington disease, stroke, retinal degeneration, or cognitive impairment in neuropsychiatric diseases.

In some embodiments, the present disclosure provides a method of preventing a disease, or symptom of a disease, comprising administering to an individual in need thereof a therapeutically effective amount of a compound of Formula (I), MIN-101, MIN-101-B, MIN-S006, or a pharmaceutically acceptable salt, prodrug, or solvate thereof, wherein the disease, or symptom of a disease, is anxiety, depression, emotional abnormality, schizophrenia, narcotic intoxication, narcotic addiction, sharp pain, dyskinesia, cerebrovascular disease, epilepsy, dementia, Parkinson's syndrome, attention deficit disorder, irritable bowel syndrome, irritable colon, spastic colon, colitis mucosus, enterocolitis, diverticulitis, dysentery, hypertension, arrhythmia, angina pectoris, amyotrophic lateral sclerosis (ALS), Huntington disease, stroke, retinal degeneration, or cognitive impairment in neuropsychiatric diseases.

In one aspect, the present disclosure provides a method of treating Alzheimer's disease comprising administering to an individual in need thereof a therapeutically effective amount of a compound of Formula (I), or a pharmaceutically acceptable salt, prodrug, or solvate thereof.

In one aspect, the present disclosure provides a method of treating a disease, or symptom of a disease, comprising administering to an individual in need thereof a therapeutically effective amount of a compound of Formula (I), or a pharmaceutically acceptable salt, prodrug, or solvate thereof, wherein the disease, or symptom of a disease, is anxiety, depression, emotional abnormality, schizophrenia, narcotic intoxication, narcotic addiction, alcoholic addition, sharp pain, dyskinesia, cerebrovascular disease, epilepsy, dementia, Parkinson's syndrome, attention deficit disorder, irritable bowel syndrome, irritable colon, spastic colon, colitis mucosus, enterocolitis, diverticulitis, dysentery, hypertension, arrhythmia, angina pectoris, amyotrophic lateral sclerosis (ALS), Huntington disease, stroke, retinal degeneration, or cognitive impairment in neuropsychiatric diseases.

In one aspect, the present disclosure provides a method of treating or preventing pain in a subject in need of treatment comprising administering to the subject a therapeutically effective amount of a compound of Formula (I), or a pharmaceutically acceptable salt, prodrug, or solvate thereof.

In one embodiment, the pain is acute pain, chronic pain, toxic pain, neuropathic pain, nociceptive pain, inflammatory pain, post-operative pain, visceral pain, chemotherapy-induced pain, peripheral neuropathy, fibromyalgia, or a combination thereof.

In one aspect, the present disclosure provides a method of promoting an antihyperalgesic effect in a subject suffering from hyperalgesia comprising administering to the subject a therapeutically effective amount of a compound of Formula (I), or a pharmaceutically acceptable salt, prodrug, or solvate thereof.

In one aspect, the present disclosure provides a method of reducing sensitivity to pain in a subject comprising administering to the subject a therapeutically effective amount of a compound of Formula (I), or a pharmaceutically acceptable salt, prodrug, or solvate thereof.

In one aspect, the present disclosure provides a method of treating cancer in a subject in need thereof comprising administering to the subject a therapeutically effective amount of a compound of any one of Formula (I), or a pharmaceutically acceptable salt, prodrug, or solvate thereof.

In one embodiment, the cancer is breast cancer, prostate cancer, colon cancer, rectal cancer, pancreatic cancer, liver cancer, bladder cancer, thyroid cancer, kidney cancer, skin cancer, non-Hodgkin lymphoma, or uterine cancer.

BRIEF DESCRIPTION OF THE FIGURES

FIG. 4A depicts the viral production in SARS-CoV-2 infected cells with a MOI of $10^{-1}$ after being treated with PB28. FIG. 4B depicts the viral production in SARS-CoV-2 infected cells with a MOI of $10^{-1}$ after being treated with MIN-5006. FIG. 4C depicts the viral production in SARS-CoV-2 infected cells with a MOI of $10^{-1}$ after being treated with compound 2. FIG. 4D depicts the viral production in SARS-CoV-2 infected cells with a MOI of $10^{-1}$ after being treated with compound 10. FIG. 4E depicts the viral production in SARS-CoV-2 infected cells with a MOI of $10^{-1}$ after being treated with MIN-101.

FIG. 4F depicts the viral production in SARS-CoV-2 infected cells with a MOI of $10^{-1}$ after being treated with a DMSO control.

FIGS. 5A-F depict viral production in SARS-CoV-2 infected cells with a MOI (multiplicity of infection) of $10^3$ after being treated with a compound. (See Example 29.) FIG. 5A depicts the viral production in SARS-CoV-2 infected cells with a MOI of $10^3$ after being treated with PB28. FIG. 5B depicts the viral production in SARS-CoV-2 infected cells with a MOI of $10^{-3}$ after being treated with MIN-5006. FIG. 5C depicts the viral production in SARS-CoV-2 infected cells with a MOI of $10^{-3}$ after being treated with compound 2. FIG. 5D depicts the viral production in SARS-CoV-2 infected cells with a MOI of $10^{-3}$ after being treated with compound 10. FIG. 5E depicts the viral production in SARS-CoV-2 infected cells with a MOI of $10^{-3}$ after being treated with MIN-101. FIG. 5F depicts the viral production in SARS-CoV-2 infected cells with a MOI of $10^{-3}$ after being treated with a DMSO control.

DETAILED DESCRIPTION

Definitions

Figure 1:
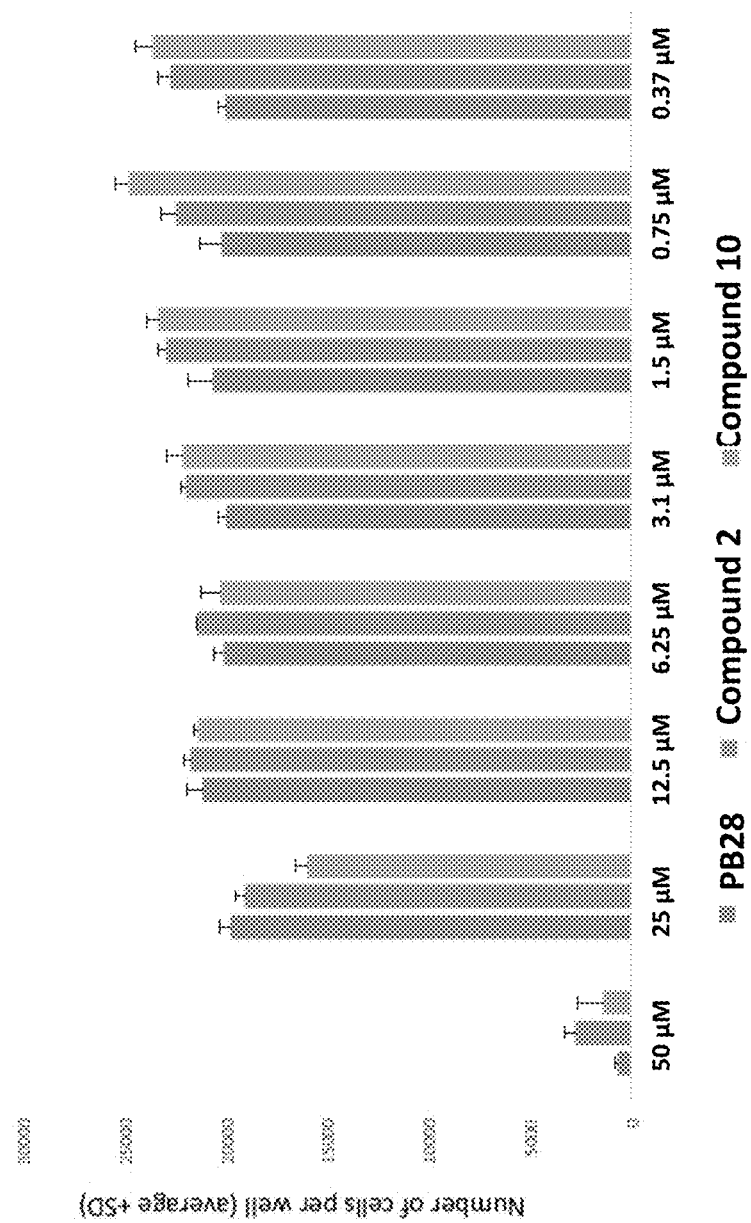
FIG. 1 depicts the cell number after exposing the cells to the toxicity protocol of Example 28, which shows that compound 2 and compound 10 are not cytotoxic to the cells.

Unless otherwise stated, the following terms used in the specification and claims have the following meanings set out below.

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_2$, $C_3$, $C_4$, $C_5$ or $C_6$ branched saturated aliphatic hydrocarbon groups. For example, $C_1$-$C_6$ alkyl is intends to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, i-pentyl, or n-hexyl. In some embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, "alkoxyl", "$C_1$, $C_2$, $C_3$, $C_4$, $C_5$ or $C_6$ alkoxyl" or "$C_1$-$C_6$ alkoxyl" is intended to include —O—$C_1$, —O—$C_2$, —O—$C_3$, —O—$C_4$, —O—$C_5$ or —O—$C_6$ straight chain (linear) saturated aliphatic hydrocarbon groups and —O—$C_2$, —O—$C_3$, —O—$C_4$, —O—$C_5$ or —O—$C_6$ branched saturated aliphatic hydrocarbon groups. For example, $C_1$-$C_6$ alkoxyl is intends to include —O—$C_1$, —O—$C_2$, —O—$C_3$, —O—$C_4$, —O—$C_5$ and —O—$C_6$ alkyl groups. Examples of alkoxyl include, moieties having from one to six carbon atoms, such as, but not limited to, methoxyl, ethoxyl, n-propoxyl, i-propoxyl, n-butoxyl, s-butoxyl, t-butoxyl, n-pentoxyl, i-pentoxyl, or n-hexoxyl. In some embodiments, a straight chain or branched alkoxyl has six or fewer carbon atoms (e.g., $C_1$-$C_6$ for straight chain, $C_3$-$C_6$ for branched chain), and in another embodiment, a straight chain or branched alkoxyl has four or fewer carbon atoms.

As used herein, the term "alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

As used herein, the term "alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain).

The term "$C_2$-$C_6$" includes alkynyl groups containing two to six carbon atoms. The term "$C_3$-$C_6$" includes alkynyl groups containing three to six carbon atoms. As used herein, "$C_2$-$C_6$ alkenylene linker" or "$C_2$-$C_6$ alkynylene linker" is intended to include $C_2$, $C_3$, $C_4$, $C_5$ or $C_6$ chain (linear or branched) divalent unsaturated aliphatic hydrocarbon groups. For example, $C_2$-$C_6$ alkenylene linker is intended to include $C_2$, $C_3$, $C_4$, $C_5$ and $C_6$ alkenylene linker groups.

The term "alkylene" or "alkylenyl" refers to a divalent alkyl radical. Any of the above mentioned monovalent alkyl groups may be an alkylene by abstraction of a second hydrogen atom from the alkyl. As herein defined, alkylene may also be a $C_1$-$C_6$ alkylene. An alkylene may further be a $C_1$-$C_4$ alkylene. Typical alkylene groups include, but are not limited to, —$CH_2$—, —$CH(CH_3)$—, —$C(CH_3)_2$—, —$CH_2CH_2$—, —$CH_2CH(CH_3)$—, —$CH_2C(CH_3)_2$—, —$CH_2CH_2CH_2$—, —$CH_2CH_2CH_2CH_2$—, and the like.

Optionally substituted moieties (such as optionally substituted alkyl, alkenyl, alkynyl, cycloalkyl, heterocycloalkyl, aryl, heteroaryl, etc.) include both the unsubstituted moieties and the moieties having one or more of the designated substituents. For example, substituted aryl moieties include those which are halogen and/or $C_1$-$C_6$ alkyl substituted; substituted heteroaryl moieties include 2,6-dimethylpyridinyl; and substituted heterocycloalkyl includes those substituted with one or more alkyl groups, such as 2,2,6,6-tetramethyl-piperidinyl, and 2,2,6,6-tetramethyl-1,2,3,6-tetrahydropyridinyl.

As used herein, the term "cycloalkyl" refers to a saturated or partially unsaturated hydrocarbon monocyclic or polycyclic (e.g., fused, bridged, or spiro rings) system having 3 to 30 carbon atoms (e.g., $C_3$-$C_{12}$, $C_3$-$C_{10}$, or $C_3$-$C_5$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, 1,2,3,4-tetrahydronaphthalenyl, and adamantyl. In the case of polycyclic cycloalkyl, only one of the rings in the cycloalkyl needs to be non-aromatic.

As used herein, the term "heterocycloalkyl" refers to a saturated or partially unsaturated 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, P, or Se), e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulphur, unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, 3'H-spiro[cyclohexane-1,1'-furo[3,4-c]pyridin]-yl, 3-azabicyclo[3.1.0]hexanyl, 3-azabicyclo[3.1.0]hexan-3-yl, 1,4,5,6-tetrahydropyrrolo[3,4-c]pyrazolyl, 3,4,5,6,7,8-hexahydropyrido[4,3-d]pyrimidinyl, 4,5,6,7-tetrahydro-1H-pyrazolo[3,4-c]pyridinyl, 5,6,7,8-tetrahydropyrido[4,3-d]pyrimidinyl, 2-azaspiro[3.3]heptanyl, 2-methyl-2-azaspiro[3.3]heptanyl, 2-azaspiro[3.5]nonanyl, 2-methyl-2-azaspiro[3.5]nonanyl, 2-azaspiro[4.5]decanyl, 2-methyl-2-azaspiro[4.5]decanyl, 2-oxa-azaspiro[3.4]octanyl, 2-oxa-azaspiro[3.4]octan-6-yl, and the like. In the case of multicyclic heterocycloalkyl, only one of the rings in the heterocycloalkyl needs to be non-aromatic (e.g., 4,5,6,7-tetrahydrobenzo[c]isoxazolyl).

As used herein, the term "aryl" includes groups with aromaticity, including "conjugated," or multicyclic systems with one or more aromatic rings and do not contain any heteroatom in the ring structure. The term aryl includes both monovalent species and divalent species. Examples of aryl groups include, but are not limited to, phenyl, biphenyl, naphthyl and the like. Conveniently, an aryl is phenyl.

As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulphur. The nitrogen atom may be substituted or unsubstituted (i.e., N or NR wherein R is H or another substituent, as defined). The nitrogen and sulphur heteroatoms may optionally be oxidized (i.e., N→O and $S(O)_p$, where p=1 or 2). It is to be noted that total number of S and O atoms in the aromatic heterocycle is not more than 1. Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like. Heteroaryl groups can also be fused or bridged with alicyclic or heterocyclic rings, which are not aromatic so as to form a multicyclic system (e.g., 4,5,6,7-tetrahydrobenzo[c]isoxazolyl).

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, quinoline, isoquinoline, naphthrydine, indole, benzofuran, purine, benzofuran, deazapurine, indolizine.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulphhydryl, alkylthio, arylthio, thiocarboxylate, sulphates, alkylsulphinyl, sulphonato, sulphamoyl, sulphonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl such as benzo[d][1,3]dioxole-5-yl).

As used herein, the term "substituted," means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., R) occurs more than one time in any constituent or formula for a compound, its definition at each occurrence is independent of its definition at every other occurrence. Thus, for example, if a group is shown to be substituted with 0-2 R moieties, then the group may optionally be substituted with up to two R moieties and R at each occurrence is selected independently from the definition of R. Also, combinations of substituents and/or variables are permissible, but only if such combinations result in stable compounds.

As used herein, the term "hydroxy" or "hydroxyl" includes groups with an —OH or the corresponding anion, —O⁻.

As used herein, the term "halo" or "halogen" refers to fluorine, chlorine, bromine and iodine.

As used herein, "haloalkyl", is intended to include "alkyl" moieties that are substituted with one or more halogens. Non-limiting examples include —CH$_2$F, —CHF$_2$, —CF$_3$, —CH$_2$CF$_3$, —CH$_2$CHF$_2$, —CH$_2$Cl, —CClF$_2$, —CCl$_3$, —CClHCF$_3$, —CCl$_2$CHF$_2$, —CClFCF$_3$, and —CF$_2$CCl$_3$.

As used herein, "haloalkoxyl", is intended to include "alkoxyl" moieties that are substituted with one or more halogens. Non-limiting examples include —OCH$_2$F, —OCHF$_2$, —OCF$_3$, —OCH$_2$CF$_3$, —OCH$_2$CHF$_2$, —OCHFCF$_3$, and —OCF$_2$CF$_3$.

As used herein, the expressions "one or more of A, B, or C," "one or more A, B, or C," "one or more of A, B, and C," "one or more A, B, and C," "selected from the group consisting of A, B, and C", "selected from A, B, and C", and the like are used interchangeably and all refer to a selection from a group consisting of A, B, and/or C, i.e., one or more As, one or more Bs, one or more Cs, or any combination thereof, unless indicated otherwise.

It is to be understood that compounds of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, 5$^{th}$ edition, John Wiley & Sons: New York, 2001; Greene, T. W., Wuts, P. G. M., *Protective Groups in Organic Synthesis*, 3$^{rd}$ edition, John Wiley & Sons: New York, 1999; R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., Encyclopedia of Reagents for Organic Synthesis, John Wiley and Sons (1995), incorporated by reference herein, are useful and recognized reference textbooks of organic synthesis known to those in the art One of ordinary skill in the art will note that, during the reaction sequences and synthetic schemes described herein, the order of certain steps may be changed, such as the introduction and removal of protecting groups. One of ordinary skill in the art will recognize that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., *Protective Groups in Organic Synthesis*, 3$^{rd}$ edition, John Wiley & Sons: New York, 1999.

Unless explicitly indicated otherwise, the terms "approximately" and "about" are synonymous. In some embodiments, "approximately" and "about" refer to the recited amount, value, dose or duration ±20%, +15%, 10%, ±8%, ±6%, +5%, ±4%, ±2%, ±1%, or ±0.5%. In another embodiment, "approximately" and "about" refer to the listed amount or duration ±10%, +8%, +6%, +5%, +4%, or +2%. In some embodiments, "approximately" and "about" refer to the listed amount, value, dose, or duration ±5%. In some embodiments, "approximately" and "about" refer to the listed amount, value, dose, or duration ±2%. In some embodiments, "approximately" and "about" refer to the listed amount, value, dose, or duration±1%.

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

As used herein, the term "unsubstituted" means that the specified group bears no substituents.

The term "solvate" refers to a complex of variable stoichiometry formed by a solute and solvent. Such solvents for the purpose of the invention may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula (I) may have one or more asymmetric carbon atom and may occur as racemates, racemic mixtures and as individual enantiomers or diastereomers.

The present invention also contemplates isotopically-labelled compounds of Formula I (e.g., those labeled with $^2$H and 14C). Deuterated (i.e., $^2$H or D) and carbon-14 (i.e., $^{14}$C) isotopes are particularly preferred for their ease of preparation and detectability. Further, substitution with heavier isotopes such as deuterium may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples herein below, by substituting an appropriate isotopically labelled reagent for a non-isotopically labelled reagent.

As used herein, the term "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzoate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate, pantothenate, phosphate/diphosphate, picrate, polygalacturonate, propionate, p-toluenesulfonate, salicylate, stearate, subacetate, succinate, sulfate, sulfosalicylate, tannate, tartrate, teoclate, tosylate, triethiodide, and valerate salts.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

As used herein, "pharmaceutically acceptable salts" and "pharmaceutically acceptable excipients" may be used interchangeably.

As used herein, the term "subject" is interchangeable with the term "subject in need thereof", both of which refer to a subject having a disease or having an increased risk of developing the disease. A "subject" includes a mammal. The mammal can be e.g., a human or appropriate non-human mammal, such as primate, mouse, rat, dog, cat, cow, horse, goat, camel, sheep or a pig. The subject can also be a bird or fowl. In one embodiment, the mammal is a human. A subject in need thereof can be one who has been previously diagnosed or identified as having a disease or disorder disclosed herein. A subject in need thereof can also be one who is suffering from a disease or disorder disclosed herein. Alternatively, a subject in need thereof can be one who has an increased risk of developing such disease or disorder relative to the population at large (i.e., a subject who is predisposed to developing such disorder relative to the population at large). A subject in need thereof can have a refractory or resistant a disease or disorder disclosed herein (i.e., a disease or disorder disclosed herein that does not respond or has not yet responded to treatment). The subject may be resistant at start of treatment or may become resistant during treatment. In some embodiments, the subject in need thereof received and failed all known effective therapies for a disease or disorder disclosed herein. In some embodiments, the subject in need thereof received at least one prior therapy.

The term "disorder" is used in this disclosure to mean, and is used interchangeably with, the terms disease, condition, or illness, unless otherwise indicated.

As used herein, the term "preventing," "prevent," or "protecting against" describes reducing or eliminating the onset of the symptoms or complications of such disease, condition or disorder, or preventing the transmission or replication of the virus causing such disease, condition, or disorder.

It is to be appreciated that references to "treating" or "treatment" include the alleviation of established symptoms of a condition. "Treating" or "treatment" of a state, infection exposure, disorder or condition therefore includes: (1) delaying the appearance of clinical symptoms of the state, infection exposure, disorder or condition developing in a human that may be afflicted with or predisposed to the state, infection exposure, disorder or condition but does not yet experience or display clinical or subclinical symptoms of the state, infection exposure, disorder or condition, (2) inhibiting the state, infection exposure, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, infection exposure, disorder or condition or at least one of its clinical or subclinical symptoms.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

In one embodiment, the term "therapeutically effective amount," as used herein, refers to the amount of a compound disclosed herein, or a composition comprising said compound, administered to a patient already suffering from a disease, condition, or disorder, that is sufficient to cure or at least partially arrest, or relieve to some extent one or more of the symptoms of the disease, disorder, or condition being treated. The effectiveness of such compositions depend upon conditions including, but not limited to, the severity and course of the disease, disorder, or condition, any previous therapy, the patient's health status and response to the drugs, and the judgment of the treating physician. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. Such an amount would be sufficient to elicit the biological or medical response of a tissue system, or patient that is sought by a researcher or clinician. Such a therapeutically effective amount can be determined by one of ordinary skill in the art having regard to their own knowledge, the state of the art, and this disclosure. By way of example only, therapeutically effective amounts may be determined by routine experimentation, including but not limited to a dose escalation clinical trial.

In one embodiment, the term "therapeutically effective amount," as used herein, refers to the amount of a compound disclosed herein, or a composition comprising said compound, this is effective for prevention of a disease, condition, or disorder.

The term "prodrug," as used in this disclosure, means a compound which is convertible in vivo by metabolic means (e.g., by hydrolysis) to a disclosed compound.

As used herein, "MOI" is equivalent to "multiplicity of infection", which refers to the number of virions that are added per cell during infection.

As used herein, PB28 refers 1-cyclohexyl-4-(3-(5-methoxy-1,2,3,4-tetrahydronaphthalen-1-yl)-n-propyl)piperazine dihydrochloride (i.e.,

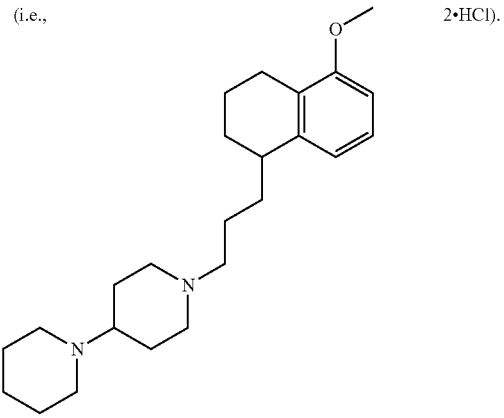 [SMILES: COc1cccc2c1CCCC2CCCN1CCC(N2CCCCC2)CC1]

2·HCl).

As used herein, MIN-101, which may also be referred to Roluperidone, has the following structure:

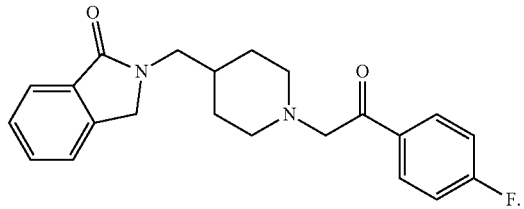 [SMILES: O=C(CN1CCC(CN2Cc3ccccc3C2=O)CC1)c1ccc(F)cc1]

The preparation of this compound is disclosed in Example 1 in U.S. Pat. No. 7,166,617, which is incorporated herein by reference in its entirety.

As used herein, MIN-S006 has the following structure:

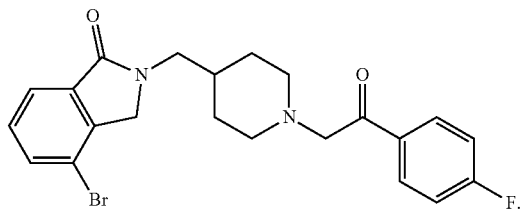 [SMILES: O=C(CN1CCC(CN2Cc3c(Br)cccc3C2=O)CC1)c1ccc(F)cc1]

The preparation of this compound is disclosed in Example 2 in U.S. Pat. No. 7,166,617.

Compounds of the Present Disclosure

In some aspects, the present disclosure provides, inter alia, a compound of Formula (I):

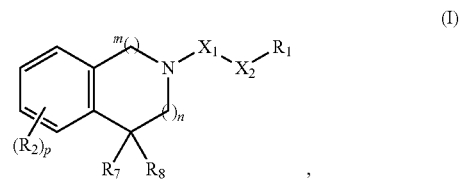

or a prodrug, solvate, or pharmaceutically acceptable salt thereof, wherein
  $X_1$ is absent, $-(CR_3R_4)_q-$, $-O-$, $-S(O)_2-$, $-C(O)-$, $-C(S)-$, $-S(O)-$, $-NR_3C(O)-$, $-C(O)NR_3-$, $-C(O)O-$, or $-OC(O)-$;
  $X_2$ is absent, $-(CR_3R_4)_q-$, $-O-$, $-S(O)_2-$, $-C(O)-$, $-C(S)-$, $-S(O)-$, $-NR_3-$ $-NR_3C(O)-$, $-C(O)NR_3-$, $-C(O)O-$, or $-OC(O)-$;
  $R_1$ is H, OH, halogen, $NH_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, $C_6$-$C_{10}$ aryl, 5- to 12-membered heteroaryl comprising 1-6 heteroatoms selected from N, O, and S, 5- to 14-membered saturated or unsaturated heterocycloalkyl comprising 1-5 heteroatoms selected from N, O, and S; wherein the alkyl, alkenyl, alkynyl, haloalkyl, alkoxyl, haloalkoxyl, cycloalkyl, aryl, heteroaryl, or heterocycloalkyl of any of the foregoing is optionally substituted with one or more $R_5$;
  each $R_2$ is H, OH, halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, $-C(O)C_1$-$C_6$alkyl, $-C(O)OC_1$-$C_6$alkyl, $-C(O)NH_2$, $-C(O)NHC_1$-

$C_6$alkyl, —C(O)N($C_1$-$C_6$alkyl)$_2$, $C_6$-$C_{10}$ aryl, 5- to 12-membered heteroaryl comprising 1-6 heteroatoms selected from N, O, and S, or 5- to 14-membered saturated or unsaturated heterocycloalkyl comprising 1-5 heteroatoms selected from N, O, and S; wherein the alkyl, alkenyl, alkynyl, haloalkyl, alkoxyl, haloalkoxyl, cycloalkyl, aryl, heteroaryl, or heterocycloalkyl of any of the foregoing is optionally substituted with one or more $R_6$;

each $R_3$ independently is H, halogen, or $C_1$-$C_6$ alkyl;

each $R_4$ independently is H, halogen, or $C_1$-$C_6$ alkyl;

each $R_5$ independently is OH, halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, $C_6$-$C_{10}$ aryl, or 5- to 14-membered saturated or unsaturated heterocycloalkyl comprising 1-5 heteroatoms selected from N, O, and S; wherein the alkyl, alkenyl, alkynyl, cycloalkyl, or aryl of any of the foregoing is optionally substituted with one or more —C(O)$C_1$-$C_6$alkyl, —C(O)O$C_1$-$C_6$alkyl, —C(O)NH$_2$, —C(O)NH$C_1$-$C_6$alkyl, or —C(O)N($C_1$-$C_6$alkyl)$_2$;

each $R_6$ independently is OH, halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, $C_6$-$C_{10}$ aryl, or 5- to 14-membered saturated or unsaturated heterocycloalkyl comprising 1-5 heteroatoms selected from N, O, and S; wherein the alkyl, alkenyl, alkynyl, cycloalkyl, aryl, or heterocycloalkyl of any of the foregoing is optionally substituted with one or more —C(O)$C_1$-$C_6$alkyl, —C(O)O$C_1$-$C_6$alkyl, —C(O)NH$_2$, —C(O)NH$C_1$-$C_6$alkyl, or —C(O)N($C_1$-$C_6$alkyl)$_2$;

$R_7$ is $C_1$-$C_6$ alkyl optionally substituted with one or more OH, halogen, or $C_1$-$C_6$ alkoxyl;

$R_8$ is $C_1$-$C_6$ alkyl optionally substituted with one or more OH, halogen, or $C_1$-$C_6$ alkoxyl; or $R_7$ and $R_8$, together with the carbon atom they are attached, form a $C_3$-$C_6$ cycloalkyl optionally substituted with one or more OH, halogen, or $C_1$-$C_6$ alkoxyl m is 0, 1, 2, or 3;

n is 0, 1, 2, or 3;

p is 0, 1, 2, 3, or 4; and each q independently is 1, 2, 3, or 4.

In some aspects, the present disclosure provides, inter alia, a compound of Formula (I):

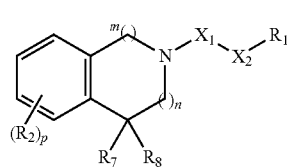

(I)

or a prodrug, solvate, or pharmaceutically acceptable salt thereof, wherein $X_1$ is absent, —(CR$_3$R$_4$)$_q$—, —O—, —S(O)$_2$—, —C(O)—, —C(S)—, —S(O)—, —NR$_3$C(O)—, —C(O)NR$_3$—, —C(O)O—, or —OC(O)—;

$X_2$ is absent, —(CR$_3$R$_4$)$_q$—, —O—, —S(O)$_2$—, —C(O)—, —C(S)—, —S(O)—, —NR$_3$— —NR$_3$C(O)—, —C(O)NR$_3$—, —C(O)O—, or —OC(O)—;

$R_1$ is H, OH, halogen, NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, $C_6$-$C_{10}$ aryl, 5- to 12-membered heteroaryl comprising 1-6 heteroatoms selected from N, O, and S, 5- to 14-membered saturated or unsaturated heterocycloalkyl comprising 1-5 heteroatoms selected from N, O, and S; wherein the alkyl, alkenyl, alkynyl, haloalkyl, alkoxyl, haloalkoxyl, cycloalkyl, aryl, heteroaryl, or heterocycloalkyl of any of the foregoing is optionally substituted with one or more $R_5$;

each $R_2$ is H, OH, halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, —C(O)$C_1$-$C_6$alkyl, —C(O)O$C_1$-$C_6$alkyl, —C(O)NH$_2$, —C(O)NH$C_1$-$C_6$alkyl, —C(O)N($C_1$-$C_6$alkyl)$_2$, $C_6$-$C_{10}$ aryl, 5- to 12-membered heteroaryl comprising 1-6 heteroatoms selected from N, O, and S, or 5- to 14-membered saturated or unsaturated heterocycloalkyl comprising 1-5 heteroatoms selected from N, O, and S; wherein the alkyl, alkenyl, alkynyl, haloalkyl, alkoxyl, haloalkoxyl, cycloalkyl, aryl, heteroaryl, or heterocycloalkyl of any of the foregoing is optionally substituted with one or more $R_6$;

each $R_3$ independently is H, halogen, or $C_1$-$C_6$ alkyl;

each $R_4$ independently is H, halogen, or $C_1$-$C_6$ alkyl;

each $R_5$ independently is OH, halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, $C_6$-$C_{10}$ aryl, or 5- to 14-membered saturated or unsaturated heterocycloalkyl comprising 1-5 heteroatoms selected from N, O, and S; wherein the alkyl, alkenyl, alkynyl, cycloalkyl, or aryl of any of the foregoing is optionally substituted with one or more —C(O)$C_1$-$C_6$alkyl, —C(O)O$C_1$-$C_6$alkyl, —C(O)NH$_2$, —C(O)NH$C_1$-$C_6$alkyl, or —C(O)N($C_1$-$C_6$alkyl)$_2$;

each $R_6$ independently is OH, halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, $C_6$-$C_{10}$ aryl, or 5- to 14-membered saturated or unsaturated heterocycloalkyl comprising 1-5 heteroatoms selected from N, O, and S; wherein the alkyl, alkenyl, alkynyl, cycloalkyl, aryl, or heterocycloalkyl of any of the foregoing is optionally substituted with one or more —C(O)$C_1$-$C_6$alkyl, —C(O)O$C_1$-$C_6$alkyl, —C(O)NH$_2$, —C(O)NH$C_1$-$C_6$alkyl, or —C(O)N($C_1$-$C_6$alkyl)$_2$;

$R_7$ is $C_1$-$C_6$ alkyl;

$R_8$ is $C_1$-$C_6$ alkyl;

m is 0, 1, 2, or 3;

n is 0, 1, 2, or 3;

p is 0, 1, 2, 3, or 4; and each q independently is 1, 2, 3, or 4.

In some aspects, the present disclosure provides, inter alia, a compound of Formula (Ia):

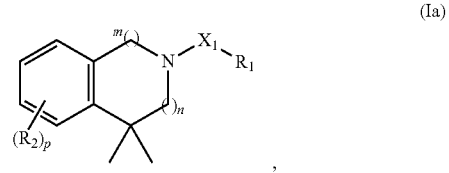

(Ia)

or a prodrug, solvate, or pharmaceutically acceptable salt thereof, wherein $X_1$ is absent, (CR$_3$R$_4$)$_q$, —C(O)—, —C(S)—, —S(O)—, —NR$_3$C(O)—, or —C(O)O—;

$R_1$ is H, OH, halogen, —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl, wherein the alkyl, alkenyl, alkynyl, haloalkyl, alkoxyl, haloalkoxyl, or cycloalkyl is optionally substituted with one or more $R_5$;

$R_2$ is H, OH, halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, —C(O)$C_1$-$C_6$alkyl, —C(O)O$C_1$-$C_6$alkyl, —C(O)NH$_2$, —C(O)NH$C_1$-$C_6$alkyl, —C(O)N($C_1$-$C_6$alkyl)$_2$, $C_6$-$C_{10}$ aryl, 5- to 12-membered heteroaryl comprising 1-6 heteroatoms selected from N, O, and S, or 5- to 14-membered saturated or unsaturated heterocycloalkyl comprising 1-5 heteroatoms selected from N, O, and S wherein the alkyl, alkenyl, alkynyl, haloalkyl, alkoxyl, haloalkoxyl, cycloalkyl, aryl, heteroaryl, or heterocycloalkyl is optionally substituted with one or more $R_6$;

each $R_3$ is H or halogen;

each $R_4$ is H or halogen;

each $R_5$ is OH, halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, or $C_6$-$C_{10}$ aryl, wherein the alkyl, alkenyl, alkynyl, cycloalkyl, or aryl is optionally substituted with one or more —C(O)$C_1$-$C_6$alkyl, —C(O)O$C_1$-$C_6$alkyl, —C(O)NH$_2$, —C(O)NH$C_1$-$C_6$alkyl, or —C(O)N($C_1$-$C_6$alkyl)$_2$;

each $R_6$ independently is OH, halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, $C_6$-$C_{10}$ aryl, or 5- to 14-membered saturated or unsaturated heterocycloalkyl comprising 1-5 heteroatoms selected from N, O, and S wherein the alkyl, alkenyl, alkynyl, cycloalkyl, aryl, or heterocycloalkyl is optionally substituted with one or more —C(O)$C_1$-$C_6$alkyl, —C(O)O$C_1$-$C_6$alkyl, —C(O)NH$_2$, —C(O)NH$C_1$-$C_6$alkyl, or —C(O)N($C_1$-$C_6$alkyl)$_2$;

m is 0, 1, 2, or 3;

n is 0, 1, 2, or 3;

p is 0, 1, 2, 3, or 4; and each q independently is 1, 2, 3, or 4.

In some embodiments, $X_1$ is absent, (CR$_3$R$_4$)$_q$, —O—, —S(O)$_2$—, —C(O)—, —C(S)—, —S(O)—, —NR$_3$C(O)—, —C(O)NR$_3$—, —C(O)O—, or —OC(O)—.

In some embodiments, $X_1$ is —O—, —S(O)$_2$—, —NR$_3$C(O)—, or —C(O)NR$_3$—.

In some embodiments, $X_1$ is a absent, —(CR$_3$R$_4$)$_q$—, —C(O)—, —C(S)—, —S(O)—, —NR$_3$C(O)—, or —C(O)O—.

In some embodiments, $X_1$ is a absent, —(CR$_3$R$_4$)$_q$—, —C(O)—, or —C(O)O—.

In some embodiments, $X_1$ is a absent.

In some embodiments, $X_1$ is —(CR$_3$R$_4$)$_q$—.

In some embodiments, $X_1$ is —C(O)— or —C(O)O—.

In some embodiments, $X_1$ is —C(O)—.

In some embodiments, $X_1$ is —C(O)O—.

In some embodiments, $X_1$ is —NR$_3$C(O)— or —C(O)NR$_3$—.

In some embodiments, $X_1$ is —O— or —S(O)$_2$—. In some embodiments, $X_1$ is —O—. In some embodiments, $X_1$ is —S(O)$_2$—. In some embodiments, $X_2$ is absent, —(CR$_3$R$_4$)$_q$—, —O—, —S(O)$_2$—, —C(O)—, —C(S)—, —S(O)—, —NR$_3$C(O)—, —C(O)NR$_3$—, —C(O)O—, or —OC(O)—.

In some embodiments, $X_2$ is —O—, —S(O)$_2$—, —NR$_3$C(O)—, or —C(O)NR$_3$—.

In some embodiments, $X_2$ is absent, —(CR$_3$R$_4$)$_q$—, —C(O)—, —C(S)—, —S(O)—, —NR$_3$C(O)—, or —C(O)O—.

In some embodiments, $X_2$ is absent, —(CR$_3$R$_4$)$_q$—, —C(O)—, or —C(O)O—.

In some embodiments, $X_2$ is absent.

In some embodiments, $X_2$ is —(CR$_3$R$_4$)$_q$—.

In some embodiments, $X_2$ is —C(O)— or —C(O)O—.

In some embodiments, $X_2$ is —C(O)—.

In some embodiments, $X_2$ is —C(O)O—.

In some embodiments, $X_2$ is —NR$_3$C(O)— or —C(O)NR$_3$—.

In some embodiments, $X_2$ is —O— or —S(O)$_2$—. In some embodiments, $X_2$ is —O—. In some embodiments, $X_2$ is —S(O)$_2$—.

In some embodiments, $R_1$ is H, OH, halogen, NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, $C_6$-$C_{10}$ aryl, 5- to 12-membered heteroaryl comprising 1-6 heteroatoms selected from N, O, and S, 5- to 14-membered saturated or unsaturated heterocycloalkyl comprising 1-5 heteroatoms selected from N, O, and S; wherein the alkyl, alkenyl, alkynyl, haloalkyl, alkoxyl, haloalkoxyl, cycloalkyl, aryl, heteroaryl, or heterocycloalkyl of any of the foregoing is optionally substituted with one or more $R_5$.

In some embodiments, $R_1$ is H, OH, halogen, NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl, wherein the alkyl, alkenyl, alkynyl, haloalkyl, alkoxyl, haloalkoxyl, or cycloalkyl of any of the foregoing is optionally substituted with one or more $R_5$.

In some embodiments, $R_1$ is H or OH. In some embodiments, $R_1$ is H. In some embodiments, $R_1$ is OH.

In some embodiments, $R_1$ is halogen.

In some embodiments, $R_1$ is NH$_2$.

In some embodiments, $R_1$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl, wherein the alkyl, alkenyl, alkynyl, haloalkyl, alkoxyl, haloalkoxyl, or cycloalkyl of any of the foregoing is optionally substituted with one or more $R_5$.

In some embodiments, $R_1$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl, wherein the alkyl, alkenyl, alkynyl, haloalkyl, alkoxyl, haloalkoxyl, or cycloalkyl of any of the foregoing is substituted with one or more $R_5$.

In some embodiments, $R_1$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl, wherein the alkyl, alkenyl, alkynyl, haloalkyl, alkoxyl, haloalkoxyl, or cycloalkyl of any of the foregoing is substituted with one $R_5$.

In some embodiments, $R_1$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl, wherein the alkyl, alkenyl, alkynyl, haloalkyl, alkoxyl, haloalkoxyl, or cycloalkyl of any of the foregoing is substituted with two $R_5$.

In some embodiments, $R_1$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl, wherein the alkyl, alkenyl, alkynyl, haloalkyl, alkoxyl, haloalkoxyl, or cycloalkyl of any of the foregoing is substituted with three $R_5$.

In some embodiments, $R_1$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl.

In some embodiments, $R_1$ is $C_1$-$C_6$ alkyl, $C_2$-$C_6$ alkenyl, or $C_2$-$C_6$ alkynyl.

In some embodiments, $R_1$ is $C_1$-$C_6$ alkyl. In some embodiments, $R_1$ is methyl. In some embodiments, $R_1$ is ethyl. In some embodiments, $R_1$ is propyl. In some embodiments, $R_1$ is butyl. In some embodiments, $R_1$ is isopropyl. In some embodiments, $R_1$ is iso-butyl. In some embodiments, $R_1$ is sec-butyl. In some embodiments, $R_1$ is tert-butyl. In some embodiments, $R_1$ is pentyl. In some embodiments, $R_1$ is iso-pentyl. In some embodiments, $R_1$ is hexyl. In some embodiments, $R_1$ is iso-hexyl.

In some embodiments, $R_1$ is $C_2$-$C_6$ alkenyl. In some embodiments, $R_1$ is $C_2$ alkenyl. In some embodiments, $R_1$ is $C_3$ alkenyl. In some embodiments, $R_1$ is $C_4$ alkenyl. In some embodiments, $R_1$ is $C_5$ alkenyl. In some embodiments, $R_1$ is $C_6$ alkenyl.

In some embodiments, $R_1$ is $C_2$-$C_6$ alkynyl. In some embodiments, $R_1$ is $C_2$ alkynyl. In some embodiments, $R_1$ is $C_3$ alkynyl. In some embodiments, $R_1$ is $C_4$ alkynyl. In some embodiments, $R_1$ is $C_5$ alkynyl. In some embodiments, $R_1$ is $C_6$ alkynyl.

In some embodiments, $R_1$ is $C_1$-$C_6$ haloalkyl, $C_1$-$C_6$ alkoxyl, $C_1$-$C_6$ haloalkoxyl, or $C_3$-$C_6$ cycloalkyl.

In some embodiments, $R_1$ is $C_1$-$C_6$ haloalkyl. In some embodiments, $R_1$ is halomethyl. In some embodiments, $R_1$ is haloethyl. In some embodiments, $R_1$ is halopropyl. In some embodiments, $R_1$ is halobutyl. In some embodiments, $R_1$ is halopentyl. In some embodiments, $R_1$ is halohexyl.

In some embodiments, $R_1$ is $C_1$-$C_6$ alkoxyl. In some embodiments, $R_1$ is methoxyl. In some embodiments, $R_1$ is ethoxyl. In some embodiments, $R_1$ is propoxyl. In some embodiments, $R_1$ is butoxyl. In some embodiments, $R_1$ is pentoxyl. In some embodiments, $R_1$ is hexoxyl.

In some embodiments, $R_1$ is $C_1$-$C_6$ haloalkoxyl. In some embodiments, $R_1$ is halomethoxyl. In some embodiments, $R_1$ is haloethoxyl. In some embodiments, $R_1$ is halopropoxyl. In some embodiments, $R_1$ is halobutoxyl. In some embodiments, $R_1$ is halopentoxyl. In some embodiments, $R_1$ is halohexoxyl.

In some embodiments, $R_1$ is $C_3$-$C_6$ cycloalkyl. In some embodiments, $R_1$ is cyclopropyl.

In some embodiments, $R_1$ is cyclobutyl. In some embodiments, $R_1$ is cyclopentyl. In some embodiments, $R_1$ is cyclohexyl.

In some embodiments, $R_1$ is $C_1$-$C_6$ alkyl, $C_2$-$C_6$ alkenyl, or $C_2$-$C_6$ alkynyl, wherein the alkyl, alkenyl, or alkynyl of any of the foregoing is optionally substituted with one or more $R_5$.

In some embodiments, $R_1$ is $C_1$-$C_6$ alkyl, $C_2$-$C_6$ alkenyl, or $C_2$-$C_6$ alkynyl, wherein the alkyl, alkenyl, or alkynyl of any of the foregoing is substituted with one or more $R_5$.

In some embodiments, $R_1$ is $C_1$-$C_6$ alkyl, $C_2$-$C_6$ alkenyl, or $C_2$-$C_6$ alkynyl, wherein the alkyl, alkenyl, or alkynyl of any of the foregoing is substituted with one $R_5$.

In some embodiments, $R_1$ is $C_1$-$C_6$ alkyl, $C_2$-$C_6$ alkenyl, or $C_2$-$C_6$ alkynyl, wherein the alkyl, alkenyl, or alkynyl of any of the foregoing is substituted with two $R_5$.

In some embodiments, $R_1$ is $C_1$-$C_6$ alkyl, $C_2$-$C_6$ alkenyl, or $C_2$-$C_6$ alkynyl, wherein the alkyl, alkenyl, or alkynyl is substituted with three $R_5$.

In some embodiments, $R_1$ is methyl substituted with one or more $R_5$. In some embodiments, $R_1$ is ethyl substituted with one or more $R_5$. In some embodiments, $R_1$ is propyl substituted with one or more $R_5$. In some embodiments, $R_1$ is butyl substituted with one or more $R_5$. In some embodiments, $R_1$ is pentyl substituted with one or more $R_5$. In some embodiments, $R_1$ is hexyl substituted with one or more $R_5$.

In some embodiments, $R_1$ is $C_6$-$C_{10}$ aryl, 5- to 12-membered heteroaryl comprising 1-6 heteroatoms selected from N, O, and S, or 5- to 14-membered saturated or unsaturated heterocycloalkyl comprising 1-5 heteroatoms selected from N, O, and S, wherein the aryl, heteroaryl, or heterocycloalkyl of any of the foregoing is optionally substituted with one or more $R_5$.

In some embodiments, $R_1$ is $C_6$-$C_{10}$ aryl, 5- to 12-membered heteroaryl comprising 1-6 heteroatoms selected from N, O, and S, or 5- to 14-membered saturated or unsaturated heterocycloalkyl comprising 1-5 heteroatoms selected from N, O, and S.

In some embodiments, $R_1$ is $C_6$-$C_{10}$ aryl, 5- to 12-membered heteroaryl comprising 1-6 heteroatoms selected from N, O, and S, or 5- to 14-membered saturated or unsaturated heterocycloalkyl comprising 1-5 heteroatoms selected from N, O, and S, wherein the aryl, heteroaryl, or heterocycloalkyl of any of the foregoing is substituted with one or more $R_5$.

In some embodiments, $R_1$ is $C_6$-$C_{10}$ aryl, 5- to 12-membered heteroaryl comprising 1-6 heteroatoms selected from N, O, and S, or 5- to 14-membered saturated or unsaturated heterocycloalkyl comprising 1-5 heteroatoms selected from N, O, and S, wherein the aryl, heteroaryl, or heterocycloalkyl of any of the foregoing is substituted with one $R_5$.

In some embodiments, $R_1$ is $C_6$-$C_{10}$ aryl, 5- to 12-membered heteroaryl comprising 1-6 heteroatoms selected from N, O, and S, or 5- to 14-membered saturated or unsaturated heterocycloalkyl comprising 1-5 heteroatoms selected from N, O, and S, wherein the aryl, heteroaryl, or heterocycloalkyl of any of the foregoing is substituted with two $R_5$.

In some embodiments, $R_1$ is $C_6$-$C_{10}$ aryl, 5- to 12-membered heteroaryl comprising 1-6 heteroatoms selected from N, O, and S, or 5- to 14-membered saturated or unsaturated heterocycloalkyl comprising 1-5 heteroatoms selected from N, O, and S, wherein the aryl, heteroaryl, or heterocycloalkyl of any of the foregoing is substituted with three $R_5$.

In some embodiments, $R_1$ is H, OH, methyl,

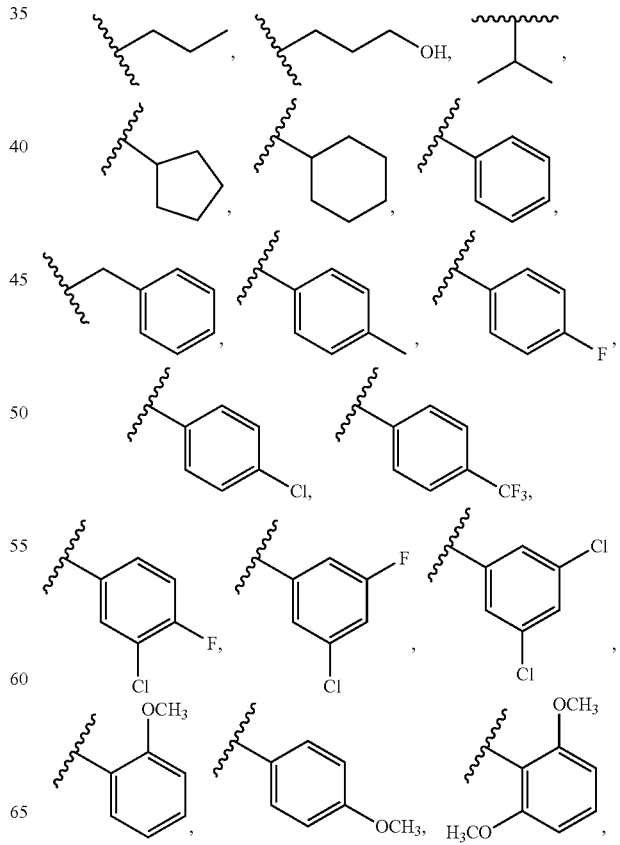

-continued
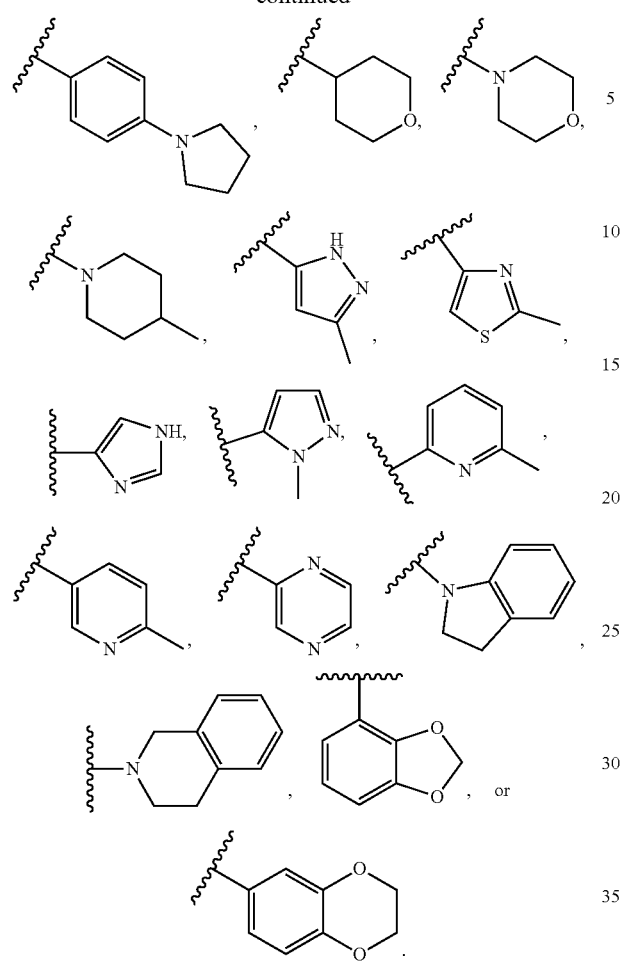
In some embodiments, $R_1$ is H, OH, methyl,
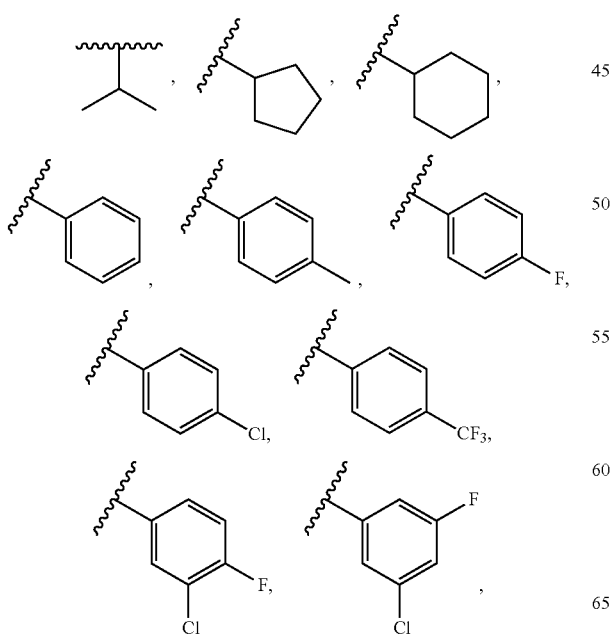
-continued
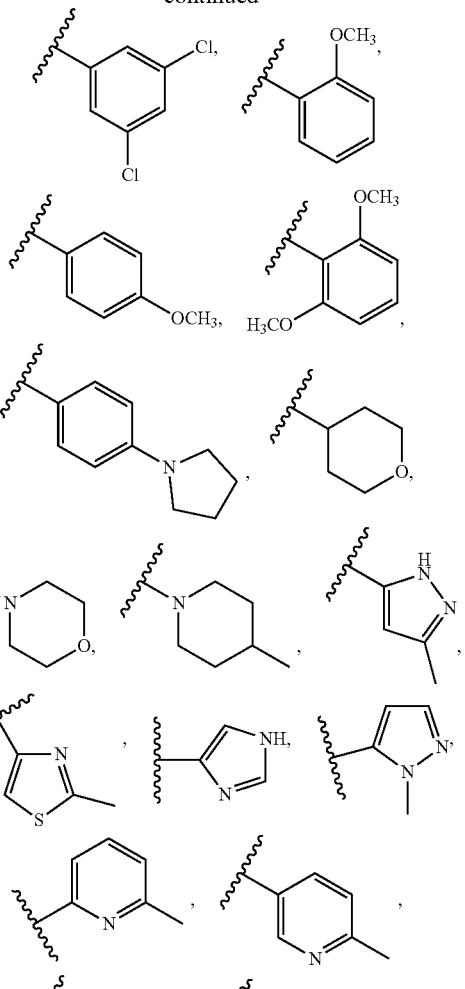
In some embodiments, $R_1$ is
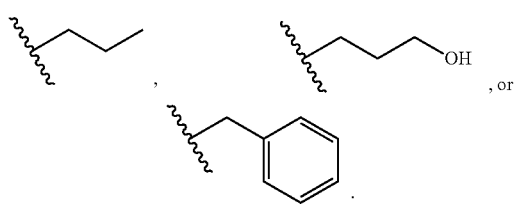

In some embodiments, $R_1$ is H, OH, methyl,

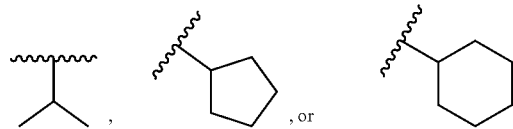

, or

In some embodiments, $R_1$ is

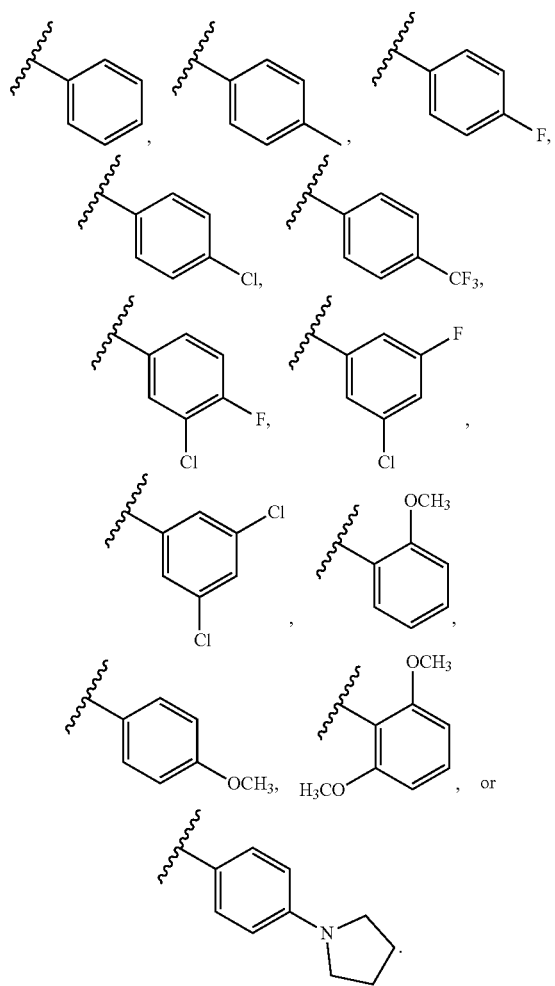

In some embodiments, $R_1$ is

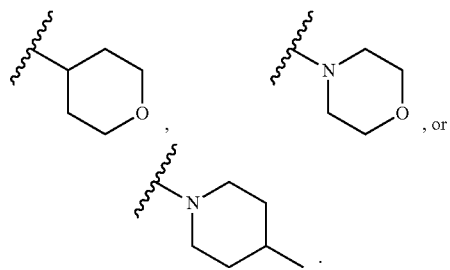

In some embodiments, $R_1$ is

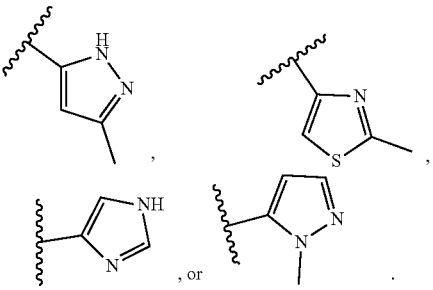

, or

In some embodiments, $R_1$ is

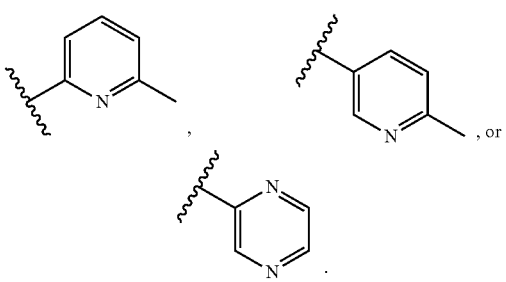

In some embodiments, $R_1$ is

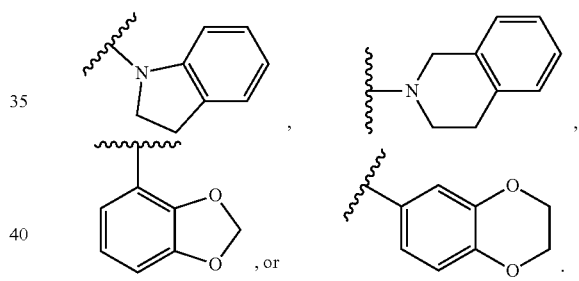

, or

In some embodiments, $R_2$ is H, OH, halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, —C(O)$C_1$-$C_6$alkyl, —C(O)O$C_1$-$C_6$alkyl, —C(O)NH$_2$, —C(O)NH$C_1$-$C_6$alkyl, —C(O)N($C_1$-$C_6$alkyl)$_2$, $C_6$-$C_{10}$ aryl, 5- to 12-membered heteroaryl comprising 1-6 heteroatoms selected from N, O, and S, or 5- to 14-membered saturated or unsaturated heterocycloalkyl comprising 1-5 heteroatoms selected from N, O, and S wherein the alkyl, alkenyl, alkynyl, haloalkyl, alkoxyl, haloalkoxyl, cycloalkyl, aryl, heteroaryl, or heterocycloalkyl is optionally substituted with one or more $R_6$.

In some embodiments, $R_2$ is OH, halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, —C(O)$C_1$-$C_6$alkyl, —C(O)O$C_1$-$C_6$alkyl, —C(O)NH$_2$, —C(O)NH$C_1$-$C_6$alkyl, —C(O)N($C_1$-$C_6$alkyl)$_2$, $C_6$-$C_{10}$ aryl, 5- to 12-membered heteroaryl comprising 1-6 heteroatoms selected from N, O, and S, or 5- to 14-membered saturated or unsaturated heterocycloalkyl comprising 1-5 heteroatoms selected from N, O, and S; wherein the alkyl, alkenyl, alkynyl, haloalkyl, alkoxyl, haloalkoxyl, cycloalkyl, aryl, heteroaryl, or heterocycloalkyl of any of the foregoing is optionally substituted with one or more $R_6$.

In some embodiments, $R_2$ is H, OH, halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, —C(O)$C_1$-$C_6$alkyl, —C(O)O$C_1$-$C_6$alkyl, —C(O)NH$_2$, —C(O)NH$C_1$-$C_6$alkyl, —C(O)N($C_1$-$C_6$alkyl)$_2$, $C_6$-$C_{10}$ aryl, 5- to 12-membered heteroaryl comprising 1-6 heteroatoms selected from N, O, and S, or 5- to 14-membered saturated or unsaturated heterocycloalkyl comprising 1-5 heteroatoms selected from N, O, and S; wherein the alkyl, alkenyl, alkynyl, haloalkyl, alkoxyl, haloalkoxyl, cycloalkyl, aryl, heteroaryl, or heterocycloalkyl of any of the foregoing is substituted with one or more $R_6$.

In some embodiments, $R_2$ is H, OH, halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, —C(O)$C_1$-$C_6$alkyl, —C(O)O$C_1$-$C_6$alkyl, —C(O)NH$_2$, —C(O)NH$C_1$-$C_6$alkyl, —C(O)N($C_1$-$C_6$alkyl)$_2$, $C_6$-$C_{10}$ aryl, 5- to 12-membered heteroaryl comprising 1-6 heteroatoms selected from N, O, and S, or 5- to 14-membered saturated or unsaturated heterocycloalkyl comprising 1-5 heteroatoms selected from N, O, and S; wherein the alkyl, alkenyl, alkynyl, haloalkyl, alkoxyl, haloalkoxyl, cycloalkyl, aryl, heteroaryl, or heterocycloalkyl of any of the foregoing is substituted with one $R_6$.

In some embodiments, $R_2$ is H, OH, halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, —C(O)$C_1$-$C_6$alkyl, —C(O)O$C_1$-$C_6$alkyl, —C(O)NH$_2$, —C(O)NH$C_1$-$C_6$alkyl, —C(O)N($C_1$-$C_6$alkyl)$_2$, $C_6$-$C_{10}$ aryl, 5- to 12-membered heteroaryl comprising 1-6 heteroatoms selected from N, O, and S, or 5- to 14-membered saturated or unsaturated heterocycloalkyl comprising 1-5 heteroatoms selected from N, O, and S; wherein the alkyl, alkenyl, alkynyl, haloalkyl, alkoxyl, haloalkoxyl, cycloalkyl, aryl, heteroaryl, or heterocycloalkyl of any of the foregoing is substituted with two $R_6$.

In some embodiments, $R_2$ is H, OH, halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, —C(O)$C_1$-$C_6$alkyl, —C(O)O$C_1$-$C_6$alkyl, —C(O)NH$_2$, —C(O)NH$C_1$-$C_6$alkyl, —C(O)N($C_1$-$C_6$alkyl)$_2$, $C_6$-$C_{10}$ aryl, 5- to 12-membered heteroaryl comprising 1-6 heteroatoms selected from N, O, and S, or 5- to 14-membered saturated or unsaturated heterocycloalkyl comprising 1-5 heteroatoms selected from N, O, and S; wherein the alkyl, alkenyl, alkynyl, haloalkyl, alkoxyl, haloalkoxyl, cycloalkyl, aryl, heteroaryl, or heterocycloalkyl of any of the foregoing is substituted with three $R_6$.

In some embodiments, $R_2$ is H, OH, halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, —C(O)$C_1$-$C_6$alkyl, —C(O)O$C_1$-$C_6$alkyl, —C(O)NH$_2$, —C(O)NH$C_1$-$C_6$alkyl, —C(O)N($C_1$-$C_6$alkyl)$_2$, $C_6$-$C_{10}$ aryl, 5- to 12-membered heteroaryl comprising 1-6 heteroatoms selected from N, O, and S, or 5- to 14-membered saturated or unsaturated heterocycloalkyl comprising 1-5 heteroatoms selected from N, O, and S.

In some embodiments, $R_2$ is H, OH, or halogen. In some embodiments, $R_2$ is H. In some embodiments, $R_2$ is OH. In some embodiments, $R_2$ is halogen. In some embodiments, $R_2$ is fluorine. In some embodiments, $R_2$ is chlorine. In some embodiments, $R_2$ is bromine. In some embodiments, $R_2$ is iodine.

In some embodiments, $R_2$ is $C_1$-$C_6$ alkyl, $C_2$-$C_6$ alkenyl, or $C_2$-$C_6$ alkynyl.

In some embodiments, $R_2$ is $C_1$-$C_6$ alkyl. In some embodiments, $R_2$ is methyl. In some embodiments, $R_2$ is ethyl. In some embodiments, $R_2$ is propyl. In some embodiments, $R_2$ is butyl.

In some embodiments, $R_2$ is isopropyl. In some embodiments, $R_2$ is iso-butyl. In some embodiments, $R_2$ is sec-butyl. In some embodiments, $R_2$ is tert-butyl. In some embodiments, $R_2$ is pentyl. In some embodiments, $R_2$ is iso-pentyl. In some embodiments, $R_2$ is hexyl. In some embodiments, $R_2$ is iso-hexyl.

In some embodiments, $R_2$ is $C_2$-$C_6$ alkenyl. In some embodiments, $R_2$ is $C_2$ alkenyl. In some embodiments, $R_2$ is $C_3$ alkenyl. In some embodiments, $R_2$ is $C_4$ alkenyl. In some embodiments, $R_2$ is $C_5$ alkenyl. In some embodiments, $R_2$ is $C_6$ alkenyl.

In some embodiments, $R_2$ is $C_2$-$C_6$ alkynyl. In some embodiments, $R_2$ is $C_2$ alkynyl. In some embodiments, $R_2$ is $C_3$ alkynyl. In some embodiments, $R_2$ is $C_4$ alkynyl. In some embodiments, $R_2$ is $C_5$ alkynyl. In some embodiments, $R_2$ is $C_6$ alkynyl.

In some embodiments, $R_2$ is $C_1$-$C_6$ haloalkyl, $C_1$-$C_6$ alkoxyl, $C_1$-$C_6$ haloalkoxyl, or $C_3$-$C_6$ cycloalkyl.

In some embodiments, $R_2$ is $C_1$-$C_6$ haloalkyl. In some embodiments, $R_2$ is halomethyl. In some embodiments, $R_2$ is haloethyl. In some embodiments, $R_2$ is halopropyl. In some embodiments, $R_2$ is halobutyl. In some embodiments, $R_2$ is halopentyl. In some embodiments, $R_2$ is halohexyl.

In some embodiments, $R_2$ is $C_1$-$C_6$ alkoxyl. In some embodiments, $R_2$ is methoxyl. In some embodiments, $R_2$ is ethoxyl. In some embodiments, $R_2$ is propoxyl. In some embodiments, $R_2$ is butoxyl. In some embodiments, $R_2$ is pentoxyl. In some embodiments, $R_2$ is hexoxyl.

In some embodiments, $R_2$ is $C_1$-$C_6$ haloalkoxyl. In some embodiments, $R_2$ is halomethoxyl. In some embodiments, $R_2$ is haloethoxyl. In some embodiments, $R_2$ is halopropoxyl. In some embodiments, $R_2$ is halobutoxyl. In some embodiments, $R_2$ is halopentoxyl. In some embodiments, $R_2$ is halohexoxyl.

In some embodiments, $R_2$ is $C_3$-$C_6$ cycloalkyl. In some embodiments, $R_2$ is cyclopropyl.

In some embodiments, $R_2$ is cyclobutyl. In some embodiments, $R_2$ is cyclopentyl. In some embodiments, $R_2$ is cyclohexyl.

In some embodiments, $R_2$ is —C(O)O$C_1$-$C_6$alkyl, —C(O)NH$_2$, —C(O)NH$C_1$-$C_6$alkyl, or —C(O)N($C_1$-$C_6$alkyl)$_2$. In some embodiments, $R_2$ is —C(O)O$C_1$-$C_6$alkyl. In some embodiments, $R_2$ is —C(O)NH$_2$. In some embodiments, $R_2$ is —C(O)NH$C_1$-$C_6$alkyl. In some embodiments, $R_2$ is —C(O)N($C_1$-$C_6$alkyl)$_2$.

In some embodiments, $R_2$ is $C_6$-$C_{10}$ aryl, 5- to 12-membered heteroaryl comprising 1-6 heteroatoms selected from N, O, and S, or 5- to 14-membered saturated or unsaturated heterocycloalkyl comprising 1-5 heteroatoms selected from N, O, and S; wherein the aryl, heteroaryl, or heterocycloalkyl is optionally substituted with one or more $R_6$.

In some embodiments, $R_2$ is $C_6$-$C_{10}$ aryl, 5- to 12-membered heteroaryl comprising 1-6 heteroatoms selected from N, O, and S, or 5- to 14-membered saturated or unsaturated heterocycloalkyl comprising 1-5 heteroatoms selected from N, O, and S; wherein the aryl, heteroaryl, or heterocycloalkyl of any of the foregoing is substituted with one or more $R_6$.

In some embodiments, $R_2$ is $C_6$-$C_{10}$ aryl, 5- to 12-membered heteroaryl comprising 1-6 heteroatoms selected from N, O, and S, or 5- to 14-membered saturated or unsaturated heterocycloalkyl comprising 1-5 heteroatoms selected from N, O, and S; wherein the aryl, heteroaryl, or heterocycloalkyl of any of the foregoing is substituted with one $R_6$.

In some embodiments, $R_2$ is $C_6$-$C_{10}$ aryl, 5- to 12-membered heteroaryl comprising 1-6 heteroatoms selected from N, O, and S, or 5- to 14-membered saturated or unsaturated heterocycloalkyl comprising 1-5 heteroatoms selected from N, O, and S; wherein the aryl, heteroaryl, or heterocycloalkyl of any of the foregoing is substituted with two $R_6$.

In some embodiments, $R_2$ is $C_6$-$C_{10}$ aryl, 5- to 12-membered heteroaryl comprising 1-6 heteroatoms selected from N, O, and S, or 5- to 14-membered saturated or unsaturated heterocycloalkyl comprising 1-5 heteroatoms selected from N, O, and S; wherein the aryl, heteroaryl, or heterocycloalkyl of any of the foregoing is substituted with three $R_6$.

In some embodiments, $R_2$ is $C_6$-$C_{10}$ aryl, 5- to 12-membered heteroaryl comprising 1-6 heteroatoms selected from N, O, and S, or 5- to 14-membered saturated or unsaturated heterocycloalkyl comprising 1-5 heteroatoms selected from N, O, and S.

In some embodiments, $R_2$ is $C_6$-$C_{10}$ aryl. In some embodiments, $R_2$ is $C_6$ aryl. In some embodiments, $R_2$ is $C_7$ aryl. In some embodiments, $R_2$ is Cs aryl. In some embodiments, $R_2$ is $C_9$ aryl. In some embodiments, $R_2$ is $C_{10}$ aryl.

In some embodiments, $R_2$ is $C_6$-$C_{10}$ aryl, wherein the aryl is substituted with one or more $R_6$.

In some embodiments, $R_2$ is $C_6$-$C_{10}$ aryl, wherein the aryl is substituted with one $R_6$.

In some embodiments, $R_2$ is $C_6$-$C_{10}$ aryl, wherein the aryl is substituted with two $R_6$.

In some embodiments, $R_2$ is $C_6$-$C_{10}$ aryl, wherein the aryl is substituted with three $R_6$.

In some embodiments, $R_2$ is 5- to 12-membered heteroaryl comprising 1-6 heteroatoms selected from N, O, and S.

In some embodiments, $R_2$ is 5- to 12-membered heteroaryl comprising 1-6 heteroatoms selected from N, O, and S, wherein the heteroaryl is substituted with one or more $R_6$.

In some embodiments, $R_2$ is 5- to 12-membered heteroaryl comprising 1-6 heteroatoms selected from N, O, and S, wherein the heteroaryl is substituted with one $R_6$.

In some embodiments, $R_2$ is 5- to 12-membered heteroaryl comprising 1-6 heteroatoms selected from N, O, and S, wherein the heteroaryl is substituted with two $R_6$.

In some embodiments, $R_2$ is 5- to 12-membered heteroaryl comprising 1-6 heteroatoms selected from N, O, and S, wherein the heteroaryl is substituted with three $R_6$.

In some embodiments, $R_2$ is 5- to 14-membered saturated or unsaturated heterocycloalkyl comprising 1-5 heteroatoms selected from N, O, and S.

In some embodiments, $R_2$ is 5- to 14-membered saturated or unsaturated heterocycloalkyl comprising 1-5 heteroatoms selected from N, O, and S, wherein the heterocycloalkyl is substituted with one or more $R_6$.

In some embodiments, $R_2$ is 5- to 14-membered saturated or unsaturated heterocycloalkyl comprising 1-5 heteroatoms selected from N, O, and S, wherein the heterocycloalkyl is substituted with one $R_6$.

In some embodiments, $R_2$ is 5- to 14-membered saturated or unsaturated heterocycloalkyl comprising 1-5 heteroatoms selected from N, O, and S, wherein the heterocycloalkyl is substituted with two $R_6$.

In some embodiments, $R_2$ is 5- to 14-membered saturated or unsaturated heterocycloalkyl comprising 1-5 heteroatoms selected from N, O, and S, wherein the heterocycloalkyl is substituted with three $R_6$.

In some embodiments, $R_2$ is 5- to 14-membered saturated heterocycloalkyl comprising 1-5 heteroatoms selected from N, O, and S.

In some embodiments, $R_2$ is 6-membered saturated heterocycloalkyl comprising 1-5 heteroatoms selected from N, O, and S.

In some embodiments, $R_2$ is 6-membered saturated heterocycloalkyl comprising 2 heteroatoms selected from N, O, and S.

In some embodiments, $R_2$ is 6-membered saturated heterocycloalkyl comprising 2 N atoms.

In some embodiments, $R_2$ is

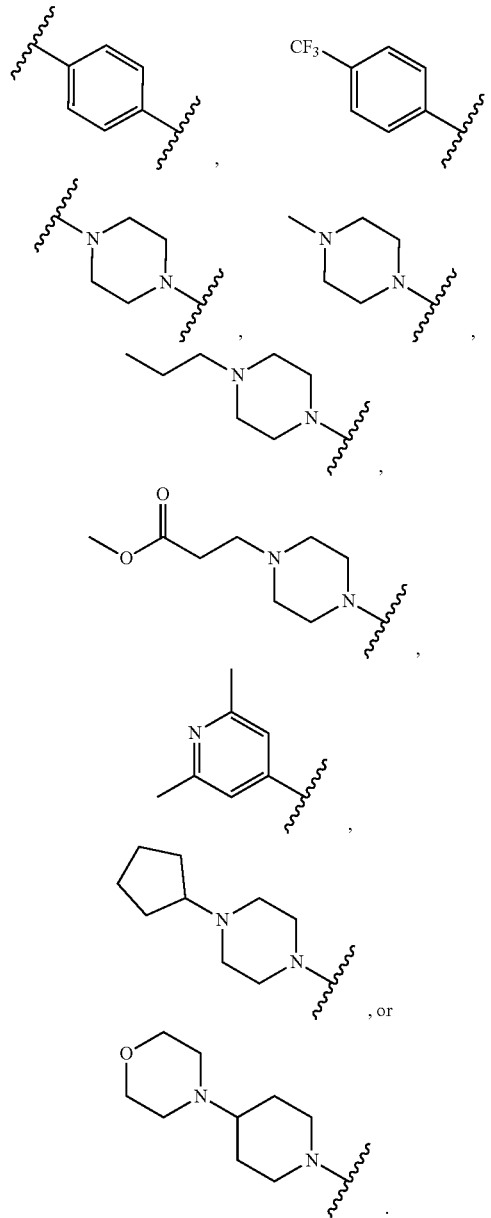

, or

In some embodiments, $R_2$ is

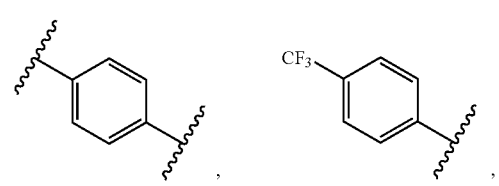

,

-continued

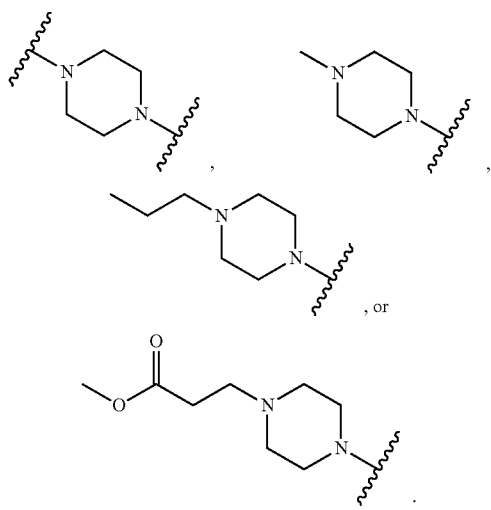

In some embodiments, $R_2$ is

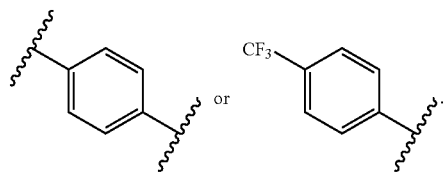 [SMILES: *c1ccc(*)cc1 ; *c1ccc(C(F)(F)F)cc1]

In some embodiments, $R_2$ is

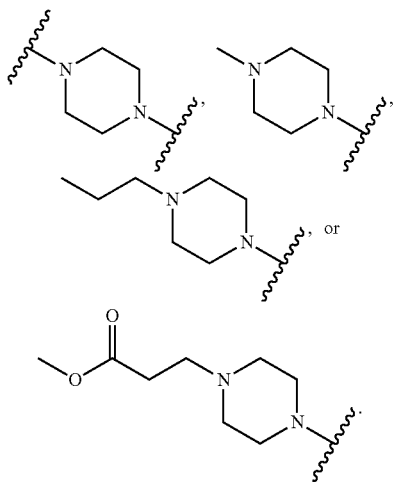

In some embodiments, $R_2$ is

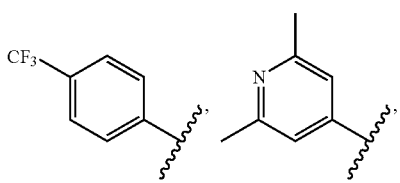

-continued

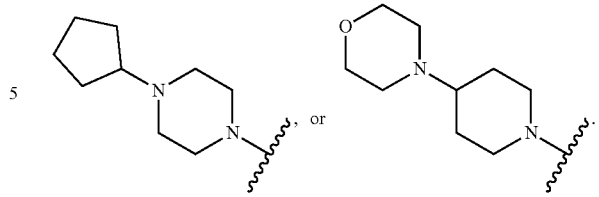

In some embodiments, $R_3$ is H or halogen. In some embodiments, $R_3$ is H. In some embodiments, $R_3$ is halogen.

In some embodiments, $R_4$ is H or halogen. In some embodiments, $R_4$ is H. In some embodiments, $R_4$ is halogen.

In some embodiments, m is 0, 1, 2, or 3. In some embodiments, m is 0. In some embodiments, m is 1. In some embodiments, m is 2. In some embodiments, m is 3.

In some embodiments, n is 0, 1, 2, or 3. In some embodiments, n is 0. In some embodiments, n is 1. In some embodiments, n is 2. In some embodiments, n is 3.

In some embodiments, m is 1 and n is 1.

In some embodiments, m is 1 and n is 2.

In some embodiments, p is 0, 1, 2, 3, or 4. In some embodiments, p is 0. In some embodiments, p is 1. In some embodiments, p is 2. In some embodiments, p is 3. In some embodiments, p is 4.

In some embodiments, q is 1, 2, 3, or 4. In some embodiments, q is 1. In some embodiments, q is 2. In some embodiments, q is 3. In some embodiments, q is 4.

In some embodiments, $R_5$ is OH, halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, $C_6$-$C_{10}$ aryl, or 5- to 14-membered saturated or unsaturated heterocycloalkyl comprising 1-5 heteroatoms selected from N, O, and S; wherein the alkyl, alkenyl, alkynyl, cycloalkyl, or aryl of any of the foregoing is optionally substituted with —C(O)$C_1$-$C_6$alkyl, —C(O)O$C_1$-$C_6$alkyl, —C(O)NH$_2$, —C(O)NH$C_1$-$C_6$alkyl, or —C(O)N($C_1$-$C_6$alkyl)$_2$.

In some embodiments, $R_5$ is OH, halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, $C_6$-$C_{10}$ aryl, or 5- to 14-membered saturated or unsaturated heterocycloalkyl comprising 1-5 heteroatoms selected from N, O, and S; wherein the alkyl, alkenyl, alkynyl, cycloalkyl, or aryl of any of the foregoing is substituted with —C(O)$C_1$-$C_6$alkyl, —C(O)O$C_1$-$C_6$alkyl, —C(O)NH$_2$, —C(O)NH$C_1$-$C_6$alkyl, or —C(O)N($C_1$-$C_6$alkyl)$_2$.

In some embodiments, $R_5$ is OH, halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, or $C_6$-$C_{10}$ aryl, wherein the alkyl, alkenyl, alkynyl, cycloalkyl, or aryl of any of the foregoing is optionally substituted with one or more —C(O)$C_1$-$C_6$alkyl, —C(O)O$C_1$-$C_6$alkyl, —C(O)NH$_2$, —C(O)NH$C_1$-$C_6$alkyl, or —C(O)N($C_1$-$C_6$alkyl)$_2$.

In some embodiments, $R_5$ is OH, halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, or $C_6$-$C_{10}$ aryl, wherein the alkyl, alkenyl, alkynyl, cycloalkyl, or aryl of any of the foregoing is substituted with one or more —C(O)$C_1$-$C_6$alkyl, —C(O)O$C_1$-$C_6$alkyl, —C(O)NH$_2$, —C(O)NH$C_1$-$C_6$alkyl, or —C(O)N($C_1$-$C_6$alkyl)$_2$.

In some embodiments, $R_5$ is OH or halogen. In some embodiments, $R_5$ is OH. In some embodiments, $R_5$ is halogen. In some embodiments, $R_5$ is fluorine. In some embodiments, $R_5$ is chlorine. In some embodiments, $R_5$ is bromine. In some embodiments, $R_5$ is iodine.

In some embodiments, $R_5$ is $C_1$-$C_6$ alkyl, $C_2$-$C_6$ alkenyl, or $C_2$-$C_6$ alkynyl.

In some embodiments, $R_5$ is $C_1$-$C_6$ alkyl. In some embodiments, $R_5$ is methyl. In some embodiments, $R_5$ is ethyl. In some embodiments, $R_5$ is propyl. In some embodiments, $R_5$ is butyl. In some embodiments, $R_5$ is isopropyl. In some embodiments, $R_5$ is iso-butyl. In some embodiments, $R_5$ is sec-butyl. In some embodiments, $R_5$ is tert-butyl. In some embodiments, $R_5$ is pentyl. In some embodiments, $R_5$ is iso-pentyl. In some embodiments, $R_5$ is hexyl. In some embodiments, $R_5$ is iso-hexyl.

In some embodiments, $R_5$ is $C_2$-$C_6$ alkenyl. In some embodiments, $R_5$ is $C_2$ alkenyl. In some embodiments, $R_5$ is $C_3$ alkenyl. In some embodiments, $R_5$ is $C_4$ alkenyl. In some embodiments, $R_5$ is $C_5$ alkenyl. In some embodiments, $R_5$ is $C_6$ alkenyl.

In some embodiments, $R_5$ is $C_2$-$C_6$ alkynyl. In some embodiments, $R_5$ is $C_2$ alkynyl. In some embodiments, $R_5$ is $C_3$ alkynyl. In some embodiments, $R_5$ is $C_4$ alkynyl. In some embodiments, $R_5$ is $C_5$ alkynyl. In some embodiments, $R_5$ is $C_6$ alkynyl.

In some embodiments, $R_5$ is $C_1$-$C_6$ haloalkyl, $C_1$-$C_6$ alkoxyl, $C_1$-$C_6$ haloalkoxyl, or $C_3$-$C_6$ cycloalkyl.

In some embodiments, $R_5$ is $C_1$-$C_6$ haloalkyl. In some embodiments, $R_5$ is halomethyl. In some embodiments, $R_5$ is haloethyl. In some embodiments, $R_5$ is halopropyl. In some embodiments, $R_5$ is halobutyl. In some embodiments, $R_5$ is halopentyl. In some embodiments, $R_5$ is halohexyl.

In some embodiments, $R_5$ is $C_1$-$C_6$ alkoxyl. In some embodiments, $R_5$ is methoxyl. In some embodiments, $R_5$ is ethoxyl. In some embodiments, $R_5$ is propoxyl. In some embodiments, $R_5$ is butoxyl. In some embodiments, $R_5$ is pentoxyl. In some embodiments, $R_5$ is hexoxyl.

In some embodiments, $R_5$ is $C_1$-$C_6$ haloalkoxyl. In some embodiments, $R_5$ is halomethoxyl. In some embodiments, $R_5$ is haloethoxyl. In some embodiments, $R_5$ is halopropoxyl. In some embodiments, $R_5$ is halobutoxyl. In some embodiments, $R_5$ is halopentoxyl. In some embodiments, $R_5$ is halohexoxyl.

In some embodiments, $R_5$ is $C_3$-$C_6$ cycloalkyl. In some embodiments, $R_5$ is cyclopropyl.

In some embodiments, $R_5$ is cyclobutyl. In some embodiments, $R_5$ is cyclopentyl. In some embodiments, $R_5$ is cyclohexyl.

In some embodiments, $R_5$ is —C(O)OC$_1$-C$_6$alkyl, —C(O)NH$_2$, —C(O)NHC$_1$-C$_6$alkyl, or —C(O)N(C$_1$-C$_6$alkyl)$_2$. In some embodiments, $R_5$ is —C(O)OC$_1$-C$_6$alkyl. In some embodiments, $R_5$ is —C(O)NH$_2$. In some embodiments, $R_5$ is —C(O)NHC$_1$-C$_6$alkyl. In some embodiments, $R_5$ is —C(O)N(C$_1$-C$_6$alkyl)$_2$.

In some embodiments, $R_5$ is alkyl substituted with with —C(O)C$_1$-C$_6$alkyl, —C(O)OC$_1$-C$_6$alkyl, —C(O)NH$_2$, —C(O)NHC$_1$-C$_6$alkyl, or —C(O)N(C$_1$-C$_6$alkyl)$_2$.

In some embodiments, $R_5$ is alkyl substituted with with —C(O)OC$_1$-C$_6$alkyl. In some embodiments, $R_5$ is alkyl substituted with with —C(O)Omethyl. In some embodiments, $R_5$ is alkyl substituted with with —C(O)Oethyl. In some embodiments, $R_5$ is alkyl substituted with with —C(O)Opropyl. In some embodiments, $R_5$ is alkyl substituted with with —C(O)Oisopropyl. In some embodiments, $R_5$ is alkyl substituted with with —C(O)Obutyl. In some embodiments, $R_5$ is alkyl substituted with with —C(O)Opentyl. In some embodiments, $R_5$ is alkyl substituted with with —C(O)Ohexyl.

In some embodiments, $R_6$ is OH, halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, $C_6$-$C_{10}$ aryl, or 5- to 14-membered saturated or unsaturated heterocycloalkyl comprising 1-5 heteroatoms selected from N, O, and S; wherein the alkyl, alkenyl, alkynyl, cycloalkyl, aryl, or heterocycloalkyl of any of the foregoing is optionally substituted with one or more —C(O)C$_1$-C$_6$alkyl, —C(O)OC$_1$-C$_6$alkyl, —C(O)NH$_2$, —C(O)NHC$_1$-C$_6$alkyl, or —C(O)N(C$_1$-C$_6$alkyl)$_2$.

In some embodiments, $R_6$ is OH, halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, $C_6$-$C_{10}$ aryl, or 5- to 14-membered saturated or unsaturated heterocycloalkyl comprising 1-5 heteroatoms selected from N, O, and S; wherein the alkyl, alkenyl, alkynyl, cycloalkyl, aryl, or heterocycloalkyl of any of the foregoing is substituted with one or more —C(O)C$_1$-C$_6$alkyl, —C(O)OC$_1$-C$_6$alkyl, —C(O)NH$_2$, —C(O)NHC$_1$-C$_6$alkyl, or —C(O)N(C$_1$-C$_6$alkyl)$_2$.

In some embodiments, $R_6$ is OH, halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, or $C_6$-$C_{10}$ aryl, wherein the alkyl, alkenyl, alkynyl, cycloalkyl, or aryl of any of the foregoing is optionally substituted with one or more —C(O)C$_1$-C$_6$alkyl, —C(O)OC$_1$-C$_6$alkyl, —C(O)NH$_2$, —C(O)NHC$_1$-C$_6$alkyl, or —C(O)N(C$_1$-C$_6$alkyl)$_2$.

In some embodiments, $R_6$ is OH, halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, or $C_6$-$C_{10}$ aryl, wherein the alkyl, alkenyl, alkynyl, cycloalkyl, or aryl of any of the foregoing is substituted with one or more —C(O)C$_1$-C$_6$alkyl, —C(O)OC$_1$-C$_6$alkyl, —C(O)NH$_2$, —C(O)NHC$_1$-C$_6$alkyl, or —C(O)N(C$_1$-C$_6$alkyl)$_2$.

In some embodiments, $R_6$ is OH or halogen. In some embodiments, $R_6$ is OH. In some embodiments, $R_6$ is halogen. In some embodiments, $R_6$ is fluorine. In some embodiments, $R_6$ is chlorine. In some embodiments, $R_6$ is bromine. In some embodiments, $R_6$ is iodine.

In some embodiments, $R_6$ is $C_1$-$C_6$ alkyl, $C_2$-$C_6$ alkenyl, or $C_2$-$C_6$ alkynyl.

In some embodiments, $R_6$ is $C_1$-$C_6$ alkyl. In some embodiments, $R_6$ is methyl. In some embodiments, $R_6$ is ethyl. In some embodiments, $R_6$ is propyl. In some embodiments, $R_6$ is butyl. In some embodiments, $R_6$ is isopropyl. In some embodiments, $R_6$ is iso-butyl. In some embodiments, $R_6$ is sec-butyl. In some embodiments, $R_6$ is tert-butyl. In some embodiments, $R_6$ is pentyl. In some embodiments, $R_6$ is iso-pentyl. In some embodiments, $R_6$ is hexyl. In some embodiments, $R_6$ is iso-hexyl.

In some embodiments, $R_6$ is $C_2$-$C_6$ alkenyl. In some embodiments, $R_6$ is $C_2$ alkenyl. In some embodiments, $R_6$ is $C_3$ alkenyl. In some embodiments, $R_6$ is $C_4$ alkenyl. In some embodiments, $R_6$ is $C_5$ alkenyl. In some embodiments, $R_6$ is $C_6$ alkenyl.

In some embodiments, $R_6$ is $C_2$-$C_6$ alkynyl. In some embodiments, $R_6$ is $C_2$ alkynyl. In some embodiments, $R_6$ is $C_3$ alkynyl. In some embodiments, $R_6$ is $C_4$ alkynyl. In some embodiments, $R_6$ is $C_5$ alkynyl. In some embodiments, $R_6$ is $C_6$ alkynyl.

In some embodiments, $R_6$ is $C_1$-$C_6$ haloalkyl, $C_1$-$C_6$ alkoxyl, $C_1$-$C_6$ haloalkoxyl, or $C_3$-$C_6$ cycloalkyl.

In some embodiments, $R_6$ is $C_1$-$C_6$ haloalkyl. In some embodiments, $R_6$ is halomethyl. In some embodiments, $R_6$ is haloethyl. In some embodiments, $R_6$ is halopropyl. In some embodiments, $R_6$ is halobutyl. In some embodiments, $R_6$ is halopentyl. In some embodiments, $R_6$ is halohexyl.

In some embodiments, $R_6$ is $C_1$-$C_6$ alkoxyl. In some embodiments, $R_6$ is methoxyl. In some embodiments, $R_6$ is ethoxyl. In some embodiments, $R_6$ is propoxyl. In some embodiments, $R_6$ is butoxyl. In some embodiments, $R_6$ is pentoxyl. In some embodiments, $R_6$ is hexoxyl.

In some embodiments, $R_6$ is $C_1$-$C_6$ haloalkoxyl. In some embodiments, $R_6$ is halomethoxyl. In some embodiments, $R_6$ is haloethoxyl. In some embodiments, $R_6$ is halopropoxyl. In some embodiments, $R_6$ is halobutoxyl. In some embodiments, $R_6$ is halopentoxyl. In some embodiments, $R_6$ is halohexoxyl.

In some embodiments, $R_6$ is $C_3$-$C_6$ cycloalkyl. In some embodiments, $R_6$ is cyclopropyl. In some embodiments, $R_6$ is cyclobutyl. In some embodiments, $R_6$ is cyclopentyl. In some embodiments, $R_6$ is cyclohexyl.

In some embodiments, $R_6$ is —C(O)OC$_1$-C$_6$alkyl, —C(O)NH$_2$, —C(O)NHC$_1$-C$_6$alkyl, or —C(O)N(C$_1$-C$_6$alkyl)$_2$. In some embodiments, $R_6$ is —C(O)OC$_1$-C$_6$alkyl. In some embodiments, $R_6$ is —C(O)NH$_2$. In some embodiments, $R_6$ is —C(O)NHC$_1$-C$_6$alkyl. In some embodiments, $R_6$ is —C(O)N(C$_1$-C$_6$alkyl)$_2$.

In some embodiments, $R_6$ is alkyl substituted with with —C(O)C$_1$-C$_6$alkyl, —C(O)OC$_1$-C$_6$alkyl, —C(O)NH$_2$, —C(O)NHC$_1$-C$_6$alkyl, or —C(O)N(C$_1$-C$_6$alkyl)$_2$.

In some embodiments, $R_6$ is alkyl substituted with with —C(O)OC$_1$-C$_6$alkyl. In some embodiments, $R_6$ is alkyl substituted with with —C(O)Omethyl. In some embodiments, $R_6$ is alkyl substituted with with —C(O)Oethyl. In some embodiments, $R_6$ is alkyl substituted with with —C(O)Opropyl. In some embodiments, $R_6$ is alkyl substituted with with —C(O)Oisopropyl. In some embodiments, $R_6$ is alkyl substituted with with —C(O)Obutyl. In some embodiments, $R_6$ is alkyl substituted with with —C(O)Opentyl. In some embodiments, $R_6$ is alkyl substituted with with —C(O)Ohexyl.

In some embodiments, $R_6$ is a 5- to 14-membered saturated or unsaturated heterocycloalkyl comprising 1-5 heteroatoms selected from N, O, and S wherein the heterocycloalkyl is optionally substituted with one or more —C(O)C$_1$-C$_6$alkyl, —C(O)OC$_1$-C$_6$alkyl, —C(O)NH$_2$, —C(O)NHC$_1$-C$_6$alkyl, or —C(O)N(C$_1$-C$_6$alkyl)$_2$.

In some embodiments, $R_6$ is a 5- to 14-membered saturated or unsaturated heterocycloalkyl comprising 1-5 heteroatoms selected from N, O, and S wherein the heterocycloalkyl is substituted with one or more —C(O)C$_1$-C$_6$alkyl, —C(O)OC$_1$-C$_6$alkyl, —C(O)NH$_2$, —C(O)NHC$_1$-C$_6$alkyl, or —C(O)N(C$_1$-C$_6$alkyl)$_2$.

In some embodiments, $R_6$ is a 5- to 14-membered saturated or unsaturated heterocycloalkyl comprising 1 heteroatom selected from N, O, and S.

In some embodiments, $R_6$ is a 5- to 14-membered saturated or unsaturated heterocycloalkyl comprising 2 heteroatoms selected from N, O, and S.

In some embodiments, $R_6$ is a 5- to 14-membered saturated or unsaturated heterocycloalkyl comprising 3 heteroatoms selected from N, O, and S.

In some embodiments, $R_6$ is a 5- to 14-membered saturated or unsaturated heterocycloalkyl comprising 4 heteroatoms selected from N, O, and S.

In some embodiments, $R_6$ is a 5- to 14-membered saturated or unsaturated heterocycloalkyl comprising 5 heteroatoms selected from N, O, and S.

In some embodiments, $R_6$ is a 5-membered saturated or unsaturated heterocycloalkyl comprising 2 heteroatoms selected from N, O, and S.

In some embodiments, $R_6$ is a 6-membered saturated or unsaturated heterocycloalkyl comprising 2 heteroatoms selected from N, O, and S.

In some embodiments, $R_6$ is a 7-membered saturated or unsaturated heterocycloalkyl comprising 2 heteroatoms selected from N, O, and S.

In some embodiments, $R_6$ is a 8-membered saturated or unsaturated heterocycloalkyl comprising 2 heteroatoms selected from N, O, and S.

In some embodiments, $R_6$ is a 9-membered saturated or unsaturated heterocycloalkyl comprising 2 heteroatoms selected from N, O, and S.

In some embodiments, $R_6$ is a 10-membered saturated or unsaturated heterocycloalkyl comprising 2 heteroatoms selected from N, O, and S.

In some embodiments, $R_6$ is a 11-membered saturated or unsaturated heterocycloalkyl comprising 2 heteroatoms selected from N, O, and S.

In some embodiments, $R_6$ is a 12-membered saturated or unsaturated heterocycloalkyl comprising 2 heteroatoms selected from N, O, and S.

In some embodiments, $R_6$ is a 13-membered saturated or unsaturated heterocycloalkyl comprising 2 heteroatoms selected from N, O, and S.

In some embodiments, $R_6$ is a 14-membered saturated or unsaturated heterocycloalkyl comprising 2 heteroatoms selected from N, O, and S.

In some embodiments, $R_6$ is

In some embodiments, $R_7$ is $C_1$-$C_6$ alkyl optionally substituted with one or more OH, halogen, or $C_1$-$C_6$ alkoxyl. In some embodiments, $R_7$ is methyl optionally substituted with one or more OH, halogen, or $C_1$-$C_6$ alkoxyl. In some embodiments, $R_7$ is ethyl optionally substituted with one or more OH, halogen, or $C_1$-$C_6$ alkoxyl. In some embodiments, $R_7$ is propyl optionally substituted with one or more OH, halogen, or $C_1$-$C_6$ alkoxyl. In some embodiments, $R_7$ is butyl optionally substituted with one or more OH, halogen, or $C_1$-$C_6$ alkoxyl. In some embodiments, $R_7$ is pentyl optionally substituted with one or more OH, halogen, or $C_1$-$C_6$ alkoxyl. In some embodiments, $R_7$ is hexyl optionally substituted with one or more OH, halogen, or $C_1$-$C_6$ alkoxyl.

In some embodiments, $R_8$ is $C_1$-$C_6$ alkyl optionally substituted with one or more OH, halogen, or $C_1$-$C_6$ alkoxyl. In some embodiments, $R_8$ is methyl optionally substituted with one or more OH, halogen, or $C_1$-$C_6$ alkoxyl. In some embodiments, $R_8$ is ethyl optionally substituted with one or more OH, halogen, or $C_1$-$C_6$ alkoxyl. In some embodiments, $R_8$ is propyl optionally substituted with one or more OH, halogen, or $C_1$-$C_6$ alkoxyl. In some embodiments, $R_8$ is butyl optionally substituted with one or more OH, halogen, or $C_1$-$C_6$ alkoxyl. In some embodiments, $R_8$ is pentyl optionally substituted with one or more OH, halogen, or $C_1$-$C_6$ alkoxyl. In some embodiments, $R_8$ is hexyl optionally substituted with one or more OH, halogen, or $C_1$-$C_6$ alkoxyl.

In some embodiments, $R_7$ is $C_1$-$C_6$ alkyl. In some embodiments, $R_7$ is methyl. In some embodiments, $R_7$ is ethyl. In some embodiments, $R_7$ is propyl. In some embodiments, $R_7$ is butyl. In some embodiments, $R_7$ is pentyl. In some embodiments, $R_7$ is hexyl.

In some embodiments, $R_8$ is $C_1$-$C_6$ alkyl. In some embodiments, $R_8$ is methyl. In some embodiments, $R_8$ is ethyl. In some embodiments, $R_8$ is propyl. In some embodiments, $R_8$ is butyl. In some embodiments, $R_8$ is pentyl. In some embodiments, $R_8$ is hexyl.

In some embodiments, $R_7$ and $R_8$ are different.

In some embodiments, $R_7$ and $R_8$ are the same.

In some embodiments, $R_7$ and $R_8$ are each methyl.

In some embodiments, $R_7$ and $R_8$, together with the carbon atom they are attached, form a $C_3$-$C_6$ cycloalkyl optionally substituted with one or more OH, halogen, or $C_1$-$C_6$ alkoxyl. In some embodiments, $R_7$ and $R_8$, together with the carbon atom they are attached, form a cyclopropyl optionally substituted with one or more OH, halogen, or $C_1$-$C_6$ alkoxyl. In some embodiments, $R_7$ and $R_8$, together with the carbon atom they are attached, form a cyclobutyl optionally substituted with one or more OH, halogen, or $C_1$-$C_6$ alkoxyl. In some embodiments, $R_7$ and $R_8$, together with the carbon atom they are attached, form a cyclopentyl optionally substituted with one or more OH, halogen, or $C_1$-$C_6$ alkoxyl. In some embodiments, $R_7$ and $R_8$, together with the carbon atom they are attached, form a cyclohexyl optionally substituted with one or more OH, halogen, or $C_1$-$C_6$ alkoxyl.

In some embodiments, $R_7$ and $R_8$, together with the carbon atom they are attached, form a $C_3$-$C_6$ cycloalkyl. In some embodiments, $R_7$ and $R_8$, together with the carbon atom they are attached, form a cyclopropyl. In some embodiments, $R_7$ and $R_8$, together with the carbon atom they are attached, form a cyclobutyl. In some embodiments, $R_7$ and $R_8$, together with the carbon atom they are attached, form a cyclopentyl. In some embodiments, $R_7$ and $R_8$, together with the carbon atom they are attached, form a cyclohexyl.

In some embodiments, m is 1, n is 1, and p is 1.

In some embodiments, m is 1, n is 1, p is 1, and $R_2$ is $C_6$-$C_{10}$ aryl.

In some embodiments, m is 1, n is 1, p is 1, and $R_2$ is phenyl.

In some embodiments, m is 1, n is 1, p is 1, and $R_2$ is a 5- to 14-membered saturated or unsaturated heterocycloalkyl comprising 1-5 heteroatoms selected from N, O, and S.

In some embodiments, m is 1, n is 2, and p is 1.

In some embodiments, m is 1, n is 2, p is 1, and $R_2$ is $C_6$-$C_{10}$ aryl.

In some embodiments, m is 1, n is 2, p is 1, and $R_2$ is phenyl.

In some embodiments, m is 1, n is 2, p is 1, and $R_2$ is a 5- to 14-membered saturated or unsaturated heterocycloalkyl comprising 1-5 heteroatoms selected from N, O, and S.

In some embodiments, m is 1, n is 1, p is 1, $X_1$ is —C(O)O— and $X_2$ is absent.

In some embodiments, m is 1, n is 1, p is 1, $X_1$ is absent, and $X_2$ is absent.

In some embodiments, m is 1, n is 1, p is 1, $X_1$ is —O—, and $X_2$ is absent.

In some embodiments, m is 1, n is 1, p is 1, $X_1$ is —S(O)$_2$—, and $X_2$ is absent.

In some embodiments, m is 1, n is 1, p is 1, $X_1$ is —C(O)NR$_3$— and $X_2$ is absent.

In some embodiments, m is 1, n is 2, p is 1, $X_1$ is absent, and $X_2$ is —O—.

In some embodiments, m is 1, n is 2, p is 1, $X_1$ is absent, and $X_2$ is S(O)$_2$.

In some embodiments, m is 1, n is 2, p is 1, $X_1$ is absent, and $X_2$ is —C(O)NR$_3$—.

In some aspects, the present disclosure provides, inter alia, a compound of Formula (I) that is a compound of Formula (I'):

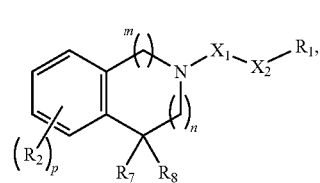

(I')

or a prodrug, solvate, or pharmaceutically acceptable salt thereof, wherein:

$X_1$ is absent or —(CR$_3$R$_4$)$_q$—;

$X_2$ is absent, —S(O)$_2$—, —C(O)—, or —C(O)O—;

$R_1$ is $C_1$-$C_6$ alkyl, $C_3$-$C_6$ cycloalkyl, $C_6$-$C_{10}$ aryl, 5- to 14-membered saturated or unsaturated heterocycloalkyl comprising 1-5 heteroatoms selected from N, O, and S; wherein the alkyl, cycloalkyl, aryl, or heterocycloalkyl of any of the foregoing is optionally substituted with one or two $R_5$;

each $R_2$ is $C_6$-$C_{10}$ aryl, 5- to 12-membered heteroaryl comprising 1-6 heteroatoms selected from N, O, and S, or 5- to 14-membered saturated or unsaturated heterocycloalkyl comprising 1-5 heteroatoms selected from N, O, and S; wherein the aryl, heteroaryl, or heterocycloalkyl of any of the foregoing is optionally substituted with one or two $R_6$;

each $R_3$ is H;

each $R_4$ is H;

each $R_5$ independently is halogen or $C_1$-$C_6$ alkyl;

each $R_6$ independently is $C_1$-$C_6$ alkyl, $C_1$-$C_6$ haloalkyl, $C_3$-$C_6$ cycloalkyl, $C_6$-$C_{10}$ aryl, or 5- to 14-membered saturated or unsaturated heterocycloalkyl comprising 1-5 heteroatoms selected from N, O, and S;

$R_7$ is $C_1$-$C_6$ alkyl;

$R_8$ is $C_1$-$C_6$ alkyl;

m is 1;

n is 1 or 2;

p is 1; and q is 2.

In some aspects, the compound of Formula (I') is a compound of Formula (I"), or a prodrug, solvate, or pharmaceutically acceptable salt thereof, wherein:

$X_1$ is absent;

$X_2$ is —S(O)$_2$— or —C(O)O—;

$R_1$ is $C_1$-$C_6$ alkyl, $C_3$-$C_6$ cycloalkyl, or $C_6$-$C_{10}$ aryl; wherein the alkyl, cycloalkyl, or aryl of any of the foregoing is optionally substituted with one or two $R_5$;

each $R_2$ is 5- to 14-membered saturated or unsaturated heterocycloalkyl comprising 1-5 heteroatoms selected from N, O, and S that is optionally substituted with one or two $R_6$;

each $R_5$ independently is halogen;

each $R_6$ independently is $C_3$-$C_6$ cycloalkyl;

$R_7$ is $C_1$-$C_6$ alkyl;

$R_8$ is $C_1$-$C_6$ alkyl;

m is 1;

n is 1; and p is 1.

In some aspects, the compound of Formula (I') is a compound of Formula (I'''), or a prodrug, solvate, or pharmaceutically acceptable salt thereof, wherein $X_1$ is absent or —(CR$_3$R$_4$)$_q$—;

$X_2$ is absent, —S(O)$_2$—, —C(O)—, or —C(O)O—;

$R_1$ is $C_1$-$C_6$ alkyl, $C_3$-$C_6$ cycloalkyl, $C_6$-$C_{10}$ aryl, 5- to 14-membered saturated or unsaturated heterocycloalkyl comprising 1-5 heteroatoms selected from N, O, and S; wherein the alkyl, cycloalkyl, aryl, or heterocycloalkyl of any of the foregoing is optionally substituted with one or two $R_5$;

each $R_2$ is $C_6$-$C_{10}$ aryl, 5- to 12-membered heteroaryl comprising 1-6 heteroatoms selected from N, O, and S, or 5- to 14-membered saturated or unsaturated heterocycloalkyl comprising 1-5 heteroatoms selected from N, O, and S; wherein the aryl, heteroaryl, or heterocycloalkyl of any of the foregoing is optionally substituted with one or two $R_6$;

each $R_3$ is H;
each $R_4$ is H;
each $R_5$ independently is halogen or $C_1$-$C_6$ alkyl;
each $R_6$ independently is $C_1$-$C_6$ alkyl, $C_1$-$C_6$ haloalkyl, $C_3$-$C_6$ cycloalkyl, $C_6$-$C_{10}$ aryl, or 5- to 14-membered saturated or unsaturated heterocycloalkyl comprising 1-5 heteroatoms selected from N, O, and S;

$R_7$ is $C_1$-$C_6$ alkyl;
$R_8$ is $C_1$-$C_6$ alkyl;
m is 1;
n is 2;
p is 1; and
q is 2.

In some embodiments, a compound of Formula (I) is a compound of Formula (II):

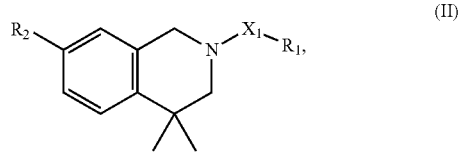

(II)

or a prodrug, solvate, or pharmaceutically acceptable salt thereof, wherein $X_1$, $R_1$, $R_2$, $R_3$, $R_4$, and $R_5$ are as described herein for Formula (I).

In some embodiments, a compound of Formula (I) is a compound of Formula (IIa):

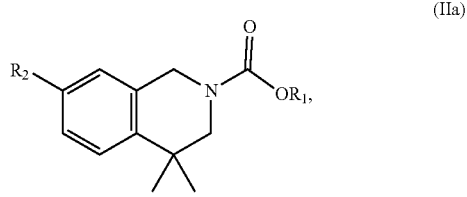

(IIa)

or a prodrug, solvate, or pharmaceutically acceptable salt thereof, wherein $R_1$, $R_2$, and $R_5$ are as described herein for Formula (I).

In some embodiments, a compound of Formula (I) is a compound of Formula (IIb):

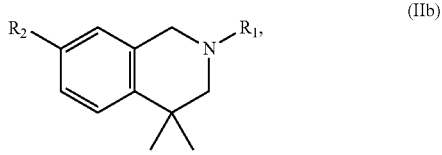

(IIb)

or a prodrug, solvate, or pharmaceutically acceptable salt thereof, wherein $R_1$, $R_2$, and $R_5$ are as described herein for Formula (I).

In some embodiments, a compound of Formula (I) is a compound of Formula (IIc):

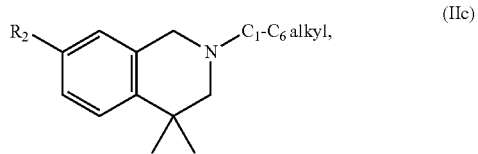

(IIc)

or a prodrug, solvate, or pharmaceutically acceptable salt thereof, wherein $R_2$ and $R_5$ are as described herein for Formula (I).

In some embodiments, a compound of Formula (I) is a compound of Formula (IId):

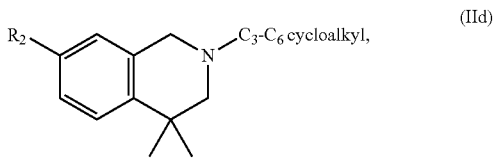

(IId)

or a prodrug, solvate, or pharmaceutically acceptable salt thereof, wherein $R_2$ and $R_5$ are as described herein for Formula (I).

In some embodiments, a compound of Formula (I) is a compound of Formula (IIe):

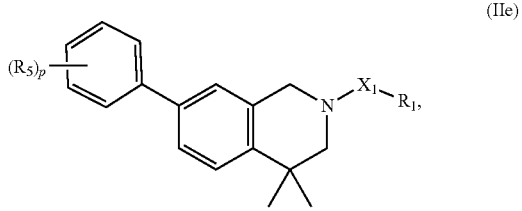

(IIe)

or a prodrug, solvate, or pharmaceutically acceptable salt thereof, wherein $X_1$, $R_1$, $R_3$, $R_4$, $R_5$, and p are as described herein for Formula (I).

In some embodiments, a compound of Formula (I) is a compound of Formula (IIf):

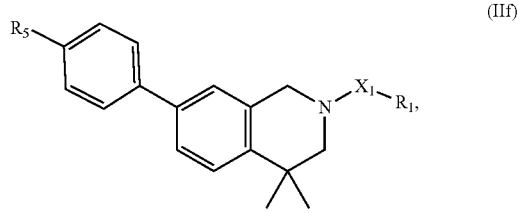

(IIf)

or a prodrug, solvate, or pharmaceutically acceptable salt thereof, wherein $X_1$, $R_1$, $R_3$, $R_4$, and $R_5$ are as described herein for Formula (I).

In some embodiments, a compound of Formula (I) is a compound of Formula (IIg):

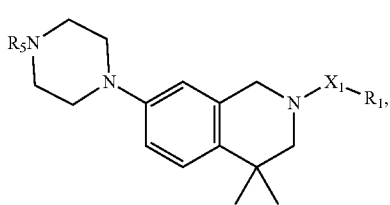

(IIg)

or a prodrug, solvate, or pharmaceutically acceptable salt thereof, wherein $X_1$, $R_1$, $R_3$, $R_4$, and $R_5$ are as described herein for Formula (I).

In some embodiments, a compound of Formula (I) is a compound of Formula (IIh):

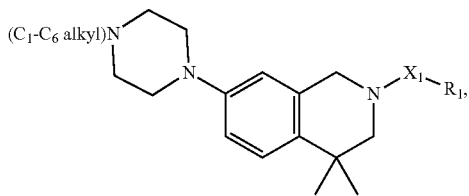

(IIh)

or a prodrug, solvate, or pharmaceutically acceptable salt thereof, wherein $X_1$, $R_1$, $R_3$, and $R_4$ are as described herein for Formula (I).

In some embodiments, a compound of Formula (I) is a compound of Formula (IIi):

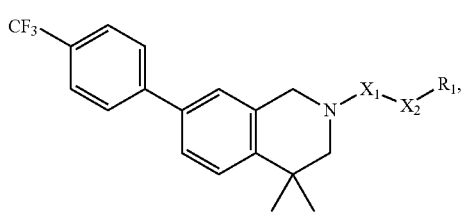

(IIi)

or a prodrug, solvate, or pharmaceutically acceptable salt thereof, wherein $X_1$, $X_2$, $R_1$, $R_3$, $R_4$, and $R_5$ are as described herein for Formula (I).

In some embodiments, a compound of Formula (I) is a compound of Formula (IIj):

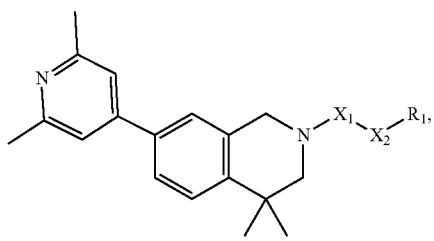

(IIj)

or a prodrug, solvate, or pharmaceutically acceptable salt thereof, wherein $X_1$, $X_2$, $R_1$, $R_3$, $R_4$, and $R_5$ are as described herein for Formula (I).

In some embodiments, a compound of Formula (I) is a compound of Formula (IIk):

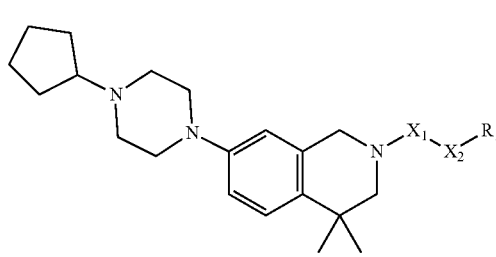

(IIk)

or a prodrug, solvate, or pharmaceutically acceptable salt thereof, wherein $X_1$, $X_2$, $R_1$, $R_3$, $R_4$, and $R_5$ are as described herein for Formula (I).

In some embodiments, a compound of Formula (I) is a compound of Formula (III):

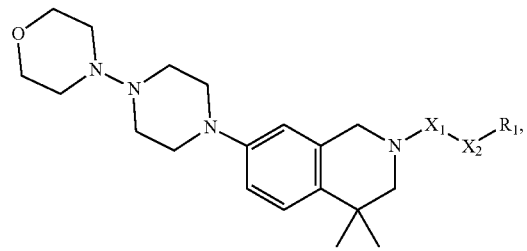

(IIl)

or a prodrug, solvate, or pharmaceutically acceptable salt thereof, wherein $X_1$, $X_2$, $R_1$, $R_3$, $R_4$, and $R_5$ are as described herein for Formula (I).

In some embodiments, a compound of Formula (I) is a compound of Formula (III):

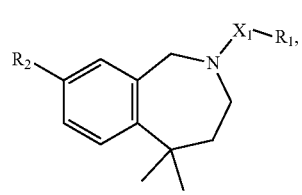

(III)

or a prodrug, solvate, or pharmaceutically acceptable salt thereof, wherein $X_1$, $R_1$, $R_2$, $R_3$, $R_4$, and $R_5$ are as described herein for Formula (I).

In some embodiments, a compound of Formula (I) is a compound of Formula (IIIa):

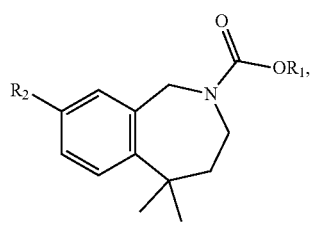

(IIIa)

or a prodrug, solvate, or pharmaceutically acceptable salt thereof, wherein $R_1$, $R_2$, and $R_5$ are as described herein for Formula (I).

In some embodiments, a compound of Formula (I) is a compound of Formula (IIIb):

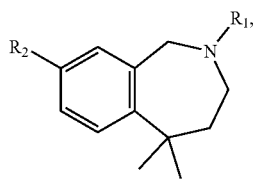

(IIIb)

or a prodrug, solvate, or pharmaceutically acceptable salt thereof, wherein $R_1$, $R_2$, and $R_5$ are as described herein for Formula (I).

In some embodiments, a compound of Formula (I) is a compound of Formula (IIIc):

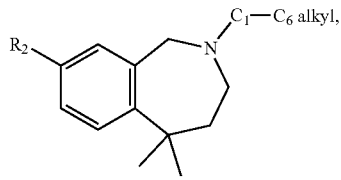

(IIIc)

or a prodrug, solvate, or pharmaceutically acceptable salt thereof, wherein $R_2$ and $R_5$ are as described herein for Formula (I).

In some embodiments, a compound of Formula (I) is a compound of Formula (IIId):

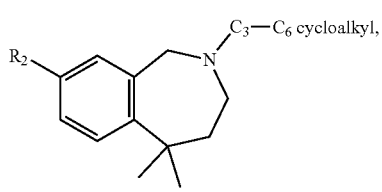

(IIId)

or a prodrug, solvate, or pharmaceutically acceptable salt thereof, wherein $R_2$ and $R_5$ are as described herein for Formula (I).

In some embodiments, a compound of Formula (I) is a compound of Formula (IIIe):

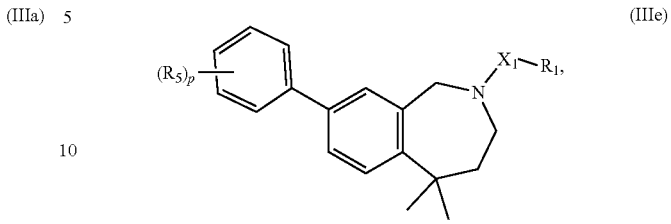

(IIIe)

or a prodrug, solvate, or pharmaceutically acceptable salt thereof, wherein $X_1$, $R_1$, $R_3$, $R_4$, $R_5$, and p are as described herein for Formula (I).

In some embodiments, a compound of Formula (I) is a compound of Formula (IIIf):

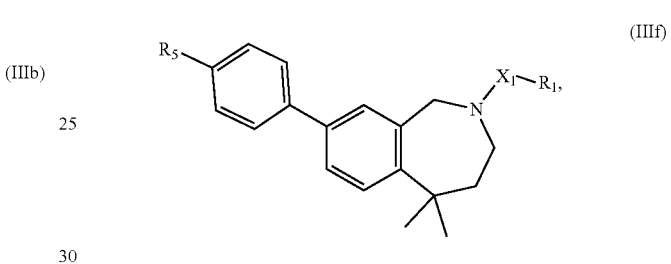

(IIIf)

or a prodrug, solvate, or pharmaceutically acceptable salt thereof, wherein $X_1$, $R_1$, $R_3$, $R_4$, and $R_5$ are as described herein for Formula (I).

In some embodiments, a compound of Formula (I) is a compound of Formula (IIIg):

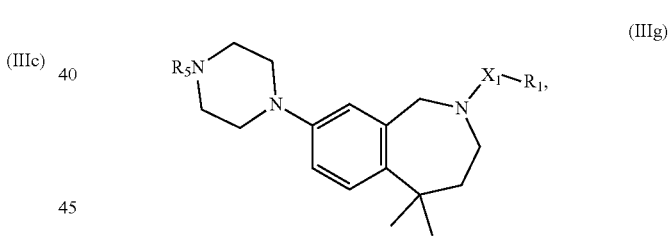

(IIIg)

or a prodrug, solvate, or pharmaceutically acceptable salt thereof, wherein $X_1$, $R_1$, $R_3$, $R_4$, and $R_5$ are as described herein for Formula (I).

In some embodiments, a compound of Formula (I) is a compound of Formula (IIIh):

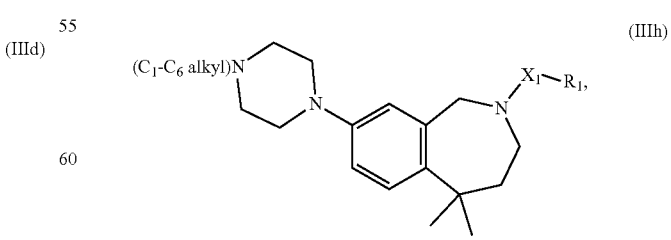

(IIIh)

or a prodrug, solvate, or pharmaceutically acceptable salt thereof, wherein $X_1$, $R_1$, $R_3$, and $R_4$ are as described herein for Formula (I).

In some embodiments, a compound of Formula (I) is a compound of Formula (IIIi):

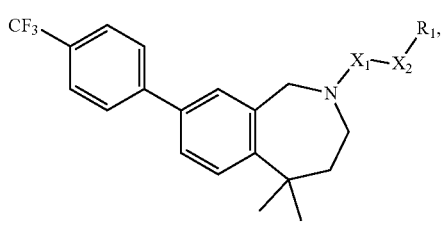

(IIIi)

or a prodrug, solvate, or pharmaceutically acceptable salt thereof, wherein $X_1$, $X_2$, $R_1$, $R_3$, $R_4$, and $R_5$ are as described herein for Formula (I).

In some embodiments, a compound of Formula (I) is a compound of Formula (IIIj):

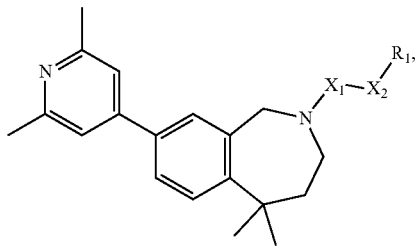

(IIIj)

or a prodrug, solvate, or pharmaceutically acceptable salt thereof, wherein $X_1$, $X_2$, $R_1$, $R_3$, $R_4$, and $R_5$ are as described herein for Formula (I).

In some embodiments, a compound of Formula (I) is a compound of Formula (IIIk):

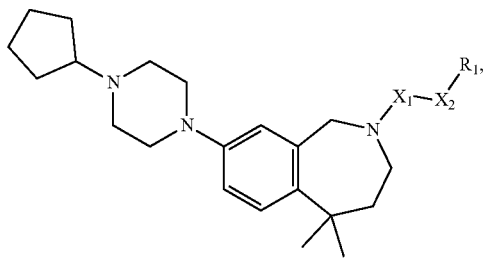

(IIIk)

or a prodrug, solvate, or pharmaceutically acceptable salt thereof, wherein $X_1$, $X_2$, $R_1$, $R_3$, $R_4$, and $R_5$ are as described herein for Formula (I).

In some embodiments, a compound of Formula (I) is a compound of Formula (IIIl):

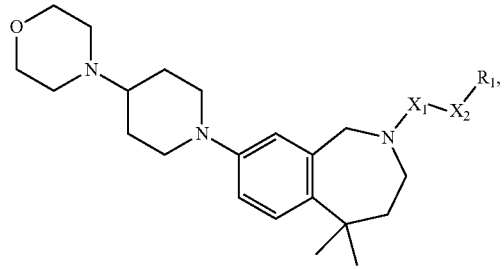

(IIIl)

or a prodrug, solvate, or pharmaceutically acceptable salt thereof, wherein $X_1$, $X_2$, $R_1$, $R_3$, $R_4$, and $R_5$ are as described herein for Formula (I).

In some aspects, the present disclosure provides a compound, 2-(2-(1-(2-(4-fluorophenyl)-2-oxoethyl)pyrrolidin-3-yl)ethyl)isoindolin-1-one, i.e., MIN-101-B:

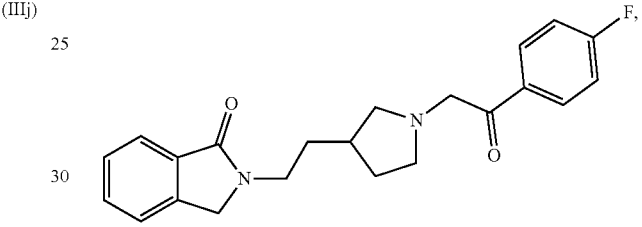

or a prodrug, solvate, or pharmaceutically acceptable salt thereof.

In one embodiment, MIN-101-B is (S)-2-2-1-2-(4-fluorophenyl)-2-oxoethyl)pyrrolidin-3-yl)ethyl)isoindolin-1-one,

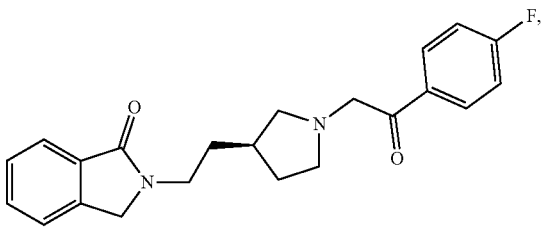 [SMILES: O=C(CN1CCC(CCN2Cc3ccccc3C2=O)C1)c1ccc(F)cc1]

or a prodrug, solvate, or pharmaceutically acceptable salt thereof.

In one embodiment, MIN-101-B is (R)-2-(2-(1-(2-(4-fluorophenyl)-2-oxoethyl)pyrrolidin-3-yl)ethyl)isoindolin-1-one,

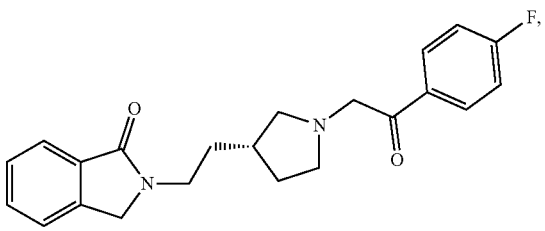 [SMILES: O=C(CN1CC[C@H](CCN2Cc3ccccc3C2=O)C1)c1ccc(F)cc1]

or a prodrug, solvate, or pharmaceutically acceptable salt thereof.

In some embodiments, the compound is selected from the compounds described in Table 1.

TABLE 1

| Compound No. | Structure and name | NMR data |
|---|---|---|
| 1 | 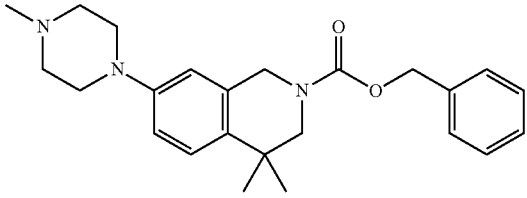 [SMILES: CN1CCN(c2ccc3c(c2)CN(C(=O)OCc2ccccc2)CC3(C)C)CC1]<br>benzyl 4,4-dimethyl-7-(4-methylpiperazin-1-yl)-3,4-dihydroisoquinoline-2(1H)-carboxylate | $^1$H NMR (300 MHz, CDCl$_3$) δ 7.43 – 7.37 (m, 5H), 7.24 (t, J = 8.5 Hz, 1H), 6.83 (d, J = 8.7 Hz, 1H), 6.61 (d, J = 12.9 Hz, 1H), 5.21 (s, 2H), 4.67 (s, 2H), 3.48 (d, J = 4.7 Hz, 2H), 3.26 (t, J = 4.9 Hz, 4H), 2.69 (s, 4H), 2.44 (s, 3H), 1.26 (d, J = 11.2 Hz, 6H). |
| 2 | 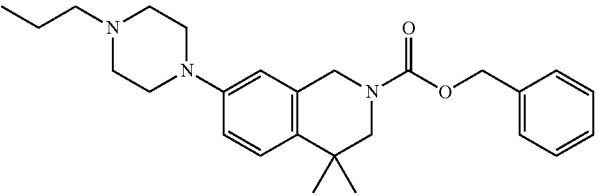 [SMILES: CCCN1CCN(c2ccc3c(c2)CN(C(=O)OCc2ccccc2)CC3(C)C)CC1]<br>benzyl 4,4-dimethyl-7-(4-propylpiperazin-1-yl)-3,4-dihydroisoquinoline-2(1H)-carboxylate | $^1$H NMR (300 MHz, CDCl$_3$) δ 7.42 – 7.33 (m, 5H), 7.23 (t, J = 8.5 Hz, 1H), 6.83 (d, J = 8.7 Hz, 1H), 6.61 (d, J = 13.1 Hz, 1H), 5.21 (s, 2H), 4.67 (s, 2H), 3.48 (d, J = 4.8 Hz, 2H), 3.20 (s, 4H), 2.62 (s, 2H), 2.38 (t, J = 7.9 Hz, 2H), 1.60 (s, 4H), 1.26 (d, J = 8.3 Hz, 6H), 0.95 (t, J = 7.48 Hz, 3H). |
| 3 | 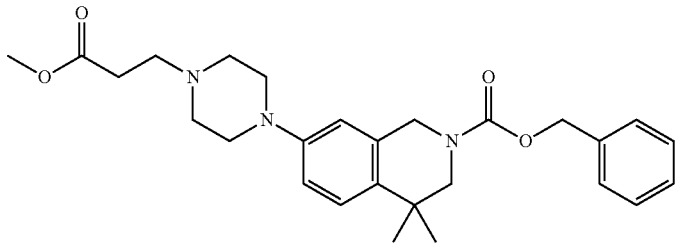 [SMILES: COC(=O)CCN1CCN(c2ccc3c(c2)CN(C(=O)OCc2ccccc2)CC3(C)C)CC1]<br>benzyl 7-(4-(3-methoxy-3-oxopropyl)piperazin-1-yl)-4,4-dimethyl-3,4-dihydroisoquinoline-2(1H)-carboxylate | $^1$H NMR (300 MHz, CDCl$_3$) δ 7.45 – 7.33 (m, 5H), 7.23 (t, J = 8.3 Hz, 1H), 6.82 (dd, J = 8.7, 2.5 Hz, 1H), 6.60 (d, J = 12.9 Hz, 1H), 5.21 (s, 2H), 4.67 (s, 2H), 3.71 (s, 3H), 3.48 (d, J = 4.7 Hz, 2H), 3.17 (t, J = 5.0 Hz, 4H), 2.78 (t, J = 7.4 Hz, 2H), 2.63 (t, J = 4.9 Hz, 4H), 2.57 (t, J = 7.3 Hz, 2H), 1.26 (d, J = 11.7 Hz, 6H). |
| 4 | 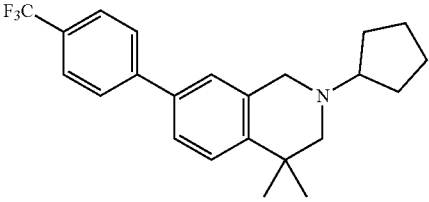 [SMILES: CC1(C)CN(C2CCCC2)Cc2cc(-c3ccc(C(F)(F)F)cc3)ccc21]<br>2-cyclopentyl-4,4-dimethyl-7-(4-(trifluoromethyl)phenyl)-1,2,3,4-tetrahydroisoquinoline | $^1$H NMR (300 MHz, DMSO-d$_6$) δ 7.92 – 7.74 (m, 4H), 7.58 – 7.35 (m, 3H), 3.67 (s, 2H), 3.31 (s, 2H), 2.45 (s, 2H), 1.89 (s, 2H), 1.65 (d, J = 7.7 Hz, 2H), 1.56 (d, J = 7.5 Hz, 2H), 1.47 (t, J = 8.7 Hz, 2H), 1.28 (s, 6H), 1.23 (d, J = 2.3 Hz, 2H). |

TABLE 1-continued

| Compound No. | Structure and name | NMR data |
|---|---|---|
| 5 | 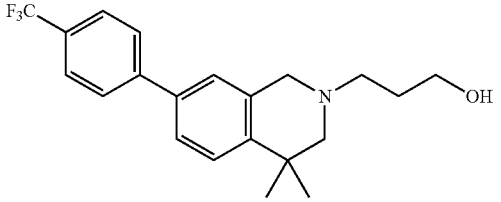 [SMILES: CC1(C)CN(CCCO)Cc2cc(-c3ccc(C(F)(F)F)cc3)ccc21]<br>3-(4,4-dimethyl-7-(4-(trifluoromethyl)phenyl)-3,4-dihydroisoquinolin-2(1H)-yl)propan-1-ol | $^1$H NMR (300 MHz, CD$_3$OD) δ 7.81–7.70 (m, 4H), 7.54–7.46 (m, 2H), 7.37 (d, J = 1.8 Hz, 1H), 3.62 (s, 2H), 3.37 (s, 1H), 2.52 (s, 2H), 2.45 (s, 3H), 1.37 (s, 6H), 1.30 (s, 2H)ppm. |
| 6 | 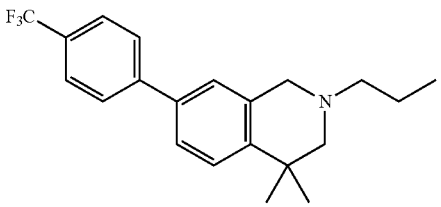 [SMILES: CCCN1Cc2cc(-c3ccc(C(F)(F)F)cc3)ccc2C(C)(C)C1]<br>4,4-dimethyl-2-propyl-7-(4-(trifluoromethyl)phenyl)-1,2,3,4-tetrahydroisoquinoline | $^1$H NMR (300 MHz, CDCl$_3$) δ 7.69 (s, 4H), 7.44 (d, J = 1.2 Hz, 2H), 7.27 (t, J = 1.2 Hz, 1H), 3.72 (s, 2H), 2.52 (s, 2H), 1.68 (p, J = 7.2 Hz, 2H), 1.39 (s, 6H), 1.29 (s, 2H), 1.00 (t, J = 7.4 Hz, 3H). |
| 7 | 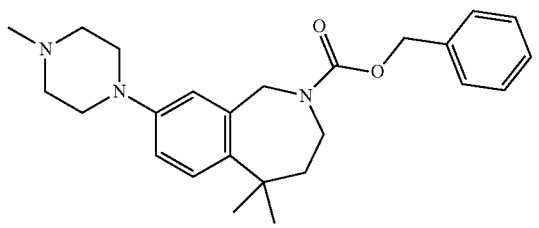 [SMILES: CN1CCN(c2ccc3c(c2)CN(C(=O)OCc2ccccc2)CCC3(C)C)CC1]<br>benzyl 5,5-dimethyl-8-(4-methylpiperazin-1-yl)-1,3,4,5-tetrahydro-2H-benzo[c]azepine-2-carboxylate | $^1$H NMR (400 MHz, CDCl$_3$, 3:2 ratio of rotamers): δ 7.38–7.18 (m, 6H), 6.83–6.72 (m, 1.4H), 6.59 (d, J = 2.7 Hz, 0.6H), 5.08 (s, 0.8H), 5.03 (s, 1.2H), 4.59 (s, 0.8H), 4.53 (s, 1.2H), 3.78–3.69 (m, 2H), 3.21 (t, J = 5.0 Hz, 1.6H), 3.08 (t, J = 5.0 Hz, 2.4H), 2.58–2.49 (m, 4H), 1.94–1.81 (m, 2H), 1.33 (s, 6H). |
| 8 | 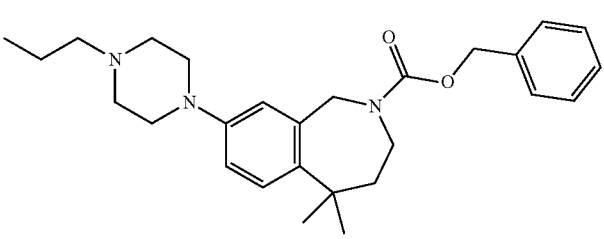 [SMILES: CCCN1CCN(c2ccc3c(c2)CN(C(=O)OCc2ccccc2)CCC3(C)C)CC1]<br>benzyl 5,5-dimethyl-8-(4-propylpiperazin-1-yl)-1,3,4,5-tetrahydro-2H-benzo[c]azepine-2-carboxylate | $^1$H NMR (400 MHz, CDCl$_3$, 3:2 ratio of rotamers): δ 7.37–7.19 (m, 6H), 6.82–6.72 (m, 1.4H), 6.59 (d, J = 2.8 Hz, 0.6H), 5.08 (s, 0.8H), 5.03 (s, 1.2H), 4.59 (s, 0.8H), 4.53 (s, 1.2H), 3.79–3.68 (m, 2H), 3.20 (t, J = 5.0 Hz, 2H), 3.08 (t, J = 5.0 Hz, 2H), 2.60–2.50 (m, 4H), 2.39–2.31 (m, 2H), 1.93–1.82 (m, 2H), 1.60–1.49 (m, 2H), 1.33 (s, 6H), 0.93 (q, J = 6.9 Hz, 3H). |

TABLE 1-continued

| Compound No. | Structure and name | NMR data |
|---|---|---|
| 9 | 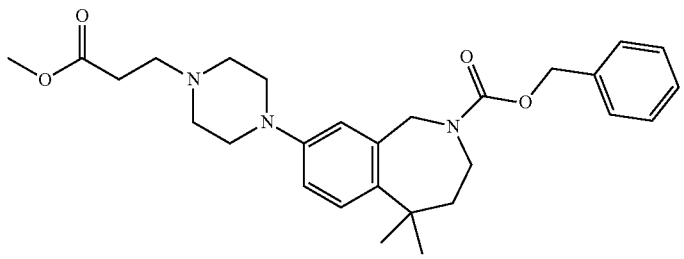 [SMILES: COC(=O)CCN1CCN(c2ccc3c(c2)CN(C(=O)OCc2ccccc2)CCC3(C)C)CC1]<br>benzyl 8-(4-(3-methoxy-3-oxopropyl)piperazin-1-yl)-5,5-dimethyl-1,3,4,5-tetrahydro-2H-benzo[c]azepine-2-carboxylate | $^1$H NMR (400 MHz, DMSO-d$_6$, 3:2 ratio of rotamers): δ 7.38 – 7.14 (m, 6H), 6.75 (ddd, J = 8.8, 6.0, 2.6 Hz, 1H), 6.68 (d, J = 2.7 Hz, 0.4H), 6.61 (d, J = 2.9 Hz, 0.6H), 5.01 (s, 0.8H), 4.97 (s, 1.2H), 4.51 (s, 1.2H), 4.50 (s, 0.8H), 3.68 – 3.57 (m, 5H), 3.06 (t, J = 5.1 Hz, 1.6H), 2.96 (t, J = 4.9 Hz, 2.4H), 2.65 – 2.56 (m, 2H), 2.56 – 2.38, m, 6H, overlaps with DMSO signal) 1.88-1.77 (m, 2H), 1.24 (s, 6H). |
| 10 | 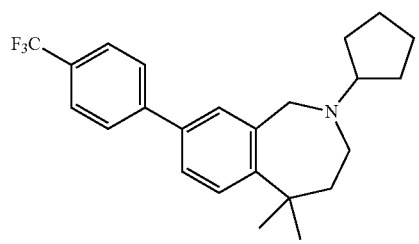 [SMILES: CC1(C)CCN(C2CCCC2)Cc2cc(-c3ccc(C(F)(F)F)cc3)ccc21]<br>2-cyclopentyl-5,5-dimethyl-8-(4-(trifluoromethyl)phenyl)-2,3,4,5-tetrahydro-1H-benzo[c]azepine | $^1$H NMR (400 MHz, DMSO-d$_6$, δ 7.88 (d, J = 8.1 Hz, 2H), 7.80 (d, J = 8.3 Hz, 2H), 7.55 (dd, J = 8.2, 2.1 Hz, 1H), 7.47 (dd, J = 5.2, 3.0 Hz, 2H), 4.00 (s, 2H), 2.99 (t, J = 5.7 Hz, 2H), 2.73 – 2.64 (m, 1H), 1.84 – 1.69 (m, 4H), 1.65 – 1.51 (m, 2H), 1.48 – 1.28 (m, 10H). |
| 11 | 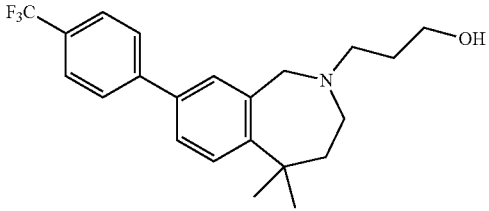 [SMILES: CC1(C)CCN(CCCO)Cc2cc(-c3ccc(C(F)(F)F)cc3)ccc21]<br>3-(5,5-dimethyl-8-(4-(trifluoromethyl)phenyl)-1,3,4,5-tetrahydro-2H-benzo[c]azepin-2-yl)propan-1-ol | $_1$H NMR (400 MHz, CDCl$_3$): δ 7.68 (s, 4H), 7.49 – 7.43 (m, 2H), 7.33 (s, 1H), 4.11 (s, 2H), 3.93 (brs, 1H), 3.80 (t, J = 5.3 Hz, 2H), 3.17 – 3.07 (m, 2H), 2.69 (t, J = 5.7 Hz, 2H), 1.88 – 1.77 (m, 2H), 1.71 (q, J = 5.6 Hz, 2H), 1.43 (s, 6H). |
| 12 | 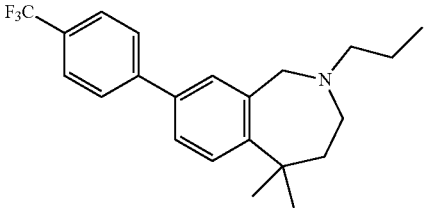 [SMILES: CCCN1CCC(C)(C)c2ccc(-c3ccc(C(F)(F)F)cc3)cc2C1]<br>5,5-dimethyl-2-propyl-8-(4-(trifluoromethyl)phenyl)-2,3,4,5-tetrahydro-1H-benzo[c]azepine | $^1$H NMR (400 MHz, CDCl$_3$) δ 7.67 (s, 4H), 7.50 – 7.40 (m, 2H), 7.29 (d, J = 2.0 Hz, 1H), 4.04 (s, 2H), 3.10 – 3.00 (m, 2H), 2.45 – 2.36 (m, 2H), 1.87 – 1.75 (m, 2H), 1.53 (sx, J = 7.6 Hz, 2H), 1.43 (s, 6H), 0.87 (t, J = 7.4 Hz, 3H). |

TABLE 1-continued

| Compound No. | Structure and name | NMR data |
|---|---|---|
| 13 | 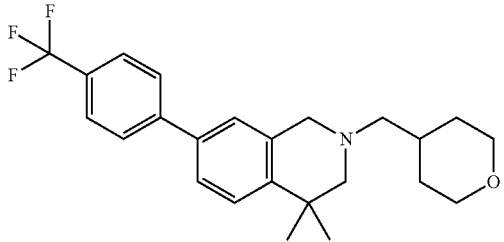 [SMILES: CC1(C)CN(CC2CCOCC2)Cc2cc(-c3ccc(C(F)(F)F)cc3)ccc21]<br>4,4-dimethyl-2-((tetrahydro-2H-pyran-4-yl)methyl)-7-(4-(trifluoromethyl)phenyl)-1,2,3,4-tetrahydroisoquinoline | $^1$H NMR (400 MHz, DMSO) δ 7.89 – 7.75 (m, 4H), 7.56 – 7.42 (m, 2H), 7.39 (d, J = 1.9 Hz, 1H), 3.85 (ddd, J = 11.6, 4.4, 1.9 Hz, 2H), 3.60 (s, 2H), 3.28 (d, J = 2.1 Hz, 1H), 2.41 (s, 2H), 2.30 (d, J = 7.3 Hz, 2H), 1.88 (ddd, J = 11.2, 7.4, 3.9 Hz, 1H), 1.71 – 1.62 (m, 2H), 1.28 (s, 6H), 1.17 (qd, J = 11.9, 4.4 Hz, 2H). 1H under solvent peaks. |
| 14 | 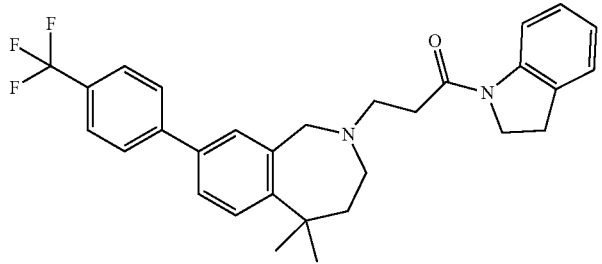 [SMILES: CC1(C)CCN(CCC(=O)N2CCc3ccccc32)Cc2cc(-c3ccc(C(F)(F)F)cc3)ccc21]<br>3-(5,5-dimethyl-8-(4-(trifluoromethyl)phenyl)-1,3,4,5-tetrahydro-2H-benzo[c]azepin-2-yl)-1-(indolin-1-yl)propan-1-one | $^1$H NMR (400 MHz, DMSO) δ 8.02 (d, J = 8.0 Hz, 1H), 7.87 (d, J = 8.2 Hz, 2H), 7.79 (d, J = 8.3 Hz, 2H), 7.60 – 7.50 (m, 2H), 7.47 (d, J = 8.2 Hz, 1H), 7.18 (d, J = 7.3 Hz, 1H), 7.10 (t, J = 7.7 Hz, 1H), 6.94 (t, J = 7.4 Hz, 1H), 4.12 – 3.98 (m, 4H), 3.02 (dt, J = 17.1, 7.0 Hz, 4H), 2.67 (dt, J = 36.8, 7.3 Hz, 4H), 1.75 (d, J = 5.9 Hz, 2H), 1.37 (s, 6H). |
| 15 | 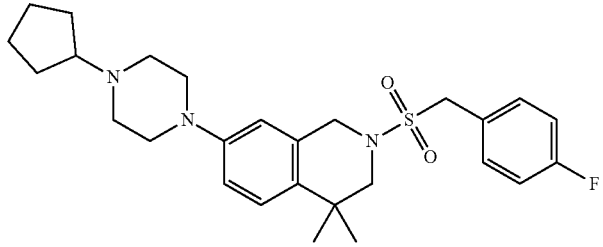 [SMILES: CC1(C)CN(S(=O)(=O)Cc2ccc(F)cc2)Cc2cc(N3CCN(C4CCCC4)CC3)ccc21]<br>7-(4-cyclopentylpiperazin-1-yl)-2-((4-fluorobenzyl)sulfonyl)-4,4-dimethyl-1,2,3,4-tetrahydroisoquinoline | $^1$H NMR (400 MHz, DMSO) δ 7.54 – 7.42 (m, 2H), 7.29 – 7.16 (m, 3H), 6.82 (dd, J = 8.8, 2.6 Hz, 1H), 6.58 (d, J = 2.5 Hz, 1H), 4.52 (s, 2H), 4.29 (s, 2H), 3.30 (s, 4H), 3.06 (d, J = 6.5 Hz, 6H), 2.46 – 2.42 (m, 1H), 1.80 (s, 2H), 1.62 (s, 2H), 1.51 (d, J = 9.3 Hz, 2H), 1.40 – 1.28 (m, 2H), 1.16 (s, 6H). |
| 16 | 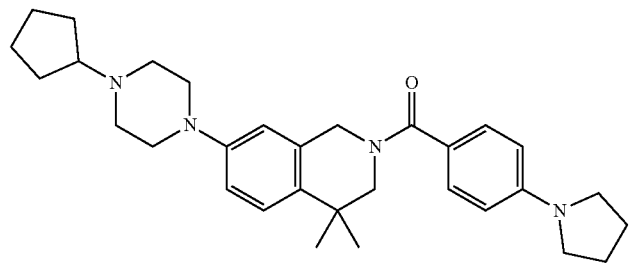 [SMILES: CC1(C)CN(C(=O)c2ccc(N3CCCC3)cc2)Cc2cc(N3CCN(C4CCCC4)CC3)ccc21]<br>(7-(4-cyclopentylpiperazin-1-yl)-4,4-dimethyl-3,4-dihydroisoquinolin-2(1H)-yl)(4-(pyrrolidin-1-yl)phenyl)methanone | $^1$H NMR (400 MHz, DMSO) δ 7.27 (d, J = 8.6 Hz, 2H), 7.19 (d, J = 8.6 Hz, 1H), 6.79 (dd, J = 8.8, 2.6 Hz, 1H), 6.60 (s, 1H), 6.57 – 6.49 (m, 2H), 4.66 (s, 2H), 3.53 (s, 2H), 3.30 – 3.22 (m, 6H), 3.05 (t, J = 5.0 Hz, 4H), 2.46 – 2.40 (m, 1H), 1.99 – 1.94 (m, 4H), 1.86 – 1.75 (m, 2H), 1.66 – 1.56 (m, 2H), 1.54 – 1.44 (m, 2H), 1.40 – 1.28 (m, 2H), 1.14 (s, 6H). 2H under solvent peaks. |

TABLE 1-continued

| Compound No. | Structure and name | NMR data |
|---|---|---|
| 17 | 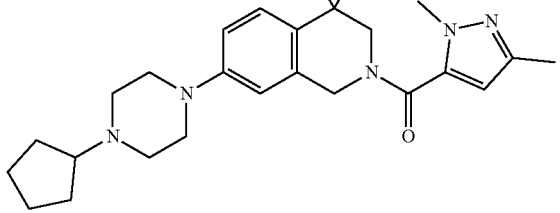<br>(7-(4-cyclopentylpiperazin-1-yl)-4,4-dimethyl-3,4-dihydroisoquinolin-2(1H)-yl)(1,3-dimethyl-1H-pyrazol-5-yl)methanone | $^1$H NMR (400 MHz, DMSO) δ 7.21 (d, J = 6.3 Hz, 1H), 6.85 – 6.77 (m, 1H), 6.66 (d, J = 66.3 Hz, 1H), 6.26 (d, J = 20.2 Hz, 1H), 4.71 (d, J = 31.1 Hz, 2H), 3.73 (s, 3H), 3.63 (br s, 1H), 3.49 (br s, 1H), 3.06 (br s, 4H), 2.47 – 2.40 (m, 1H), 2.18 (s, 3H), 1.80 (br s, 2H), 1.61 (br s, 2H), 1.50 (d, J = 7.4 Hz, 2H), 1.34 (br s, 2H), 1.16 (d, J = 47.7 Hz, 6H). 4H under solvent peaks. |
| 18 | 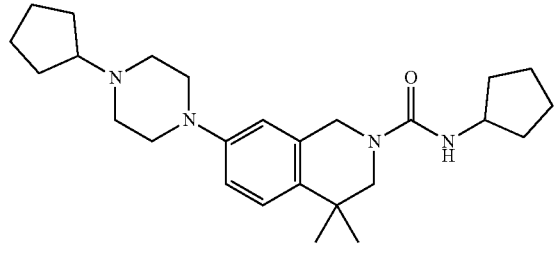 [SMILES: CC1(C)CN(C(=O)NC2CCCC2)Cc2cc(N3CCN(C4CCCC4)CC3)ccc21]<br>N-cyclopentyl-7-(4-cyclopentylpiperazin-1-yl)-4,4-dimethyl-3,4-dihydroisoquinoline-2(1H)-carboxamide | $^1$H NMR (400 MHz, DMSO) δ 7.17 (d, J = 8.6 Hz, 1H), 6.78 (dd, J = 8.6, 2.6 Hz, 1H), 6.56 (d, J = 2.5 Hz, 1H), 6.16 (d, J = 7.0 Hz, 1H), 4.45 (s, 2H), 3.96 (p, J = 7.0 Hz, 1H), 3.31 – 3.28 (m, 3H), 3.06 (t, J = 5.0 Hz, 4H), 2.55 – 2.52 (m, 3H), 2.47 – 2.41 (m, 1H), 1.78 (dt, J = 11.6, 7.3 Hz, 4H), 1.69 – 1.57 (m, 4H), 1.54 – 1.30 (m, 8H), 1.14 (s, 6H). |
| 19 | 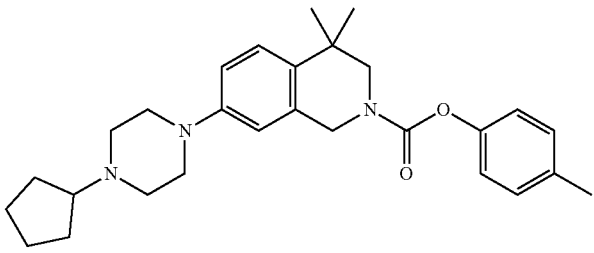 [SMILES: Cc1ccc(OC(=O)N2Cc3cc(N4CCN(C5CCCC5)CC4)ccc3C(C)(C)C2)cc1]<br>p-tolyl 7-(4-cyclopentylpiperazin-1-yl)-4,4-dimethyl-3,4-dihydroisoquinoline-2(1H)-carboxylate | $^1$H NMR (400 MHz, DMSO) δ 7.24 (d, J = 8.7 Hz, 1H), 7.21 – 7.15 (m, 2H), 7.00 (dd, J = 13.2, 8.2 Hz, 2H), 6.83 (dd, J = 8.8, 2.5 Hz, 1H), 6.70 (br s, 1H), 4.76 (s, 1H), 4.59 (s, 1H), 3.57 (s, 1H), 3.42 (s, 1H), 3.08 (t, J = 5.0 Hz, 4H), 2.53 (s, 2H), 2.46 – 2.42 (m, 1H), 2.29 (s, 3H), 1.86 – 1.74 (m, 2H), 1.68 – 1.57 (m, 2H), 1.51 (dq, J = 12.9, 4.9 Hz, 2H), 1.41 – 1.29 (m, 2H), 1.23 (d, J = 16.1 Hz, 6H). 2H under solvent peaks. |
| 20 | 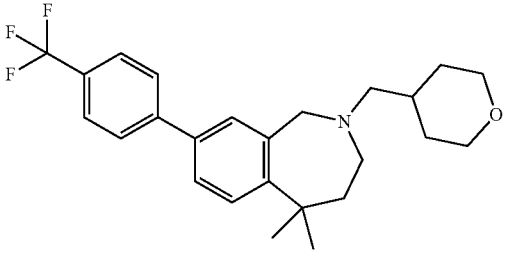 [SMILES: CC1(C)CCN(CC2CCOCC2)Cc2cc(-c3ccc(C(F)(F)F)cc3)ccc21]<br>5,5-dimethyl-2-((tetrahydro-2H-pyran-4-yl)methyl)-8-(4-(trifluoromethyl)phenyl)-2,3,4,5-tetrahydro-1H-benzo[c]azepine | $^1$H NMR (400 MHz, DMSO) δ 7.88 (d, J = 8.2 Hz, 2H), 7.80 – (d, J = 8.2 Hz, 2H), 7.55 (dd, J = 8.1, 2.2 Hz, 1H), 7.47 (d, J = 8.3 Hz, 2H), 3.96 (s, 2H), 3.78 (ddd, J = 11.4, 4.5, 2.0 Hz, 2H), 3.27 – 3.21 (m, 2H), 2.91 (t, J = 5.7 Hz, 2H), 2.23 (d, J = 7.1 Hz, 2H), 1.74 (tt, J = 6.8, 4.0 Hz, 3H), 1.58 – 1.48 (m, 2H), 1.37 (s, 6H), 1.06 (qd, |

TABLE 1-continued

| Compound No. | Structure and name | NMR data |
|---|---|---|
| | | J = 11.9, 4.5 Hz, 2H). |
| 21 | 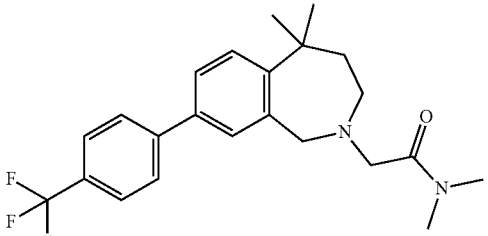<br>2-(5,5-dimethyl-8-(4-(trifluoromethyl)phenyl)-1,3,4,5-tetrahydro-2H-benzo[c]azepin-2-yl)-N,N-dimethylacetamide | $^1$H NMR (400 MHz, DMSO) δ 7.87 (d, J = 8.3 Hz, 2H), 7.80 (d, J = 8.2 Hz, 2H), 7.56 (dd, J = 8.2, 2.1 Hz, 1H), 7.48 (d, J = 8.3 Hz, 1H), 7.40 (d, J = 2.2 Hz, 1H), 4.04 (s, 2H), 3.24 (s, 2H), 2.95 (s, 5H), 2.79 (s, 3H), 1.75 (t, J = 5.7 Hz, 2H), 1.37 (s, 6H). |
| 22 | 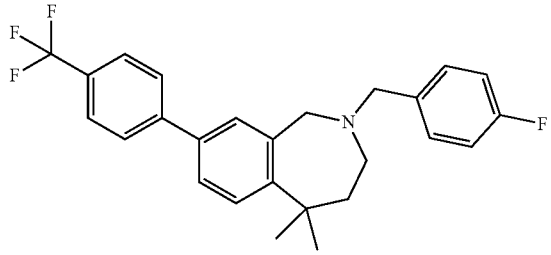 [SMILES: CC1(C)CCN(Cc2ccc(F)cc2)Cc2cc(-c3ccc(C(F)(F)F)cc3)ccc21]<br>2-(4-fluorobenzyl)-5,5-dimethyl-8-(4-(trifluoromethyl)phenyl)-2,3,4,5-tetrahydro-1H-benzo[c]azepine | $^1$H NMR (400 MHz, DMSO) δ 7.82 (q, J = 8.4 Hz, 4H), 7.57 (dd, J = 8.2, 2.1 Hz, 1H), 7.50 (d, J = 8.3 Hz, 1H), 7.34 – 7.25 (m, 3H), 7.17 – 7.08 (m, 2H), 3.99 (s, 2H), 3.56 (s, 2H), 2.91 (t, J = 5.6 Hz, 2H), 1.76 (dd, J = 7.5, 3.9 Hz, 2H), 1.38 (s, 6H). |
| 23 | 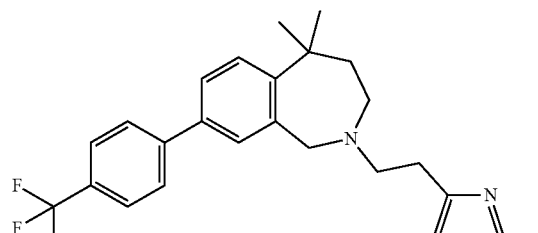<br>4-(2-(5,5-dimethyl-8-(4-(trifluoromethyl)phenyl)-1,3,4,5-tetrahydro-2H-benzo[c]azepin-2-yl)ethyl)-2-methylthiazole | $^1$H NMR (400 MHz, DMSO) δ 7.89 (d, J = 8.2 Hz, 2H), 7.80 (d, J = 8.3 Hz, 2H), 7.58 – 7.51 (m, 2H), 7.46 (d, J = 8.2 Hz, 1H), 7.07 (s, 1H), 4.04 (s, 2H), 3.00 (t, J = 5.6 Hz, 2H), 2.83 (t, J = 7.6 Hz, 2H), 2.67 (t, J = 7.5 Hz, 2H), 2.56 (s, 3H), 1.74 (t, J = 5.7 Hz, 2H), 1.36 (s, 6H). |
| 24 | 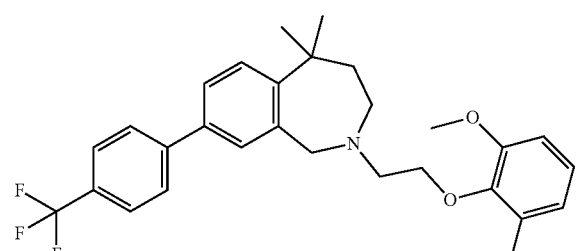<br>2-(2-(2,6-dimethoxyphenoxy)ethyl)-5,5-dimethyl-8-(4-(trifluoromethyl)phenyl)-2,3,4,5-tetrahydro-1H-benzo[c]azepine | $^1$H NMR (400 MHz, DMSO) δ 7.86 (d, J = 8.2 Hz, 2H), 7.79 (d, J = 8.2 Hz, 2H), 7.56 (dd, J = 8.1, 2.2 Hz, 1H), 7.51 – 7.44 (m, 2H), 6.96 (t, J = 8.4 Hz, 1H), 6.63 (d, J = 8.3 Hz, 2H), 4.07 (s, 2H), 3.93 (t, J = 6.1 Hz, 2H), 3.69 (s, 6H), 3.04 (t, J = 5.7 Hz, 2H), 2.72 (t, J = 6.1 Hz, 2H), 1.75 (t, J = 5.4 Hz, 2H), 1.38 (s, 6H). |

TABLE 1-continued

| Compound No. | Structure and name | NMR data |
|---|---|---|
| 25 | 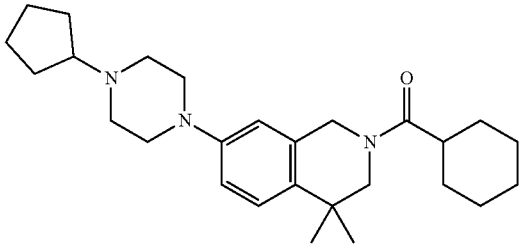 [SMILES: CC1(C)CN(C(=O)C2CCCCC2)Cc2cc(N3CCN(C4CCCC4)CC3)ccc21]
cyclohexyl(7-(4-cyclopentylpiperazin-1-yl)-4,4-dimethyl-3,4-dihydroisoquinolin-2(1H)-yl)methanone | $^1$H NMR (400 MHz, DMSO) δ 7.18 (d, J = 8.5 Hz, 1H), 6.79 (dt, J = 8.7, 3.0 Hz, 1H), 6.67 (dd, J = 21.4, 2.7 Hz, 1H), 4.66 (s, 1H), 4.54 (s, 1H), 3.45 (d, J = 10.9 Hz, 2H), 3.07 (q, J = 5.7 Hz, 4H), 2.77 – 2.68 (m, 1H), 2.59 – 2.51 (m, 4H), 2.47 – 2.41 (m, 1H), 1.86 – 1.75 (m, 2H), 1.74 – 1.42(m, 10H), 1.35 (q, J = 12.5 Hz, 6H), 1.15 (d, J = 32.8 Hz, 6H). 4 + 1H under solvent peaks. |
| 26 | 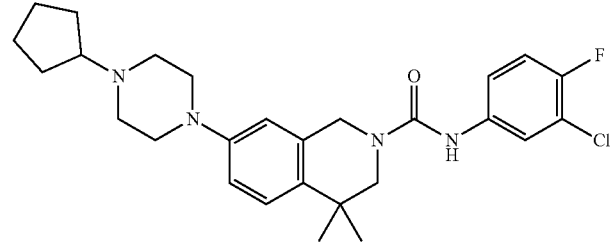 [SMILES: CC1(C)CN(C(=O)Nc2ccc(F)c(Cl)c2)Cc2cc(N3CCN(C4CCCC4)CC3)ccc21]
N-(3-chloro-4-fluorophenyl)-7-(4-cyclopentylpiperazin-1-yl)-4,4-dimethyl-3,4-dihydroisoquinoline-2(1H)-carboxamide | $^1$H NMR (400 MHz, DMSO) δ 8.69 (s, 1H), 7.77 (dd, J = 6.9, 2.6 Hz, 1H), 7.45 (ddd, J = 9.1, 4.3, 2.6 Hz, 1H), 7.30 (t, J = 9.1 Hz, 1H), 7.21 (d, J = 8.6 Hz, 1H), 6.82 (dd, J = 8.7, 2.6 Hz, 1H), 6.62 (d, J = 2.5 Hz, 1H), 4.63 (s, 2H), 3.47 (s, 2H), 3.08 (t, J = 5.0 Hz, 4H), 2.56 – 2.52 (m, 4H), 2.47 – 2.44 (m, 1H), 1.80 (t, J = 9.1 Hz, 2H), 1.62 (qd, J = 10.5, 9.2, 5.4 Hz, 2H), 1.57 – 1.46 (m, 2H), 1.41 – 1.29 (m, 2H), 1.19 (s, 6H). |
| 27 | 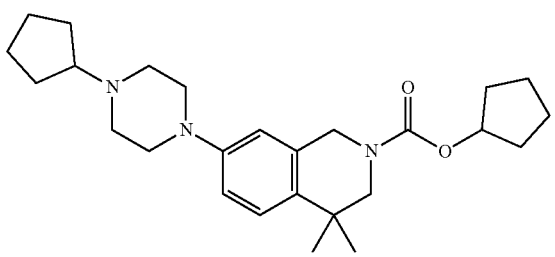 [SMILES: CC1(C)CN(C(=O)OC2CCCC2)Cc2cc(N3CCN(C4CCCC4)CC3)ccc21]
cyclopentyl 7-(4-cyclopentylpiperazin-1-yl)-4,4-dimethyl-3,4-dihydroisoquinoline-2(1H)-carboxylate | $^1$H NMR (400 MHz, DMSO) δ 7.19 (d, J = 8.6 Hz, 1H), 6.79 (dd, J = 8.7, 2.6 Hz, 1H), 6.64 (d, J = 2.9 Hz, 1H), 5.03 (tt, J = 5.4, 2.3 Hz, 1H), 4.50 (s, 2H), 3.06 (t, J = 4.9 Hz, 4H), 2.46 – 2.41 (m, 1H), 1.86 – 1.72 (m, 4H), 1.68 – 1.47 (m, 10H), 1.34 (dq, J = 16.2, 8.0 Hz, 2H), 1.14 (s, 6H). 2 + 4H under solvent peaks. |
| 28 | 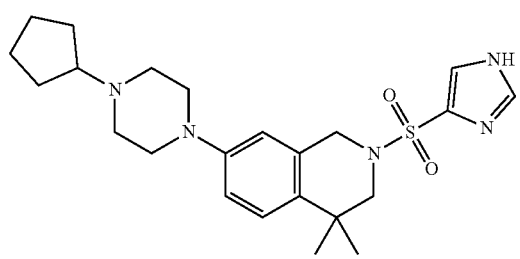 [SMILES: CC1(C)CN(S(=O)(=O)c2c[nH]cn2)Cc2cc(N3CCN(C4CCCC4)CC3)ccc21]
2-((1H-imidazol-4-yl)sulfonyl)-7-(4-cyclopentylpiperazin-1-yl)-4,4-dimethyl-1,2,3,4-tetrahydroisoquinoline | $^1$H NMR (400 MHz, DMSO) δ 12.90 (br s, 1H), 8.17 (s, 1.24H formic acid), 7.87 (d, J = 17.9 Hz, 2H), 7.19 (d, J = 8.7 Hz, 1H), 6.80 (dd, J = 8.7, 2.6 Hz, 1H), 6.63 (d, J = 2.6 Hz, 1H), 4.15 (s, 2H), 3.06 (t, J = 4.9 Hz, 4H), 2.97 (s, 2H), 2.54 – 2.52 (m, 2H), 2.48 – 2.43 (m, 1H), 1.87 – 1.73 (m, 2H), 1.68 – 1.56 (m, 2H), |

TABLE 1-continued

| Compound No. | Structure and name | NMR data |
|---|---|---|
|  |  | 1.56 – 1.43 (m, 2H), 1.42 – 1.28 (m, 2H), 1.20 (s, 6H). 2H under solvent peaks. |
| 29 | 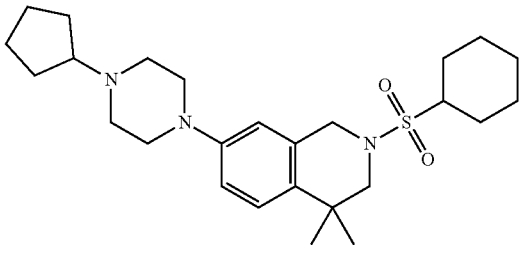 [SMILES: CC1(C)CN(S(=O)(=O)C2CCCCC2)Cc2cc(N3CCN(C4CCCC4)CC3)ccc21]<br>2-(cyclohexylsulfonyl)-7-(4-cyclopentylpiperazin-1-yl)-4,4-dimethyl-1,2,3,4-tetrahydroisoquinoline | $^1$H NMR (400 MHz, DMSO) δ 7.21 (d, J = 8.7 Hz, 1H), 6.82 (dd, J = 8.8, 2.6 Hz, 1H), 6.62 (d, J = 2.6 Hz, 1H), 4.39 (s, 2H), 3.24 (s, 2H), 3.27 – 3.16 (m, 2H), 3.06 (t, J = 5.0 Hz, 4H), 2.56 – 2.52 (m, 2H), 2.45 (d, J = 7.7 Hz, 1H), 2.03 (d, J = 12.2 Hz, 2H), 1.84 – 1.73 (m, 4H), 1.66 – 1.58 (m, 3H), 1.55 – 1.20 (m, 9H), 1.19 (s, 6H), 1.18 – 1.11 (m, 1H). |
| 30 | 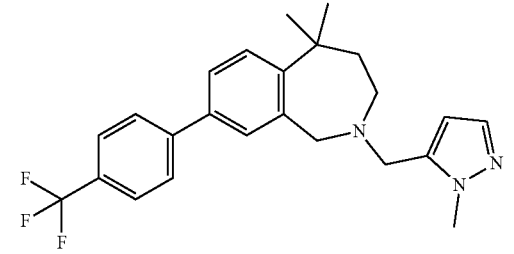 [SMILES: Cn1nccc1CN1CCC(C)(C)c2ccc(-c3ccc(C(F)(F)F)cc3)cc2C1]<br>5,5-dimethyl-2-((1-methyl-1H-pyrazol-5-yl)methyl)-8-(4-(trifluoromethyl)phenyl)-2,3,4,5-tetrahydro-1H-benzo[c]azepine | 1H NMR (400 MHz, DMSO) δ 7.86 (d, J = 8.3 Hz, 2H), 7.81 (d, J = 8.4 Hz, 2H), 7.58 (dd, J = 8.2, 2.1 Hz, 1H), 7.50 (d, J = 8.2 Hz, 1H), 7.32 (dd, J = 15.7, 2.0 Hz, 2H), 6.07 (d, J = 1.7 Hz, 1H), 4.02 (s, 2H), 3.73 (s, 3H), 3.59 (s, 2H), 2.93 (t, J = 5.6 Hz, 2H), 1.76 (t, J = 5.5 Hz, 2H), 1.38 (s, 6H). |
| 31 | 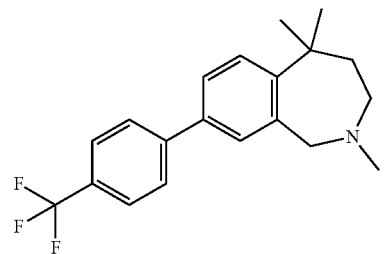 [SMILES: CN1CCC(C)(C)c2ccc(-c3ccc(C(F)(F)F)cc3)cc2C1]<br>2,5,5-trimethyl-8-(4-(trifluoromethyl)phenyl)-2,3,4,5-tetrahydro-1H-benzo[c]azepine | $^1$H NMR (400 MHz, DMSO) δ 8.18 (s, 1H, formic acid), 7.89 (d, J = 8.2 Hz, 2H), 7.81 (d, J = 8.3 Hz, 2H), 7.59 (dd, J = 8.2, 2.2 Hz, 1H), 7.52 (d, J = 2.2 Hz, 1H), 7.48 (d, J = 8.2 Hz, 1H), 3.99 (s, 2H), 2.93 (t, 2H), 2.32 (s, 3H), 1.77 (t, 2H), 1.37 (s, 6H). |
| 32 | 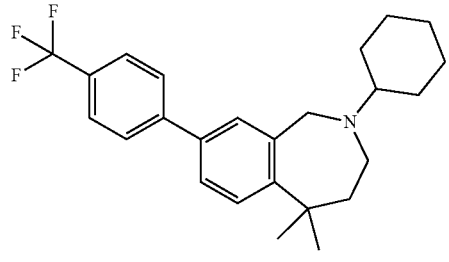 [SMILES: CC1(C)CCN(C2CCCCC2)Cc2cc(-c3ccc(C(F)(F)F)cc3)ccc21]<br>2-cyclohexyl-5,5-dimethyl-8-(4-(trifluoromethyl)phenyl)-2,3,4,5-tetrahydro-1H-benzo[c]azepine | $^1$H NMR (400 MHz, DMSO) δ 8.18 (s, 1H, formic acid), 7.88 (d, J = 8.1 Hz, 2H), 7.79 (d, J = 8.2 Hz, 2H), 7.53 (dd, J = 8.1, 2.2 Hz, 1H), 7.51 – 7.44 (m, 2H), 3.96 (s, 2H), 2.97 (t, J = 5.8 Hz, 2H), 2.46 – 2.38 (m, 1H), 1.81 – 1.66 (m, 6H), 1.54 (t, J = 9.5 Hz, 1H), 1.39 – 1.06 (m, 1H). |

TABLE 1-continued

| Compound No. | Structure and name | NMR data |
|---|---|---|
| 33 | 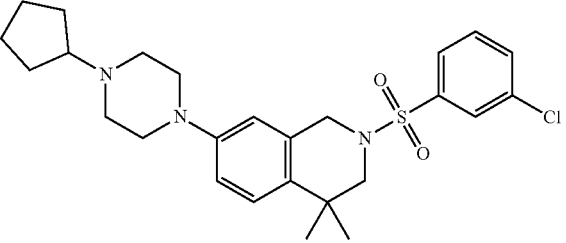 [SMILES: CC1(C)CN(S(=O)(=O)c2cccc(Cl)c2)Cc2cc(N3CCN(C4CCCC4)CC3)ccc21]<br>2-((3-chlorophenyl)sulfonyl)-7-(4-cyclopentylpiperazin-1-yl)-4,4-dimethyl-1,2,3,4-tetrahydroisoquinoline | $^1$H NMR (400 MHz, DMSO) δ 7.86 – 7.77 (m, 3H), 7.71 (t, J = 7.8 Hz, 1H), 7.19 (d, J = 8.7 Hz, 1H), 6.81 (dd, J = 8.6, 2.6 Hz, 1H), 6.65 (d, J = 2.6 Hz, 1H), 4.11 (s, 2H), 3.05 (t, J = 5.0 Hz, 4H), 2.99 (s, 2H), 2.47 – 2.41 (m, 1H), 1.85 – 1.74 (m, 2H), 1.61 (tq, J = 9.4, 5.5, 3.9 Hz, 2H), 1.56 – 1.45 (m, 2H), 1.40 – 1.27 (m, 2H), 1.21 (s, 6H). 4H under solvent peaks. |
| 34 | 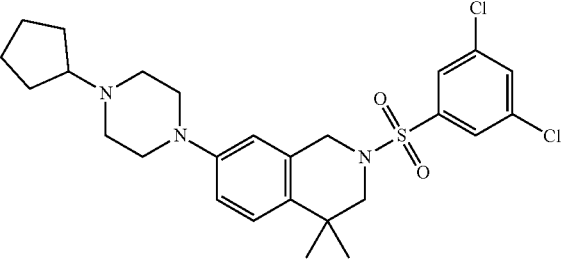 [SMILES: CC1(C)CN(S(=O)(=O)c2cc(Cl)cc(Cl)c2)Cc2cc(N3CCN(C4CCCC4)CC3)ccc21]<br>7-(4-cyclopentylpiperazin-1-yl)-2-((3,5-dichlorophenyl)sulfonyl)-4,4-dimethyl-1,2,3,4-tetrahydroisoquinoline | $^1$H NMR (400 MHz, DMSO) δ 8.05 (t, J = 1.9 Hz, 1H), 7.84 (d, J = 1.9 Hz, 2H), 7.20 (d, J = 8.6 Hz, 1H), 6.81 (dd, J = 8.7, 2.7 Hz, 1H), 6.65 (d, J = 2.8 Hz, 1H), 4.16 (s, 2H), 3.05 (t, J = 5.8 Hz, 6H), 2.43 (s, 1H), 1.84 – 1.75 (m, 2H), 1.68 – 1.56 (m, 2H), 1.54 – 1.45 (m, 2H), 1.41 – 1.28 (m, 2H), 1.21 (s, 6H). 4H under solvent peaks. |
| 35 | 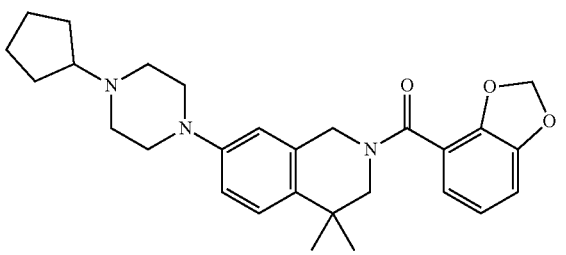 [SMILES: CC1(C)CN(C(=O)c2cccc3c2OCO3)Cc2cc(N3CCN(C4CCCC4)CC3)ccc21]<br>benzo[d][1,3]dioxol-4-yl(7-(4-cyclopentylpiperazin-1-yl)-4,4-dimethyl-3,4-dihydroisoquinolin-2(1H)-yl)methanone | $^1$H NMR (400 MHz, DMSO) δ 7.19 (dd, J = 12.2, 8.6 Hz, 1H), 7.01 (dd, J = 7.9, 4.3 Hz, 1H), 6.91 (t, J = 7.8 Hz, 1H), 6.83 (dd, J = 7.9, 1.2 Hz, 1H), 6.81 – 6.75 (m, 1H), 6.57 (d, J = 2.7 Hz, 1H), 6.06 (d, J = 4.9 Hz, 2H), 4.76 (s, 1H), 4.50 (s, 1H), 3.63 (s, 1H), 3.09 (t, J = 5.2 Hz, 2H), 3.02 (t, J = 4.8 Hz, 2H), 2.56 – 2.52 (m, 2H), 2.49 – 2.46 (m, 2H), 2.43 (d, J = 8.2 Hz, 1H), 1.87 – 1.73 (m, 2H), 1.68 – 1.56 (m, 2H), 1.55 – 1.42 (m, 2H), 1.41 – 1.26 (m, 2H), 1.22 (s, 3H), 1.05 (s, 3H). 1H under solvent peaks. |

TABLE 1-continued

| Compound No. | Structure and name | NMR data |
|---|---|---|
| 36 | 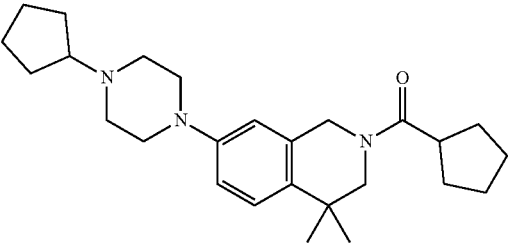 [SMILES: CC1(C)CN(C(=O)C2CCCC2)Cc2cc(N3CCN(C4CCCC4)CC3)ccc21]<br>cyclopentyl(7-(4-cyclopentylpiperazin-1-yl)-4,4-dimethyl-3,4-dihydroisoquinolin-2(1H)-yl)methanone | 1H NMR (400 MHz, DMSO) δ 7.19 (dd, J = 8.6, 2.6 Hz, 1H), 6.79 (t, J = 7.9 Hz, 1H), 6.67 (dd, J = 10.8, 2.5 Hz, 1H), 4.67 (s, 1H), 4.56 (s, 1H), 3.47 (d, J = 9.5 Hz, 2H), 3.07 (q, J = 3.6, 3.0 Hz, 5H), 1.78 (d, J = 11.0 Hz, 4H), 1.72 – 1.43 (m, 11H), 1.34 (t, J = 9.7 Hz, 2H), 1.15 (d, J = 27.7 Hz, 6H). 4H under solvent peaks. |
| 37 | 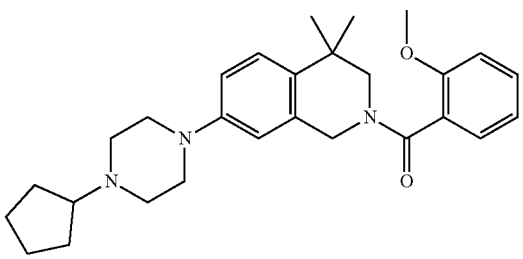 [SMILES: COc1ccccc1C(=O)N1Cc2cc(N3CCN(C4CCCC4)CC3)ccc2C(C)(C)C1]<br>(7-(4-cyclopentylpiperazin-1-yl)-4,4-dimethyl-3,4-dihydroisoquinolin-2(1H)-yl)(2-methoxyphenyl)methanone | $^1$H NMR (400 MHz, DMSO) δ 7.41 (tt, J = 7.5, 2.2 Hz, 1H), 7.24 – 7.14 (m, 2H), 7.10 (d, J = 8.4 Hz, 1H), 7.00 (t, J = 7.4 Hz, 1H), 6.77 (ddd, J = 20.1, 11.7, 2.7 Hz, 1.5H), 6.45 (d, J = 2.5 Hz, 0.5H), 4.98 – 4.49 (m, 1H), 4.38 – 4.20 (m, 1H), 3.77 (s, 1.33H), 3.66 (s, 1.66H), 3.62 (s, 1H), 3.14 (d, J = 2.3 Hz, 1H), 3.04 (dt, J = 33.9, 5.1 Hz, 4H), 2.43 – 2.38 (m, 1H), 1.86 – 1.72 (m, 2H), 1.66 – 1.54 (m, 2H), 1.53 – 1.47 (m, 2H), 1.43 – 1.27 (m, 2H), 1.23 (d, J = 5.0 Hz, 3H), 1.02 (d, J = 30.3 Hz, 3H). 4H under solvent peaks. |
| 38 | 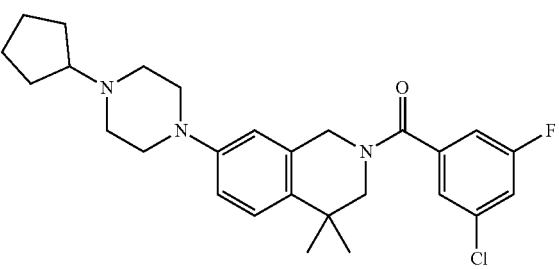 [SMILES: CC1(C)CN(C(=O)c2cc(F)cc(Cl)c2)Cc2cc(N3CCN(C4CCCC4)CC3)ccc21]<br>(3-chloro-5-fluorophenyl)(7-(4-cyclopentylpiperazin-1-yl)-4,4-dimethyl-3,4-dihydroisoquinolin-2(1H)-yl)methanone | $^1$H NMR (400 MHz, DMSO) δ 7.58 (d, J = 5.7 Hz, 1H), 7.36 (t, J = 1.6 Hz, 1H), 7.32 (d, J = 8.7 Hz, 1H), 7.20 (dd, J = 15.1, 8.6 Hz, 1H), 6.85 – 6.77 (m, 1H), 6.64 (d, J = 85.3 Hz, 1H), 4.75 (s, 1H), 4.48 (s, 1H), 3.62 (s, 1H), 3.30 (s, 1H), 3.05 (d, J = 26.8 Hz, 4H), 2.45 – 2.39 (m, 1H), 1.79 (br s, 2H), 1.61 (br s, 2H), 1.50 (br s, 2H), 1.42 – 1.28 (m, 2H), 1.23 (s, 3H), 1.07 (s, 3H). 4H under solvent peaks. |

TABLE 1-continued

| Compound No. | Structure and name | NMR data |
|---|---|---|
| 39 | 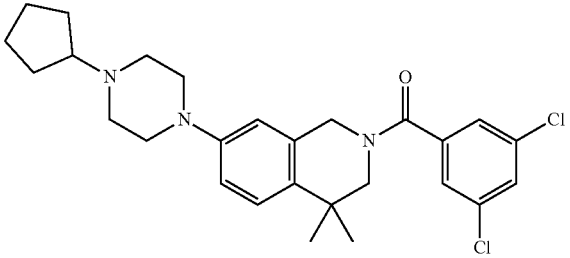 [SMILES: CC1(C)CN(C(=O)c2cc(Cl)cc(Cl)c2)Cc2cc(N3CCN(C4CCCC4)CC3)ccc21]<br>(7-(4-cyclopentylpiperazin-1-yl)-4,4-dimethyl-3,4-dihydroisoquinolin-2(1H)-yl)(3,5-dichlorophenyl)methanone | ¹H NMR (400 MHz, DMSO) δ 7.75 (s, 1H), 7.49 (d, J = 2.0 Hz, 2H), 7.20 (dd, J = 14.8, 8.5 Hz, 1H), 6.81 (s, 1H), 6.65 (d, J = 83.0 Hz, 1H), 4.75 (s, 1H), 4.48 (s, 1H), 3.62 (s, 1H), 3.29 (s, 1H), 3.05 (d, J = 26.2 Hz, 4H), 2.42 (s, 1H), 1.80 (br s, 2H), 1.61 (br s, 2H), 1.50 (br s, 2H), 1.34 (br s, 2H), 1.24 (s, 3H), 1.08 (s, 3H). 4H under solvent peaks. |
| 40 | 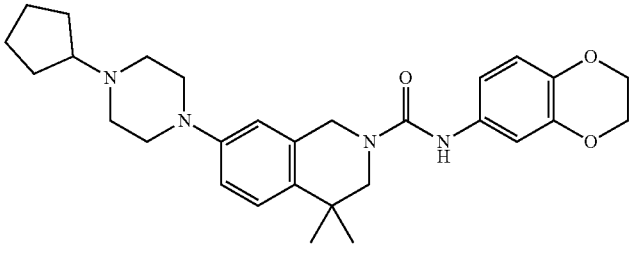 [SMILES: CC1(C)CN(C(=O)Nc2ccc3c(c2)OCCO3)Cc2cc(N3CCN(C4CCCC4)CC3)ccc21]<br>7-(4-cyclopentylpiperazin-1-yl)-N-(2,3-dihydrobenzo[b][1,4]dioxin-6-yl)-4,4-dimethyl-3,4-dihydroisoquinoline-2(1H)-carboxamide | ¹H NMR (400 MHz, DMSO) δ 8.29 (s, 1H), 7.20 (d, J = 8.7 Hz, 1H), 7.06 (d, J = 2.5 Hz, 1H), 6.89 (dd, J = 8.8, 2.5 Hz, 1H), 6.81 (dd, J = 8.7, 2.6 Hz, 1H), 6.71 (d, J = 8.8 Hz, 1H), 6.61 (d, J = 2.6 Hz, 1H), 4.60 (s, 2H), 4.23 – 4.14 (m, 4H), 3.44 (s, 2H), 3.07 (t, J = 5.0 Hz, 4H), 2.55 – 2.52 (m, 4H), 2.47 – 2.41 (m, 1H), 1.85 – 1.76 (m, 2H), 1.66 – 1.56 (m, 2H), 1.56 – 1.47 (m, 2H), 1.36 (q, J = 10.1, 9.1 Hz, 2H), 1.18 (s, 6H). 1H under solvent peaks. |
| 41 | 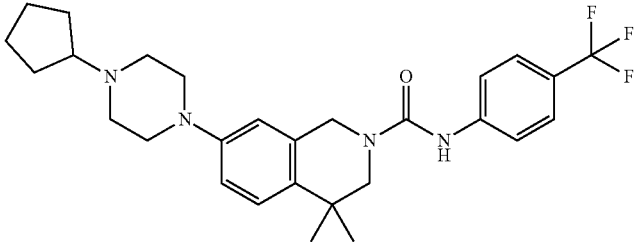 [SMILES: CC1(C)CN(C(=O)Nc2ccc(C(F)(F)F)cc2)Cc2cc(N3CCN(C4CCCC4)CC3)ccc21]<br>7-(4-cyclopentylpiperazin-1-yl)-4,4-dimethyl-N-(4-(trifluoromethyl)phenyl)-3,4-dihydroisoquinoline-2(1H)-carboxamide | ¹H NMR (400 MHz, DMSO) δ 8.89 (s, 1H), 7.72 (d, J = 8.7 Hz, 2H), 7.59 (d, J = 8.7 Hz, 2H), 7.22 (d, J = 8.7 Hz, 1H), 6.82 (dd, J = 8.7, 2.7 Hz, 1H), 6.64 (d, J = 2.5 Hz, 1H), 4.67 (s, 2H), 3.50 (s, 2H), 3.08 (t, J = 5.0 Hz, 4H), 2.56 – 2.52 (m, 4H), 2.47 – 2.44 (m, 1H), 1.86 – 1.77 (m, 2H), 1.67 – 1.57 (m, 2H), 1.54 – 1.45 (m, 2H), 1.41 – 1.30 (m, 2H), 1.20 (s, 6H). |

TABLE 1-continued

| Compound No. | Structure and name | NMR data |
|---|---|---|
| 42 | 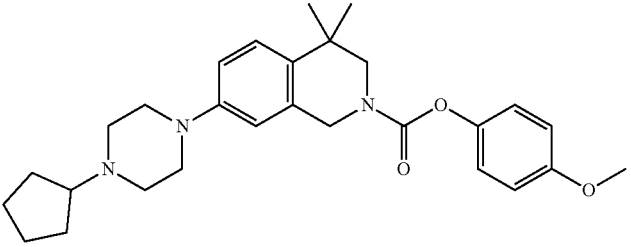 [SMILES: COc1ccc(OC(=O)N2Cc3cc(N4CCN(C5CCCC5)CC4)ccc3C(C)(C)C2)cc1]<br>4-methoxyphenyl 7-(4-cyclopentylpiperazin-1-yl)-4,4-dimethyl-3,4-dihydroisoquinoline-2(1H)-carboxylate | $^1$H NMR (400 MHz, DMSO) δ 7.24 (d, J = 8.6 Hz, 1H), 7.06 (d, J = 8.7 Hz, 1H), 7.02 (d, J = 8.9 Hz, 1H), 6.96 – 6.88 (m, 2H), 6.83 (dd, J = 8.9, 2.7 Hz, 1H), 6.70 (br s, 1H), 4.76 (s, 1H), 4.58 (s, 1H), 3.74 (s, 3H), 3.57 (s, 1H), 3.41 (s, 1H), 3.08 (t, J = 5.0 Hz, 4H), 2.56 – 2.51 (m, 4H), 2.47 – 2.41 (m, 1H), 1.80 (td, J = 10.8, 6.1 Hz, 2H), 1.68 – 1.56 (m, 2H), 1.56 – 1.43 (m, 2H), 1.42 – 1.29 (m, 2H), 1.23 (d, J = 16.9 Hz, 6H). |
| 43 | 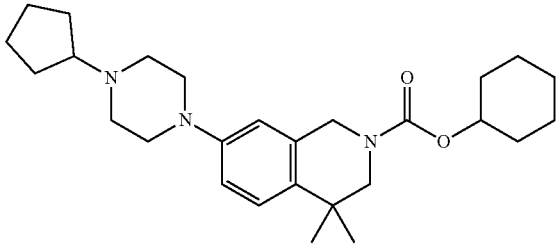 [SMILES: CC1(C)CN(C(=O)OC2CCCCC2)Cc2cc(N3CCN(C4CCCC4)CC3)ccc21]<br>cyclohexyl 7-(4-cyclopentylpiperazin-1-yl)-4,4-dimethyl-3,4-dihydroisoquinoline-2(1H)-carboxylate | $^1$H NMR (400 MHz, DMSO) δ 7.19 (d, J = 8.7 Hz, 1H), 6.79 (dd, J = 8.7, 2.6 Hz, 1H), 6.65 (d, J = 2.5 Hz, 1H), 4.65 – 4.57 (m, 1H), 4.52 (d, J = 13.7 Hz, 2H), 3.37 (br s, 1H), 3.06 (t, J = 4.9 Hz, 4H), 2.54 – 2.52 (m, 1H), 2.46 – 2.41 (m, 1H), 1.80 (q, J = 9.9, 9.3 Hz, 4H), 1.72 – 1.57 (m, 4H), 1.57 – 1.26 (m, 10H), 1.15 (s, 6H). 1 + 3H under solvent peaks. |
| 44 | 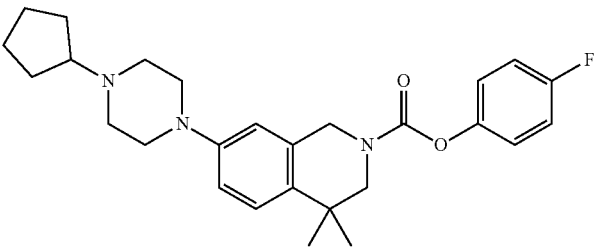 [SMILES: CC1(C)CN(C(=O)Oc2ccc(F)cc2)Cc2cc(N3CCN(C4CCCC4)CC3)ccc21]<br>4-fluorophenyl 7-(4-cyclopentylpiperazin-1-yl)-4,4-dimethyl-3,4-dihydroisoquinoline-2(1H)-carboxylate | $^1$H NMR (400 MHz, DMSO) δ 7.27 – 7.12 (m, 5H), 6.83 (d, J = 8.3 Hz, 1H), 6.70 (d, J = 2.6 Hz, 1H), 4.77 (s, 1H), 4.59 (s, 1H), 3.58 (s, 1H), 3.42 (s, 1H), 3.08 (t, J = 5.0 Hz, 4H), 2.47 – 2.41 (m, 1H), 1.86 – 1.74 (m, 2H), 1.69 – 1.56 (m, 2H), 1.55 – 1.44 (m, 2H), 1.40 – 1.29 (m, 2H), 1.23 (d, J = 16.1 Hz, 6H). 4H under solvent peaks. |
| 45 | 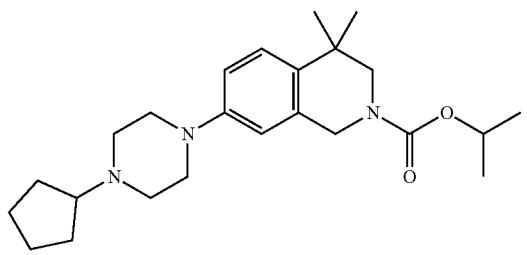 [SMILES: CC(C)OC(=O)N1Cc2cc(N3CCN(C4CCCC4)CC3)ccc2C(C)(C)C1]<br>isopropyl 7-(4-cyclopentylpiperazin-1-yl)-4,4-dimethyl-3,4-dihydroisoquinoline-2(1H)-carboxylate | $^1$H NMR (400 MHz, DMSO) δ 7.19 (d, J = 8.8 Hz, 1H), 6.79 (dd, J = 8.7, 2.6 Hz, 1H), 6.64 (d, J = 2.6 Hz, 1H), 4.82 (p, J = 6.2 Hz, 1H), 4.51 (s, 2H), 3.06 (t, J = 4.9 Hz, 4H), 2.47 – 2.39 (m, 1H), 1.86 – 1.74 (m, 2H), 1.68 – 1.57 (m, 2H), 1.57 – 1.43 (m, 2H), 1.42 – 1.27 (m, 2H), 1.20 (d, J = 6.2 Hz, 6H), 1.15 (s, 6H). 2 + 4H under solvent peaks. |

TABLE 1-continued

| Compound No. | Structure and name | NMR data |
|---|---|---|
| 46 | 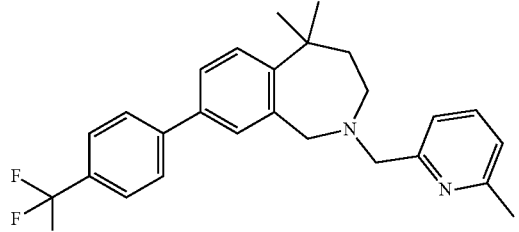<br>5,5-dimethyl-2-((6-methylpyridin-2-yl)methyl)-8-(4-(trifluoromethyl)phenyl)-2,3,4,5-tetrahydro-1H-benzo[c]azepine | 1H NMR (400 MHz, DMSO) δ 7.84 (d, J = 8.4 Hz, 2H), 7.79 (d, J = 8.4 Hz, 2H), 7.62 (t, J = 7.7 Hz, 1H), 7.58 (dd, J = 8.1, 2.2 Hz, 1H), 7.50 (d, J = 8.2 Hz, 1H), 7.31 (d, J = 2.2 Hz, 1H), 7.19 (d, J = 7.7 Hz, 1H), 7.09 (d, J = 7.5 Hz, 1H), 4.02 (s, 2H), 3.65 (s, 2H), 2.95 (t, J = 5.6 Hz, 2H), 2.40 (s, 3H), 1.83 – 1.72 (m, 2H), 1.39 (s, 6H). |
| 47 | 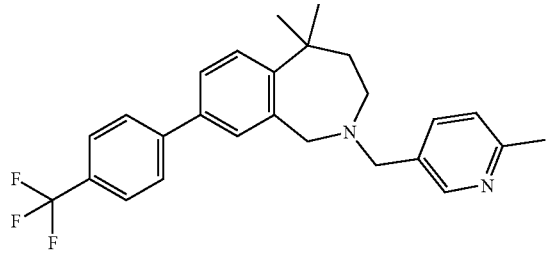 [SMILES: Cc1ccc(CN2CCC(C)(C)c3ccc(-c4ccc(C(F)(F)F)cc4)cc3C2)cn1]<br>5,5-dimethyl-2-((6-methylpyridin-3-yl)methyl)-8-(4-(trifluoromethyl)phenyl)-2,3,4,5-tetrahydro-1H-benzo[c]azepine | 1H NMR (400 MHz, DMSO) δ 8.29 (d, J = 2.2 Hz, 1H), 7.85 (d, J = 8.3 Hz, 2H), 7.80 (d, J = 8.4 Hz, 2H), 7.57 (td, J = 8.4, 2.2 Hz, 2H), 7.50 (d, J = 8.2 Hz, 1H), 7.31 (d, J = 2.3 Hz, 1H), 7.19 (d, J = 7.9 Hz, 1H), 4.00 (s, 2H), 3.55 (s, 2H), 2.90 (t, J = 5.6 Hz, 2H), 2.43 (s, 3H), 1.76 (t, J = 5.7 Hz, 2H), 1.38 (s, 6H). |
| 48 | 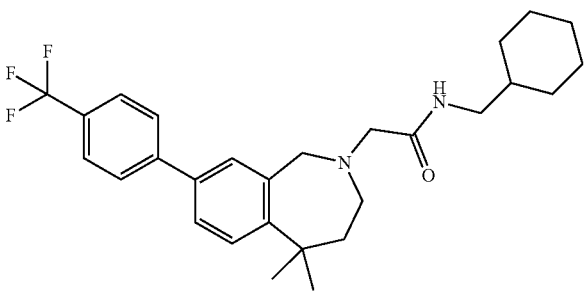 [SMILES: CC1(C)CCN(CC(=O)NCC2CCCCC2)Cc2cc(-c3ccc(C(F)(F)F)cc3)ccc21]<br>N-(cyclohexylmethyl)-2-(5,5-dimethyl-8-(4-(trifluoromethyl)phenyl)-1,3,4,5-tetrahydro-2H-benzo[c]azepin-2-yl)acetamide | $^{1}$H NMR (400 MHz, DMSO) δ 7.86 (d, J = 8.2 Hz, 2H), 7.80 (d, J = 8.3 Hz, 2H), 7.58 (dd, J = 8.1, 2.1 Hz, 1H), 7.53 (t, J = 6.0 Hz, 1H), 7.50 (d, J = 8.3 Hz, 1H), 7.40 (d, J = 2.1 Hz, 1H), 4.00 (s, 2H), 3.03 – 2.95 (m, 4H), 2.89 (t, J = 6.4 Hz, 2H), 1.76 (t, J = 5.4 Hz, 2H), 1.52 (d, J = 12.5 Hz, 5H), 1.38 (s, 6H), 1.34 – 1.21 (m, 1H), 1.09 – 0.94 (m, 3H), 0.83 – 0.70 (m, 2H). |
| 49 | 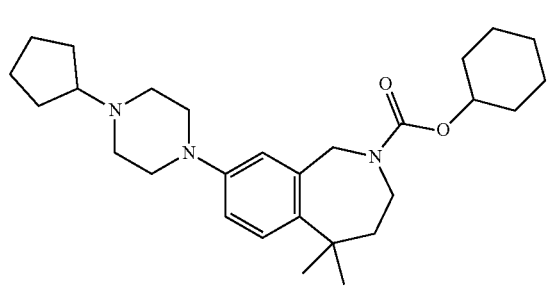 [SMILES: CC1(C)CCN(C(=O)OC2CCCCC2)Cc2cc(N3CCN(C4CCCC4)CC3)ccc21]<br>cyclohexyl 8-(4-cyclopentylpiperazin-1-yl)-5,5-dimethyl-1,3,4,5-tetrahydro-2H-benzo[c]azepine-2-carboxylate | $^{1}$H NMR (400 MHz, DMSO) δ 7.20 (dd, J = 8.6, 4.3 Hz, 1H), 6.74 (dt, J = 8.1, 3.9 Hz, 1H), 6.65 (d, J = 2.8 Hz, 1H), 4.53 – 4.42 (m, 3H), 3.64 – 3.54 (m, 2H), 3.07 (t, J = 5.0 Hz, 4H), 2.54 – 2.52 (m, 2H), 2.46 – 2.41 (m, 1H), 1.86 – 1.74 (m, 4H), 1.73 – 1.55 (m, 4H), 1.55 – 1.43 (m, 4H), 1.41 – 1.25 (m, 8H), 1.24 (s, 6H). 2H under solvent peaks. |

TABLE 1-continued

| Compound No. | Structure and name | NMR data |
|---|---|---|
| 50 | 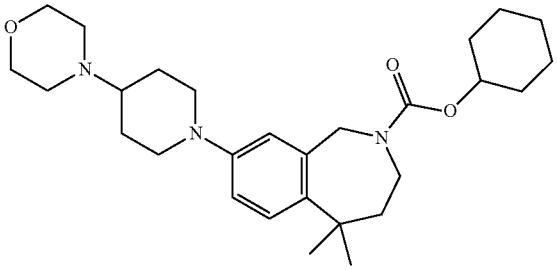 [SMILES: CC1(C)CCN(C(=O)OC2CCCCC2)Cc2cc(N3CCC(N4CCOCC4)CC3)ccc21]<br>cyclohexyl 5,5-dimethyl-8-(4-morpholinopiperidin-1-yl)-1,3,4,5-tetrahydro-2H-benzo[c]azepine-2-carboxylate | $^1$H NMR (400 MHz, DMSO) δ 7.19 (dd, J = 8.8, 3.8 Hz, 1H), 6.75 (dt, J = 9.0, 3.3 Hz, 1H), 6.66 (d, J = 2.8 Hz, 1H), 4.52 – 4.41 (m, 3H), 3.67 (d, J = 12.9 Hz, 2H), 3.62 – 3.53 (m, 6H), 2.66 – 2.56 (m, 2H), 2.48 – 2.43 (m, 4H), 2.29 – 2.18 (m, 1H), 1.80 (dd, J = 22.6, 7.4 Hz, 4H), 1.71 – 1.26 (m, 12H), 1.24 (s, 6H). |
| 51 | 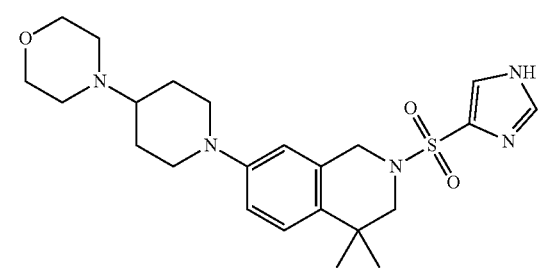 [SMILES: CC1(C)CN(S(=O)(=O)c2c[nH]cn2)Cc2cc(N3CCC(N4CCOCC4)CC3)ccc21]<br>4-(1-(2-((1H-imidazol-4-yl)sulfonyl)-4,4-dimethyl-1,2,3,4-tetrahydroisoquinolin-7-yl)piperidin-4-yl)morpholine | $^1$H NMR (400 MHz, DMSO) δ 12.88 (br s, 1H), 7.84 (d, J = 16.4 Hz, 2H), 7.18 (d, J = 8.7 Hz, 1H), 6.80 (dd, J = 8.7, 2.6 Hz, 1H), 6.64 (d, J = 2.6 Hz, 1H), 4.14 (s, 2H), 3.70 – 3.61 (m, 2H), 3.56 (t, J = 4.6 Hz, 4H), 2.96 (s, 2H), 2.59 (td, J = 12.3, 2.4 Hz, 2H), 2.48 – 2.43 (m, 4H), 2.23 (tt, J = 11.2, 3.8 Hz, 1H), 1.82 (d, J = 11.6 Hz, 2H), 1.43 (qd, J = 12.0, 3.9 Hz, 2H), 1.20 (s, 6H). |
| 52 | 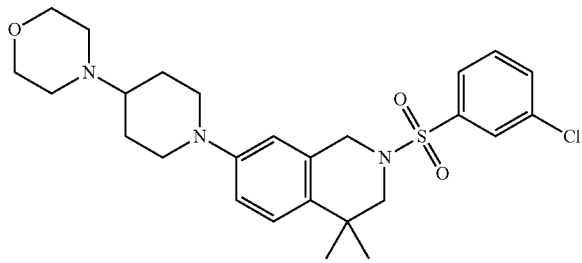 [SMILES: CC1(C)CN(S(=O)(=O)c2cccc(Cl)c2)Cc2cc(N3CCC(N4CCOCC4)CC3)ccc21]<br>4-(1-(2-((3-chlorophenyl)sulfonyl)-4,4-dimethyl-1,2,3,4-tetrahydroisoquinolin-7-yl)piperidin-4-yl)morpholine | $^1$H NMR (400 MHz, DMSO) δ 7.86 – 7.77 (m, 3H), 7.71 (t, J = 7.8 Hz, 1H), 7.18 6.81 (dd, J = 8.7, 2.6 Hz, 1H), 6.66 (d, J = 2.7 Hz, 1H), 4.10 (s, 2H), 3.65 (d, J = 12.3 Hz, 2H), 3.56 (t, J = 4.6 Hz, 4H), 2.99 (s, 2H), 2.59 (t, J = 11.9 Hz, 2H), 2.47 – 2.42 (m, 4H), 2.28 – 2.18 (m, 1H), 1.82 (d, J = 12.2 Hz, 2H), 1.42 (qd, J = 12.0, 11.6, 3.8 Hz, 2H), 1.21 (s, 6H). |
| 53 | 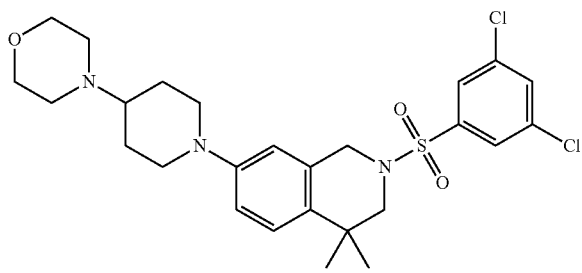 [SMILES: CC1(C)CN(S(=O)(=O)c2cc(Cl)cc(Cl)c2)Cc2cc(N3CCC(N4CCOCC4)CC3)ccc21]<br>4-(1-(2-((3,5-dichlorophenyl)sulfonyl)-4,4-dimethyl-1,2,3,4-tetrahydroisoquinolin-7-yl)piperidin-4-yl)morpholine | $^1$H NMR (400 MHz, DMSO) δ 8.05 (t, J = 1.9 Hz, 1H), 7.84 (d, J = 1.8 Hz, 2H), 7.18 (d, J = 8.7 Hz, 1H), 6.82 (dd, J = 8.7, 2.6 Hz, 1H), 6.67 (d, J = 2.7 Hz, 1H), 4.16 (s, 2H), 3.66 (d, J = 12.4 Hz, 2H), 3.56 (t, J = 4.6 Hz, 4H), 3.05 (s, 2H), 2.60 (t, J = 11.7 Hz, 2H), 2.46 (t, J = 4.6 Hz, 4H), 2.24 (qt, J = 7.2, 3.4 Hz, 1H), 1.82 (d, J = 12.3 Hz, 2H), 1.43 (qd, J = 12.3, 2.8 Hz, 2H), 1.21 (s, 6H). |

TABLE 1-continued

| Compound No. | Structure and name | NMR data |
|---|---|---|
| 54 | 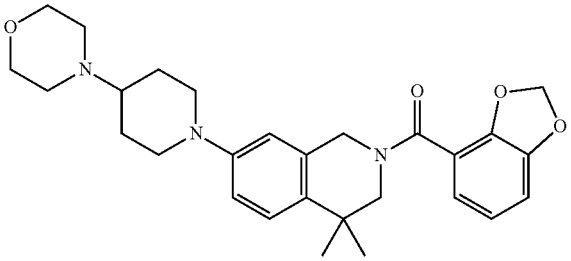 [SMILES: CC1(C)CN(C(=O)c2cccc3c2OCO3)Cc2cc(N3CCC(N4CCOCC4)CC3)ccc21]<br>benzo[d][1,3]dioxol-4-yl(4,4-dimethyl-7-(4-morpholinopiperidin-1-yl)-3,4-dihydroisoquinolin-2(1H)-yl)methanone | 1H NMR (400 MHz, DMSO) δ 7.18 (dd, J = 12.1, 8.6 Hz, 1H), 7.01 (dd, J = 7.9, 3.9 Hz, 1H), 6.91 (t, J = 7.8 Hz, 1H), 6.86 – 6.77 (m, 2H), 6.67 (dd, J = 63.9, 2.4 Hz, 1H), 6.06 (d, J = 3.0 Hz, 2H), 4.76 (s, 1H), 4.50 (s, 1H), 3.74 – 3.50 (m, 7H), 2.66 – 2.53 (m, 2H), 2.47 – 2.41 (m, 3H), 2.29 – 2.14 (m, 1H), 1.82 (t, J = 15.9 Hz, 2H), 1.43 (tt, J = 21.2, 11.7 Hz, 2H), 1.22 (s, 3H), 1.05 (s, 3H). 2H under solvent peaks. |
| 55 | 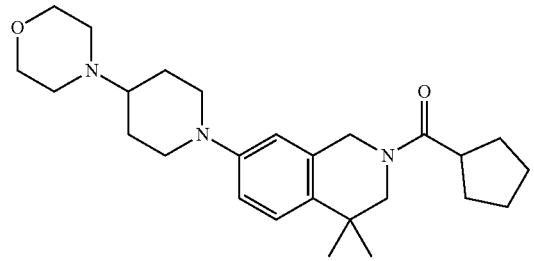 [SMILES: CC1(C)CN(C(=O)C2CCCC2)Cc2cc(N3CCC(N4CCOCC4)CC3)ccc21]<br>cyclopentyl(4,4-dimethyl-7-(4-morpholinopiperidin-1-yl)-3,4-dihydroisoquinolin-2(1H)-yl)methanone | $^1$H NMR (400 MHz, DMSO) δ 7.17 (dd, J = 8.7, 2.2 Hz, 1H), 6.83 – 6.77 (m, 1H), 6.68 (dd, J = 12.5, 2.5 Hz, 1H), 4.67 (s, 1H), 4.56 (s, 1H), 3.66 (dd, J = 12.7, 3.8 Hz, 2H), 3.57 (t, J = 4.6 Hz, 4H), 3.47 (d, J = 9.0 Hz, 2H), 3.08 (p, J = 7.6 Hz, 1H), 2.65 – 2.54 (m, 2H), 2.48 – 2.44 (m, 4H), 2.29 – 2.18 (m, 1H), 1.90 – 1.73 (m, 4H), 1.72 – 1.37 (m, 8H), 1.19 (s, 3H), 1.12 (s, 3H). |
| 56 | 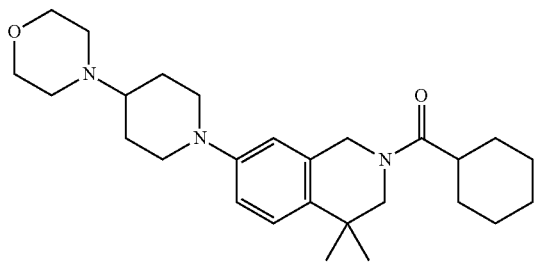 [SMILES: CC1(C)CN(C(=O)C2CCCCC2)Cc2cc(N3CCC(N4CCOCC4)CC3)ccc21]<br>cyclohexyl(4,4-dimethyl-7-(4-morpholinopiperidin-1-yl)-3,4-dihydroisoquinolin-2(1H)-yl)methanone | $^1$H NMR (400 MHz, DMSO) δ 7.17 (d, J = 8.6 Hz, 1H), 6.84 – 6.76 (m, 1H), 6.68 (dd, J = 22.8, 2.6 Hz, 1H), 4.66 (s, 1H), 4.54 (s, 1H), 3.66 (d, J = 12.2 Hz, 2H), 3.60 – 3.52 (m, 4H), 3.45 (d, J = 10.4 Hz, 2H), 2.76 – 2.55 (m, 3H), 2.48 – 2.44 (m, 4H), 2.29 – 2.18 (m, 1H), 1.84 (br s, 2H), 1.67 (dd, J = 25.4, 9.5 Hz, 5H), 1.49 – 1.27 (m, 6H), 1.19 (s, 3H), 1.18 – 1.12 (m, 1H), 1.11 (s, 3H). |

TABLE 1-continued

| Compound No. | Structure and name | NMR data |
|---|---|---|
| 57 | 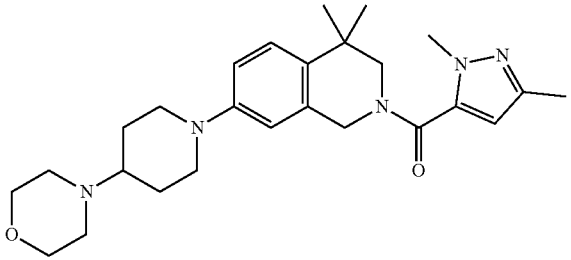 [SMILES: Cc1cc(C(=O)N2Cc3cc(N4CCC(N5CCOCC5)CC4)ccc3C(C)(C)C2)n(C)n1]<br>(1,3-dimethyl-1H-pyrazol-5-yl)(4,4-dimethyl-7-(4-morpholinopiperidin-1-yl)-3,4-dihydroisoquinolin-2(1H)-yl)methanone | $^1$H NMR (400 MHz, DMSO) δ 7.19 (br s, 1H), 6.82 (dd, J = 8.6, 2.2 Hz, 1H), 6.67 (d, J = 65.2 Hz, 1H), 6.26 (d, J = 20.0 Hz, 1H), 4.71 (d, J = 31.4 Hz, 2H), 3.73 (s, 3H), 3.69 – 3.46 (m, 8H), 2.65 – 2.56 (m, 2H), 2.48 – 2.43 (m, 4H), 2.23 (br s, 1H), 2.18 (s, 3H), 1.83 (br s, 2H), 1.51 – 1.34 (m, 2H), 1.22 (s, 3H), 1.10 (s, 3H). |
| 58 | 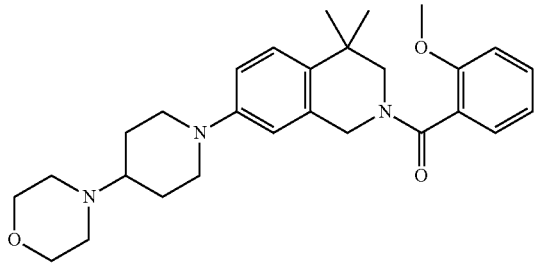 [SMILES: COc1ccccc1C(=O)N1Cc2cc(N3CCC(N4CCOCC4)CC3)ccc2C(C)(C)C1]<br>(4,4-dimethyl-7-(4-morpholinopiperidin-1-yl)-3,4-dihydroisoquinolin-2(1H)-yl)(2-methoxyphenyl)methanone | $^1$H NMR (400 MHz, DMSO) δ 7.38 (d, J = 4.8 Hz, 3H), 7.35 – 7.29 (m, 1H), 7.18 (d, J = 8.7 Hz, 1H), 6.80 (dd, J = 8.6, 2.7 Hz, 1H), 6.67 (d, J = 2.9 Hz, 1H), 5.13 (s, 2H), 4.56 (d, J = 23.5 Hz, 2H), 3.66 (d, J = 12.3 Hz, 2H), 3.56 (t, J = 4.6 Hz, 4H), 3.44 – 3.39 (m, 3H), 2.59 (t, J = 12.0 Hz, 2H), 2.48 – 2.43 (m, 4H), 2.22 (d, J = 11.3 Hz, 1H), 1.83 (d, J = 12.2 Hz, 2H), 1.44 (q, J = 11.8 Hz, 2H), 1.15 (br s, 6H). |
| 59 | 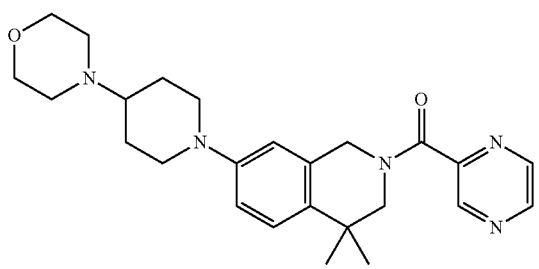 [SMILES: CC1(C)CN(C(=O)c2cnccn2)Cc2cc(N3CCC(N4CCOCC4)CC3)ccc21]<br>(4,4-dimethyl-7-(4-morpholinopiperidin-1-yl)-3,4-dihydroisoquinolin-2(1H)-yl)(pyrazin-2-yl)methanone | $^1$H NMR (400 MHz, DMSO) δ 8.86 (d, J = 1.5 Hz, 1H), 8.77 (t, J = 2.7 Hz, 1H), 8.71 (t, J = 2.2 Hz, 1H), 7.20 (dd, J = 17.8, 8.7 Hz, 1H), 6.82 (ddd, J = 9.0, 7.0, 2.6 Hz, 1H), 6.64 (dd, J = 111.6, 2.6 Hz, 1H), 4.81 (s, 1H), 4.59 (s, 1H), 3.73 – 3.66 (m, 2H), 3.64 – 3.53 (m, 5H), 3.44 (s, 1H), 2.66 – 2.54 (m, 2H), 2.48 – 2.41 (m, 4H), 2.22 (dddd, J = 20.6, 10.9, 8.3, 4.6 Hz, 1H), 1.83 (dd, J = 22.1, 12.3 Hz, 2H), 1.52 – 1.33 (m, 2H), 1.25 (s, 3H), 1.07 (s, 3H). |

TABLE 1-continued

| Compound No. | Structure and name | NMR data |
|---|---|---|
| 60 | 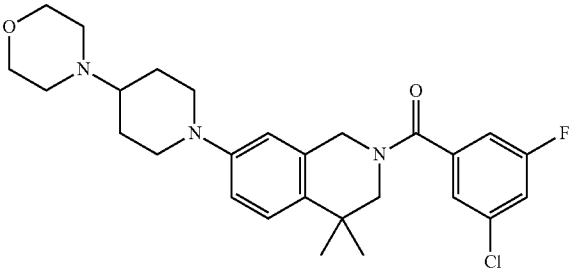 [SMILES: CC1(C)CN(C(=O)c2cc(F)cc(Cl)c2)Cc2cc(N3CCC(N4CCOCC4)CC3)ccc21]<br>(3-chloro-5-fluorophenyl)(4,4-dimethyl-7-(4-morpholinopiperidin-1-yl)-3,4-dihydroisoquinolin-2(1H)-yl)methanone | ¹H NMR (400 MHz, DMSO) δ 7.57 (d, J = 8.7 Hz, 1H), 7.36 (d, J = 1.6 Hz, 1H), 7.32 (dt, J = 9.0, 2.1 Hz, 1H), 7.19 (dd, J = 14.9, 8.6 Hz, 1H), 6.86 – 6.78 (m, 1H), 6.66 (d, J = 84.9 Hz, 1H), 4.74 (s, 1H), 4.48 (s, 1H), 3.77 – 3.49 (m, 8H), 2.66 – 2.53 (m, 2H), 2.48 – 2.40 (m, 4H), 2.30 – 2.16 (m, 1H), 1.82 (dd, J = 21.8, 12.6 Hz, 2H), 1.53 – 1.32 (m, 2H), 1.23 (s, 3H), 1.07 (s, 3H). |
| 61 | 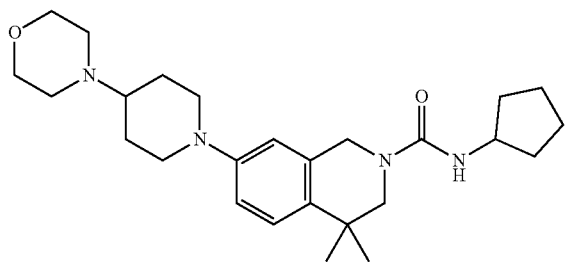<br>N-cyclopentyl-4,4-dimethyl-7-(4-morpholinopiperidin-1-yl)-3,4-dihydroisoquinoline-2(1H)-carboxamide | ¹H NMR (400 MHz, DMSO) δ 7.16 (d, J = 8.7 Hz, 1H), 6.79 (dd, J = 8.7, 2.6 Hz, 1H), 6.58 (d, J = 2.6 Hz, 1H), 6.15 (d, J = 7.0 Hz, 1H), 4.45 (s, 2H), 3.95 (h, J = 6.9 Hz, 1H), 3.64 (d, J = 12.4 Hz, 2H), 3.56 (t, J = 4.6 Hz, 4H), 3.30 – 3.29 (m, 2H), 2.60 (td, J = 12.3, 2.4 Hz, 2H), 2.48 – 2.45 (m, 4H), 2.28 – 2.19 (m, 1H), 1.88 – 1.73 (m, 4H), 1.69 – 1.59 (m, 2H), 1.53 – 1.35 (m, 6H), 1.14 (s, 6H). |
| 62 | 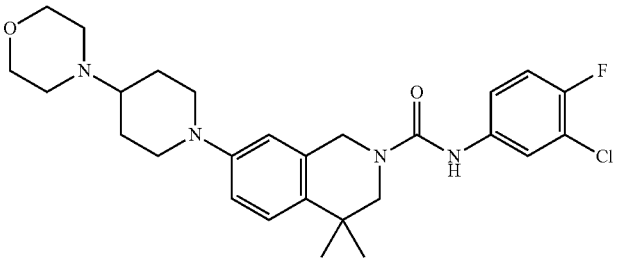 [SMILES: CC1(C)CN(C(=O)Nc2ccc(F)c(Cl)c2)Cc2cc(N3CCC(N4CCOCC4)CC3)ccc21]<br>N-(3-chloro-4-fluorophenyl)-4,4-dimethyl-7-(4-morpholinopiperidin-1-yl)-3,4-dihydroisoquinoline-2(1H)-carboxamide | ¹H NMR (400 MHz, DMSO) δ 8.68 (s, 1H), 7.77 (dd, J = 6.8, 2.7 Hz, 1H), 7.45 (ddd, J = 9.1, 4.4, 2.6 Hz, 1H), 7.30 (t, J = 9.1 Hz, 1H), 7.20 (d, J = 8.6 Hz, 1H), 6.83 (dd, J = 8.7, 2.7 Hz, 1H), 6.64 (d, J = 2.7 Hz, 1H), 4.63 (s, 2H), 3.67 (d, J = 12.3 Hz, 2H), 3.57 (t, J = 4.6 Hz, 4H), 3.47 (s, 2H), 2.62 (td, J = 12.5, 2.1 Hz, 2H), 2.48 – 2.45 (m, 4H), 2.29 – 2.20 (m, 1H), 1.85 (d, J = 12.3 Hz, 2H), 1.46 (qd, J = 12.1, 3.8 Hz, 2H), 1.19 (s, 6H). |

TABLE 1-continued

| Compound No. | Structure and name | NMR data |
|---|---|---|
| 63 | 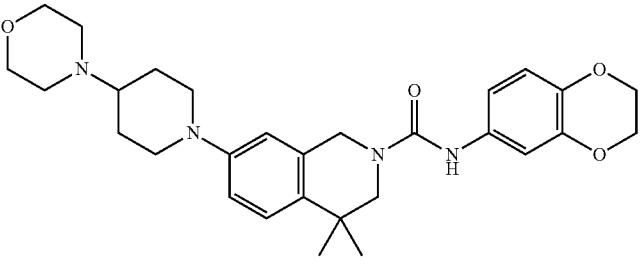 [SMILES: CC1(C)CN(C(=O)Nc2ccc3c(c2)OCCO3)Cc2cc(N3CCC(N4CCOCC4)CC3)ccc21]<br>N-(2,3-dihydrobenzo[b][1,4]dioxin-6-yl)-4,4-dimethyl-7-(4-morpholinopiperidin-1-yl)-3,4-dihydroisoquinoline-2(1H)-carboxamide | $^1$H NMR (400 MHz, DMSO) δ 8.28 (s, 1H), 7.19 (d, J = 8.6 Hz, 1H), 7.06 (d, J = 2.5 Hz, 1H), 6.89 (dd, J = 8.7, 2.5 Hz, 1H), 6.82 (dd, J = 8.6, 2.7 Hz, 1H), 6.71 (d, J = 8.8 Hz, 1H), 6.63 (d, J = 2.6 Hz, 1H), 4.60 (s, 2H), 4.19 (dt, J = 10.4, 3.1 Hz, 4H), 3.66 (d, J = 12.2 Hz, 2H), 3.57 (t, J = 4.5 Hz, 4H), 2.70 – 2.58 (m, 8H), 2.25 (t, J = 11.3 Hz, 1H), 1.85 (d, J = 12.3 Hz, 2H), 1.51 – 1.40 (m, 2H), 1.18 (s, 6H). |
| 64 | 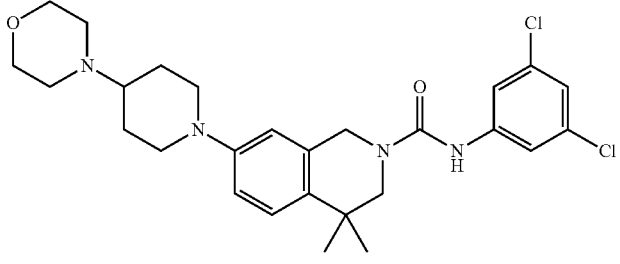 [SMILES: CC1(C)CN(C(=O)Nc2cc(Cl)cc(Cl)c2)Cc2cc(N3CCC(N4CCOCC4)CC3)ccc21]<br>N-(3,5-dichlorophenyl)-4,4-dimethyl-7-(4-morpholinopiperidin-1-yl)-3,4-dihydroisoquinoline-2(1H)-carboxamide | $^1$H NMR (400 MHz, DMSO) δ 8.84 (s, 1H), 7.64 (d, J = 2.0 Hz, 2H), 7.20 (d, J = 8.7 Hz, 1H), 7.13 (t, J = 1.9 Hz, 1H), 6.83 (dd, J = 8.7, 2.7 Hz, 1H), 6.64 (d, J = 2.5 Hz, 2H), 4.63 (s, 2H), 3.67 (d, J = 12.4 Hz, 2H), 3.57 (t, J = 4.6 Hz, 4H), 3.47 (s, 2H), 2.62 (t, J = 11.9 Hz, 2H), 2.47 – 2.45 (m, 4H), 2.29 – 2.19 (m, 1H), 1.85 (d, J = 12.4 Hz, 2H), 1.46 (qd, J = 12.4, 3.5 Hz, 2H), 1.19 (s, 6H). |
| 65 | 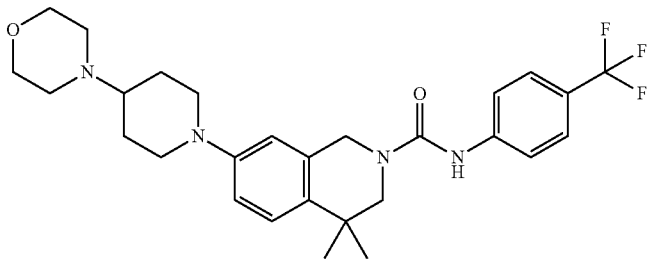 [SMILES: CC1(C)CN(C(=O)Nc2ccc(C(F)(F)F)cc2)Cc2cc(N3CCC(N4CCOCC4)CC3)ccc21]<br>4,4-dimethyl-7-(4-morpholinopiperidin-1-yl)-N-(4-(trifluoromethyl)phenyl)-3,4-dihydroisoquinoline-2(1H)-carboxamide | $^1$H NMR (400 MHz, DMSO) δ 8.88 (s, 1H), 7.72 (d, J = 8.5 Hz, 2H), 7.59 (d, J = 8.6 Hz, 2H), 7.21 (d, J = 8.7 Hz, 1H), 6.83 (dd, J = 8.7, 2.6 Hz, 1H), 6.65 (d, J = 2.8 Hz, 1H), 4.66 (s, 2H), 3.67 (d, J = 12.3 Hz, 2H), 3.57 (t, J = 4.6 Hz, 4H), 3.50 (s, 2H), 2.63 (td, J = 12.4, 2.2 Hz, 2H), 2.47 (t, J = 4.6 Hz, 4H), 2.25 (tt, J = 11.5, 4.0 Hz, 1H), 1.85 (d, J = 11.6 Hz, 2H), 1.46 (qd, J = 12.1, 3.8 Hz, 2H), 1.20 (s, 6H). |

TABLE 1-continued

| Compound No. | Structure and name | NMR data |
|---|---|---|
| 66 | 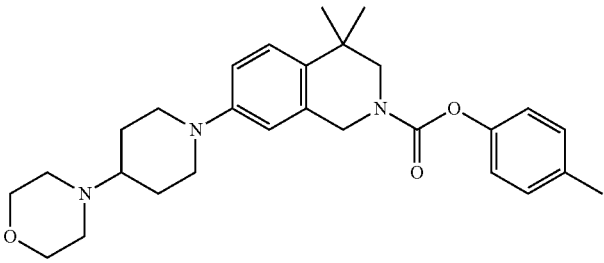 [SMILES: Cc1ccc(OC(=O)N2Cc3cc(N4CCC(N5CCOCC5)CC4)ccc3C(C)(C)C2)cc1]<br>p-tolyl 4,4-dimethyl-7-(4-morpholinopiperidin-1-yl)-3,4-dihydroisoquinoline-2(1H)-carboxylate | $^1$H NMR (400 MHz, DMSO) δ 7.22 (d, J = 8.6 Hz, 1H), 7.18 (d, J = 8.0 Hz, 2H), 7.00 (dd, J = 13.7, 8.1 Hz, 2H), 6.83 (dd, J = 8.7, 2.4 Hz, 1H), 6.71 (s, 1H), 4.76 (s, 1H), 4.58 (s, 1H), 3.68 (d, J = 12.3 Hz, 2H), 3.62 – 3.53 (m, 5H), 3.43 – 3.40 (m, 1H), 2.61 (td, J = 11.9, 2.2 Hz, 2H), 2.48 – 2.45 (m, 4H), 2.29 (s, 3H), 2.29 – 2.19 (m, 1H), 1.84 (d, J = 12.3 Hz, 2H), 1.45 (qd, J = 11.4, 2.8 Hz, 2H), 1.23 (d, J = 15.9 Hz, 6H). |
| 67 | 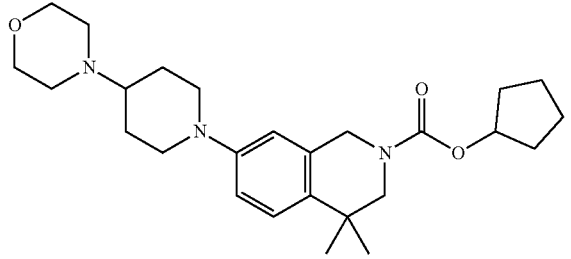 [SMILES: CC1(C)CN(C(=O)OC2CCCC2)Cc2cc(N3CCC(N4CCOCC4)CC3)ccc21]<br>cyclopentyl 4,4-dimethyl-7-(4-morpholinopiperidin-1-yl)-3,4-dihydroisoquinoline-2(1H)-carboxylate | $^1$H NMR (400 MHz, DMSO) δ 7.17 (d, J = 8.5 Hz, 1H), 6.80 = (dd, J = 8.7, 2.6 Hz, 1H), 6.65 (d, J = 2.6 Hz, 1H), 5.03 (tt, J = 5.6, 2.4 Hz, 1H), 4.49 (s, 2H), 3.66 (d, J = 12.3 Hz, 2H), 3.56 (t, J = 4.6 Hz, 4H), 3.32 – 3.31 (m, 2H), 2.60 (td, J = 12.2, 2.4 Hz, 2H), 2.46 (t, J = 4.7 Hz, 4H), 2.28 – 2.19 (m, 1H), 1.87 – 1.73 (m, 4H), 1.69 – 1.50 (m, 6H), 1.44 (qd, J = 12.0, 3.8 Hz, 2H), 1.14 (s, 6H). |
| 68 | 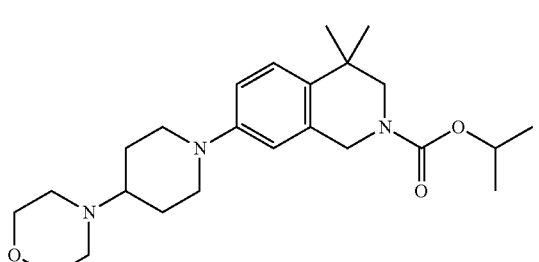<br>isopropyl 4,4-dimethyl-7-(4-morpholinopiperidin-1-yl)-3,4-dihydroisoquinoline-2(1H)-carboxylate | $^1$H NMR (400 MHz, DMSO) δ 7.18 (d, J = 8.8 Hz, 1H), 6.80 (dd, J = 8.8, 2.7 Hz, 1H), 6.66 (d, J = 2.6 Hz, 1H), 4.82 (p, J = 6.2 Hz, 1H), 4.51 (br s, 2H), 3.71 – 3.63 (m, 2H), 3.56 (t, J = 4.6 Hz, 4H), 3.32 – 3.30 (m, 2H), 2.60 (td, J = 12.2, 2.4 Hz, 2H), 2.46 (t, J = 4.7 Hz, 4H), 2.24 (tt, J = 11.0, 3.6 Hz, 1H), 1.83 (d, J = 11.3 Hz, 2H), 1.44 (qd, J = 12.1, 3.9 Hz, 2H), 1.20 (d, J = 6.1 Hz, 6H), 1.15 (s, 6H). |

TABLE 1-continued

| Compound No. | Structure and name | NMR data |
|---|---|---|
| 69 | 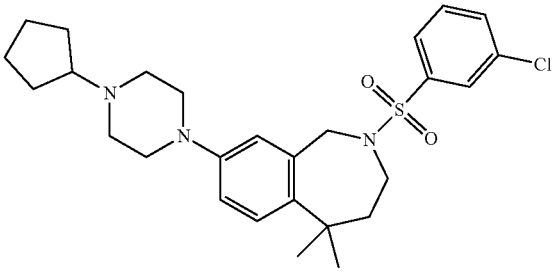 [SMILES: CC1(C)CCN(S(=O)(=O)c2cccc(Cl)c2)Cc2cc(N3CCN(C4CCCC4)CC3)ccc21]<br>2-((3-chlorophenyl)sulfonyl)-8-(4-cyclopentylpiperazin-1-yl)-5,5-dimethyl-2,3,4,5-tetrahydro-1H-benzo[c]azepine | ¹H NMR (400 MHz, DMSO) δ 7.76 – 7.66 (m, 3H), 7.59 (t, J = 7.9 Hz, 1H), 7.18 (d, J = 9.2 Hz, 1H), 6.78 – 6.71 (m, 2H), 4.46 (s, 2H), 3.39 (s, 2H), 3.10 (t, J = 5.0 Hz, 4H), 2.54 (t, J = 5.0 Hz, 4H), 2.49 – 2.43 (m, 1H), 1.87 – 1.72 (m, 4H), 1.69 – 1.57 (m, 2H), 1.57 – 1.46 (m, 2H), 1.43 – 1.29 (m, 2H), 1.20 (s, 6H). |
| 70 | 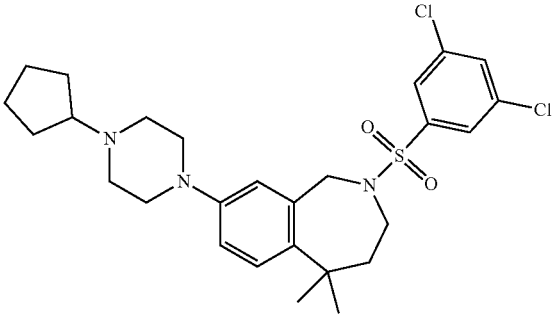 [SMILES: CC1(C)CCN(S(=O)(=O)c2cc(Cl)cc(Cl)c2)Cc2cc(N3CCN(C4CCCC4)CC3)ccc21]<br>8-(4-cyclopentylpiperazin-1-yl)-2-((3,5-dichlorophenyl)sulfonyl)-5,5-dimethyl-2,3,4,5-tetrahydro-1H-benzo[c]azepine | ¹H NMR (400 MHz, DMSO) δ 7.93 (t, J = 1.9 Hz, 1H), 7.69 (d, J = 1.8 Hz, 2H), 7.17 (d, J = 8.7 Hz, 1H), 6.79 (d, J = 2.8 Hz, 1H), 6.75 (dd, J = 8.8, 2.7 Hz, 1H), 4.51 (s, 2H), 3.45 (t, J = 5.7 Hz, 2H), 3.11 (t, J = 5.0 Hz, 4H), 2.54 (t, J = 5.0 Hz, 4H), 2.48 – 2.43 (m, 1H), 1.87 – 1.74 (m, 4H), 1.69 – 1.57 (m, 2H), 1.54 – 1.46 (m, 2H), 1.42 – 1.29 (m, 2H), 1.20 (s, 6H). |
| 71 | 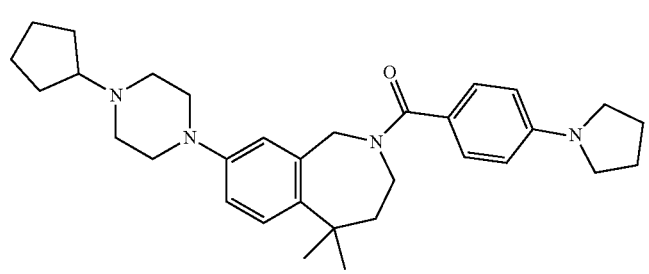 [SMILES: CC1(C)CCN(C(=O)c2ccc(N3CCCC3)cc2)Cc2cc(N3CCN(C4CCCC4)CC3)ccc21]<br>(8-(4-cyclopentylpiperazin-1-yl)-5,5-dimethyl-1,3,4,5-tetrahydro-2H-benzo[c]azepin-2-yl)(4-(pyrrolidin-1-yl)phenyl)methanone | ¹H NMR (400 MHz, DMSO) δ 7.37 – 6.88 (m, 3H), 6.76 (d, J = 7.9 Hz, 1.5H), 6.46 (br s, 2H), 6.10 (br s, 0.5H), 4.56 (br s, 2H), 3.67 (t, J = 6.1 Hz, 2H), 3.27 – 3.19 (m, 4H), 3.05 (br s, 4H), 2.59 – 2.53 (m, 4H), 2.47 – 2.43 (m, 1H), 2.02 – 1.87 (m, 6H), 1.85 – 1.76 (m, 2H), 1.66 – 1.57 (m, 2H), 1.57 – 1.47 (m, 2H), 1.40 – 1.31 (m, 2H), 1.19 (br s, 6H). |
| 72 | 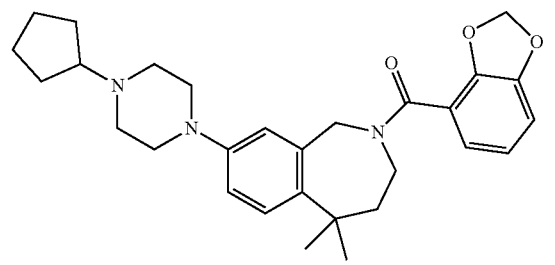 [SMILES: CC1(C)CCN(C(=O)c2cccc3c2OCO3)Cc2cc(N3CCN(C4CCCC4)CC3)ccc21]<br>benzo[d][1,3]dioxol-4-yl(8-(4-cyclopentylpiperazin-1-yl)-5,5-dimethyl-1,3,4,5-tetrahydro-2H-benzo[c]azepin-2-yl)methanone | ¹H NMR (400 MHz, DMSO) δ 7.22 (dd, J = 8.6, 3.1 Hz, 1H), 6.97 (t, J = 7.3 Hz, 1H), 6.86 (t, J = 7.8 Hz, 0.5H), 6.82 – 6.73 (m, 2H), 6.72 (d, J = 7.8 Hz, 1H), 6.38 (d, J = 7.8 Hz, 0.5H), 6.04 (s, 1H), 5.86 – 5.77 (m, 1H), 4.69 (s, 1H), 4.42 (s, 1H), 3.78 (t, J = 5.9 Hz, 1H), 3.56 (t, J = 6.0 Hz, 1H), 3.10 (t, J = 5.0 Hz, 2H), 2.88 (t, J = 4.9 Hz, 2H), 2.57 – 2.53 (m, 2H), 2.48 – 2.43 (m, 3H), 1.94 (d, J = 6.2 Hz, |

TABLE 1-continued

| Compound No. | Structure and name | NMR data |
|---|---|---|
| | | 1H), 1.90 – 1.74 (m, 3H), 1.68 – 1.56 (m, 2H), 1.56 – 1.47 (m, 2H), 1.36 (dt, J = 18.9, 9.8 Hz, 2H), 1.27 (s, 3H), 1.18 (s, 3H). |
| 73 | 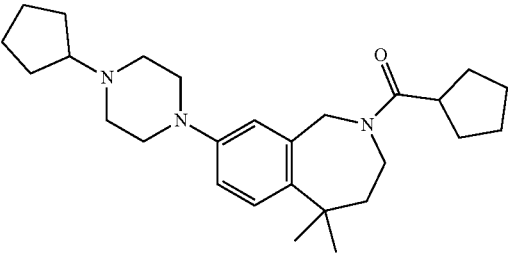 [SMILES: CC1(C)CCN(C(=O)C2CCCC2)Cc2cc(N3CCN(C4CCCC4)CC3)ccc21]  cyclopentyl(8-(4-cyclopentylpiperazin-1-yl)-5,5-dimethyl-1,3,4,5-tetrahydro-2H-benzo[c]azepin-2-yl)methanone | ¹H NMR (400 MHz, DMSO) δ 7.21 (dd, J = 13.1, 8.7 Hz, 1H), 6.83 (d, J = 2.9 Hz, 0.5H), 6.79 – 6.65 (m, 1.5H), 4.59 (d, J = 30.1 Hz, 2H), 3.67 (dt, J = 31.6, 5.9 Hz, 2H), 3.12 – 3.02 (m, 4H), 2.93 (dq, J = 14.9, 7.3 Hz, 1H), 2.56 – 2.51 (m, 4H), 2.49 – 2.42 (m, 1H), 1.92 – 1.68 (m, 5H), 1.64 – 1.31 (m, 13H), 1.23 (d, J = 28.2 Hz, 6H). |
| 74 | 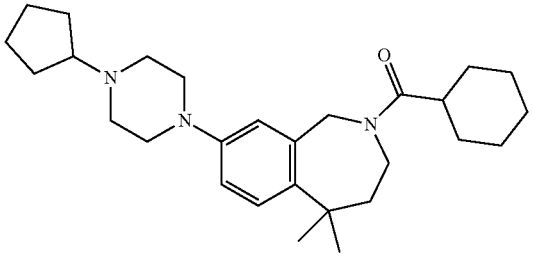 [SMILES: CC1(C)CCN(C(=O)C2CCCCC2)Cc2cc(N3CCN(C4CCCC4)CC3)ccc21]  cyclohexyl(8-(4-cyclopentylpiperazin-1-yl)-5,5-dimethyl-1,3,4,5-tetrahydro-2H-benzo[c]azepin-2-yl)methanone | ¹H NMR (400 MHz, DMSO) δ 7.21 (dd, J = 12.1, 8.8 Hz, 1H), 6.85 – 6.66 (m, 2H), 4.57 (d, J = 33.9 Hz, 2H), 3.65 (dt, J = 33.2, 6.2 Hz, 2H), 3.08 (q, J = 8.2, 6.3 Hz, 4H), 2.63 – 2.53 (m, 4H), 2.47 – 2.42 (m, 1H), 1.91 – 1.76 (m, 4H), 1.70 – 1.46 (m, 8H), 1.41 – 1.31 (m, 2H), 1.26 (s, 3H), 1.22 – 1.05 (m, 10H). |
| 75 | 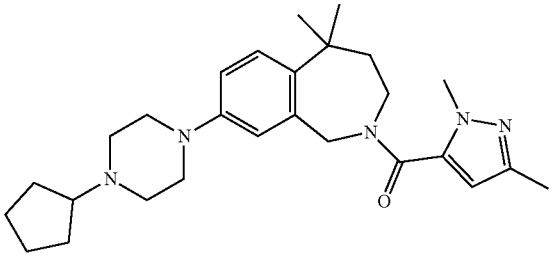 [SMILES: Cc1cc(C(=O)N2CCC(C)(C)c3ccc(N4CCN(C5CCCC5)CC4)cc3C2)n(C)n1]  (8-(4-cyclopentylpiperazin-1-yl)-5,5-dimethyl-1,3,4,5-tetrahydro-2H-benzo[c]azepin-2-yl)(1,3-dimethyl-1H-pyrazol-5-yl)methanone | ¹H NMR (400 MHz, DMSO) δ 7.25 (dd, J = 16.5, 8.7 Hz, 1H), 6.83 – 6.72 (m, 1.5H), 6.26 (s, 0.5H), 6.05 (d, J = 2.7 Hz, 0.5H), 5.87 (s, 0.5H), 4.62 (d, J = 64.3 Hz, 2H), 3.73 (dt, J = 28.9, 6.1 Hz, 2H), 3.65 (s, 1H), 3.29 (s, 2H), 3.10 (t, J = 5.0 Hz, 2H), 3.00 (t, J = 4.9 Hz, 2H), 2.56 – 2.51 (m, 3H), 2.48 – 2.42 (m, 2H), 2.13 (d, J = 9.0 Hz, 3H), 1.97 (t, J = 5.9 Hz, 1H), 1.89 (t, J = 5.6 Hz, 1H), 1.81 (s, 2H), 1.65 – 1.57 (m, 2H), 1.57 – 1.45 (m, 2H), 1.41 – 1.30 (m, 2H), 1.27 (s, 3H), 1.21 (s, 3H). |

TABLE 1-continued

| Compound No. | Structure and name | NMR data |
|---|---|---|
| 76 | 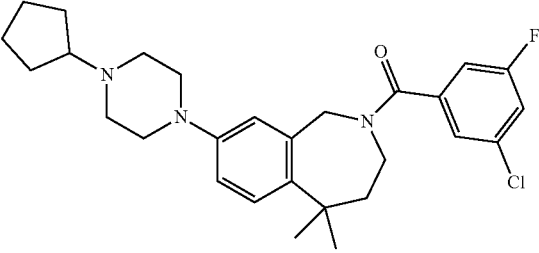 [SMILES: CC1(C)CCN(C(=O)c2cc(F)cc(Cl)c2)Cc2cc(N3CCN(C4CCCC4)CC3)ccc21]<br>(3-chloro-5-fluorophenyl)(8-(4-cyclopentylpiperazin-1-yl)-5,5-dimethyl-1,3,4,5-tetrahydro-2H-benzo[c]azepin-2-yl)methanone | $^1$H NMR (400 MHz, DMSO) δ 7.55 (ddt, J = 9.0, 6.9, 2.2 Hz, 1H), 7.34 – 7.19 (m, 2H), 6.87 – 6.75 (m, 2.4H), 6.06 (d, J = 2.6 Hz, 0.6H), 4.70 (s, 0.7H), 4.39 (s, 1.3H), 3.74 (t, J = 6.1 Hz, 1H), 3.52 (t, J = 5.9 Hz, 1H), 3.10 (t, J = 5.1 Hz, 2H), 2.98 (t, J = 5.0 Hz, 2H), 2.57 – 2.52 (m, 2H), 2.48 – 2.40 (m, 3H), 2.01 (t, J = 6.1 Hz, 1.3H), 1.87 (t, J = 5.9 Hz, 0.7H), 1.80 (s, 2H), 1.69 – 1.57 (m, 2H), 1.54 – 1.43 (m, 2H), 1.35 (q, J = 12.4, 9.8 Hz, 2H), 1.28 (s, 4H), 1.18 (s, 2H). |
| 77 | 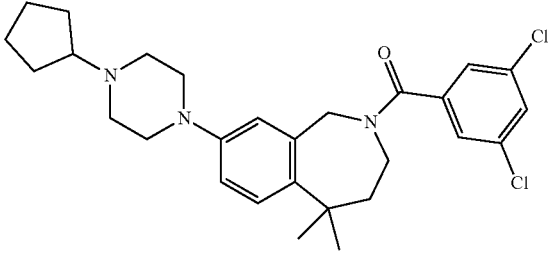 [SMILES: CC1(C)CCN(C(=O)c2cc(Cl)cc(Cl)c2)Cc2cc(N3CCN(C4CCCC4)CC3)ccc21]<br>(8-(4-cyclopentylpiperazin-1-yl)-5,5-dimethyl-1,3,4,5-tetrahydro-2H-benzo[c]azepin-2-yl)(3,5-dichlorophenyl)methanone | $^1$H NMR (400 MHz, DMSO) δ 7.74 – 7.70 (m, 1H), 7.45 (d, J = 1.9 Hz, 0.6H), 7.27 (dd, J = 35.0, 8.7 Hz, 1H), 6.95 (d, J = 1.9 Hz, 1.4H), 6.88 – 6.73 (m, 1.4H), 6.08 (d, J = 2.7 Hz, 0.6H), 4.54 (d, J = 123.4 Hz, 2H), 3.63 (dt, J = 85.5, 6.1 Hz, 2H), 3.05 (dt, J = 39.2, 4.9 Hz, 4H), 2.59 – 2.52 (m, 4H), 2.45 (s, 1H), 1.94 (dt, J = 55.2, 6.0 Hz, 2H), 1.79 (d, J = 10.3 Hz, 2H), 1.62 (q, J = 8.2, 5.3 Hz, 2H), 1.52 (td, J = 8.4, 4.9 Hz, 2H), 1.36 (d, J = 14.3 Hz, 2H), 1.23 (d, J = 36.6 Hz, 6H). |
| 78 | 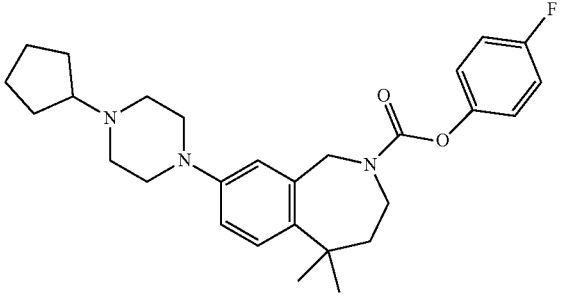 [SMILES: CC1(C)CCN(C(=O)Oc2ccc(F)cc2)Cc2cc(N3CCN(C4CCCC4)CC3)ccc21]<br>4-fluorophenyl 8-(4-cyclopentylpiperazin-1-yl)-5,5-dimethyl-1,3,4,5-tetrahydro-2H-benzo[c]azepine-2-carboxylate | $^1$H NMR (400 MHz, DMSO) δ 7.27 (dd, J = 8.6, 1.5 Hz, 1H), 7.17 (td, J = 8.8, 5.3 Hz, 2H), 7.12 – 7.03 (m, 1H), 6.97 – 6.88 (m, 1H), 6.77 (ddt, J = 7.7, 4.9, 2.8 Hz, 1.5H), 6.66 (d, J = 2.8 Hz, 0.5H), 4.66 (s, 1H), 4.55 (s, 1H), 3.80 (t, J = 5.9 Hz, 1H), 3.66 (t, J = 5.8 Hz, 1H), 3.06 (t, J = 5.0 Hz, 4H), 2.46 – 2.38 (m, 1H), 1.91 (dt, J = 25.4, 5.9 Hz, 2H), 1.85 – 1.72 (m, 2H), 1.67 – 1.42 (m, 4H), 1.41 – 1.24 (m, 8H). 4H under solvent peaks. |

TABLE 1-continued

| Compound No. | Structure and name | NMR data |
|---|---|---|
| 79 | 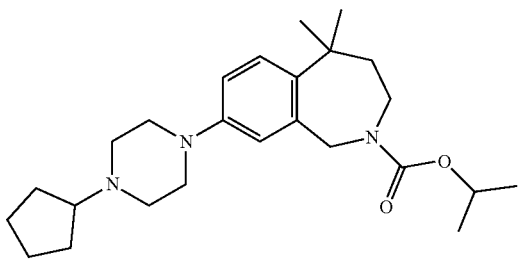 [SMILES: CC(C)OC(=O)N1CCC(C)(C)c2ccc(N3CCN(C4CCCC4)CC3)cc2C1]<br>isopropyl 8-(4-cyclopentylpiperazin-1-yl)-5,5-dimethyl-1,3,4,5-tetrahydro-2H-benzo[c]azepine-2-carboxylate | $^1$H NMR (400 MHz, DMSO) δ 7.20 (dd, J = 8.7, 6.0 Hz, 1H), 6.77 – 6.70 (m, 1H), 6.65 (dd, J = 6.6, 2.8 Hz, 1H), 4.65 (dp, J = 40.6, 6.4 Hz, 1H), 4.44 (d, J = 12.6 Hz, 2H), 3.57 (br s, 2H), 3.07 (t, J = 5.0 Hz, 4H), 2.55 – 2.51 (m, 4H), 2.47 – 2.42 (m, 1H), 1.86 – 1.72(m, 4H), 1.67 – 1.57(m, 2H), 1.54 – 1.44(m, 2H), 1.41 – 1.28 (m, 2H), 1.25 (d, J = 6.1 Hz, 6H), 1.13 (d, J = 6.2 Hz, 3H), 1.06 (d, J = 6.1 Hz, 3H). |
| 80 | 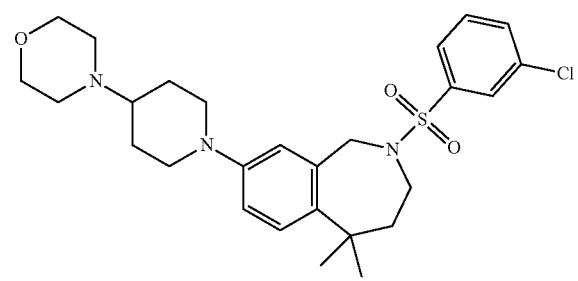 [SMILES: CC1(C)CCN(S(=O)(=O)c2cccc(Cl)c2)Cc2cc(N3CCC(N4CCOCC4)CC3)ccc21]<br>4-(1-(2-((3-chlorophenyl)sulfonyl)-5,5-dimethyl-2,3,4,5-tetrahydro-1H-benzo[c]azepin-8-yl)piperidin-4-yl)morpholine | $^1$H NMR (400 MHz, DMSO) δ 7.72 (ddd, J = 31.3, 12.2, 2.3 Hz, 3H), 7.58 (t, J = 7.8 Hz, 1H), 7.19 – 7.13 (m, 1H), 6.77 (dq, J = 5.1, 2.8 Hz, 2H), 4.45 (s, 2H), 3.70 (d, J = 12.3 Hz, 2H), 3.57 (t, J = 4.5 Hz, 4H), 3.41 – 3.38 (m, 2H), 2.69 – 2.58 (m, 2H), 2.47 (d, J = 4.4 Hz, 4H), 2.32 – 2.21 (m, 1H), 1.87 (d, J = 12.5 Hz, 2H), 1.77 (t, J = 5.8 Hz, 2H), 1.47 (qd, J = 12.5, 3.1 Hz, 2H), 1.20 (s, 6H). |
| 81 | 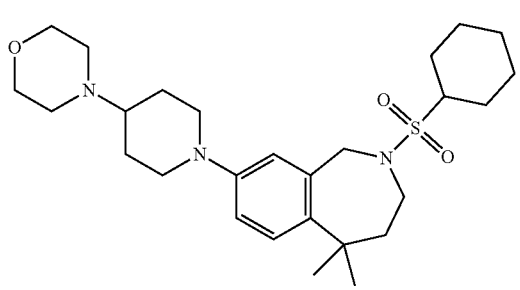 [SMILES: CC1(C)CCN(S(=O)(=O)C2CCCCC2)Cc2cc(N3CCC(N4CCOCC4)CC3)ccc21]<br>4-(1-(2-(cyclohexylsulfonyl)-5,5-dimethyl-2,3,4,5-tetrahydro-1H-benzo[c]azepin-8-yl)piperidin-4-yl)morpholine | $^1$H NMR (400 MHz, DMSO) 7.21 (d, J = 8.8 Hz, 1H), 6.76 (dd, J = 8.8, 2.8 Hz, 1H), 6.65 (d, J = 2.8 Hz, 1H), 4.46 (s, 2H), 3.67 (d, J = 12.5 Hz, 2H), 3.54 (dt, J = – 19.2, 5.2 H 6H), 3.14 – 3.06 (m, 1H), 2.61 (t, J = 11.9 Hz, 2H), 2.48 – 2.44 (m, 4H), 2.29 – 2.20 (m, 1H), 1.95 – 1.71 (m, 8H), 1.60 (d, J = 12.6 Hz, 1H), 1.52 – 1.38 (m, 3H), 1.28 (s, 9H), 1.13 (dd, J = 23.7, 11.1 Hz, 1H). |

TABLE 1-continued

| Compound No. | Structure and name | NMR data |
|---|---|---|
| 82 | 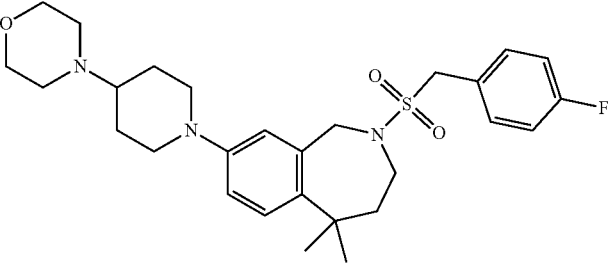 [SMILES: CC1(C)CCN(S(=O)(=O)Cc2ccc(F)cc2)Cc2cc(N3CCC(N4CCOCC4)CC3)ccc21]

4-(1-(2-((4-fluorobenzyl)sulfonyl)-5,5-dimethyl-2,3,4,5-tetrahydro-1H-benzo[c]azepin-8-yl)piperidin-4-yl)morpholine | $^1$H NMR (400 MHz, DMSO) δ 7.35 – 7.29 (m, 2H), 7.24 – 7.15 (m, 3H), 6.78 (dd, J = 8.6, 2.8 Hz, 1H), 6.59 (d, J = 2.8 Hz, 1H), 4.33 (s, 4H), 3.66 (d, J = 12.4 Hz, 2H), 3.56 (t, J = 4.6 Hz, 4H), 3.40 (t, J = 5.9 Hz, 2H), 2.61 (dd, J = 13.0, 10.6 Hz, 2H), 2.47 – 2.41 (m, 5H), 2.30 – 2.20 (m, 1H), 1.84 (d, J = 12.4 Hz, 2H), 1.75 (t, J = 5.8 Hz, 2H), 1.45 (qd, J = 12.1, 3.7 Hz, 2H), 1.26 (s, 6H). |
| 83 | 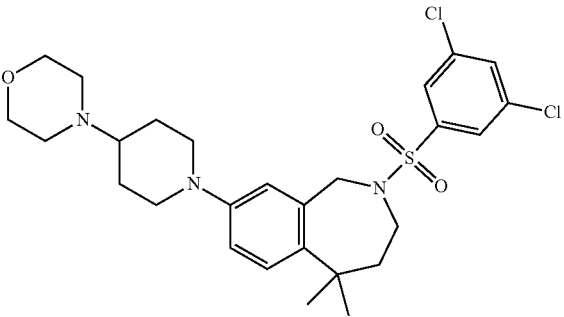 [SMILES: CC1(C)CCN(S(=O)(=O)c2cc(Cl)cc(Cl)c2)Cc2cc(N3CCC(N4CCOCC4)CC3)ccc21]

4-(1-(2-((3,5-dichlorophenyl)sulfonyl)-5,5-dimethyl-2,3,4,5-tetrahydro-1H-benzo[c]azepin-8-yl)piperidin-4-yl)morpholine | $^1$H NMR (400 MHz, DMSO) δ 7.93 (t, J = 1.9 Hz, 1H), 7.69 (d, J = 2.0 Hz, 2H), 7.16 (d, J = 8.6 Hz, 1H), 6.81 – 6.74 (m, 2H), 4.50 (s, 2H), 3.70 (d, J = 12.4 Hz, 2H), 3.57 (t, J = 4.7 Hz, 4H), 3.49 – 3.41 (m, 2H), 2.67 – 2.60 (m, 2H), 2.48 – 2.44 (m, 4H), 2.26 (t, J = 11.0 Hz, 1H), 1.87 (d, J = 12.5 Hz, 2H), 1.77 (t, J = 5.9 Hz, 2H), 1.48 (qd, J = 11.9, 11.5, 3.8 Hz, 2H), 1.20 (s, 6H). |
| 84 | 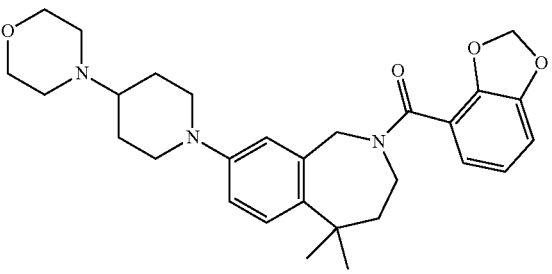 [SMILES: CC1(C)CCN(C(=O)c2cccc3c2OCO3)Cc2cc(N3CCC(N4CCOCC4)CC3)ccc21]

benzo[d][1,3]dioxol-4-yl(5,5-dimethyl-8-(4-morpholinopiperidin-1-yl)-1,3,4,5-tetrahydro-2H-benzo[c]azepin-2-yl)methanone | $^1$H NMR (400 MHz, DMSO) δ 7.21 (dd, J = 8.7, 2.2 Hz, 1H), 6.97 (td, J = 7.9, 1.2 Hz, 1H), 6.86 (t, J = 7.8 Hz, 0.5H), 6.82 – 6.70 (m, 2.5H), 6.38 (dd, J = 7.9, 1.1 Hz, 0.5H), 6.04 (s, 1H), 5.84 (s, 1H), 5.82 (d, J = 2.8 Hz, 0.5H), 4.69 (s, 1H), 4.42 (s, 1H), 3.81 – 3.74 (m, 1H), 3.69 (d, J = 12.4 Hz, 1H), 3.62 – 3.52 (m, 5H), 3.43 (d, J = 12.2 Hz, 1H), 2.63 (td, J = 12.7, 2.5 Hz, 1H), 2.48 – 2.41 (m, 5H), 2.29 – 2.15 (m, 1H), 1.96 – 1.82 (m, 3H), 1.78 (d, J = 12.2 Hz, 1H), 1.54-1.29 (m, 2H), 1.27 (s, 3H), 1.18 (s, 3H). |

TABLE 1-continued

| Compound No. | Structure and name | NMR data |
|---|---|---|
| 85 | 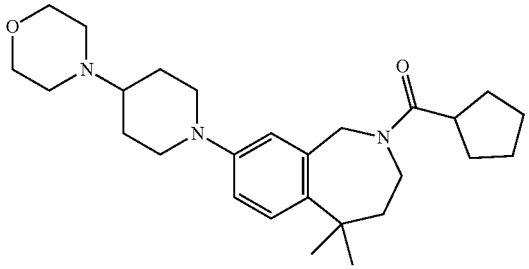 [SMILES: CC1(C)CCN(C(=O)C2CCCC2)Cc2cc(N3CCC(N4CCOCC4)CC3)ccc21]<br>cyclopentyl(5,5-dimethyl-8-(4-morpholinopiperidin-1-yl)-1,3,4,5-tetrahydro-2H-benzo[c]azepin-2-yl)methanone | ¹H NMR (400 MHz, DMSO) δ 7.20 (dd, J = 12.3, 8.7 Hz, 1H), 6.85 (d, J = 2.8 Hz, 0.5H), 6.79 – 6.65 (m, 1.5H), 4.58 (d, J = 31.5 Hz, 2H), 3.76 – 3.50 (m, 8H), 3.00 – 2.89 (m, 1H), 2.66 – 2.55 (m, 2H), 2.48 – 2.43 (m, 4H), 2.31 – 2.18 (m, 1H), 1.91 – 1.78 (m, 4H), 1.71 (d, J = 11.1 Hz, 1H), 1.64 – 1.35 (m, 9H), 1.22 (d, J = 29.4 Hz, 6H). |
| 86 | 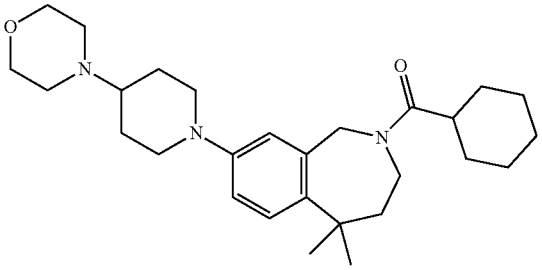 [SMILES: CC1(C)CCN(C(=O)C2CCCCC2)Cc2cc(N3CCC(N4CCOCC4)CC3)ccc21]<br>cyclohexyl(5,5-dimethyl-8-(4-morpholinopiperidin-1-yl)-1,3,4,5-tetrahydro-2H-benzo[c]azepin-2-yl)methanone | ¹H NMR (400 MHz, DMSO) δ 7.19 (dd, J = 11.2, 8.7 Hz, 1H), 6.84 (d, J = 2.8 Hz, 0.5H), 6.79 – 6.67 (m, 1.5H), 4.57 (d, J = 34.2 Hz, 2H), 3.75 – 3.52 (m, 8H), 2.66 – 2.58 (m, 2H), 2.48 – 2.41 (m, 4H), 2.30 – 2.19 (m, 1H), 1.90 – 1.79 (m, 4H), 1.70 – 1.37 (m, 6H), 1.31 – 1.04 (m, 13H). |
| 87 | 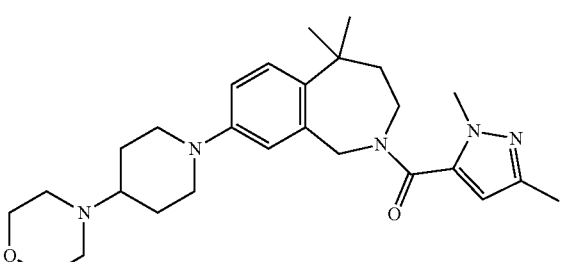<br>(1,3-dimethyl-1H-pyrazol-5-yl)(5,5-dimethyl-8-(4-morpholinopiperidin-1-yl)-1,3,4,5-tetrahydro-2H-benzo[c]azepin-2-yl)methanone | ¹H NMR (400 MHz, DMSO) δ 7.23 (dd, J = 16.5, 8.6 Hz, 1H), 6.84 – 6.74 (m, 1.5H) 6.25 (s, 0.5H), 6.08 (d, J = 2.7 Hz, 0.5H), 5.86 (s, 0.5H), 4.61 (d, J = 63.0 Hz, 2H), 3.77 (t, J = 5.9 Hz, 1H), 3.72 – 3.68 (m, 1H), 3.64 (s, 1H), 3.57 (t, J = 4.6 Hz, 5H), 3.31 (s, 3H), 2.65 – 2.54 (m, 2H), 2.48 – 2.43 (m, 4H), 2.30 – 2.20 (m, 1H), 2.13 (d, J = 7.3 Hz, 3H), 1.97 (t, J = 6.1 Hz, 1H), 1.93 – 1.77 (m, 3H), 1.54 – 1.37 (m, 2H), 1.24 (d, J = 22.5 Hz, 6H). |
| 88 | 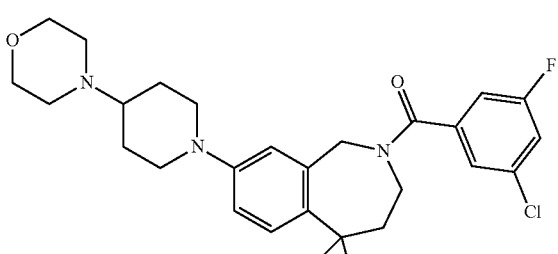<br>(3-chloro-5-fluorophenyl)(5,5-dimethyl-8-(4-morpholinopiperidin-1-yl)-1,3,4,5-tetrahydro-2H-benzo[c]azepin-2-yl)methanone | ¹H NMR (400 MHz, DMSO) δ 7.55 (ddd, J = 8.9, 4.7, 2.4 Hz, 1H), 7.26 (dd, J = 31.7, 8.7 Hz, 2H), 6.90 – 6.77 (m, 2.4H), 6.07 (d, J = 2.7 Hz, 0.6H), 4.69 (s, 0.8H), 4.40 (s, 1.2H), 3.79 – 3.64 (m, 2H), 3.61 – 3.48 (m, 6H), 2.66 – 2.53 (m, 2H), 2.48 – 2.44 (m, 4H), 2.27 – 2.16 (m, 1H), 2.00 (t, J = 6.1 Hz, 1H), 1.91 – 1.78 (m, 3H), 1.51 – 1.36 (m, 2H), 1.28 (s, 4H), 1.18 (s, 2H). |

TABLE 1-continued

| Compound No. | Structure and name | NMR data |
|---|---|---|
| 89 | 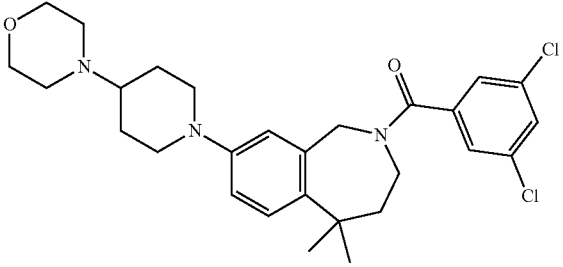 [SMILES: CC1(C)CCN(C(=O)c2cc(Cl)cc(Cl)c2)Cc2cc(N3CCC(N4CCOCC4)CC3)ccc21]<br>(3,5-dichlorophenyl)(5,5-dimethyl-8-(4-morpholinopiperidin-1-yl)-1,3,4,5-tetrahydro-2H-benzo[c]azepin-2-yl)methanone | $^1$H NMR (400 MHz, DMSO) δ 7.72 (q, J = 1.9 Hz, 1H), 7.44 (d, J = 2.0 Hz, 0.7H), 7.26 (dd, J = 34.1, 8.8 Hz, 1H), 6.97 (d, J = 1.8 Hz, 1.3H), 6.88 – 6.81 (m, 0.66H), 6.78 (d, J = 10.3 Hz, 0.66H), 6.09 (d, J = 2.6 Hz, 0.66H), 4.69 (s, 0.7H), 4.39 (s, 1.3H), 3.71 (d, J = 25.8 Hz, 3H), 3.57 (d, J = 5.0 Hz, 7H), 2.62 (d, J = 11.5 Hz, 2H), 2.22 (s, 1H), 2.01 (t, J = 6.3 Hz, 1H), 1.85 (t, J = 12.8 Hz, 3H), 1.54 – 1.39 (m, 3H), 1.28 (s, 4H), 1.24 (s, 1H), 1.18 (s, 2H). |
| 90 | 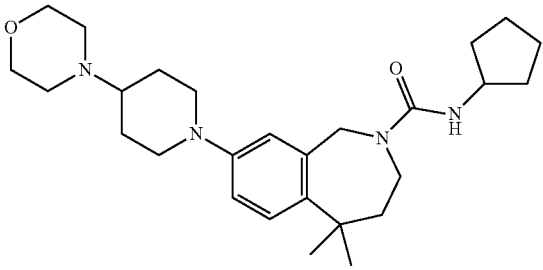 [SMILES: CC1(C)CCN(C(=O)NC2CCCC2)Cc2cc(N3CCC(N4CCOCC4)CC3)ccc21]<br>N-cyclopentyl-5,5-dimethyl-8-(4-morpholinopiperidin-1-yl)-1,3,4,5-tetrahydro-2H-benzo[c]azepine-2-carboxamide | $^1$H NMR (400 MHz, DMSO) δ 7.17 (d, J = 8.7 Hz, 1H), 6.82 (d, J = 2.7 Hz, 1H), 6.72 (dd, J = 8.8, 2.7 Hz, 1H), 5.80 (d, J = 7.2 Hz, 1H), 4.44 (s, 2H), 3.79 (p, J = 7.1 Hz, 1H), 3.68 (d, J = 12.6 Hz, 2H), 3.60 – 3.48 (m, 6H), 2.61 (td, J = 12.3, 2.3 Hz, 2H), 2.48 – 2.44 (m, 4H), 2.25 (tt, J = 11.0, 3.3 Hz, 1H), 1.84 (d, J = 12.3 Hz, 2H), 1.75 (t, J = 5.9 Hz, 2H), 1.71– 1.62 (m, 2H), 1.58 – 1.39 (m, 6H), 1.33 – 1.26 (m, 2H), 1.23 (s, 6H). |
| 91 | 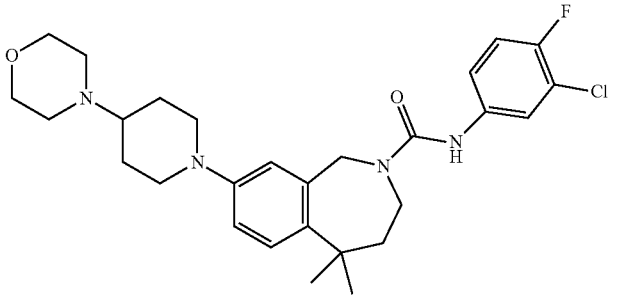 [SMILES: CC1(C)CCN(C(=O)Nc2ccc(F)c(Cl)c2)Cc2cc(N3CCC(N4CCOCC4)CC3)ccc21]<br>N-(3-chloro-4-fluorophenyl)-5,5-dimethyl-8-(4-morpholinopiperidin-1-yl)-1,3,4,5-tetrahydro-2H-benzo[c]azepine-2-carboxamide | $^1$H NMR (400 MHz, DMSO) δ 8.43 (s, 1H), 7.72 (dd, J = 6.9, 2.6 Hz, 1H), 7.41 (ddd, J = 9.1, 4.3, 2.6 Hz, 1H), 7.25 (t, J = 9.1 Hz, 1H), 7.19 (d, J = 8.7 Hz, 1H), 6.89 (s, 1H), 6.73 (dd, J = 8.8, 2.7 Hz, 1H), 4.62 (s, 2H), 3.74 – 3.65 (m, 4H), 3.54 (t, J = 4.6 Hz, 4H), 2.63 (td, J = 12.1, 1.9 Hz, 2H), 2.43 (t, J = 4.7 Hz, 4H), 2.26 (ddt, J = 11.1, 7.5, 3.8 Hz, 1H), 1.89 – 1.78 (m, 4H), 1.41 (qd, J = 12.0, 3.8 Hz, 2H), 1.27 (s, 6H). |

TABLE 1-continued

| Compound No. | Structure and name | NMR data |
|---|---|---|
| 92 | 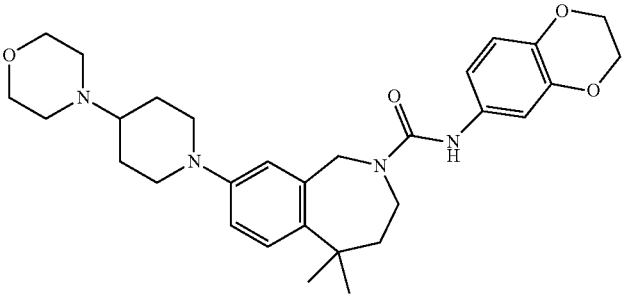 [SMILES: CC1(C)CCN(C(=O)Nc2ccc3c(c2)OCCO3)Cc2cc(N3CCC(N4CCOCC4)CC3)ccc21]<br>N-(2,3-dihydrobenzo[b][1,4]dioxin-6-yl)-5,5-dimethyl-8-(4-morpholinopiperidin-1-yl)-1,3,4,5-tetrahydro-2H-benzo[c]azepine-2-carboxamide | $^1$H NMR (400 MHz, DMSO) δ 7.99 (s, 1H), 7.19 (d, J = 8.6 Hz, 1H), 7.00 (d, J = 2.5 Hz, 1H), 6.91 (d, J = 2.9 Hz, 1H), 6.84 (dd, J = 8.8, 2.5 Hz, 1H), 6.72 (dd, J = 8.7, 2.8 Hz, 1H), 6.66 (d, J = 8.7 Hz, 1H), 4.59 (s, 2H), 4.15 (tq, J = 6.9, 3.1 Hz, 4H), 3.75 – 3.62 (m, 4H), 3.55 (t, J = 4.5 Hz, 4H), 2.63 (t, J = 12.2 Hz, 2H), 2.44 (t, J = 4.7 Hz, 4H), 2.31 – 2.21 (m, 1H), 1.86 – 1.77 (m, 4H), 1.43 (qd, J = 12.1, 3.6 Hz, 2H), 1.26 (s, 6H). |
| 93 | 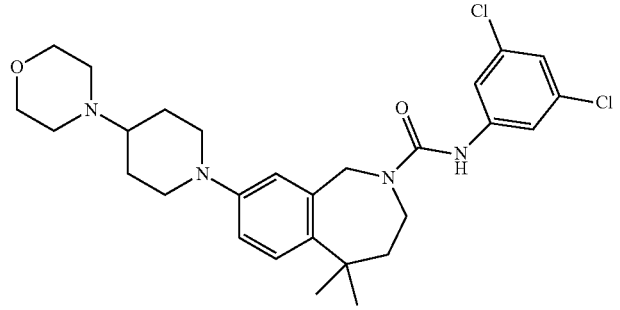 [SMILES: CC1(C)CCN(C(=O)Nc2cc(Cl)cc(Cl)c2)Cc2cc(N3CCC(N4CCOCC4)CC3)ccc21]<br>N-(3,5-dichlorophenyl)-5,5-dimethyl-8-(4-morpholinopiperidin-1-yl)-1,3,4,5-tetrahydro-2H-benzo[c]azepine-2-carboxamide | $^1$H NMR (400 MHz, DMSO) δ 8.58 (s, 1H), 7.60 (d, J = 1.8 Hz, 2H), 7.19 (d, J = 8.8 Hz, 1H), 7.08 (t, J = 1.9 Hz, 1H), 6.90 (br s, 1H), 6.73 (dd, J = 8.7, 2.7 Hz, 1H), 4.63 (s, 2H), 3.75 – 3.64 (m, 4H), 3.54 (t, J = 4.5 Hz, 4H), 2.64 (t, J = 12.3 Hz, 2H), 2.42 (t, J = 4.7 Hz, 4H), 2.32 – 2.20 (m, 1H), 1.83 (t, J = 12.1 Hz, 4H), 1.41 (q, J = 11.1, 10.6 Hz, 2H), 1.27 (s, 6H). |
| 94 | 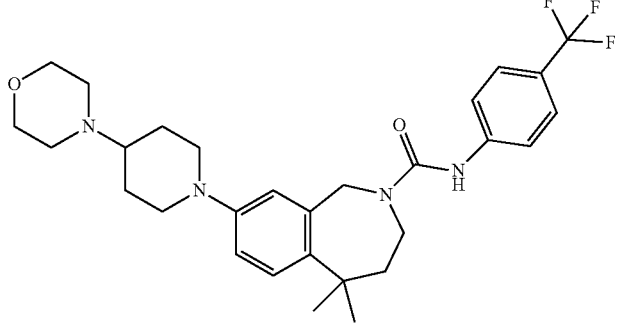<br>5,5-dimethyl-8-(4-morpholinopiperidin-1-yl)-N-(4-(trifluoromethyl)phenyl)-1,3,4,5-tetrahydro-2H-benzo[c]azepine-2-carboxamide | $^1$H NMR (400 MHz, DMSO) δ 8.61 (s, 1H), 7.67 (d, J = 8.6 Hz, 2H), 7.54 (d, J = 8.6 Hz, 2H), 7.20 (d, J = 8.8 Hz, 1H), 6.90 (br s, 1H), 6.73 (dd, J = 8.6, 2.7 Hz, 1H), 4.65 (s, 2H), 3.75 – 3.65 (m, 4H), 3.54 (t, J = 4.6 Hz, 4H), 2.63 (td, J = 12.8, 2.4 Hz, 2H), 2.43 (t, J = 4.7 Hz, 4H), 2.29 – 2.19 (m, 1H), 1.90 – 1.78 (m, 4H), 1.41 (q, J = 12.8, 12.1 Hz, 2H), 1.28 (s, 6H). |

TABLE 1-continued

| Compound No. | Structure and name | NMR data |
|---|---|---|
| 95 | 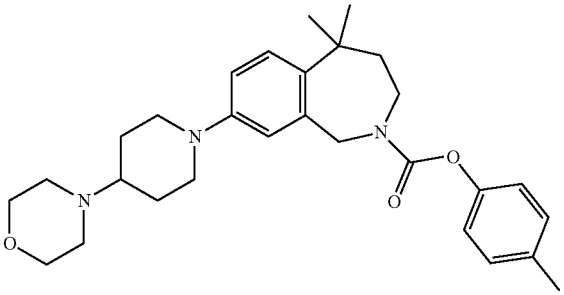 [SMILES: Cc1ccc(OC(=O)N2CCC(C)(C)c3ccc(N4CCC(N5CCOCC5)CC4)cc3C2)cc1]<br>p-tolyl 5,5-dimethyl-8-(4-morpholinopiperidin-1-yl)-1,3,4,5-tetrahydro-2H-benzo[c]azepine-2-carboxylate | $^1$H NMR (400 MHz, DMSO) δ 7.28 – 7.21 (m, 1H), 7.12 (dd, J = 10.9, 8.2 Hz, 2H), 6.92 – 6.87 (m, 1H), 6.82 – 6.74 (m, 2.5H), 6.67 (d, J = 2.8 Hz, 0.5H), 4.59 (d, J = 41.2 Hz, 2H), 3.80 (t, J = 5.8 Hz, 1H), 3.71 – 3.61 (m, 3H), 3.55 (q, J = 4.8 Hz, 4H), 2.60 (t, J = 12.2 Hz, 2H), 2.47 – 2.39 (m, 4H), 2.27 – 2.19 (m, 4H), 1.97 – 1.74 (m, 4H), 1.50 – 1.37 (m, 2H), 1.30 (d, J = 9.8 Hz, 6H). |
| 96 | 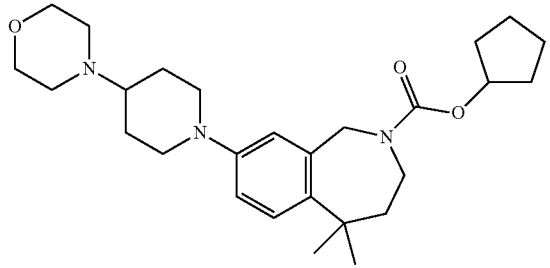 [SMILES: CC1(C)CCN(C(=O)OC2CCCC2)Cc2cc(N3CCC(N4CCOCC4)CC3)ccc21]<br>cyclopentyl 5,5-dimethyl-8-(4-morpholinopiperidin-1-yl)-1,3,4,5-tetrahydro-2H-benzo[c]azepine-2-carboxylate | $^1$H NMR (400 MHz, DMSO) δ 7.19 (dd, J = 8.7, 4.4 Hz, 1H), 6.78 – 6.72 (m, 1H), 6.64 (dd, J = 16.2, 2.4 Hz, 1H), 4.89 (d, J = 19.4 Hz, 1H), 4.42 (d, J = 19.4 Hz, 2H), 3.67 (d, J = 12.2 Hz, 2H), 3.62 – 3.51 (m, 6H), 2.61 (t, J = 12.0 Hz, 2H), 2.48 – 2.44 (m, 4H), 2.29 – 2.19 (m, 1H), 1.89 – 1.76 (m, 4H), 1.66 – 1.39 (m, 10H), 1.24 (s, 6H). |
| 97 | 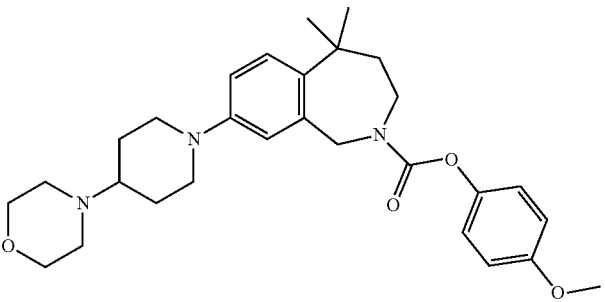 [SMILES: COc1ccc(OC(=O)N2CCC(C)(C)c3ccc(N4CCC(N5CCOCC5)CC4)cc3C2)cc1]<br>4-methoxyphenyl 5,5-dimethyl-8-(4-morpholinopiperidin-1-yl)-1,3,4,5-tetrahydro-2H-benzo[c]azepine-2-carboxylate | $^1$H NMR (400 MHz, DMSO) δ 7.29 – 7.22 (m, 1H), 7.01 – 6.91 (m, 1H), 6.90 – 6.82 (m, 2H), 6.82 – 6.75 (m, 2.5H), 6.67 (d, J = 2.8 Hz, 0.5H), 4.59 (d, J = 41.3 Hz, 2H), 3.83 – 3.62 (m, 7H), 3.55 (q, J = 5.1 Hz, 4H), 2.60 (t, J = 12.2 Hz, 2H), 2.48 – 2.39 (m, 4H), 2.29 – 2.16 (m, 1H), 1.93 (t, J = 6.0 Hz, 1H), 1.90 – 1.75 (m, 3H), 1.43 (t, J = 11.3 Hz, 2H), 1.30 (d, J = 10.3 Hz, 6H). |
| 98 | 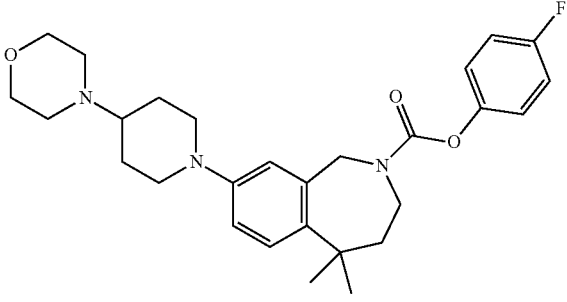 [SMILES: CC1(C)CCN(C(=O)Oc2ccc(F)cc2)Cc2cc(N3CCC(N4CCOCC4)CC3)ccc21]<br>4-fluorophenyl 5,5-dimethyl-8-(4-morpholinopiperidin-1-yl)-1,3,4,5-tetrahydro-2H-benzo[c]azepine-2-carboxylate | $^1$H NMR (400 MHz, DMSO) δ 7.25 (d, J = 8.6 Hz, 1H), 7.21 – 7.11 (m, 2H), 7.11 – 7.04 (m, 1H), 6.95 – 6.88 (m, 1H), 6.83 – 6.74 (m, 1.5H), 6.68 (d, J = 2.5 Hz, 0.5H), 4.60 (d, J = 42.1 Hz, 2H), 3.81 (t, J = 5.9 Hz, 1H), 3.71 – 3.61 (m, 3H), 3.60 – 3.50 (m, 4H), 2.60 (t, J = 12.1 Hz, 2H), 2.44 (dt, J = 14.3, 4.7 Hz, 4H), 2.23 (ddd, J = 14.4, 6.4, 3.1 Hz, 1H), 1.87 (ddd, J = 35.5, 16.9, 9.3 Hz, |

| Compound No. | Structure and name | NMR data |
|---|---|---|
| | | 4H), 1.42 (dtd, J = 23.4, 12.0, 4.1 Hz, 2H), 1.30 (d, J = 10.5 Hz, 6H). |
| 99 | 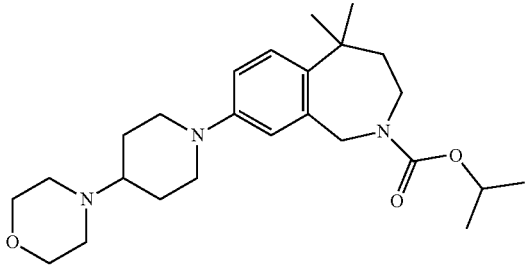 [SMILES: CC(C)OC(=O)N1CCC(C)(C)c2ccc(N3CCC(N4CCOCC4)CC3)cc2C1]<br>isopropyl 5,5-dimethyl-8-(4-morpholinopiperidin-1-yl)-1,3,4,5-tetrahydro-2H-benzo[c]azepine-2-carboxylate | $^1$H NMR (400 MHz, DMSO) δ 7.19 (dd, J = 8.8, 5.8 Hz, 1H), 6.75 (dt, J = 9.1, 2.7 Hz, 1H), 6.68 − 6.63 (m, 1H), 4.65 (dp, J = 37.5, 6.1 Hz, 1H), 4.43 (d, J = 12.0 Hz, 2H), 3.72 − 3.62 (m, 2H), 3.61 − 3.52 (m, 6H), 2.61 (t, J = 12.5 Hz, 2H), 2.48 − 2.44 (m, 4H), 2.30 − 2.18 (m, 1H), 1.90 − 1.72 (m, 4H), 1.45 (qd, J = 12.0, 4.0 Hz, 2H), 1.25 (d, J = 4.9 Hz, 6H), 1.09 (dd, J = 28.3, 6.2 Hz, 6H). |
| 100 | 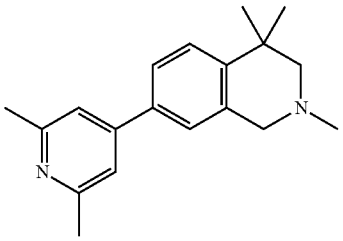<br>7-(2,6-dimethylpyridin-4-yl)-2,4,4-trimethyl-1,2,3,4-tetrahydroisoquinoline | $^1$H NMR (400 MHz, DMSO) δ 7.54 (dd, J = 8.3, 2.0 Hz, 1H), 7.46 (d, J = 8.2 Hz, 1H), 7.41 (d, J = 2.2 Hz, 1H), 7.32 (s, 2H), 3.52 (s, 2H), 2.46 (s, 6H), 2.36 (s, 2H), 2.34 (s, 3H), 1.27 (s, 6H). |
| 101 | 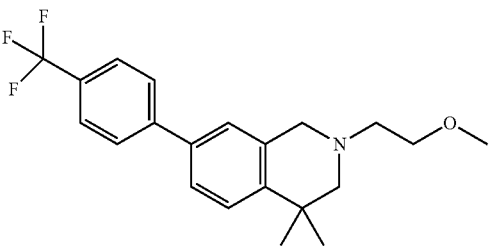 [SMILES: COCCN1Cc2cc(-c3ccc(C(F)(F)F)cc3)ccc2C(C)(C)C1]<br>2-(2-methoxyethyl)-4,4-dimethyl-7-(4-(trifluoromethyl)phenyl)-1,2,3,4-tetrahydroisoquinoline | $^1$H NMR (400 MHz, DMSO) δ 7.86 (d, J = 8.2 Hz, 2H), 7.79 (d, J = 8.3 Hz, 2H), 7.52 (dd, J = 8.2, 2.0 Hz, 1H), 7.46 (d, J = 8.1 Hz, 1H), 7.38 (d, J = 2.0 Hz, 1H), 3.67 (s, 2H), 3.54 (t, J = 5.9 Hz, 2H), 3.28 (s, 3H), 2.65 (t, J = 5.9 Hz, 2H), 2.47 (s, 2H), 1.27 (s, 6H). |
| 102 | 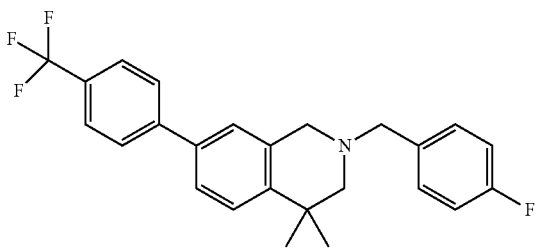 [SMILES: CC1(C)CN(Cc2ccc(F)cc2)Cc2cc(-c3ccc(C(F)(F)F)cc3)ccc21]<br>2-(4-fluorobenzyl)-4,4-dimethyl-7-(4-(trifluoromethyl)phenyl)-1,2,3,4-tetrahydroisoquinoline | $^1$H NMR (400 MHz, DMSO) δ 7.85 (d, J = 8.2 Hz, 2H), 7.78 (d, J = 8.2 Hz, 2H), 7.53 (dd, J = 8.3, 2.0 Hz, 1H), 7.48 (d, J = 8.2 Hz, 1H), 7.46 − 7.40 (m, 2H), 7.38 (d, J = 2.1 Hz, 1H), 7.23 − 7.13 (m, 2H), 3.64 (s, 2H), 3.63 (s, 2H), 2.41 (s, 2H), 1.26 (s, 6H). |

TABLE 1-continued

| Compound No. | Structure and name | NMR data |
|---|---|---|
| 103 | 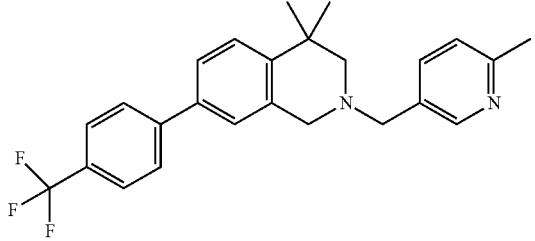 [SMILES: Cc1ccc(CN2Cc3cc(-c4ccc(C(F)(F)F)cc4)ccc3C(C)(C)C2)cn1]<br>4,4-dimethyl-2-((6-methylpyridin-3-yl)methyl)-7-(4-(trifluoromethyl)phenyl)-1,2,3,4-tetrahydroisoquinoline | $^1$H NMR (400 MHz, DMSO) δ 8.43 (d, J = 2.3 Hz, 1H), 7.85 (d, J = 8.2 Hz, 2H), 7.78 (d, J = 8.2 Hz, 2H), 7.67 (dd, J = 7.9, 2.2 Hz, 1H), 7.53 (dd, J = 8.2, 2.0 Hz, 1H), 7.47 (d, J = 8.2 Hz, 1H), 7.39 (d, J = 1.9 Hz, 1H), 7.24 (d, J = 7.8 Hz, 1H), 3.64 (s, 4H), 2.46 (s, 3H), 2.41 (s, 2H), 1.25 (s, 6H). |
| 104 | 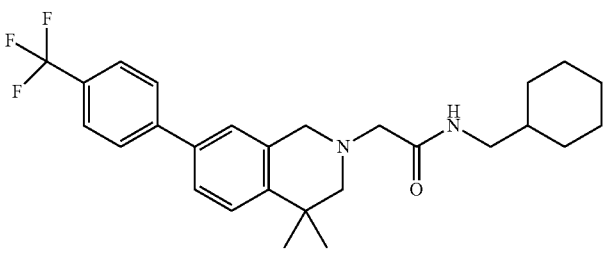 [SMILES: CC1(C)CN(CC(=O)NCC2CCCCC2)Cc2cc(-c3ccc(C(F)(F)F)cc3)ccc21]<br>N-(cyclohexylmethyl)-2-(4,4-dimethyl-7-(4-(trifluoromethyl)phenyl)-3,4-dihydroisoquinolin-2(1H)-yl)acetamide | $^1$H NMR (400 MHz, DMSO) δ 7.86 (d, J = 8.2 Hz, 2H), 7.79 (d, J = 8.4 Hz, 2H), 7.65 (t, J = 6.1 Hz, 1H), 7.55 (dd, J = 8.2, 2.0 Hz, 1H), 7.50 (d, J = 8.2 Hz, 1H), 7.40 (d, J = 2.1 Hz, 1H), 3.71 (s, 2H), 3.10 (s, 2H), 2.97 (t, J = 6.4 Hz, 2H), 1.72 – 1.53 (m, 5H), 1.40 (ddd, J = 11.2, 7.1, 3.1 Hz, 1H), 1.31 (s, 6H), 1.19 – 1.04 (m, 3H), 0.95 – 0.78 (m, 2H). 2H under solvent peaks. |
| 105 | 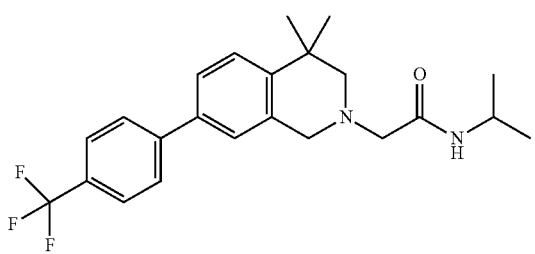 [SMILES: CC(C)NC(=O)CN1Cc2cc(-c3ccc(C(F)(F)F)cc3)ccc2C(C)(C)C1]<br>2-(4,4-dimethyl-7-(4-(trifluoromethyl)phenyl)-3,4-dihydroisoquinolin-2(1H)-yl)-N-isopropylacetamide | $^1$H NMR (400 MHz, DMSO) δ 7.86 (d, J = 8.2 Hz, 2H), 7.79 (d, J = 8.3 Hz, 2H), 7.55 (dd, J = 8.2, 2.0 Hz, 1H), 7.50 (d, J = 8.2 Hz, 1H), 7.46 – 7.36 (m, 2H), 3.92 (dp, J = 8.3, 6.4 Hz, 1H), 3.72 (s, 2H), 3.06 (s, 2H), 2.46 (s, 2H), 1.31 (s, 6H), 1.08 (d, J = 6.6 Hz, 6H). |
| 106 | 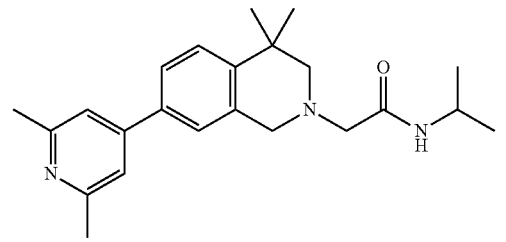 [SMILES: Cc1cc(-c2ccc3c(c2)CN(CC(=O)NC(C)C)CC3(C)C)cc(C)n1]<br>2-(7-(2,6-dimethylpyridin-4-yl)-4,4-dimethyl-3,4-dihydroisoquinolin-2(1H)-yl)-N-isopropylacetamide | $^1$H NMR (400 MHz, DMSO) δ 7.57 (dd, J = 8.2, 2.0 Hz, 1H), 7.48 (d, J = 8.2 Hz, 1H), 7.45 – 7.38 (m, 2H), 7.33 (s, 2H), 3.92 (dp, J = 8.2, 6.5 Hz, 1H), 3.71 (s, 2H), 3.05 (s, 2H), 2.46 (s, 6H), 2.45 (s, 2H), 1.30 (s, 6H), 1.07 (d, J = 6.5 Hz, 6H). |

TABLE 1-continued

| Compound No. | Structure and name | NMR data |
|---|---|---|
| 107 | 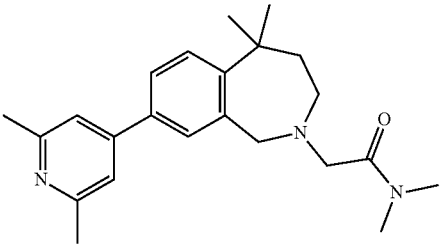<br>2-(8-(2,6-dimethylpyridin-4-yl)-5,5-dimethyl-1,3,4,5-tetrahydro-2H-benzo[c]azepin-2-yl)-N,N-dimethylacetamide | $^1$H NMR (400 MHz, DMSO) δ 7.57 (dd, J = 8.3, 2.1 Hz, 1H), 7.46 (d, J = 8.2 Hz, 1H), 7.42 (d, J = 2.1 Hz, 1H), 7.33 (s, 2H), 4.04 (s, 2H), 3.23 (s, 2H), 2.97 (d, J = 5.3 Hz, 2H), 2.95 (s, 3H), 2.79 (s, 3H), 2.47 (s, 6H), 1.74 (t, J = 5.9 Hz, 2H), 1.36 (s, 6H). |
| 108 | 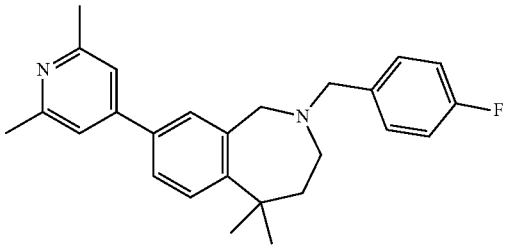 [SMILES: Cc1cc(-c2ccc3c(c2)CN(Cc2ccc(F)cc2)CCC3(C)C)cc(C)n1]<br>8-(2,6-dimethylpyridin-4-yl)-2-(4-fluorobenzyl)-5,5-dimethyl-2,3,4,5-tetrahydro-1H-benzo[c]azepine | $^1$H NMR (400 MHz, DMSO) δ 7.58 (dd, J = 8.2, 2.1 Hz, 1H), 7.48 (d, J = 8.2 Hz, 1H), 7.32 – 7.26 (m, 5H), 7.15 – 7.09 (m, 2H), 4.00 (s, 2H), 3.55 (s, 2H), 2.90 (t, J = 5.6 Hz, 2H), 2.46 (s, 6H), 1.74 (br s, 2H), 1.37 (s, 6H). |
| 109 | 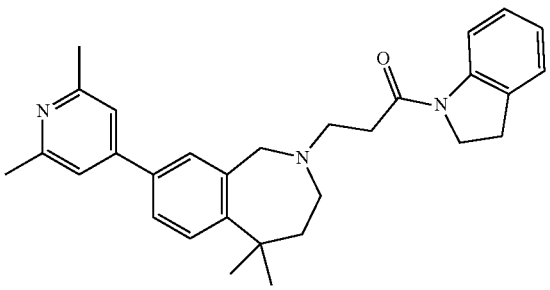 [SMILES: Cc1cc(-c2ccc3c(c2)CN(CCC(=O)N2CCc4ccccc42)CCC3(C)C)cc(C)n1]<br>3-(8-(2,6-dimethylpyridin-4-yl)-5,5-dimethyl-1,3,4,5-tetrahydro-2H-benzo[c]azepin-2-yl)-1-(indolin-1-yl)propan-1-one | $^1$H NMR (400 MHz, DMSO) δ 8.03 (d, J = 7.9 Hz, 1H), 7.61 – 7.52 (m, 2H), 7.45 (d, J = 8.4 Hz, 1H), 7.34 (s, 2H), 7.18 (d, J = 7.3 Hz, 1H), 7.10 (t, J = 7.7 Hz, 1H), 6.94 (td, J = 7.4, 1.1 Hz, 1H), 4.08 (t, J = 8.5 Hz, 2H), 4.03 (s, 2H), 3.05 (t, J = 8.5 Hz, 2H), 2.99 (t, J = 5.5 Hz, 2H), 2.74 – 2.68 (m, 2H), 2.66 – 2.58 (m, 2H), 2.47 (s, 6H), 1.74 (br s, 2H), 1.36 (s, 6H). |
| 110 | 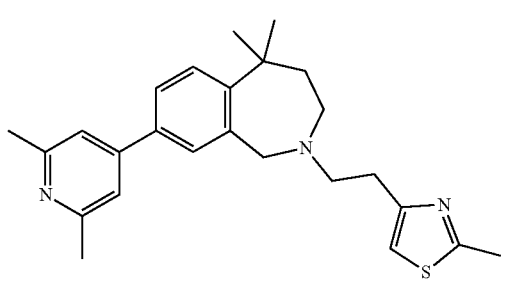<br>4-(2-(8-(2,6-dimethylpyridin-4-yl)-5,5-dimethyl-1,3,4,5-tetrahydro-2H-benzo[c]azepin-2-yl)ethyl)-2-methylthiazole | $^1$H NMR (400 MHz, DMSO) δ 7.61 – 7.50 (m, 2H), 7.44 (d, J = 8.2 Hz, 1H), 7.35 (s, 2H), 7.07 (s, 1H), 4.03 (s, 2H), 3.00 (t, J = 5.6 Hz, 2H), 2.82 (t, J = 7.5 Hz, 2H), 2.66 (dd, J = 8.7, 6.4 Hz, 2H), 2.56 (s, 3H), 2.47 (s, 6H), 1.73 (br s, 2H), 1.36 (s, 6H). |

TABLE 1-continued

| Compound No. | Structure and name | NMR data |
|---|---|---|
| 111 | 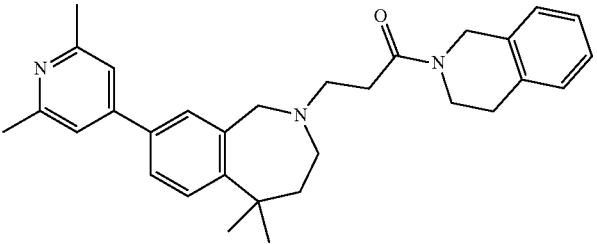 [SMILES: Cc1cc(-c2ccc3c(c2)CN(CCC(=O)N2CCc4ccccc4C2)CCC3(C)C)cc(C)n1]<br>1-(3,4-dihydroisoquinolin-2(1H)-yl)-3-(8-(2,6-dimethylpyridin-4-yl)-5,5-dimethyl-1,3,4,5-tetrahydro-2H-benzo[c]azepin-2-yl)propan-1-one | ¹H NMR (400 MHz, DMSO) δ 7.63 – 7.52 (m, 2H), 7.44 (d, J = 8.1 Hz, 1H), 7.36 (s, 2H), 7.19 – 6.97 (m, 4H), 4.56 (d, J = 19.1 Hz, 2H), 4.01 (d, J = 10.3 Hz, 2H), 3.61 (dt, J = 11.0, 6.0 Hz, 2H), 3.03 – 2.91 (m, 2H), 2.70 (q, J = 6.6 Hz, 2H), 2.65 – 2.54 (m, 4H), 2.47 (d, J = 2.1 Hz, 6H), 1.70 (br s, 2H), 1.35 (s, 6H). |
| 112 | 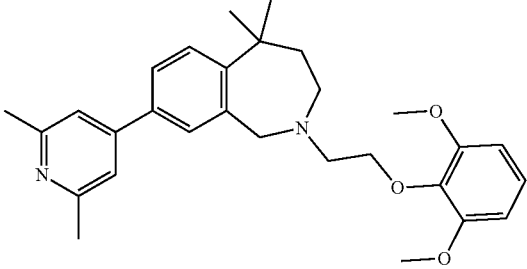 [SMILES: COc1cccc(OC)c1OCCN1CCC(C)(C)c2ccc(-c3cc(C)nc(C)c3)cc2C1]<br>2-(2-(2,6-dimethoxyphenoxy)ethyl)-8-(2,6-dimethylpyridin-4-yl)-5,5-dimethyl-2,3,4,5-tetrahydro-1H-benzo[c]azepine | ¹H NMR (400 MHz, DMSO) δ 7.57 (dd, J = 8.1, 2.1 Hz, 1H), 7.52 (d, J = 2.2 Hz, 1H), 7.45 (d, J = 8.2 Hz, 1H), 7.32 (s, 2H), 6.97 (t, J = 8.4 Hz, 1H), 6.64 (d, J = 8.4 Hz, 2H), 4.08 (s, 2H), 3.93 (t, J = 6.1 Hz, 2H), 3.70 (s, 6H), 3.04 (t, J = 5.6 Hz, 2H), 2.71 (t, J = 6.1 Hz, 2H), 2.45 (s, 6H), 1.73 (br s, 2H), 1.37 (s, 6H). |
| 113 | 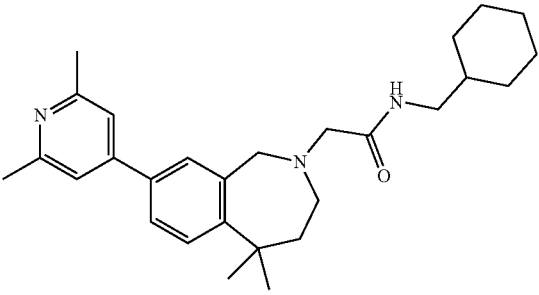 [SMILES: Cc1cc(-c2ccc3c(c2)CN(CC(=O)NCC2CCCCC2)CCC3(C)C)cc(C)n1]<br>N-(cyclohexylmethyl)-2-(8-(2,6-dimethylpyridin-4-yl)-5,5-dimethyl-1,3,4,5-tetrahydro-2H-benzo[c]azepin-2-yl)acetamide | ¹H NMR (400 MHz, DMSO) δ 7.59 (dd, J = 8.1, 2.1 Hz, 1H), 7.55 J = 6.1 Hz, 1H), 7.48 (d, J = 8.1 Hz, 1H), 7.42 (d, J = 2.2 Hz, 1H), 7.32 (s, 2H), 4.00 (s, 2H), 3.03 – 2.95 (m, 4H), 2.90 (t, J = 6.4 Hz, 2H), 2.46 (s, 6H), 1.75 (br s, 2H), 1.59 – 1.47 (m, 5H), 1.37 (s, 6H), 1.30 (dq, J = 7.6, 3.8 Hz, 1H), 1.10 – 0.98 (m, 3H), 0.85 – 0.72 (m, 2H). |
| 114 | 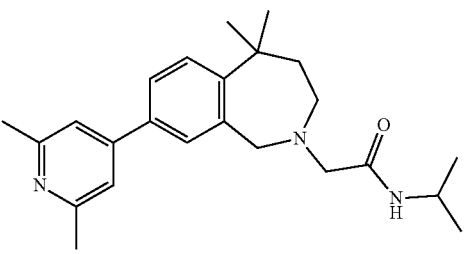 [SMILES: Cc1cc(-c2ccc3c(c2)CN(CC(=O)NC(C)C)CCC3(C)C)cc(C)n1]<br>2-(8-(2,6-dimethylpyridin-4-yl)-5,5-dimethyl-1,3,4,5-tetrahydro-2H-benzo[c]azepin-2-yl)-N-isopropylacetamide | ¹H NMR (400 MHz, DMSO) δ 7.60 (dd, J = 8.2, 2.1 Hz, 1H), 7.47 (d, J = 8.2 Hz, 1H), 7.45 (d, J = 2.2 Hz, 1H), 7.38 – 7.29 (m, 3H), 3.99 (s, 2H), 3.87 (dp, J = 8.3, 6.6 Hz, 1H), 3.02 – 2.93 (m, 4H), 2.46 (s, 6H), 1.74 (br s, 2H), 1.37 (s, 6H), 1.00 (d, J = 6.6 Hz, 6H). |

TABLE 1-continued

| Compound No. | Structure and name | NMR data |
|---|---|---|
| 115 | 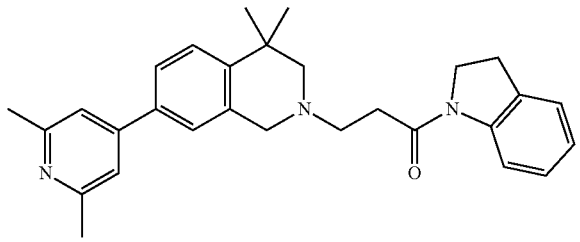 [SMILES: Cc1cc(-c2ccc3c(c2)CN(CCC(=O)N2CCc4ccccc42)CC3(C)C)cc(C)n1]<br>3-(7-(2,6-dimethylpyridin-4-yl)-4,4-dimethyl-3,4-dihydroisoquinolin-2(1H)-yl)-1-(indolin-1-yl)propan-1-one | $^1$H NMR (400 MHz, DMSO) δ 8.08 (d, J = 8.0 Hz, 1H), 7.54 (dd, J = 8.2, 2.0 Hz, 1H), 7.45 (d, J = 8.2 Hz, 1H), 7.42 (d, J = 2.0 Hz, 1H), 7.32 (s, 2H), 7.23 (d, J = 7.3 Hz, 1H), 7.14 (t, J = 7.7 Hz, 1H), 6.98 (t, J = 7.4 Hz, 1H), 4.16 (t, J = 8.5 Hz, 2H), 3.68 (s, 2H), 3.14 (t, J = 8.4 Hz, 2H), 2.82 (t, J = 6.8 Hz, 2H), 2.74 (t, J = 6.9 Hz, 2H), 2.46 (s, 6H), 1.27 (s, 6H). 2H under solvent peaks. |
| 116 | 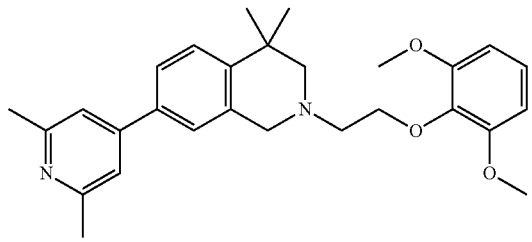<br>2-(2-(2,6-dimethoxyphenoxy)ethyl)-7-(2,6-dimethylpyridin-4-yl)-4,4-dimethyl-1,2,3,4-tetrahydroisoquinoline | $^1$H NMR (400 MHz, DMSO) δ 7.54 (dd, J = 8.2, 2.0 Hz, 1H), 7.45 (d, J = 8.2 Hz, 1H), 7.42 (d, J = 2.1 Hz, 1H), 7.32 (s, 2H), 6.99 (t, J = 8.4 Hz, 1H), 6.67 (d, J = 8.3 Hz, 2H), 4.03 (t, J = 5.8 Hz, 2H), 3.77 (s, 6H), 3.73 (s, 2H), 2.82 (t, J = 5.7 Hz, 2H), 2.55 (s, 2H), 2.46 (s, 6H), 1.27 (s, 6H). |
| 117 | 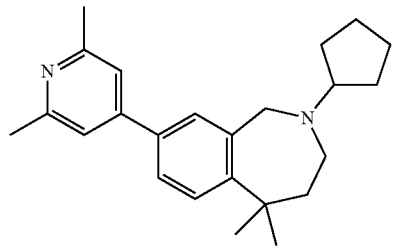 [SMILES: Cc1cc(-c2ccc3c(c2)CN(C2CCCC2)CCC3(C)C)cc(C)n1]<br>2-cyclopentyl-8-(2,6-dimethylpyridin-4-yl)-5,5-dimethyl-2,3,4,5-tetrahydro-1H-benzo[c]azepine | $^1$H NMR (400 MHz, DMSO) δ 7.56 (dd, J = 8.3, 2.2 Hz, 1H), 7.49 (d, J = 2.1 Hz, 1H), 7.44 (d, J = 8.2 Hz, 1H), 7.34 (s, 2H), 3.99 (s, 2H), 2.98 (t, J = 5.6 Hz, 2H), 2.67 (tq, J = 11.4, 5.7, 4.6 Hz, 1H), 2.47 (s, 6H), 1.84 – 1.67 (m, 4H), 1.65 – 1.51 (m, 2H), 1.47 – 1.28 (m, 4H), 1.35 (s, 6H). |
| 118 | 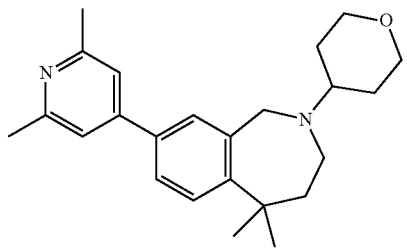 [SMILES: Cc1cc(-c2ccc3c(c2)CN(C2CCOCC2)CCC3(C)C)cc(C)n1]<br>8-(2,6-dimethylpyridin-4-yl)-5,5-dimethyl-2-(tetrahydro-2H-pyran-4-yl)-2,3,4,5-tetrahydro-1H-benzo[c]azepine | $^1$H NMR (400 MHz, DMSO) δ 7.60 – 7.50 (m, 2H), 7.45 (d, J = 7.9 Hz, 1H), 7.35 (s, 2H), 3.98 (s, 2H), 3.85 (dd, J = 11.8, 2.5 Hz, 2H), 3.20 (td, J = 11.7, 1.9 Hz, 2H), 2.99 (t, J = 5.7 Hz, 2H), 2.59 – 2.53 (m, 1H), 2.47 (s, 6H), 1.79 – 1.64 (m, 4H), 1.46 (qd, J = 11.8, 4.3 Hz, 2H), 1.35 (s, 6H). |

TABLE 1-continued

| Compound No. | Structure and name | NMR data |
|---|---|---|
| 119 | 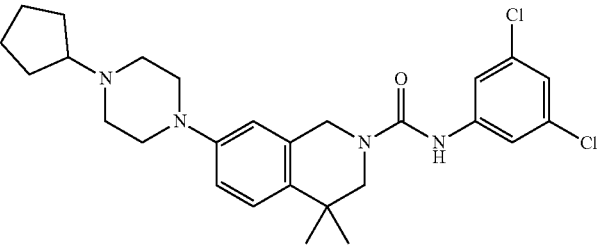 [SMILES: CC1(C)CN(C(=O)Nc2cc(Cl)cc(Cl)c2)Cc2cc(N3CCN(C4CCCC4)CC3)ccc21]<br>7-(4-cyclopentylpiperazin-1-yl)-N-(3,5-dichlorophenyl)-4,4-dimethyl-3,4-dihydroisoquinoline-2(1H)-carboxamide | $^1$H NMR (400 MHz, DMSO) δ 8.84 (s, 1H), 7.64 (d, J = 1.8 Hz, 2H), 7.22 (d, J = 8.7 Hz, 1H), 7.13 (t, J = 1.9 Hz, 1H), 6.82 (dd, J = 8.6, 2.6 Hz, 1H), 6.62 (d, J = 2.6 Hz, 1H), 4.64 (s, 2H), 3.48 (s, 2H), 3.08 (t, J = 5.0 Hz, 4H), 2.56 – 2.52 (m, 4H), 2.48 – 2.41 (m, 1H), 1.86 – 1.75 (m, 2H), 1.68 – 1.56 (m, 2H), 1.55 – 1.44 (m, 2H), 1.35 (dq, J = 16.2, 8.4 Hz, 2H), 1.19 (s, 6H). |
| 120 | 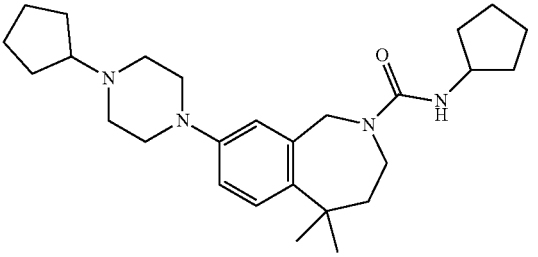 [SMILES: CC1(C)CCN(C(=O)NC2CCCC2)Cc2cc(N3CCN(C4CCCC4)CC3)ccc21]<br>N-cyclopentyl-8-(4-cyclopentylpiperazin-1-yl)-5,5-dimethyl-1,3,4,5-tetrahydro-2H-benzo[c]azepine-2-carboxamide | $^1$H NMR (400 MHz, DMSO) δ 7.18 (d, J = 8.8 Hz, 1H), 6.80 (s, 1H), 6.71 (dd, J = 8.7, 2.7 Hz, 1H), 5.79 (d, J = 7.2 Hz, 1H), 4.45 (s, 2H), 3.80 (q, J = 6.9 Hz, 1H), 3.52 (t, J = 5.8 Hz, 2H), 3.07 (t, J = 5.0 Hz, 4H), 2.55 – 2.51 (m, 4H), 2.47 – 2.44 (m, 1H), 1.85 – 1.73 (m, 4H), 1.71 – 1.59 (m, 4H), 1.57 – 1.47 (m, 4H), 1.43 – 1.26 (m, 6H), 1.23 (s, 6H). |
| 121 | 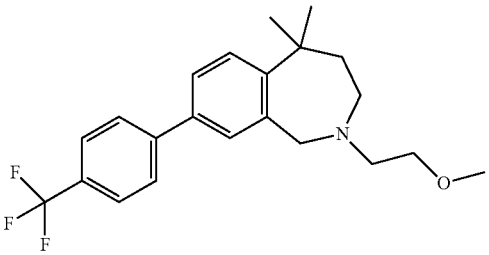 [SMILES: COCCN1CCC(C)(C)c2ccc(-c3ccc(C(F)(F)F)cc3)cc2C1]<br>2-(2-methoxyethyl)-5,5-dimethyl-8-(4-(trifluoromethyl)phenyl)-2,3,4,5-tetrahydro-1H-benzo[c]azepine | $^1$H NMR (400 MHz, DMSO) δ 7.88 (d, J = 8.2 Hz, 2H), 7.80 (d, J = 8.3 Hz, 2H), 7.56 (dd, J = 8.1, 2.2 Hz, 1H), 7.48 (d, J = 2.1 Hz, 1H), 7.47 (d, J = 8.1 Hz, 1H), 4.00 (s, 2H), 3.42 (t, J = 6.0 Hz, 2H), 3.21 (s, 3H), 2.96 (t, J = 5.6 Hz, 2H), 2.54 (t, J = 6.1 Hz, 2H), 1.72 (br s, 2H), 1.36 (s, 6H). |
| 122 | 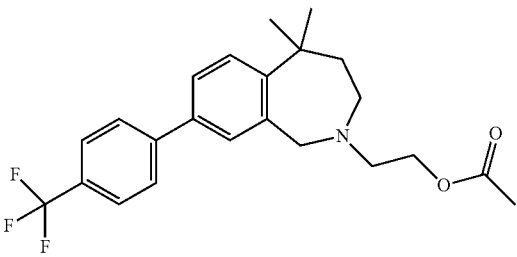 [SMILES: CC(=O)OCCN1CCC(C)(C)c2ccc(-c3ccc(C(F)(F)F)cc3)cc2C1]<br>2-(5,5-dimethyl-8-(4-(trifluoromethyl)phenyl)-1,3,4,5-tetrahydro-2H-benzo[c]azepin-2-yl)ethyl acetate | $^1$H NMR (400 MHz, DMSO) δ 7.89 (d, J = 8.2 Hz, 2H), 7.80 (d, J = 8.3 Hz, 2H), 7.57 (dd, J = 8.1, 2.2 Hz, 1H), 7.51 (d, J = 2.2 Hz, 1H), 7.47 (d, J = 8.2 Hz, 1H), 4.09 (t, J = 6.1 Hz, 2H), 4.04 (s, 2H), 2.99 (t, J = 5.5 Hz, 2H), 2.60 (t, J = 6.1 Hz, 2H), 1.97 (s, 3H), 1.72 (br s, 2H), 1.37 (s, 6H). |

TABLE 1-continued

| Compound No. | Structure and name | NMR data |
|---|---|---|
| 123 | 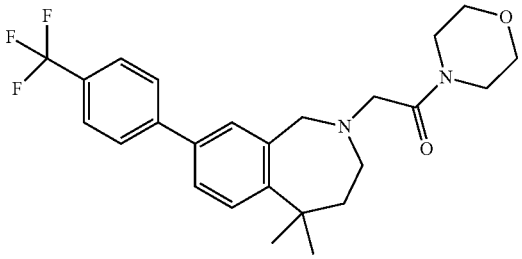 [SMILES: CC1(C)CCN(CC(=O)N2CCOCC2)Cc2cc(-c3ccc(C(F)(F)F)cc3)ccc21]<br>2-(5,5-dimethyl-8-(4-(trifluoromethyl)phenyl)-1,3,4,5-tetrahydro-2H-benzo[c]azepin-2-yl)-1-morpholinoethan-1-one | $^1$H NMR (400 MHz, DMSO) δ 7.87 (d, J = 8.2 Hz, 2H), 7.80 (d, J = 8.3 Hz, 2H), 7.57 (dd, J = 8.3, 2.1 Hz, 1H), 7.49 (d, J = 8.1 Hz, 1H), 7.40 (d, J = 2.2 Hz, 1H), 4.01 (s, 2H), 3.51 – 3.44 (m, 4H), 3.40 (dd, J = 13.1, 4.9 Hz, 4H), 3.25 (s, 2H), 2.95 (t, J = 5.6 Hz, 2H), 1.76 (br s, 2H), 1.37 (s, 6H). |
| 124 | 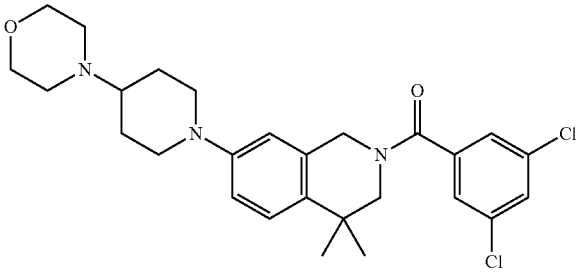 [SMILES: CC1(C)CN(C(=O)c2cc(Cl)cc(Cl)c2)Cc2cc(N3CCC(N4CCOCC4)CC3)ccc21]<br>(3,5-dichlorophenyl)(4,4-dimethyl-7-(4-morpholinopiperidin-1-yl)-3,4-dihydroisoquinolin-2(1H)-yl)methanone | $^1$H NMR (400 MHz, DMSO) δ 7.74 (s, 1H), 7.49 (d, J = 1.8 Hz, 2H), 7.19 (dd, J = 14.8, 8.7 Hz, 1H), 6.85 – 6.78 (m, 1H), 6.55 (s, 1H), 4.74 (s, 1H), 4.47 (s, 1H), 3.72 – 3.59 (m, 3H), 3.59 – 3.53 (m, 4H), 3.30 – 3.26 (m, 1H), 2.69 – 2.54 (m, 2H), 2.48 – 2.41 (m, 4H), 2.30 – 2.16 (m, 1H), 1.90 – 1.74 (m, 2H), 1.49 – 1.33 (m, 2H), 1.23 (s, 3H), 1.07 (s, 3H). |
| 125 | 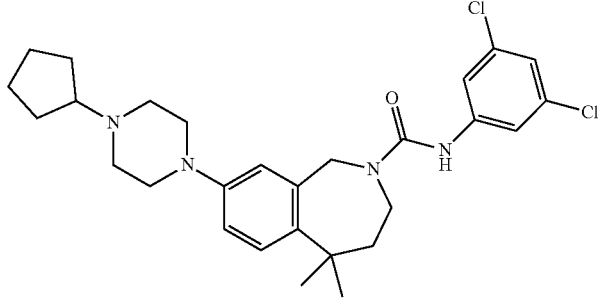 [SMILES: CC1(C)CCN(C(=O)Nc2cc(Cl)cc(Cl)c2)Cc2cc(N3CCN(C4CCCC4)CC3)ccc21]<br>8-(4-cyclopentylpiperazin-1-yl)-N-(3,5-dichlorophenyl)-5,5-dimethyl-1,3,4,5-tetrahydro-2H-benzo[c]azepine-2-carboxamide | $^1$H NMR (400 MHz, DMSO) δ 8.59 (s, 1H), 7.59 (d, J = 1.9 Hz, 2H), 7.21 (d, J = 8.7 Hz, 1H), 7.09 (t, J = 1.9 Hz, 1H), 6.86 (br s, 1H), 6.73 (dd, J = 8.7, 2.7 Hz, 1H), 4.62 (s, 2H), 3.74 – 3.64 (m, 2H), 3.12 – 2.51 (m, 4H), 2.48 – 2.40 (m, 1H), 1.86 3.03 (m, 4H), 2.55 – (br s, 2H), 1.83 – 1.75 (m, 2H), 1.66 – 1.56 (m, 2H), 1.56 – 1.46 (m, 2H), 1.40 – 1.31 (m, 2H), 1.27 (s, 6H). |
| 126 | 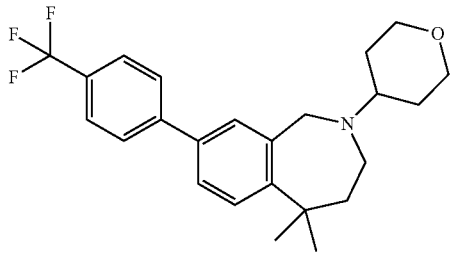 [SMILES: CC1(C)CCN(C2CCOCC2)Cc2cc(-c3ccc(C(F)(F)F)cc3)ccc21]<br>5,5-dimethyl-2-(tetrahydro-2H-pyran-4-yl)-8-(4-(trifluoromethyl)phenyl)-2,3,4,5-tetrahydro-1H-benzo[c]azepine | $^1$H NMR (400 MHz, DMSO) δ 7.88 (d, J = 8.2 Hz, 2H), 7.79 (d, J = 8.3 Hz, 2H), 7.56 – 7.51 (m, 2H), 7.47 (d, J = 8.1 Hz, 1H), 4.00 (s, 2H), 3.85 (d, J = 10.6 Hz, 2H), 3.20 (t, J = 11.4 Hz, 2H), 3.00 (t, J = 5.7 Hz, 2H), 2.60 – 2.53 (m, 1H), 1.78 – 1.67 (m, 4H), 1.46 (qd, J = 11.9, 4.4 Hz, 2H), 1.36 (s, 6H). |

TABLE 1-continued

| Compound No. | Structure and name | NMR data |
|---|---|---|
| 127 | 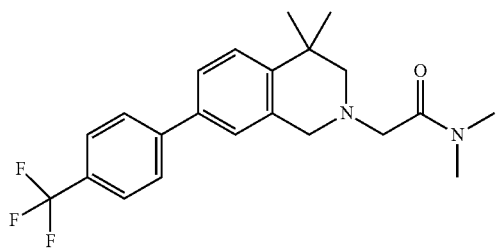 [SMILES: CN(C)C(=O)CN1Cc2cc(-c3ccc(C(F)(F)F)cc3)ccc2C(C)(C)C1]<br>2-(4,4-dimethyl-7-(4-(trifluoromethyl)phenyl)-3,4-dihydroisoquinolin-2(1H)-yl)-N,N-dimethylacetamide | $^1$H NMR (400 MHz, DMSO) δ 7.87 (d, J = 8.2 Hz, 2H), 7.79 (d, J = 8.2 Hz, 2H), 7.53 (dd, J = 8.2, 2.0 Hz, 1H), 7.48 (d, J = 8.2 Hz, 1H), 7.40 (d, J = 2.0 Hz, 1H), 3.68 (s, 2H), 3.08 (s, 3H), 2.84 (s, 3H), 1.28 (s, 6H). 2 + 2H under solvent peaks. |
| 128 | 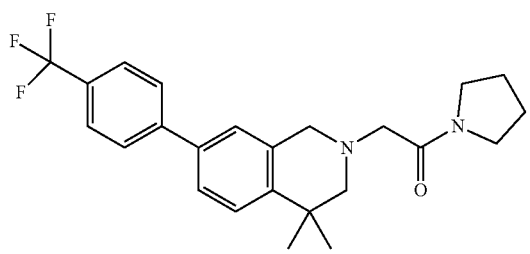 [SMILES: CC1(C)CN(CC(=O)N2CCCC2)Cc2cc(-c3ccc(C(F)(F)F)cc3)ccc21]<br>2-(4,4-dimethyl-7-(4-(trifluoromethyl)phenyl)-3,4-dihydroisoquinolin-2(1H)-yl)-1-(pyrrolidin-1-yl)ethan-1-one | $^1$H NMR (400 MHz, DMSO) δ 7.86 (d, J = 8.3 Hz, 2H), 7.79 (d, J = 8.3 Hz, 2H), 7.53 (dd, J = 8.2, 2.0 Hz, 1H), 7.48 (d, J = 8.2 Hz, 1H), 7.40 (d, J = 1.9 Hz, 1H), 3.71 (s, 2H), 3.55 (t, J = 6.7 Hz, 2H), 3.32 – 3.29 (m, 2H), 3.27 (s, 2H), 1.84 (p, J = 6.6 Hz, 2H), 1.76 (p, J = 6.8, 6.3 Hz, 2H), 1.28 (s, 6H). 2H under solvent peaks. |
| 129 | 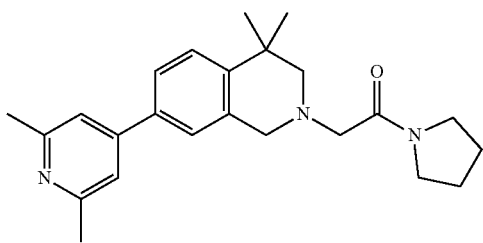 [SMILES: Cc1cc(-c2ccc3c(c2)CN(CC(=O)N2CCCC2)CC3(C)C)cc(C)n1]<br>2-(7-(2,6-dimethylpyridin-4-yl)-4,4-dimethyl-3,4-dihydroisoquinolin-2(1H)-yl)-1-(pyrrolidin-1-yl)ethan-1-one | $^1$H NMR (400 MHz, DMSO) δ 8.25 (s, 1H, formic acid), 7.55 (dd, J = 8.1, 2.0 Hz, 1H), 7.46 (d, J = 8.2 Hz, 1H), 7.43 (d, J = 2.0 Hz, 1H), 7.33 (s, 2H), 3.69 (s, 2H), 3.55 (t, J = 6.6 Hz, 2H), 3.32 (d, J = 6.9 Hz, 2H), 3.26 (s, 2H), 2.46 (s, 6H), 1.80 (dp, J = 26.1, 6.8 Hz, 4H), 1.27 (s, 6H). 2H under solvent peaks. |
| 130 | 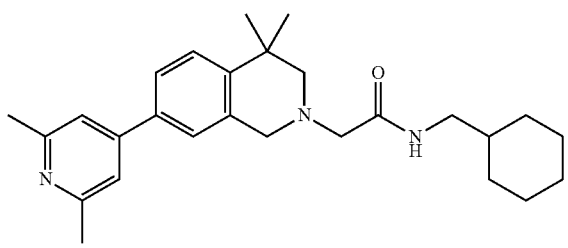 [SMILES: Cc1cc(-c2ccc3c(c2)CN(CC(=O)NCC2CCCCC2)CC3(C)C)cc(C)n1]<br>N-(cyclohexylmethyl)-2-(7-(2,6-dimethylpyridin-4-yl)-4,4-dimethyl-3,4-dihydroisoquinolin-2(1H)-yl)acetamide | $^1$H NMR (400 MHz, DMSO) δ 7.64 (t, J = 6.2 Hz, 1H), 7.57 (dd, J = 8.1, 2.0 Hz, 1H), 7.48 (d, J = 8.2 Hz, 1H), 7.42 (d, J = 2.0 Hz, 1H), 7.32 (s, 2H) 3.69 (s, 2H), 3.10 (s, 2H), 2.97 (t, J = 6.5 Hz, 2H), 2.46 (s, 6H), 1.71 – 1.54 (m, 5H), 1.47 – 1.36 (m, 1H), 1.30 (s, 6H), 1.21 – 1.06 (m, 3H), 0.94 – 0.79 (m, 2H). 2H under solvent peaks. |

TABLE 1-continued

| Compound No. | Structure and name | NMR data |
|---|---|---|
| 131 | 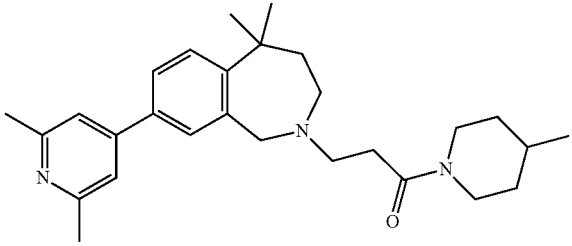
3-(8-(2,6-dimethylpyridin-4-yl)-5,5-dimethyl-1,3,4,5-tetrahydro-2H-benzo[c]azepin-2-yl)-1-(4-methylpiperidin-1-yl)propan-1-one | $^1$H NMR (400 MHz, DMSO) δ 8.21 (s, 1.28H, formic acid), 7.60 – 7.53 (m, 2H), 7.46 – 7.42 (m, 1H), 7.35 (s, 2H), 4.29 (d, J = 13.0 Hz, 1H), 4.00 (s, 2H), 3.80 (d, J = 13.6 Hz, 1H), 2.96 (t, J = 5.6 Hz, 2H), 2.85 (td, J = 13.0, 2.6 Hz, 1H), 2.60 – 2.54 (m, 2H), 2.47 (s, 6H), 2.46 – 2.36 (m, 3H), 1.71 (br s, 2H), 1.57 – 1.42 (m, 3H), 1.35 (s, 6H), 0.93 – 0.76 (m, 5H). |
| 132 | 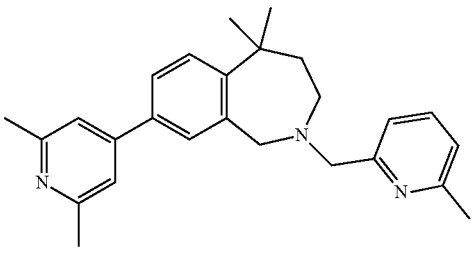
8-(2,6-dimethylpyridin-4-yl)-5,5-dimethyl-2-((6-methylpyridin-2-yl)methyl)-2,3,4,5-tetrahydro-1H-benzo[c]azepine | $^1$H NMR (400 MHz, DMSO) δ 8.26 (s, 1.68H, formic acid), 7.66 – 7.55 (m, 2H), 7.48 (d, J = 8.2 Hz, 1H), 7.34 (d, J = 2.2 Hz, 1H), 7.30 (s, 2H), 7.19 (d, J = 7.6 Hz, 1H), 7.10 (d, J = 7.5 Hz, 1H), 4.02 (s, 2H), 3.64 (s, 2H), 2.95 (t, J = 5.6 Hz, 2H), 2.46 (s, 6H), 2.41 (s, 3H), 1.76 (br s, 2H), 1.38 (s, 6H). |
| 133 | 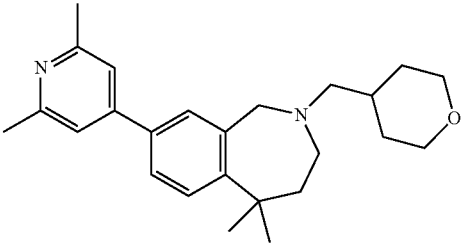 [SMILES: Cc1cc(-c2ccc3c(c2)CN(CC2CCOCC2)CCC3(C)C)cc(C)n1]
8-(2,6-dimethylpyridin-4-yl)-5,5-dimethyl-2-((tetrahydro-2H-pyran-4-yl)methyl)-2,3,4,5-tetrahydro-1H-benzo[c]azepine | $^1$H NMR (400 MHz, DMSO) δ 8.22 (s, 1.57H formic acid), 7.56 (dd, J = 8.2, 2.1 Hz, 1H), 7.49 (d, J = 2.1 Hz, 1H), 7.45 (d, J = 8.2 Hz, 1H), 7.34 (s, 2H), 3.95 (s, 2H), 3.78 (ddd, J = 11.3, 4.5, 1.9 Hz, 2H), 3.26 (td, J = 11.6, 2.1 Hz, 2H), 2.91 (t, J = 5.7 Hz, 2H), 2.47 (s, 6H), 2.22 (d, J = 7.1 Hz, 2H), 1.80 – 1.66 (m, 3H), 1.53 (dd, J = 13.6, 3.5 Hz, 2H), 1.36 (s, 6H), 1.06 (qd, J = 11.9, 4.4 Hz, 2H). |
| 134 | 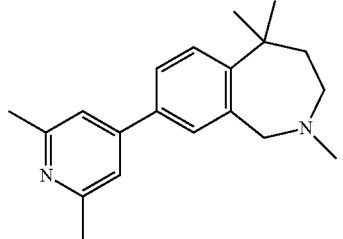
8-(2,6-dimethylpyridin-4-yl)-2,5,5-trimethyl-2,3,4,5-tetrahydro-1H-benzo[c]azepine | $^1$H NMR (400 MHz, DMSO) δ 8.21 (s, 1H, formic acid), 7.58 (dd, J = 8.2, 2.1 Hz, 1H), 7.51 (d, J = 2.2 Hz, 1H), 7.45 (d, J = 8.2 Hz, 1H), 7.35 (s, 2H), 3.92 (s, 2H), 2.87 (t, J = 5.6 Hz, 2H), 2.47 (s, 6H), 2.26 (s, 3H), 1.78 – 1.68 (m, 2H), 1.36 (s, 6H). |

TABLE 1-continued

| Compound No. | Structure and name | NMR data |
|---|---|---|
| 135 | 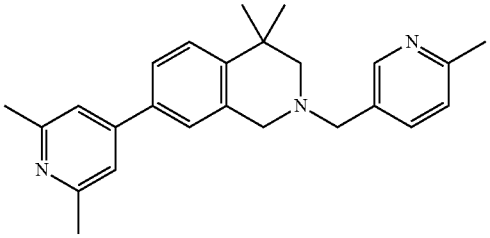<br>7-(2,6-dimethylpyridin-4-yl)-4,4-dimethyl-2-((6-methylpyridin-3-yl)methyl)-1,2,3,4-tetrahydroisoquinoline | ¹H NMR (400 MHz, DMSO) δ 8.43 (d, J = 2.1 Hz, 1H), 8.26 (s, 1.42H, formic acid), 7.67 (dd, J = 7.9, 2.3 Hz, 1H), 7.55 (dd, J = 8.1, 2.0 Hz, 1H), 7.45 (d, J = 8.2 Hz, 1H), 7.41 (d, J = 2.1 Hz, 1H), 7.32 (s, 2H), 7.24 (d, J = 7.8 Hz, 1H), 3.64 (s, 2H), 3.61 (s, 2H), 2.46 (s, 3H), 2.45 (s, 6H), 2.42 (s, 2H), 1.25 (s, 6H). |
| 136 | 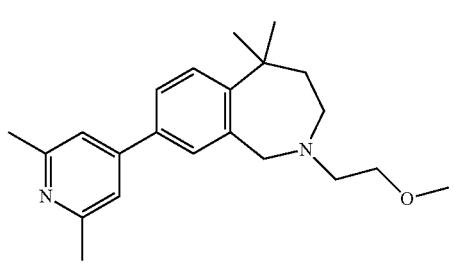<br>8-(2,6-dimethylpyridin-4-yl)-2-(2-methoxyethyl)-5,5-dimethyl-2,3,4,5-tetrahydro-1H-benzo[c]azepine | ¹H NMR (400 MHz, DMSO) δ 8.22 (s, 0.72H, formic acid), 7.57 (dd, J = 8.1, 2.2 Hz, 1H), 7.50 (d, J = 2.1 Hz, 1H), 7.44 (d, J = 8.2 Hz, 1H), 7.35 (s, 2H), 4.00 (s, 2H), 3.42 (t, J = 6.1 Hz, 2H), 3.21 (s, 3H), 2.96 (t, J = 5.6 Hz, 2H), 2.54 (t, J = 6.1 Hz, 2H), 2.47 (s, 6H), 1.75 – 1.67 (m, 2H), 1.35 (s, 6H). |
| 137 | 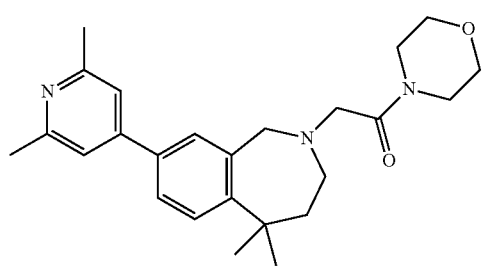 [SMILES: Cc1cc(-c2ccc3c(c2)CN(CC(=O)N2CCOCC2)CCC3(C)C)cc(C)n1]<br>2-(8-(2,6-dimethylpyridin-4-yl)-5,5-dimethyl-1,3,4,5-tetrahydro-2H-benzo[c]azepin-2-yl)-1-morpholinoethan-1-one | ¹H NMR (400 MHz, DMSO) δ 8.24 (s, 1.81H, formic acid), 7.58 (dd, J = 8.2, 2.1 Hz, 1H), 7.47 (d, J = 8.2 Hz, 1H), 7.42 (d, J = 2.2 Hz, 1H), 7.33 (s, 2H), 4.00 (s, 2H), 3.25 (s, 2H), 2.94 (t, J = 5.6 Hz, 2H), 2.47 (s, 6H), 1.78 – 1.73 (m, 2H), 1.36 (s, 6H). 8H under solvent peaks. |

A general route for the preparation of a compound of the application is described in Scheme I and Scheme II.

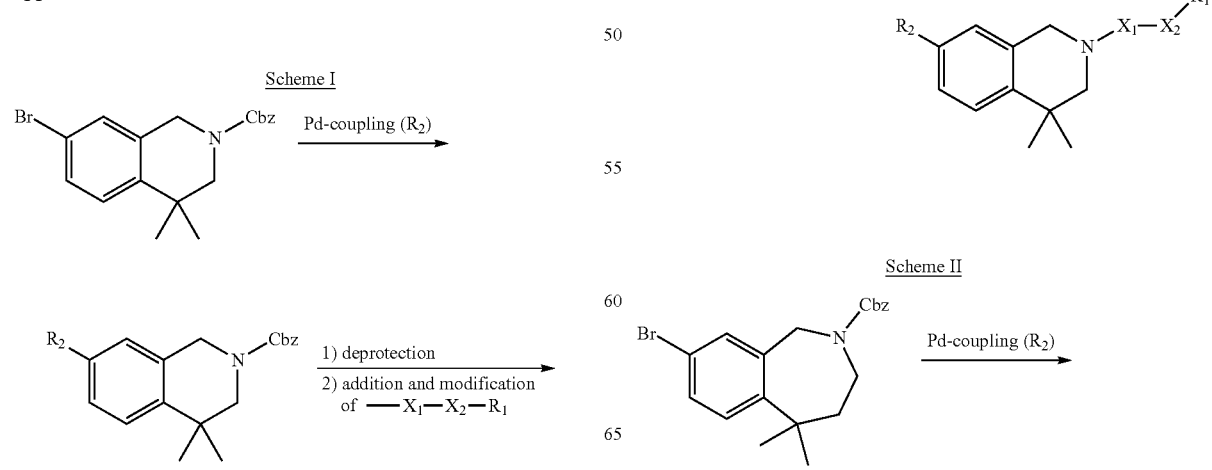

Methods of Treating Viral Infections, Pain, Cancer, and Other Diseases or Disorders In some embodiments, the present disclosure provides a method of modulating a Sigma receptor (e.g., Sigma-1 or Sigma-2, e.g., in vitro or in vivo) comprising contacting a cell with an effective amount of a compound of the present disclosure or a pharmaceutically acceptable salt, prodrug, or solvate thereof.

In some embodiments, modulating a Sigma receptor (e.g., Sigma-1 or Sigma-2, e.g., in vitro or in vivo) treats or prevents a disease or disorder associated with the Sigma receptor.

In some embodiments, modulating a Sigma receptor (e.g., Sigma-1 or Sigma-2, e.g., in vitro or in vivo) treats or prevents a disease or disorder associated with a viral infection.

In some embodiments, modulating a Sigma receptor (e.g., Sigma-1 or Sigma-2, e.g., in vitro or in vivo) prevents the replication or transmission of a viral infection.

In one aspect, the present disclosure provides a method of treating or preventing an infectious disease or disorder, wherein the infectious disease or disorder is caused by a bacterium, a fungus, or a virus.

In one aspect, the present disclosure provides a method of treating a viral infection in a subject, or an illness resulting from the viral infection, comprising administering to an individual in need thereof a therapeutically effective amount of a compound of Formula (I), MIN-101, MIN-101-B, MIN-S006, or a pharmaceutically acceptable salt, prodrug, or solvate thereof.

In one aspect, the present disclosure provides a compound of Formula (I), MIN-101, MIN-101-B, MIN-S006, or a pharmaceutically acceptable salt, prodrug, or solvate thereof, for use in treating a viral infection in a subject, or an illness resulting from the viral infection.

In one aspect, the present disclosure provides the use of a compound of Formula (I), MIN-101, MIN-101-B, MIN-S006, or a pharmaceutically acceptable salt, prodrug, or solvate thereof, in the manufacture of a medicament, for the treatment of a viral infection in a subject, or an illness resulting from the viral infection.

In one aspect, the present disclosure provides a method of preventing a viral infection in a subject, comprising administering to an individual in need thereof a therapeutically effective amount of a compound of Formula (I), MIN-101, MIN-101-B, MIN-S006, or a pharmaceutically acceptable salt, prodrug, or solvate thereof.

In one aspect, the present disclosure provides a method of preventing transmission of a virus, comprising administering to an individual in need thereof a therapeutically effective amount of a compound of Formula (I), MIN-101, MIN-101-B, MIN-S006, or a pharmaceutically acceptable salt, prodrug, or solvate thereof.

In some embodiments, the present disclosure provides a method of binding a Sigma receptor (e.g., Sigma-1 or Sigma-2) with a compound of Formula (I), MIN-101, MIN-101-B, MIN-S006, or a pharmaceutically acceptable salt, prodrug, or solvate thereof.

In one embodiment, the viral infection is caused by a coronavirus, herpes simplex virus, human immunodeficiency virus, influenza virus, or human papillomavirus.

In one embodiment, the coronavirus is Middle East respiratory syndrome-related coronavirus, severe acute respiratory syndrome coronavirus, or severe acute respiratory syndrome coronavirus 2 (i.e., SARS-CoV-2 or COVID-19).

In one embodiment, the illness resulting from the viral infection is severe acute respiratory syndrome, Middle East respiratory syndrome, acquired immune deficiency syndrome, influenza, or viral hepatitis.

In some embodiments, the present disclosure provides a method of treating a viral infection in a subject, or an illness resulting from the viral infection, comprising administering to a subject in need thereof a therapeutically effective amount of a compound of Formula (I), MIN-101, MIN-101-B, MIN-S006, or a pharmaceutically acceptable salt, prodrug, or solvate thereof, wherein the subject is at risk of viral infection. Examples of subjects at risk of viral infection include subjects who work in or have visited high-risk environments (e.g., college students and staff, cruise line participants, healthcare workers, first responders, doctors, nurses, subjects in assisted living facilities, or subjects in nursing homes). Examples of subjects at risk of viral infection include subjects who are known to be at a high risk of infection (e.g., healthcare workers, first responders, doctors, nurses, the elderly, a subject with a previous positive test for SARS-CoV-2, or subjects cohabiting with a subject who is known to be at high risk for infection).

In one aspect, the present disclosure provides a method of treating Alzheimer's disease comprising administering to an individual in need thereof a therapeutically effective amount of a compound of Formula (I), MIN-101, MIN-101-B, MIN-S006, or a pharmaceutically acceptable salt, prodrug, or solvate thereof.

In one aspect, the present disclosure provides a compound of Formula (I), MIN-101, MIN-101-B, MIN-S006, or a pharmaceutically acceptable salt, prodrug, or solvate thereof for use in treating Alzheimer's disease.

In one aspect, the present disclosure provides the use of a compound of Formula (I), MIN-101, MIN-101-B, MIN-S006, or a pharmaceutically acceptable salt, prodrug, or solvate thereof, in the manufacture of a medicament, for the treatment of Alzheimer's disease.

In one aspect, the present disclosure provides a method of preventing Alzheimer's disease comprising administering to an individual in need thereof a therapeutically effective amount of a compound of Formula (I), MIN-101, MIN-101-B, MIN-S006, or a pharmaceutically acceptable salt, prodrug, or solvate thereof.

In one aspect, the present disclosure provides a method of treating a disease, or symptom of a disease, comprising administering to an individual in need thereof a therapeutically effective amount of a compound of Formula (I), MIN-101, MIN-101-B, MIN-S006, or a pharmaceutically acceptable salt, prodrug, or solvate thereof, wherein the disease, or symptom of a disease, is anxiety, depression, emotional abnormality, schizophrenia, narcotic intoxication, narcotic addiction, sharp pain, dyskinesia, cerebrovascular disease, epilepsy, dementia, Parkinson's syndrome, attention deficit disorder, irritable bowel syndrome, irritable colon, spastic colon, colitis *mucosus*, enterocolitis, diverticulitis, dysentery, hypertension, arrhythmia, angina pectoris, amyotrophic lateral sclerosis (ALS), Huntington disease, stroke, retinal degeneration, or cognitive impairment in neuropsychiatric diseases.

In one aspect, the present disclosure provides a compound of Formula (I), MIN-101, MIN-101-B, MIN-S006, or a pharmaceutically acceptable salt, prodrug, or solvate thereof, for use in treating a disease, or symptom of a disease, wherein the disease, or symptom of a disease, is anxiety, depression, emotional abnormality, schizophrenia, narcotic intoxication, narcotic addiction, sharp pain, dyskinesia, cerebrovascular disease, epilepsy, dementia, Parkinson's syndrome, attention deficit disorder, irritable bowel syndrome, irritable colon, spastic colon, colitis mucosus, enterocolitis, diverticulitis, dysentery, hypertension, arrhythmia, angina pectoris, amyotrophic lateral sclerosis (ALS), Huntington disease, stroke, retinal degeneration, or cognitive impairment in neuropsychiatric diseases.

In one aspect, the present disclosure provides the use of a compound of Formula (I), MIN-101, MIN-101-B, MIN-S006, or a pharmaceutically acceptable salt, prodrug, or solvate thereof, in the manufacture of a medicament, for treatment of a disease, or symptom of a disease, wherein the disease, or symptom of a disease, is anxiety, depression, emotional abnormality, schizophrenia, narcotic intoxication, narcotic addiction, sharp pain, dyskinesia, cerebrovascular disease, epilepsy, dementia, Parkinson's syndrome, attention deficit disorder, irritable bowel syndrome, irritable colon, spastic colon, colitis mucosus, enterocolitis, diverticulitis, dysentery, hypertension, arrhythmia, angina pectoris, amyotrophic lateral sclerosis (ALS), Huntington disease, stroke, retinal degeneration, or cognitive impairment in neuropsychiatric diseases.

In one aspect, the present disclosure provides a method of preventing a disease, or symptom of a disease, comprising administering to an individual in need thereof a therapeutically effective amount of a compound of Formula (I), MIN-101, MIN-101-B, MIN-S006, or a pharmaceutically acceptable salt, prodrug, or solvate thereof, wherein the disease, or symptom of a disease, is anxiety, depression, emotional abnormality, schizophrenia, narcotic intoxication, narcotic addiction, sharp pain, dyskinesia, cerebrovascular disease, epilepsy, dementia, Parkinson's syndrome, attention deficit disorder, irritable bowel syndrome, irritable colon, spastic colon, colitis mucosus, enterocolitis, diverticulitis, dysentery, hypertension, arrhythmia, angina pectoris, amyotrophic lateral sclerosis (ALS), Huntington disease, stroke, retinal degeneration, or cognitive impairment in neuropsychiatric diseases.

In one aspect, the present disclosure provides a method of treating and/or preventing pain in a subject in need of treatment comprising administering to the subject a therapeutically effective amount of a compound of Formula (I), MIN-101, MIN-101-B, MIN-S006, or a pharmaceutically acceptable salt, prodrug, or solvate thereof.

In one embodiment, the pain is acute pain, chronic pain, toxic pain, neuropathic pain, nociceptive pain, inflammatory pain, post-operative pain, visceral pain, chemotherapy-induced pain, peripheral neuropathy, fibromyalgia, or a combination thereof.

In one aspect, the present disclosure provides a method of promoting an antihyperalgesic effect in a subject suffering from hyperalgesia comprising administering to the subject a therapeutically effective amount of a compound of Formula (I), MIN-101, MIN-101-B, MIN-S006, or a pharmaceutically acceptable salt, prodrug, or solvate thereof.

In one aspect, the present disclosure provides a method of reducing sensitivity to pain in a subject comprising administering to the subject a therapeutically effective amount of a compound of Formula (I), MIN-101, MIN-101-B, MIN-S006, or a pharmaceutically acceptable salt, prodrug, or solvate thereof.

In one aspect, this application pertains to methods of treating and preventing pain comprising administering to a subject in need of treatment a therapeutically effective amount of a compound of Formula (I), MIN-101, MIN-101-B, MIN-S006, or a pharmaceutically acceptable salt, prodrug, or solvate thereof.

In one embodiment, the pain treated and/or prevented by the methods of this application is acute pain.

Acute pain includes, but is not limited to, nociceptive or inflammatory pain arising from thermal, mechanical, or chemical stimulation of sensory nerve fibers responding to stimuli approaching or exceeding harmful intensity caused by injury and/or visceral pain, including, but not limited to, irritable bowel syndrome (IBS) with or without chronic fatigue syndrome (CFS), inflammatory bowel disease (IBD), Crohn's disease, food poisoning, food allergies, pain associated with gas, hernia, pain associate with gallstones and/or kidney stones, endometriosis, gastroesophageal reflux disease (GERD), appendicitis, interstitial cystitis, deep somatic pain (e.g., sprains, broken bones), neuropathic pain caused by damage or disease affecting the somatosensory nervous system, and superficial somatic pain (e.g., burns).

In one embodiment, the pain treated and/or prevented by the methods of this application is nociceptive pain.

Nociceptive pain includes, but is not limited to, pain arising from physical damage to the body from heat, cold, pressure, pinching, twisting, rubbing, chemicals, among others. Specific examples of nociceptive pain include sprains, bone fractures, burns, bruises, contusions, inflammation, obstructions, and myofascial pain.

In one embodiment, the pain treated and/or prevented by the methods of this application is inflammatory pain.

Inflammatory pain includes, but is not limited to, pain arising from inflammation, including arthritis.

In one embodiment, the pain treated and/or prevented by the methods of this application is visceral pain.

Visceral pain includes, but is not limited to, pain arising from the distension, ischemia, and inflammation of the nociceptors of the thoracic, pelvic, or abdominal organs.

In one embodiment, the pain treated and/or prevented by the methods of this application is chronic, i.e., persistent pain.

Chronic pain includes, but is not limited to, post-operative pain, cancer pain (e.g., chemotherapy-induced pain), degenerative major joint disease pain (e.g., osteoarthritis, rheumatoid arthritis, ankylosing spondylitis, Reiter's syndrome, psoriatic arthritis, gout, pseudogout, infectious arthritis, tendonitis, bursitis, bone lesions, and joint soft tissue inflammation) headaches (e.g., cluster headaches, migraine headaches, tension-type headaches), vascular pain (e.g., arteriosclerosis obliterans, thromboangiitis obliterans, acute arterial occlusion, embolism, congenital arteriovenous aneurysm, vasospastic disease, Raynaud's disease, acrocyanosis, acute venous occlusion, thrombophlebitis, varicose veins, and lymphedema), myofascial or muscle pain (e.g., temporomandibular joint (TMJ) disease/syndrome, chronic musculoskeletal pain, fibromyalgia with or without chronic fatigue syndrome, myofascial pain syndrome or referred pain), neuralgias (trigeminal, postherpetic, glossopharyngeal), shingles, neuropathy, central pain syndrome, complex regional pain syndrome, hyperalgesia, allodynia, central sensitization, peripheral sensitization, disinhibition, and augmented facilitation.

In one embodiment, the pain treated and/or prevented by the methods of this application is chemotherapy induced-pain.

In one embodiment, the pain treated and/or prevented by the methods of this application is post-operative pain.

Post-operative pain includes, but is not limited to, tissue injury together optionally combined with muscle spasm after surgery.

In one embodiment, the pain treated and/or prevented by the methods of this application is fibromyalgia and/or a symptom of fibromyalgia. Fibromyalgia is a disorder characterized by widespread musculoskeletal pain often accompanied by fatigue and/or sleep disorders.

In one embodiment, the pain treated and/or prevented by the methods of this application is fibromyalgia with chronic fatigue syndrome and/or a symptom of fibromyalgia with chronic fatigue syndrome.

In one embodiment, the pain treated and/or prevented by the methods of this application is neuropathic pain, i.e., neuropathy. In one embodiment, neuropathic pain may be caused by damage or disease to any part of the nervous system or somatosensory system. Types of neuropathic pain include, but are not limited to, diabetic neuropathy, peripheral neuropathy, and diabetic peripheral neuropathy, i.e., diabetic peripheral neuropathic pain.

Neuropathic pain caused by damage or disease to any part of the somatosensory system include, but is not limited to, phantom limb pain, multiple chemical sensitivity, sick building syndrome, repetition stress injury, chronic whiplash, chronic lime disease, side effects of silicone breast implants, candidiasis hypersensitivity, the Gulf War Syndrome, food allergies, mitral valve prolapse, and hypoglycemia.

In one embodiment, the pain treated and/or prevented by the methods of this application is diabetic neuropathy, i.e., nerve damage caused by diabetes.

In one embodiment, the pain treated and/or prevented by the methods of this application is peripheral neuropathy, i.e., peripheral neuropathic pain, which is damage or disease affecting sensory, motor, and/or autonomic nerves of the peripheral nervous system.

Peripheral neuropathic pain occurs when peripheral nerves fail to carry information to and from the brain and spinal cord, resulting in pain, loss of sensation, or inability to control muscles. In some cases, the failure of nerves that control blood vessels, intestines, and other organs results in abnormal blood pressure, digestion problems, and loss of other basic body processes. Symptoms also depend on whether the condition affects the whole body or just one nerve. Risk factors for neuropathy include diabetes, heavy alcohol use, exposure to certain chemicals and drugs, prolonged pressure on a nerve. Some people have a hereditary predisposition for peripheral neuropathy.

In one embodiment, the peripheral neuropathy in a subject results from an exposure to toxins, alcohol abuse, malnutrition, diabetes, Guillain-Barre syndrome, or complications from kidney failure, complications from cancer, infections (e.g., AIDS, shingles, Lyme disease), kidney disease, thyroid disease, parathyroid disease, and/or carpal tunnel syndrome.

Causes of peripheral neuropathic pain include, without limitation, neuropathies associated with systemic disease like diabetic neuropathy, neuropathies associated with metabolic conditions like alcoholic neuropathy and burning feet syndrome, neuropathies associated with viral infections like herpes zoster and HIV, neuropathies associated with nutritional deficiencies, neuropathies associated with toxins, neuropathies associated with tumor compression, neuropathies associated with remote manifestations of malignancies, neuropathies associated with drugs like chemotherapy, neuropathies associated with radiation, neuropathies associated with immune mediated disorders, and neuropathies associated with physical trauma to a nerve trunk.

The four cardinal patterns of peripheral neuropathic pain are mononeuropathy, mononeuropathic multiplex, polyneuropathy, and autonomic neuropathy.

In one embodiment, the pain treated and/or prevented by the methods of this application is peripheral neuropathy that is peripheral mononeuropathy. A mononeuropathy is a peripheral neuropathy involving functional loss or pathological change affecting a single nerve or nerve group. Mononeuropathy is most often caused by damage to a local area resulting from injury or trauma, although occasionally systemic disorders may cause isolated nerve damage. The usual causes are direct trauma, prolonged pressure on the nerve, and compression of the nerve by swelling or injury to nearby body structures.

In one embodiment, the damage from a mononeuropathy includes destruction of the myelin sheath (covering) of the nerve or of part of the nerve cell (the axon). This damage slows or prevents conduction of impulses through the nerve. Mononeuropathy may involve any part of the body. Mononeuropathic pain is associated with, e.g., a sciatic nerve dysfunction, a common peroneal nerve dysfunction, a radial nerve dysfunction, an ulnar nerve dysfunction, a cranial mononeuropathy VI, a cranial mononeuropathy VII, a cranial mononeuropathy III (compression type), a cranial mononeuropathy III (diabetic type), an axillary nerve dysfunction, a carpal tunnel syndrome, a femoral nerve dysfunction, a tibial nerve dysfunction, a Bell's palsy, a thoracic outlet syndrome, a carpal tunnel syndrome or other focal entrapment neuropathy, and a sixth (abducent) nerve palsy. For example, the mononeuropathy is ulnar nerve palsy, radial nerve palsy, or peroneal nerve palsy.

In one embodiment, the pain treated and/or prevented by the methods of this application is peripheral neuropathy that is a mononeuropathic multiplex. A mononeuropathic multiplex is a peripheral neuropathy involving functional loss or pathological change that sequentially or simultaneously affects several non-contiguous nerves in an asymmetric manner. A neuropathic pain based on mononeuropathy multiplex may develop over days to years and typically presents with acute or subacute loss of sensory and motor function of individual nerves. The pattern of involvement is asymmetric; however, as the disease progresses deficit(s) becomes more confluent and symmetrical, making it difficult to differentiate from polyneuropathy. Mononeuropathic multiplex may also cause pain characterized as deep, aching pain that is worse at night, and frequently present in the lower back, hip, or leg. Mononeuropathic multiplex may also cause pain characterized as acute, unilateral, severe limb pain followed by anterior muscle weakness and loss of knee reflex. Mononeuropathic multiplex pain is associated with, e.g., diabetes mellitus, infections, such as, e.g., leprosy, Lyme disease, HIV, and toxicity.

In one embodiment, the pain treated and/or prevented by the methods of this application is peripheral neuropathy that is peripheral polyneuropathy, which is a peripheral neuropathy involving functional loss or pathological change affecting multiple nerves throughout the body in a symmetric manner. A polyneuropathy may be acute and appear without warning, or chronic and develop gradually over a longer period of time. Many polyneuropathies have both motor and sensory involvement, and some also involve dysfunction of the autonomic nervous system. These disorders are often symmetrical, and usually due to various systematic illnesses and disease processes that affect the peripheral nervous system in its entirety. A polyneuropathy frequently affect the feet and hands, causing weakness, loss of sensation, pins-and-needle sensations or burning pain. Polyneuropathies can be classified in different ways, such as by cause, by speed of progression, or by the parts of the body involved. Classes of polyneuropathy are also distinguished by which part of the nerve cell is mainly affected: the axon, the myelin sheath, or the cell body.

Causes of polyneuropathic pain, include, without limitation, post-polio syndrome, postmastectomy syndrome, diabetic neuropathy, alcohol neuropathy, amyloid, toxins, AIDS, hypothyroidism, uremia, vitamin deficiencies, chemotherapy-induced pain, 2',3'-didexoycytidine (ddC) treatment, Guillain-Barre syndrome, and Fabry's disease.

In one embodiment, the pain treated and/or prevented by the methods of this application is peripheral neuropathy that is an autonomic neuropathy. An autonomic neuropathy is a peripheral neuropathy involving functional loss or pathological change affecting the non-voluntary, non-sensory nervous system (i.e., the autonomic nervous system). Autonomic neuropathy is a form of polyneuropathy which affects mostly the internal organs such as the bladder, muscles, the cardiovascular system, the digestive tract, and the genital organs.

In one embodiment, the treatment and/or prevention of pain in a subject with peripheral and/or diabetic neuropathy includes the reduction in one or more symptoms in the subject selected from the group consisting of tingling, numbness, loss of sensation (e.g., in the arms and/or legs), and a burning sensation (e.g. in the feet and/or hands).

In one embodiment, the pain treated by the methods of this application is neuropathy induced by chemotherapy.

In one embodiment, the pain prevented by the methods of this application is neuropathy induced by chemotherapy.

In one aspect, the present disclosure provides a method of treating and/or preventing cancer in a subject in need thereof comprising administering to the subject a therapeutically effective amount of a compound of any one of Formula (I), MIN-101, MIN-101-B, MIN-S006, or a pharmaceutically acceptable salt, prodrug, or solvate thereof.

In one embodiment, the cancer is breast cancer, prostate cancer, colon cancer, rectal cancer, pancreatic cancer, liver cancer, bladder cancer, thyroid cancer, kidney cancer, skin cancer, non-Hodgkin lymphoma, or uterine cancer.

In one aspect, treating cancer results in a reduction in size of a tumor. A reduction in size of a tumor may also be referred to as "tumor regression." Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. In a preferred aspect, size of a tumor may be measured as a diameter of the tumor.

In another aspect, treating cancer results in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

In another aspect, treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. In a preferred aspect, number of tumors may be measured by counting tumors visible to the naked eye or at a specified magnification. In a preferred aspect, the specified magnification is 2×, 3×, 4×, 5×, 10×, or 50×.

In another aspect, treating cancer results in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. In a preferred aspect, the number of metastatic lesions may be measured by counting metastatic lesions visible to the naked eye or at a specified magnification. In a preferred aspect, the specified magnification is 2×, 3×, 4×, 5×, 10×, or 50×.

In another aspect, treating cancer results in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means.

In a preferred aspect, an increase in average survival time of a population may be measured, for example, by calculating for a population the average length of survival following initiation of treatment with a compound of Formula (I). In another preferred aspect, an increase in average survival time of a population may also be measured, for example, by calculating for a population the average length of survival following completion of a first round of treatment with a compound of Formula (I).

In another aspect, treating cancer results in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with a compound of Formula (I). In another preferred aspect, an increase in average survival time of a population may also be measured, for example, by calculating for a population the average length of survival following completion of a first round of treatment with a compound of Formula (I).

In another aspect, treating cancer results in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. In a preferred aspect, tumor growth rate is measured according to a change in tumor diameter per unit time.

In another aspect, treating cancer results in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. In a preferred aspect, tumor regrowth is measured, for example, by measuring an increase in the diameter of a tumor after a prior tumor shrinkage that followed treatment. In another preferred aspect, a decrease in tumor regrowth is indicated by failure of tumors to reoccur after treatment has stopped.

Compounds designed, selected and/or optimized by methods described above, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) High Throughput Screening, Marcel Dekker; and U.S. Pat. No. 5,763,263. High-throughput assays can use one or more different assay techniques including, but not limited to, those described below.

Various in vitro or in vivo biological assays are may be suitable for detecting the effect of the compounds of the present disclosure. These in vitro or in vivo biological assays can include, but are not limited to, enzymatic activity assays, electrophoretic mobility shift assays, reporter gene assays, in vitro cell viability assays, and the assays described herein.

The biological activity of the compounds of the present disclosure may be determined utilizing a binding assay or a patch clamp assay. The binding assay may be for Sigma-1, Sigma-2, or 5-HT$_{2A}$. The patch clamp assay may be for hERG.

Results showing an inhibition (or stimulation for assays run in basal conditions) higher than 50% are considered to represent significant effects of the test compounds. 50% is the most common cut-off value for further investigation (determination of IC$_{50}$ or EC$_{50}$ values from concentration-response curves) that we would recommend. Results showing an inhibition (or stimulation) between 25% and 50% are indicative of weak to moderate effects (in most assays, they should be confirmed by further testing as they are within a range where more inter-experimental variability can occur).

Results showing an inhibition (or stimulation) lower than 25% are not considered significant and mostly attributable to variability of the signal around the control level. Low to moderate negative values have no real meaning and are attributable to variability of the signal around the control level. High negative values (≥50%) that are sometimes obtained with high concentrations of test compounds are generally attributable to nonspecific effects of the test compounds in the assays. On rare occasion they could suggest an allosteric effect of the test compound.

The toxicity of the compounds of the present disclosure may be determined utilizing a toxicity evaluation assay. The toxicity evaluation assay may be performed on vero-E6 cell lines.

A toxicity evaluation assay may be performed according to the following procedure. On day 1, cells may be seeded in 96 wells plate, Vero E6, P40, 10000 cells/well. Growth conditions may include medium DMEM high glucose. On day 2 compounds may be diluted in a mix of 50% DMSO and 50% growth medium to. 10 mM concentration may be used for PB28 (10 mg vial from Tocris, 1-Cyclohexyl-4-(3-(5-methoxy-1,2,3,4-tetrahydronaphthalen-1-yl)-n-propyl) piperazine dihydrochloride, see Gordon et al. Nature 2020, 583, 4459-468). Other compounds may be prepared at 2 mM concentration stock solution. Cells may be treated from 50 µM to 0.39 µM by serial dilution two-fold dilution in triplicate. Controls may be designed to include the same concentration of DMSO for each tested products. On day 5, cells may be fixed with formalin and stained with Hoetsch33342 for a 72 h post treatment. Cells may be imaged using a Cell Insight CX7 high content screening microscope. Number of cells and nuclear parameters may be assessed using an internal cytotoxicity testing protocol.

The biological activity of the compounds of the present disclosure on SARS-CoV-2 may be determined utilizing an antiviral evaluation assay. The antiviral evaluation assay may be performed on SARS-CoV-2 infected cells.

An antiviral evaluation assay may be performed according to the following procedure. On day 1, cells may be seeded in 96 wells plate. Growth conditions may include medium DMEM high glucose (Dutscher L0104-500, lot MS008A). On day 2, compounds may be diluted in a mix of 50% DMSO and 50% growth. Compounds may be diluted first in pure DMSO then diluted with medium. Stock compounds were prepared at 10 mM for PB28 (10 mg vial from Tocris) Other compounds may be made at 2 mM stock solution.

Examples

For exemplary purpose, neutral compounds of Formula (I) are synthesized and tested in the examples. It is understood that the neutral compounds of Formula (I) may be converted to the corresponding pharmaceutically acceptable salts of the compounds using routine techniques in the art (e.g., by saponification of an ester to the carboxylic acid salt, or by hydrolyzing an amide to form a corresponding carboxylic acid and then converting the carboxylic acid to a carboxylic acid salt).

Nuclear magnetic resonance (NMR) spectra were recorded at 400 MHz or 300 MHz as stated; the chemical shifts (δ) are reported in parts per million (ppm). Spectra were recorded using a Bruker or Varian instrument with 8, 16, or 32 scans.

UPLC-MS chromatograms and spectra were recorded using a Waters Aqcuity instrument using a C-18 column such as a Xtimate C18 100×2.1 mm, 1.7 µm, in 2 min chromatography, unless otherwise stated. Detection methods were diode array (DAD), photodiode array (PDA), or evaporative light scattering (ELSD) as well as positive ion electrospray ionization. MS range was 100-1000 Da. Solvents were gradients of water and acetonitrile both containing a modifier (typically 0.01-0.1%) such as formic acid or ammonium carbonate.

Abbreviations

ACN Acetonitrile
BMS borane dimethyl sulfide complex
Cbz benzyloxycarbonyl
$CDCl_3$ Chloroform-d
DCM Dichloromethane
DMF N,N-dimethylformamide
DMSO dimethylsulphoxide
DMSO-$d_6$ Hexadeuterodimethylsulphoxide
dppf 1,1'-bis(diphenylphosphino)ferrocene
eq. Equivalents
ESI Electrospray ionization
EtOAc ethyl acetate
FA Formic acid
FCC flash column chromatography
h hour(s)
$^1$H NMR Proton nuclear magnetic resonance spectroscopy
HPLC high performance liquid chromatography
LC-MS Liquid chromatography-mass spectrometry
MeOD Methanol-$d_4$
MeOH Methanol
min minute(s)
NaOAc Sodium acetate
PE petroleum ether
ppm parts per million
r.t. room temperature
$R_f$ retention factor
$R_t$ retention time.
SCX strong cation exchange
STAB sodium triacetoxyborohydride
TEA Triethylamine
TFA trifluoroacetic acid
THF Tetrahydrofuran
TLC thin layer chromatography
Y Yield General Synthetic Route 1:

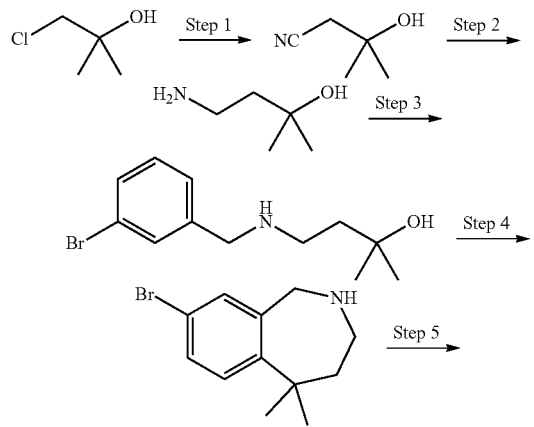

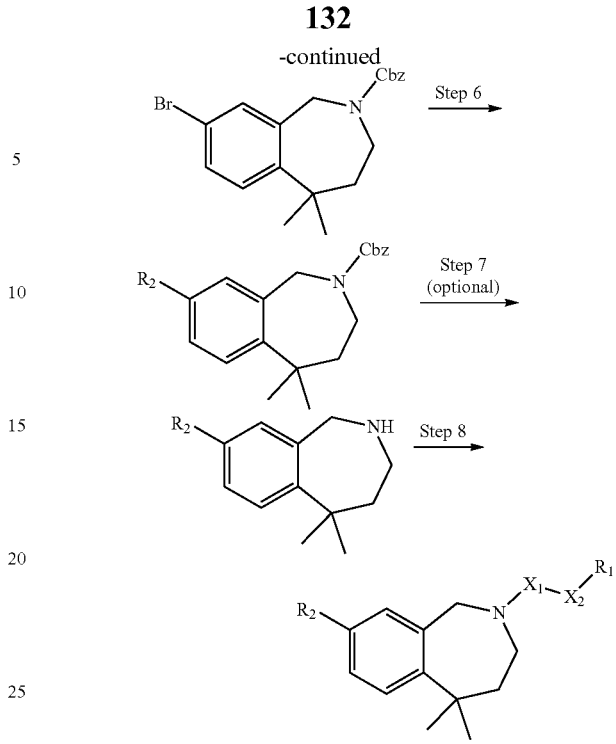

Step 1: Synthesis of 3-hydroxy-3-methylbutanenitrile 1-chloro-2-methyl-2-propanol (16.42 mL, 160 mmol) was added to a mixture of EtOH (320 mL) and water (55 mL). Next, Sodium cyanide (9.41 g, 192 mmol) was added and the reaction mixture was stirred under reflux (110° C.) for 3 hours. Next, the reaction mixture was cooled to room temperature and evaporated in vacuo. The crude product was dissolved in 300 mL water and 300 mL EtOAc. The water layer was washed with EtOAc (2×100 mL). The combined organic layers were dried over $Na_2SO_4$, filtered and evaporated in vacuo. 3-hydroxy-3-methylbutanenitrile was obtained in 84% yield.

Step 2: Synthesis of 4-amino-2-methylbutan-2-ol 3-hydroxy-3-methylbutanenitrile (13.3 g, 134 mmol) was dissolved in anhydrous THE (200 mL) and stirred at 0° C. Next, Borane dimethyl sulfide complex (38.2 mL, 402 mmol) was added slowly (over about 15 minutes) and the reaction mixture was stirred at room temperature for about 30 minutes. Next, the reaction mixture was stirred under reflux conditions (87° C.). No peaks related to the starting material could be detected by $^1$HNMR after about 2 hours. The reaction mixture was cooled down to 0° C. and quenched with MeOH (slow addition, gas formation, about 60 mL). Next, the reaction mixture was evaporated in vacuo. The reaction mixture was purified by normal phase chromatography. Starting with 1% MeOH in DCM to 10% MeOH in DCM in 5 min, staying on 10% MeOH in DCM for 5 min and finally switching to DCM/MeOH/7 N $NH_3$ in MeOH (5:4:1, v/v/v) for about 20 min. Fractions corresponding to the product were pooled together evaporated in vacuo. 4-amino-2-methylbutan-2-ol was obtained in 88% yield

Step 3: Synthesis of 4-((3-bromobenzyl)amino)-2-methylbutan-2-ol 4-amino-2-methylbutan-2-ol (51.3 mg, 0.497 mmol) was dissolved in MeOH (2.5 mL). Next, 3-bromobenzaldehyde (58.3 µL, 0.498 mmol) was added and the reaction mixture was stirred at room temperature. After 1 hour sodium triacetoxyborohydride (STAB, 211 mg, 0.995 mmol) was added and the resulting mixture was stirred at room temperature. After 20 minutes LCMS Therefore, glacial acetic acid (28.7 µL, 0.497 mmol) and additional STAB (52.7 mg, 0.249 mmol) were added. After about 30 minutes additional STAB (52.7 mg, 0.249 mmol) was added. After about 10 minutes the reaction mixture was directly submitted to reversed phase chromatography. Fractions corresponding to the product were pooled together and evaporated in vacuo. 4-((3-bromobenzyl)amino)-2-methylbutan-2-ol was obtained in 76% yield.

Step 4: Synthesis of Benzyl 8-bromo-5,5-dimethyl-1,3,4,5-tetrahydro-2H-benzo[c]azepine-2-carboxylate 4-((3-bromobenzyl)amino)-2-methylbutan-2-ol formate (49.0 mg, 0.154 mmol) was cooled to ° C. Next, cold (0° C.) sulfuric acid (85%, v/v) (2 mL, 37.5 mmol) was added and the reaction mixture was stirred at 0° C. The reaction mixture was stirred at room temperature until completeness, as determined by LCMS. Next, about 10 mL of crushed ice was added to the reaction mixture and resulting mixture was slowly basified with 4 N NaOH until the pH was basic (white precipitate was formed). The mixture was washed with DCM (3×25 mL). The combined organic layers were dried over $Na_2SO_4$, filtered and evaporated in vacuo. LCMS showed good purity.

Step 5: Synthesis of Benzyl 8-bromo-5,5-dimethyl-1,3,4,5-tetrahydro-2H-benzo[c]azepine-2-carboxylate 8-bromo-5,5-dimethyl-2,3,4,5-tetrahydro-1H-benzo[c] azepine (22.9 mg, 0.090 mmol) was dissolved in dichloromethane (1 mL) at room temperature. Next, benzyl chloroformate (0.017 ml, 0.117 mmol) and DIPEA (0.022 mL, 0.126 mmol) were added and the reaction mixture was stirred at room temperature until completeness, as determined by LCMS. The reaction mixture was dilute with DCM (9 mL) and the resulting solution was washed with sat. aq. $NaHCO_3$ (10 mL) and 10% aq. $KHSO_4$ (10 mL), dried over $Na_2SO_4$, filtered and evaporated in vacuo. The crude product was purified by reversed phase chromatography. Fractions corresponding to the product were pooled together and evaporated in vacuo.

Step 6: Coupling Reaction

General Procedure for Suzuki Coupling

To an 8 mL vial was added the aryl bromide (1 equiv.), boronic acid (1.4 equiv.), potassium carbonate (2.0 equiv.), and $Pd(dppf)Cl_2$ (5 mol %) 0.027 mmol). Next, toluene (0.5 mL), ethanol (0.250 mL) and water (0.250 mL) were added, and the vial was flushed with argon (30 s), capped, and the reaction was stirred at 120° C. The reaction was run until completeness, as determined by LCMS. The reaction mixture was allowed to cool to room temperature, the reaction mixture was diluted with EtOAc (10 mL) and the resulting solution was washed with water (10 mL) and brine (10 mL). The organic layer was dried over $Na_2SO_4$, filtered and evaporated in vacuo. The crude product was purified by normal phase flash chromatography (0 to 30% EtOAc in heptane). Fractions corresponding to the product were pooled together and evaporated in vacuo to yield the product.

General Procedure for Buchwald Coupling

A 40 mL vial containing sodium tert-butoxide (1.2 equiv.), $Pd_2(dba)_3$ (20 mol %), 2-Dicyclohexylphosphino-2',6'-diisopropoxybiphenyl (RuPhos) (5 mol %) and 1-cyclopentylpiperazine (1.2 equiv.) was flushed with argon for about 5 minutes. Next, toluene (22.11 ml) was added to the aryl bromide (1 equiv.) and the resulting solution was first degassed with argon for about 30 seconds and afterwards added to the vial. The vial was flushed with argon for about 1 min, capped and the reaction mixture was stirred at 120° C. The reaction was run until completeness, as determined by LCMS. The reaction mixture was allowed to cool down to room temperature, diluted with DCM (200 mL) and the resulting solution was washed with sat. aq. $NaHCO_3$ (200 mL). The water layer was washed with DCM (150 mL). The combined organic layers were dried over $Na_2SO_4$, filtered and evaporated in vacuo. The crude product was purified by normal phase chromatography (0 to 50% EtOAc in heptane). Fractions corresponding to the product were pooled together and evaporated in vacuo to yield the product.

Step 7: Deprotection of the Protecting Group

To the protected building block was added anisole (3 equiv.) and HBr (33 wt % in acetic acid) (~20 equiv.). The reaction was swirled and the viscous mixture left to stand for 1 hour to 3 hours at room temperature, swirling occasionally. The reaction was run until completeness, as determined by LCMS. $Et_2O$ (~10 volume equiv.) was added and mixed vigorously. The mixture was filtered off and the residue was washed with $Et_2O$ (2×~5 vol eq). The residue was partitioned between EtOAc (~10 vol eq) and 1M aq. NaOH (~10 volume equiv.). The phases were separated and the aqueous phase was extracted with EtOAc (~10 volume equiv.). The combined organics were dried over $Na_2SO_4$, filtered and concentrated in vacuo affording the product.

Step 8: N-Atom Functionalization

The N-atom of the compound from step 7 (herein referred to as "the amine") was functionalized according to one of the procedures as described below.

General Procedure for Coupling the Amine to Acids:

To the acid (0.125 mmol, 1.25 eq) was added HATU (0.044 g, 0.115 mmol, 1.15 eq; stock solution in DMAc (0.5 mL)), DIPEA (0.040 mL, 0.230 mmol, ~2.3 eq) and the reaction was shaken for 30 minutes. Then, the amine (0.1 mmol, 1 eq; stock solution/suspension in DMAc (0.5 mL)) was added and the reaction was shaken overnight at room temperature.

General Procedure for Coupling the Amine to Sulfonyl Chlorides, Acid Chlorides, Isocyanates, and Chloroformates (Herein Referred to as "the Electrophile"):

To the electrophile (0.125 mmol, 1.25 eq) was added DMAc (0.5 mL)*, DIPEA (0.040 mL, 0.230 mmol*, ~2.3 eq) and the amine (0.1 mmol, 1 eq; stock solution in DMAc (0.5 mL)) and the reaction was shaken overnight at room temperature. (For aliphatic sulfonylchlorides, pyridine (0.5 mL, 6.18 mmol) was added instead of DMAc and DIPEA.)

General Procedure for Coupling the Amine to Alcohols:

Bis(p-Nitrophenyl) carbonate (0.033 g, 0.110 mmol) (1.1 eq), the alcohol (0.125 mmol, 1.25 eq) and NaH (60% dispersion, 8.00 mg, 0.200 mmol, 2 eq) were dissolved in DMAc (0.5 mL) and the reaction was shaken for 30 minutes. Then, the amine (0.1 mmol, 1 eq, stock solution in DMAc (0.5 mL)) was added and the reaction was shaken overnight at room temperature.

General Procedure for Coupling the Amine to Aldehydes or Ketones:

To the aldehyde/ketone (0.150 mmol, 1.5 eq) and the amine (0.1 mmol, 1 eq, stock solution/suspension in DMAc (0.5 mL)) was added zinc chloride (0.027 g, 0.200 mmol, 2 eq) and STAB (0.064 g, 0.300 mmol, 3 eq, both in one stock suspension in DMAc (0.5 mL)) and the reaction was shaken overnight at room temperature.

General Procedure for Coupling the Amine to Alkyl Halides:

To the alkyl halide (0.110 mmol, 1.1 eq) and the amine (0.1 mmol, 1 eq, stock solution/suspension in DMAc (0.5 mL)) was added $K_2CO_3$ (0.035 g, 0.250 mmol, ~2.5 eq) and DMAc (0.5 mL) and the reactions were shaken overnight at 50° C.

General Procedure for Purifications:

The reactions were analyzed by LCMS. For reductive aminations, 35% aq. $NH_3$ (0.2 mL, ~1.75 mmol) was added. All reactions were filtered (0.45 m) and purified by basic preparative HPLC-MS. Product fractions were concentrated, combined with acetonitrile into vials, water was added and the products were lyophilized.

General Synthetic Route 2:

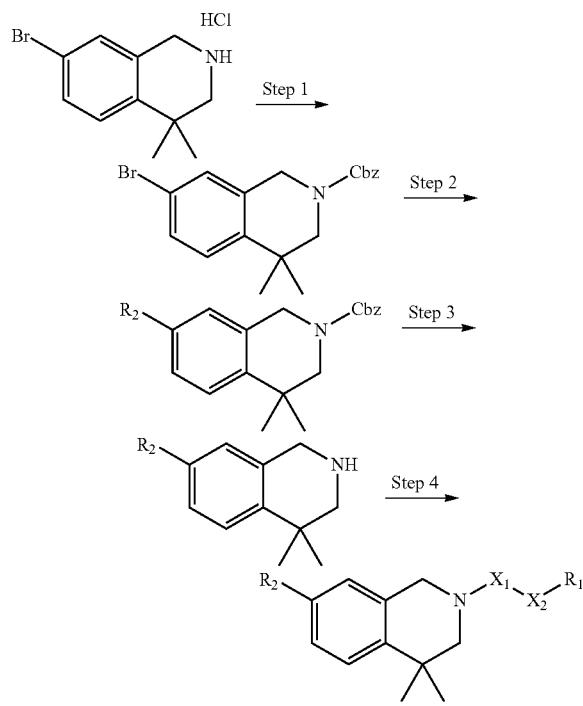

Step 1: Synthesis of Benzyl 7-bromo-4,4-dimethyl-3,4-dihydroisoquinoline-2(1H)-carboxylate 7-bromo-4,4-dimethyl-1,2,3,4-tetrahydroisoquinoline hydrochloride (2 g, 7.23 mmol; Millipore Sigma Product ID: ADVH0430AD62) was dissolved in dichloromethane (26 mL) and cooled to 0° C. DIPEA (2.78 mL, 15.91 mmol) was added, followed by benzyl chloroformate (1.135 mL, 7.95 mmol) and the reaction mixture was stirred at room temperature. The reaction was stopped after about 4 hours. The reaction mixture was evaporated in vacuo. The crude residue was dissolved in EtOAc (50 mL) and the resulting solution was washed with 0.5 N $KHSO_4$ (50 mL), sat. aq. $NaHCO_3$ (50 mL) and brine (30 mL), dried over $Na_2SO_4$, filtered and evaporated in vacuo. The crude product was purified by normal phase flash chromatography (0 to 35% EtOAc in heptane). Fractions corresponding to the product were pooled together and evaporated in vacuo to yield a colorless oil.

Step 2: Coupling Reaction

General Procedure for Suzuki Coupling

To an 8 mL vial was added the aryl bromide (1 equiv.), boronic acid (1.4 equiv.), potassium carbonate (2.0 equiv.), and Pd(dppf)$Cl_2$ (5 mol %) 0.027 mmol). Next, toluene (0.5 mL), ethanol (0.250 mL) and water (0.250 mL) were added, and the vial was flushed with argon (30 s), capped, and the reaction was stirred at 120° C. The reaction was run until completeness, as determined by LCMS. The reaction mixture was allowed to cool to room temperature, the reaction mixture was diluted with EtOAc (10 mL) and the resulting solution was washed with water (10 mL) and brine (10 mL). The organic layer was dried over $Na_2SO_4$, filtered and evaporated in vacuo. The crude product was purified by normal phase flash chromatography (0 to 30% EtOAc in heptane). Fractions corresponding to the product were pooled together and evaporated in vacuo to yield the product.

General Procedure for Buchwald Coupling

A 40 mL vial containing sodium tert-butoxide (1.2 equiv.), $Pd_2(dba)_3$ (20 mol %), 2-Dicyclohexylphosphino-2',6'-diisopropoxybiphenyl (RuPhos) (5 mol %) and 1-cyclopentylpiperazine (1.2 equiv.) was flushed with argon for about 5 minutes. Next, toluene (22.11 ml) was added to the aryl bromide (1 equiv.) and the resulting solution was first degassed with argon for about 30 seconds and afterwards added to the vial. The vial was flushed with argon for about 1 min, capped and the reaction mixture was stirred at 120° C. The reaction was run until completeness, as determined by LCMS. The reaction mixture was allowed to cool down to room temperature, diluted with DCM (200 mL) and the resulting solution was washed with sat. aq. $NaHCO_3$ (200 mL). The water layer was washed with DCM (150 mL). The combined organic layers were dried over $Na_2SO_4$, filtered and evaporated in vacuo. The crude product was purified by normal phase chromatography (0 to 50% EtOAc in heptane). Fractions corresponding to the product were pooled together and evaporated in vacuo to yield the product.

Step 3: Deprotection of the Protecting Group

To the protected building block was added anisole (3 equiv.) and HBr (33 wt % in acetic acid) (~20 equiv.). The reaction was swirled and the viscous mixture left to stand for 1 hour to 3 hours at room temperature, swirling occasionally. The reaction was run until completeness, as determined by LCMS. $Et_2O$ (~10 volume equiv.) was added and mixed vigorously. The mixture was filtered off and the residue was washed with $Et_2O$ (2×~5 vol eq). The residue was partitioned between EtOAc (~10 vol eq) and 1M aq. NaOH (~10 volume equiv.). The phases were separated and the aqueous phase was extracted with EtOAc (~10 volume equiv.). The combined organics were dried over Na₂SO₄, filtered and concentrated in vacuo affording the product.

Step 4: N-Atom Functionalization

The N-atom of the compound from step 3 (herein referred to as "the amine") was functionalized according to one of the procedures as described below.
General Procedure for Coupling the Amine to Acids:
To the acid (0.125 mmol, 1.25 eq) was added HATU (0.044 g, 0.115 mmol, 1.15 eq; stock solution in DMAc (0.5 mL)), DIPEA (0.040 mL, 0.230 mmol, ~2.3 eq) and the reaction was shaken for 30 minutes. Then, the amine (0.1 mmol, 1 eq; stock solution/suspension in DMAc (0.5 mL)) was added and the reaction was shaken overnight at room temperature.
General Procedure for Coupling the Amine to Sulfonyl Chlorides, Acid Chlorides, Isocyanates, and Chloroformates (Herein Referred to as "the Electrophile"):
To the electrophile (0.125 mmol, 1.25 eq) was added DMAc (0.5 mL)*, DIPEA (0.040 mL, 0.230 mmol*, ~2.3 eq) and the amine (0.1 mmol, 1 eq; stock solution in DMAc (0.5 mL)) and the reaction was shaken overnight at room temperature. (For aliphatic sulfonylchlorides, pyridine (0.5 mL, 6.18 mmol) was added instead of DMAc and DIPEA.)
General Procedure for Coupling the Amine to Alcohols:
Bis(p-Nitrophenyl) carbonate (0.033 g, 0.110 mmol) (1.1 eq), the alcohol (0.125 mmol, 1.25 eq) and NaH (60% dispersion, 8.00 mg, 0.200 mmol, 2 eq) were dissolved in DMAc (0.5 mL) and the reaction was shaken for 30 minutes. Then, the amine (0.1 mmol, 1 eq, stock solution in DMAc (0.5 mL)) was added and the reaction was shaken overnight at room temperature.
General Procedure for Coupling the Amine to Aldehydes or Ketones:
To the aldehyde/ketone (0.150 mmol, 1.5 eq) and the amine (0.1 mmol, 1 eq, stock solution/suspension in DMAc (0.5 mL)) was added zinc chloride (0.027 g, 0.200 mmol, 2 eq) and STAB (0.064 g, 0.300 mmol, 3 eq, both in one stock suspension in DMAc (0.5 mL)) and the reaction was shaken overnight at room temperature.
General Procedure for Coupling the Amine to Alkyl Halides:
To the alkyl halide (0.110 mmol, 1.1 eq) and the amine (0.1 mmol, 1 eq, stock solution/suspension in DMAc (0.5 mL)) was added K₂CO₃ (0.035 g, 0.250 mmol, ~2.5 eq) and DMAc (0.5 mL) and the reactions were shaken overnight at 50° C.
General Procedure for Purification:
The reactions were analyzed by LCMS. For reductive aminations, 35% aq. NH₃ (0.2 mL, ~1.75 mmol) was added. All reactions were filtered (0.45 m) and purified by basic preparative HPLC-MS. Product fractions were concentrated, combined with acetonitrile into vials, water was added and the products were lyophilized.

Example 1. Synthesis of Benzyl 4,4-dimethyl-7-(4-propylpiperazin-1-yl)-3,4-dihydroisoquinoline-2(1H)-carboxylate (Compound 2)

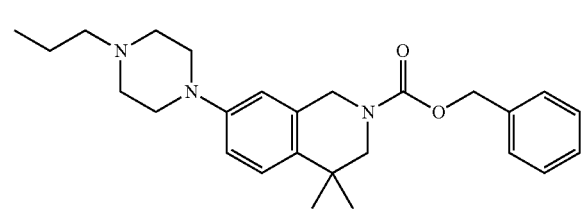 [SMILES: CCCN1CCN(c2ccc3c(c2)CN(C(=O)OCc2ccccc2)CC3(C)C)CC1]

Step 1: Synthesis of Benzyl 7-bromo-4,4-dimethyl-3,4-dihydroisoquinoline-2(1H)-carboxylate

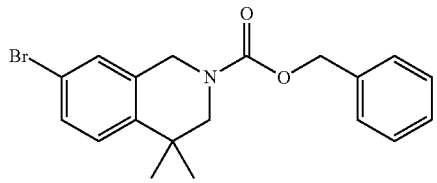 [SMILES: CC1(C)CN(C(=O)OCc2ccccc2)Cc2cc(Br)ccc21]

Benzyl 7-bromo-4,4-dimethyl-3,4-dihydroisoquinoline-2 (1H)-carboxylate was prepared following Step 1 of General Procedure 2. Benzyl 7-bromo-4,4-dimethyl-3,4-dihydroisoquinoline-2(1H)-carboxylate was isolated in 95% yield.

Step 2: Synthesis of Benzyl 4,4-dimethyl-7-(4-propylpiperazin-1-yl)-3,4-dihydroisoquinoline-2(1H)-carboxylate Benzyl 7-bromo-4,4-dimethyl-3,4-dihydroisoquinoline-2 (1H)-carboxylate was reacted with 1-propylpiperazine dihydrogen bromide in toluene in the presence of Pd(OAc)₂, JohnPhos, and t-BuONA at 80° C. Benzyl 4,4-dimethyl-7-(4-propylpiperazin-1-yl)-3,4-dihydroisoquinoline-2(1H)-carboxylate was produced in 30% yield. M/Z+1=422.32

Example 2. Synthesis of Benzyl 7-(4-(3-methoxy-3-oxopropyl)piperazin-1-yl)-4,4-dimethyl-3,4-dihydroisoquinoline-2(1H)-carboxylate (Compound 3)

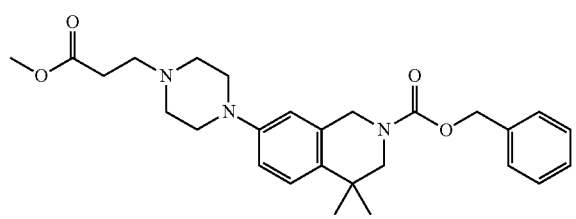 [SMILES: COC(=O)CCN1CCN(c2ccc3c(c2)CN(C(=O)OCc2ccccc2)CC3(C)C)CC1]

Compound 3 was synthesized according to general synthetic route 2 using the general procedure for Buchwald coupling and the general procedure for sulfonyl chlorides, acid chlorides, isocyanates, and chloroformates. UPLC-MS: M/Z+1=466.09.

Example 3. Synthesis of Benzyl 5,5-dimethyl-8-(4-propylpiperazin-1-yl)-1,3,4,5-tetrahydro-2H-benzo[c]azepine-2-carboxylate (Compound 8)

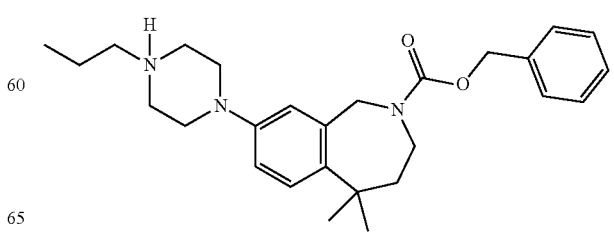

Compound 8 was synthesized according to general synthetic route 1 using the general procedure for Buchwald coupling and the general procedure for sulfonyl chlorides, acid chlorides, isocyanates, and chloroformates. UPLC-MS: M/Z+1=436.4.

Example 4. Synthesis of Benzyl 8-(4-(3-methoxy-3-oxopropyl)piperazin-1-yl)-5,5-dimethyl-1,3,4,5-tetrahydro-2H-benzo[c]azepine-2-carboxylate (Compound 9)

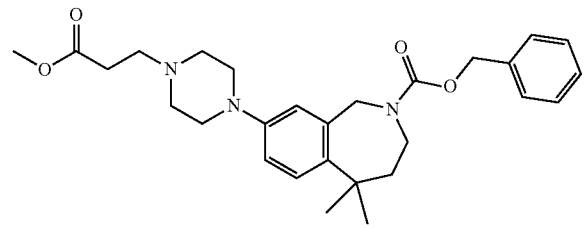 [SMILES: COC(=O)CCN1CCN(c2ccc3c(c2)CN(C(=O)OCc2ccccc2)CCC3(C)C)CC1]

Compound 9 was synthesized according to general synthetic route 1 using the general procedure for Buchwald coupling and the general procedure for sulfonyl chlorides, acid chlorides, isocyanates, and chloroformates. UPLC-MS: M/Z+1=480.4.

Example 5. Synthesis of 2-cyclopentyl-5,5-dimethyl-8-(4-(trifluoromethyl)phenyl)-2,3,4,5-tetrahydro-1H-benzo[c]azepine (Compound 10)

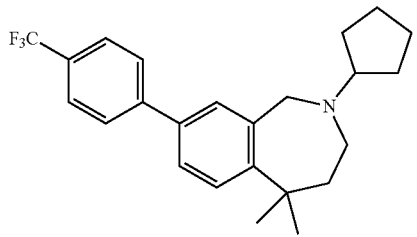 [SMILES: CC1(C)CCN(C2CCCC2)Cc2cc(-c3ccc(C(F)(F)F)cc3)ccc21]

Compound 10 was synthesized according to general synthetic route 1 using the general procedure for Buchwald coupling and the general procedure for aldehydes/ketones. UPLC-MS: M/Z+1=388.4.

Example 6. Synthesis of 5,5-dimethyl-2-propyl-8-(4-(trifluoromethyl)phenyl)-2,3,4,5-tetrahydro-1H-benzo[c]azepine (Compound 12)

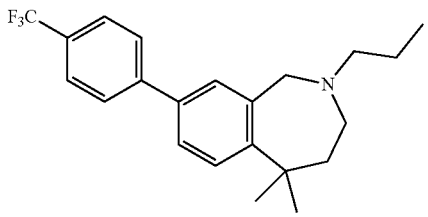 [SMILES: CCCN1CCC(C)(C)c2ccc(-c3ccc(C(F)(F)F)cc3)cc2C1]

Compound 12 was synthesized according to general synthetic route 1 using the general procedure for Suzuki coupling and the general procedure for aldehydes/ketones. UPLC-MS: M/Z+1=362.4.

Example 7. Synthesis of 2-cyclohexyl-5,5-dimethyl-8-(4-(trifluoromethyl)phenyl)-2,3,4,5-tetrahydro-1H-benzo[c]azepine (Compound 32)

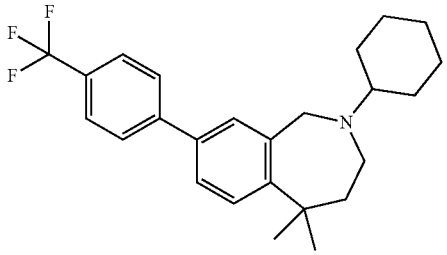 [SMILES: CC1(C)CCN(C2CCCCC2)Cc2cc(-c3ccc(C(F)(F)F)cc3)ccc21]

Compound 32 was synthesized according to general synthetic route 1 using the general procedure for Suzuki coupling and the general procedure for aldehydes/ketones.

Example 8. Synthesis of 2-((3-chlorophenyl)sulfonyl)-7-(4-cyclopentylpiperazin-1-yl)-4,4-dimethyl-1,2,3,4-tetrahydroisoquinoline (Compound 33)

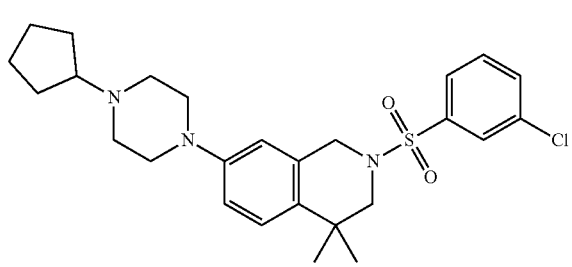 [SMILES: CC1(C)CN(S(=O)(=O)c2cccc(Cl)c2)Cc2cc(N3CCN(C4CCCC4)CC3)ccc21]

Compound 33 was synthesized according to general synthetic route 2 using the general procedure for Buchwald coupling and the general procedure for sulfonyl chlorides, acid chlorides, isocyanates, and chloroformates.

Example 9. Synthesis of (3-chloro-5-fluorophenyl)(7-(4-cyclopentylpiperazin-1-yl)-4,4-dimethyl-3,4-dihydroisoquinolin-2(1H)-yl)methanone (Compound 38)

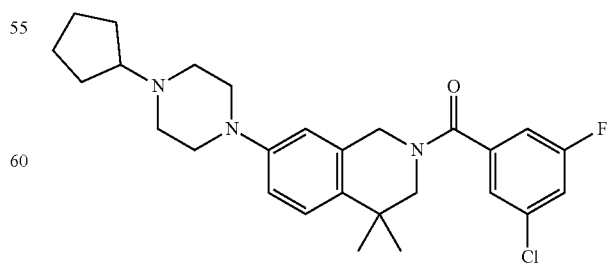

Compound 38 was synthesized according to general synthetic route 2 using the general procedure for Buchwald coupling and the general procedure for sulfonyl chlorides, acid chlorides, isocyanates, and chloroformates.

Example 10. Synthesis of Cyclohexyl 7-(4-cyclopentylpiperazin-1-yl)-4,4-dimethyl-3,4-dihydroisoquinoline-2(1H)-carboxylate (Compound 43)

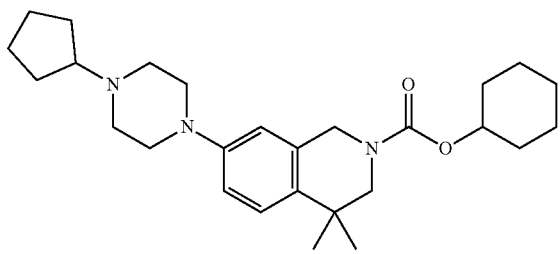 [SMILES: CC1(C)CN(C(=O)OC2CCCCC2)Cc2cc(N3CCN(C4CCCC4)CC3)ccc21]

Compound 43 was synthesized according to general synthetic route 2 using the general procedure for Buchwald coupling and the general procedure for sulfonyl chlorides, acid chlorides, isocyanates, and chloroformates.

Example 11. Synthesis of Isopropyl 7-(4-cyclopentylpiperazin-1-yl)-4,4-dimethyl-3,4-dihydroisoquinoline-2(1H)-carboxylate (Compound 45)

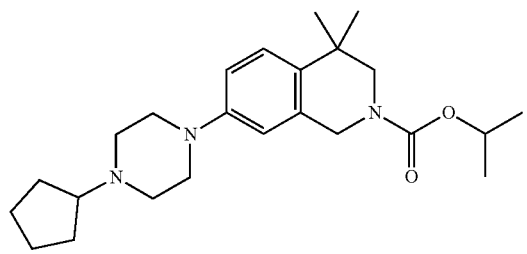 [SMILES: CC(C)OC(=O)N1Cc2cc(N3CCN(C4CCCC4)CC3)ccc2C(C)(C)C1]

Compound 45 was synthesized according to general synthetic route 2 using the general procedure for Buchwald coupling and the general procedure for sulfonyl chlorides, acid chlorides, isocyanates, and chloroformates.

Example 12. Synthesis of Cyclopentyl(8-(4-cyclopentylpiperazin-1-yl)-5,5-dimethyl-1,3,4,5-tetrahydro-2H-benzo[c]azepin-2-yl)methanone (Compound 73)

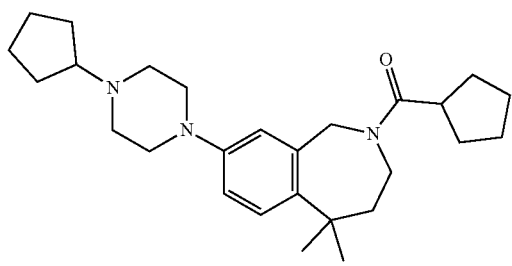 [SMILES: CC1(C)CCN(C(=O)C2CCCC2)Cc2cc(N3CCN(C4CCCC4)CC3)ccc21]

Compound 73 was synthesized according to general synthetic route 1 using the general procedure for Buchwald coupling and the general procedure for sulfonyl chlorides, acid chlorides, isocyanates, and chloroformates.

Example 13. Synthesis of Isopropyl 8-(4-cyclopentylpiperazin-1-yl)-5,5-dimethyl-1,3,4,5-tetrahydro-2H-benzo[c]azepine-2-carboxylate (Compound 79)

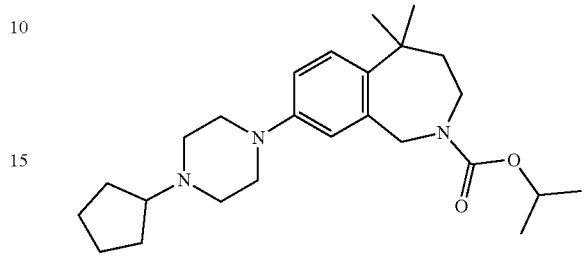

Compound 79 was synthesized according to general synthetic route 1 using the general procedure for Buchwald coupling and the general procedure for sulfonyl chlorides, acid chlorides, isocyanates, and chloroformates.

Example 14. Synthesis of 4-(1-(2-((3-chlorophenyl)sulfonyl)-5,5-dimethyl-2,3,4,5-tetrahydro-1H-benzo[c]azepin-8-yl)piperidin-4-yl)morpholine (Compound 80)

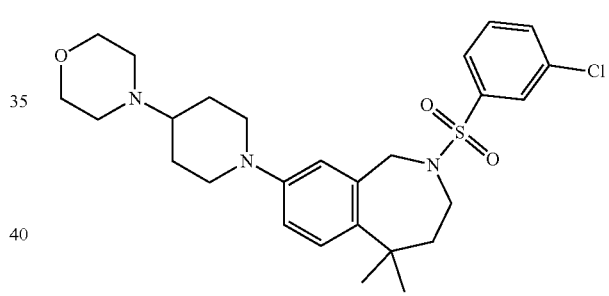

Compound 80 was synthesized according to general synthetic route 1 using the general procedure for Buchwald coupling and the general procedure for sulfonyl chlorides, acid chlorides, isocyanates, and chloroformates.

Example 15. Synthesis of Benzo[d][1,3]dioxol-4-yl (5,5-dimethyl-8-(4-morpholinopiperidin-1-yl)-1,3,4,5-tetrahydro-2H-benzo[c]azepin-2-yl)methanone (Compound 84)

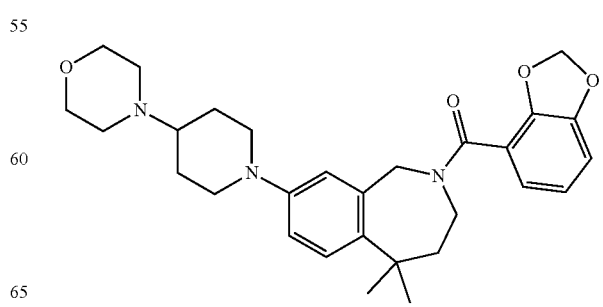

Compound 84 was synthesized according to general synthetic route 1 using the general procedure for Buchwald coupling and the general procedure for acids.

Example 16. Synthesis of Cyclopentyl(5,5-dimethyl-8-(4-morpholinopiperidin-1-yl)-1,3,4,5-tetrahydro-2H-benzo[c]azepin-2-yl)methanone (Compound 85)

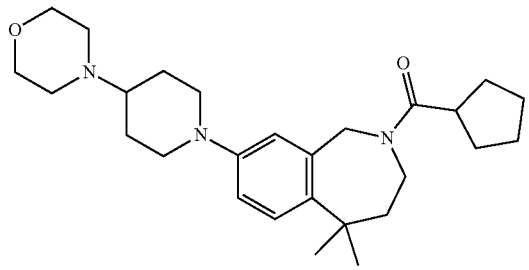 [SMILES: CC1(C)CCN(C(=O)C2CCCC2)Cc2cc(N3CCC(N4CCOCC4)CC3)ccc21]

Compound 85 was synthesized according to general synthetic route 1 using the general procedure for Buchwald coupling and the general procedure for sulfonyl chlorides, acid chlorides, isocyanates, and chloroformates.

Example 17. Synthesis of Cyclohexyl(5,5-dimethyl-8-(4-morpholinopiperidin-1-yl)-1,3,4,5-tetrahydro-2H-benzo[c]azepin-2-yl)methanone (Compound 86)

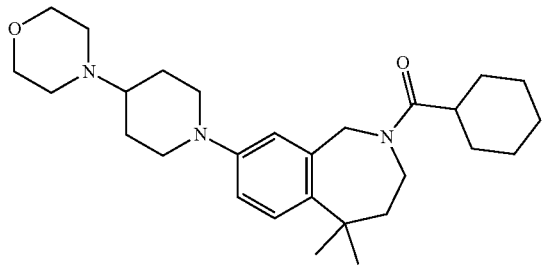 [SMILES: CC1(C)CCN(C(=O)C2CCCCC2)Cc2cc(N3CCC(N4CCOCC4)CC3)ccc21]

Compound 86 was synthesized according to general synthetic route 1 using the general procedure for Buchwald coupling and the general procedure for sulfonyl chlorides, acid chlorides, isocyanates, and chloroformates.

Example 18. Synthesis of 1-(3,4-dihydroisoquinolin-2(1H)-yl)-3-(8-(2,6-dimethylpyridin-4-yl)-5,5-dimethyl-1,3,4,5-tetrahydro-2H-benzo[c]azepin-2-yl)propan-1-one (Compound 111)

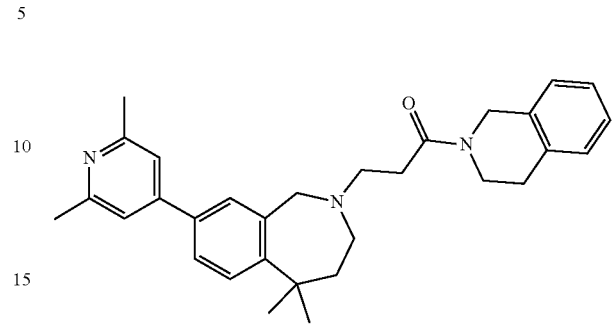

Compound 111 was synthesized according to general synthetic route 1 using the general procedure for Suzuki coupling and the general procedure for alkyl halides.

Example 19. Synthesis of 3-(8-(2,6-dimethylpyridin-4-yl)-5,5-dimethyl-1,3,4,5-tetrahydro-2H-benzo[c]azepin-2-yl)-1-(4-methylpiperidin-1-yl)propan-1-one (Compound 131)

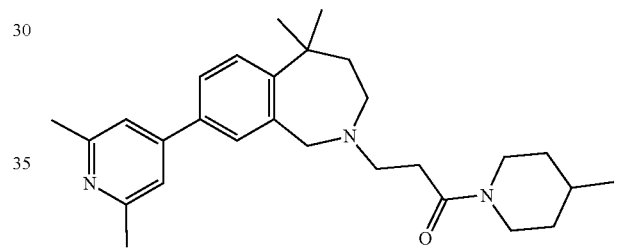

Compound 131 was synthesized according to general synthetic route 1 using the general procedure for Suzuki coupling and the general procedure for alkyl halides.

Example 20. Binding Assays for Sigma-1 and Sigma-2

Assays for determining Sigma-1 and Sigma-2 binding values were performed according to Ganapathy, M. E. et al. (1999), *J. Pharmacol. Exp. Ther.*, 289: 251-260.

| Receptors | Source | Ligand | Conc. (nM) | $K_d$ (nM) | Non-specific | Incubation | Detection Method |
|---|---|---|---|---|---|---|---|
| sigma 1 (h)(agonist radioligand) | Human endogenous (Jurkat cells) | [$^3$H] (+) pentazocine | 15 | 16 | Haloperidol (10 µM) | 120 min 37° C. | Scintillation counting |
| Sigma 2 (h)(agonist radioligand) | Human endogenous (Jurkat cells) | [$^3$H] DTG (+1 µM (+) pentazocine) | 25 | 80.84 | Haloperidol (10 µM) | 60 min rt | Scintillation counting |

Results showing an inhibition (or stimulation for assays run in basal conditions) higher than 50% are considered to represent significant effects of the test compounds. 50% is the most common cut-off value for further investigation (determination of $IC_{50}$ or $EC_{50}$ values from concentration-response curves) that we would recommend. Results showing an inhibition (or stimulation) between 25% and 50% are indicative of weak to moderate effects (in most assays, they should be confirmed by further testing as they are within a range where more inter-experimental variability can occur). Results showing an inhibition (or stimulation) lower than 25% are not considered significant and mostly attributable to variability of the signal around the control level. Low to moderate negative values have no real meaning and are attributable to variability of the signal around the control level. High negative values (≥50%) that are sometimes obtained with high concentrations of test compounds are generally attributable to nonspecific effects of the test compounds in the assays. On rare occasion they could suggest an allosteric effect of the test compound.

Measured $K_i$ values of compounds of the present disclosure are shown in Table A below (A means >0.1 nM and ≤5 nM; B means >5 and ≤50; C means >50 and ≤100 nM; D means >100 nM and ≤500 nM; E means >500 nM).

TABLE A $K_i$ values of compounds of the present disclosure.

| Compound | Sigma-1 $K_i$ | Sigma-2 $K_i$ |
|---|---|---|
| 1 | D | D |
| 2 | B | B |
| 3 | D | B |
| 4 | E | D |

TABLE A-continued $K_i$ values of compounds of the present disclosure.

| Compound | Sigma-1 $K_i$ | Sigma-2 $K_i$ |
|---|---|---|
| 5 | D | D |
| 6 | E | E |
| 7 | B | D |
| 8 | A | B |
| 9 | B | B |
| 10 | E | B |
| 11 | E | D |
| 12 | E | C |
| 32 | | C |
| 33 | A | A |
| 38 | A | A |
| 43 | A | A |
| 45 | A | B |
| 73 | A | B |
| 79 | A | B |
| 80 | A | C |
| 84 | B | |
| 85 | B | |
| 86 | A | |
| 111 | | C |
| 131 | | C |

Example 21. Assays for Determining 5-$HT_{2A}$ Binding

Assays for determining 5-$HT_{2A}$ binding values were performed according to: Bonhaus, D. W. et al. (1995), *Brit. J. Pharmacol.*, 115: 622-628; Schwinn, D. A. et al. (1995), *J. Pharmacol. Exp. Ther.*, 272: 134-142; and Vicentic, A. et al. (2002), *J. Pharmacol. Exp. Ther.*, 302: 58-65; Bylund D B et al. (1994), *Pharmacol. Rev.* 46: 121-136. Each of which is incorporated by reference in its entirety.

| Receptors | Source | Ligand | Conc. (nM) | $K_d$ (nM) | Non-specific | Incubation | Detection Method |
|---|---|---|---|---|---|---|---|
| 5-$HT_{2A}$ (h) (antagonist radioligand) | Human recombinant (HEK-293 cells) | [$^3$H] kentanserin | 0.5 | 0.6 | Kentanserin (1 μM) | 60 min rt | Scintillation counting |

| Receptors | Source | Stimulus | Incubation | Measured component | Detection method |
|---|---|---|---|---|---|
| $\alpha_{1a}$ (h) (agonist effect) | Human recombinant (CHO cells) | None (100 nM epinephrine for control) | rt | Intracellular [$Ca^{2+}$] | Fluorimetry |
| $\alpha_{1a}$ (h) (antagonist effect) | Human recombinant (CHO cells) | Epinephrine (3 nM) | rt | Intracellular [$Ca^{2+}$] | Fluorimetry |
| $\alpha_{1b}$ (h) (agonist effect) | Human recombinant (CHO cells) | None (100 nM epinephrine for control) | 30 min 37° C. | cAMP | HTRF |
| $\alpha_{1b}$ (h) (antagonist effect) | Human recombinant (CHO cells) | Epinephrine (3000 nM) | 30 min 37° C. | cAMP | HTRF |
| $\alpha_{1d}$ (h) (agonist effect) | Human recombinant (CHO cells) | None (1 μM epinephrine for control) | rt | Intracellular [$Ca^{2+}$] | Fluorimetry |
| $\alpha_{1d}$ (h) (antagonist effect) | Human recombinant (CHO cells) | Epinephrine (2.3 nM) | rt | Intracellular [$Ca^{2+}$] | Fluorimetry |

Results showing an inhibition (or stimulation for assays run in basal conditions) higher than 50% are considered to represent significant effects of the test compounds. 50% is the most common cut-off value for further investigation (determination of $IC_{50}$ or $EC_{50}$ values from concentration-response curves) that we would recommend. Results showing an inhibition (or stimulation) between 25% and 50% are indicative of weak to moderate effects (in most assays, they should be confirmed by further testing as they are within a range where more inter-experimental variability can occur). Results showing an inhibition (or stimulation) lower than 25% are not considered significant and mostly attributable to variability of the signal around the control level. Low to moderate negative values have no real meaning and are attributable to variability of the signal around the control level. High negative values ($\geq$50%) that are sometimes obtained with high concentrations of test compounds are generally attributable to nonspecific effects of the test compounds in the assays. On rare occasion they could suggest an allosteric effect of the test compound.

Measured $IC_{50}$ values of compounds of the present disclosure are shown in Table B below.

TABLE B $IC_{50}$ values of compounds of the present disclosure.

| Compound | 5-HT$_{2A}$ IC$_{50}$ | $\alpha_{1A}$ adrenergic (agonist) | $\alpha_{1B}$ adrenergic (agonist) | $\alpha_{1D}$ adrenergic (agonist) | $\alpha_{1A}$ adrenergic (antagonist) | $\alpha_{1B}$ adrenergic (antagonist) | $\alpha_{1D}$ adrenergic (antagonist) |
|---|---|---|---|---|---|---|---|
| 2 | >1 µM | >1 µM | >1 µM | >1 µM | >1 µM | >1 µM | >1 µM |
| 10 | >1 µM | >1 µM | >1 µM | >1 µM | >1 µM | >1 µM | >1 µM |

Example 22. D2S Human Dopamine

Assays for determining dopamine D2S receptor binding values were performed according to Eurofins Cerep protocol item 1322 and the results are represented in Table C below. The parameters used for the assay are described below. The compounds in Table C do not bind dopamine D2S receptor. Common antipsychotics, in contrast, block dopamine receptors (Keefe, et al., J Clin Psychiatry. 2018; 79(3): 17m11753).

Ligand [$^3$H]7-OH-DPAT

Ligand K$_d$(nM) 0.68

Ligand concentration 1 nM

Non-specific 10 µM Butaclamol

Incubation 60 min at RT

Control inhibitor 7-OH-DPAT

TABLE C

Inhibition of D2S human dopamine.

| Compound | % inhibition of control specific binding (1 µM) |
|---|---|
| 32 | 8 |
| 33 | 13 |
| 38 | 1 |
| 43 | 11 |
| 45 | −5 |
| 73 | 6 |
| 79 | 19 |
| 80 | 4 |
| 84 | −1 |
| 85 | −3 |
| 86 | 2 |
| 111 | 37 |
| 131 | 21 |

Example 23. α1a(h) (Agonist Effect) of the Compounds

Assays for determining the agonist effect on α1A(h) were performed according to the procedure described in Example 21, and the results are represented in Table D below. The compounds in Table D do not have an agonist effect on α1A(h).

TABLE D

Stimulation of α1A(h).

| Compound | % stimulation relative to control (1 µM) |
|---|---|
| 32 | 0 |
| 33 | −1 |
| 38 | 0 |
| 43 | 0 |
| 45 | 0 |
| 73 | 0 |
| 79 | 0 |
| 80 | 0 |
| 84 | 0 |
| 85 | 1 |
| 86 | 0 |
| 111 | 0 |
| 131 | −1 |

Example 24. α1A(h) (Antagonist Effect)

Assays for determining the antagonist effect on α1A(h) were performed according to the procedure described in Example 21, and the results are represented in Table E below. Compounds 38 and 111 show a small antagonist effect. No antagonist effect is observed for the other compounds.

TABLE E

Stimulation of α1A(h).

| Compound | % inhibition of control values (1 μM) |
|---|---|
| 32 | 25 |
| 33 | 9 |
| 38 | 51 |
| 43 | 15 |
| 45 | 19 |
| 73 | 31 |
| 79 | 13 |
| 80 | 15 |
| 84 | 19 |
| 85 | 10 |
| 86 | −3 |
| 111 | 57 |
| 131 | 31 |

Example 25. 5HT$_{2A}$ (Agonist Effect)

Assays for determining the agonist effect on 5HT$_{2A}$ were performed according to the procedure described in Example 21, and the results are represented in Table F below. The compounds in Table F have no agonist effect on 5HT$_{2A}$ at 1 μM and 100 nM.

TABLE F

Stimulation of 5HT$_{2A}$ (agonist effect).

| Compound | % stimulation relative to control (1 μM) | % stimulation relative to control (100 nM) |
|---|---|---|
| 32 | 2 | 1 |
| 33 | −1 | 0 |
| 38 | −1 | 0 |
| 43 | 0 | −4 |
| 45 | −1 | −4 |
| 73 | 0 | 2 |
| 79 | 0 | 1 |
| 80 | 1 | 0 |
| 84 | −2 | −2 |
| 85 | 0 | −2 |
| 86 | 1 | 2 |
| 111 | −2 | −1 |
| 131 | −1 | 1 |

Example 26. 5HT$_{2A}$ (Antagonist Effect)

Assays for determining the antagonist effect on 5HT$_{2A}$ were performed according to the procedure described in Example 21, and the results are represented in Table G below. The compounds in Table G have no agonist effect on 5HT$_{2A}$ at 1 μM and 100 nM.

TABLE G

Stimulation of 5HT$_{2A}$ (antagonist effect).

| Compound | % stimulation relative to control (1 μM) | % stimulation relative to control (100 nM) |
|---|---|---|
| 32 | −12 | −21 |
| 33 | −5 | −23 |
| 38 | −6 | −11 |
| 43 | 4 | −8 |
| 45 | −6 | −5 |
| 73 | −10 | −19 |
| 79 | −5 | −14 |
| 80 | −9 | −3 |
| 84 | −6 | −11 |
| 85 | 9 | −1 |
| 86 | 6 | −16 |
| 111 | −6 | −2 |
| 131 | 0 | −16 |

Example 27. Assays for Determining hERG Inhibition

Measured K$_i$ values of compounds of the present disclosure are shown in Table H below. These compounds do not significantly inhibit hERG. Thus, these compounds, when administered to humans, are not expected to result in QT interval prolongations.

TABLE H

K$_i$ values of compounds of the present disclosure.

| Compound | hERG IC$_{50}$ |
|---|---|
| 2 | >3 μM |
| 10 | >3 μM |
| 32 | >3 |
| 33 | >3 |
| 38 | 2.04 |
| 43 | 2.77 |
| 45 | >3 |
| 73 | 2.6 |
| 79 | >3 |
| 80 | >3 |
| 84 | >3 |
| 85 | >3 |
| 86 | >3 |
| 111 | 2.22 |
| 131 | >3 |

Example 28. Toxicity Evaluation of Compounds on Vero-E6 Cell Line

The testing protocol is described below.

Day 1: Cell were seeded in 96 wells plate, Vero E6, P40, 10000 cells/well. Growth conditions included medium DMEM high glucose.

Day 2: Compounds were diluted in a mix of 50% DMSO and 50% growth medium to. 10 mM concentration was used for PB28 (10 mg vial from Tocris, 1-Cyclohexyl-4-(3-(5-methoxy-1,2,3,4-tetrahydronaphthalen-1-yl)-n-propyl)piperazine dihydrochloride, see Gordon et al. Nature 2020, 583, 4459-468). Other compounds were prepared at 2 mM concentration stock solution. Cells were treated from 50 μM to 0.37 μM by serial dilution two-fold dilution in triplicate. Controls were designed to include the same concentration of DMSO for each tested products.

Day 5: For a 72 h post treatment, cells were fixed with formalin and stained with Hoetsch33342. Cells were imaged using a Cell Insight CX7 high content screening microscope. Number of cells and nuclear parameters were assessed using an internal cytotoxicity testing protocol.

FIG. 1 depicts the cell number after exposing the cells to the conditions described above, which shows that compound 2 and compound 10 are not cytotoxic to the cells.

Example 29. Antiviral Evaluation of Compounds on Vero-E6 Cell Line Infected with SARS-CoV-2

Figure 2:
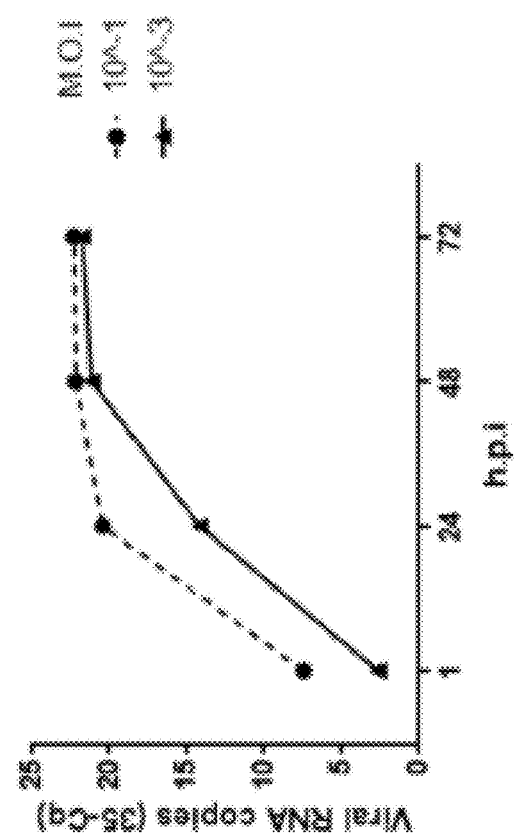
FIG. 2 depicts the replication kinetics of SARS-CoV-2 over time under untreated conditions at an MOI (multiplicity of infection) of $10^1$ and $10^3$.
Figure 3:
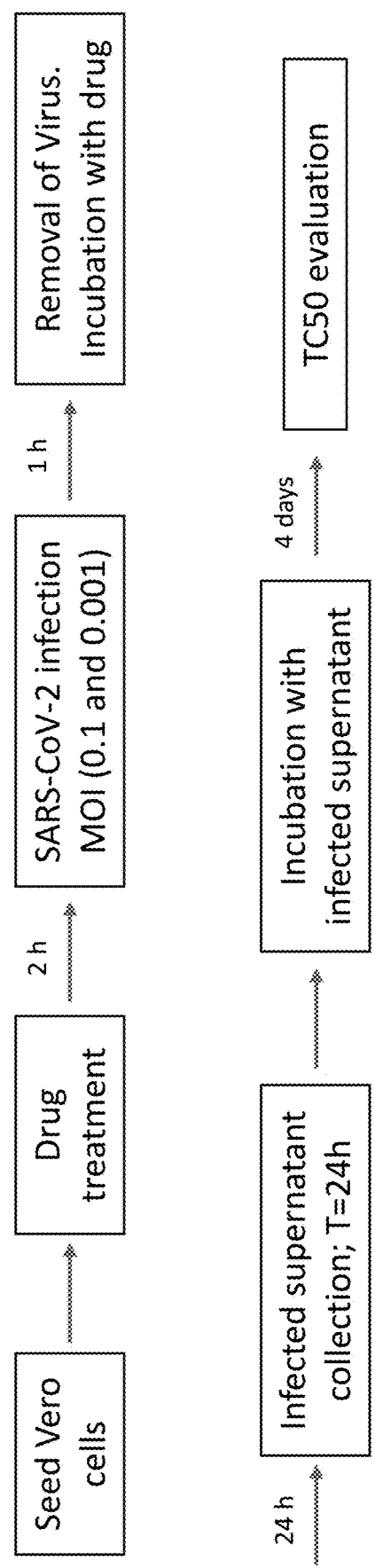
FIG. 3 depicts a schematic of the viral infectivity assay detailed in Example 29.

The testing protocol is described below and is illustrated in FIG. 3. The replication kinetics of untreated SARS-CoV-2 over time is shown in FIG. 2.

Day 1: Cells were seeded in 96 wells plate, Vero E6, P38. Growth conditions included medium DMEM high glucose (Dutscher L0104-500, lot MS008A).

Day 2: Compounds were diluted in a mix of 50% DMSO and 50% growth. Compounds were diluted first in pure DMSO then diluted with medium. Stock compounds were prepared at 10 mM for PB28 (10 mg vial from Tocris) Other compounds at 2 mM stock solution.

Figures 4A, 4B, 4C, 4D, 4E, 4F:
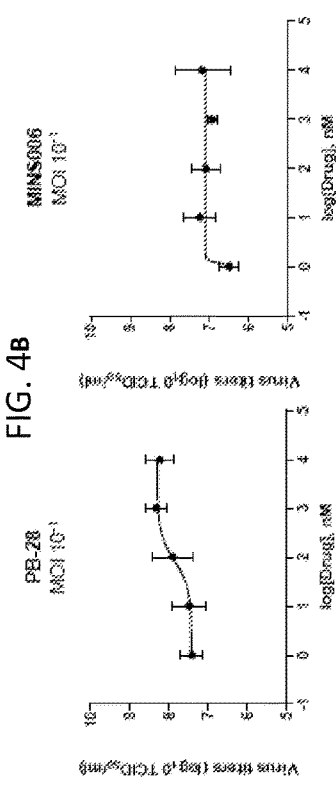
FIGS. 4A-F depict viral production in SARS-CoV-2 infected cells with a MOI of $10^1$ after being treated with a compound. (See Example 29.)

FIG. 4 depicts viral production in SARS-CoV-2 infected cells with MOI (multiplicity of infection) of $10^{-1}$ when treated with PB28, MIN-S006, Compound 2, Compound 10, MIN101, and a DMSO control.

FIG. 5 depicts viral production in SARS-CoV-2 infected cells with MOI (multiplicity of infection) of $10^{-3}$ when treated with PB28, MIN-S006, Compound 2, Compound 10, MIN101, and a DMSO control

EQUIVALENTS

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the disclosure to the precise form disclosed, but by the claims appended hereto.

The invention is further described with reference to the following clauses:

A. A compound of Formula (I) as hereinbefore described, or a prodrug, solvate, or pharmaceutically acceptable salt thereof, for use in a method of treating or preventing a viral infection in a subject, or an illness resulting from the viral infection.

B. The compound for use of clause A, wherein the viral infection is caused by a coronavirus, herpes simplex virus, human immunodeficiency virus, influenza, or human papillomavirus.

C. The compound for use of clause B, wherein the coronavirus is SARS-CoV-2.

D. The compound for use of any one of clauses A-C wherein the illness resulting from the viral infection is severe acute respiratory syndrome or COVID-19.

E. A compound of Formula (I) as hereinbefore described, or a prodrug, solvate, or pharmaceutically acceptable salt thereof, for use in a method of treating Alzheimer's disease.

F. A compound of Formula (I) as hereinbefore described, or a prodrug, solvate, or pharmaceutically acceptable salt thereof, for use in a method of treating a disease, or symptom of a disease, wherein said disease or symptom of a disease is anxiety, depression, emotional abnormality, schizophrenia, narcotic intoxication, narcotic addiction, sharp pain, dyskinesia, cerebrovascular disease, epilepsy, dementia, Parkinson's syndrome, attention deficit disorder, irritable bowel syndrome, irritable colon, spastic colon, colitis mucosus, enterocolitis, diverticulitis, dysentery, hypertension, arrhythmia, angina pectoris, amyotrophic lateral sclerosis (ALS), Huntington disease, stroke, retinal degeneration, or cognitive impairment in neuropsychiatric diseases.

G. A compound of Formula (I) as hereinbefore described, or a prodrug, solvate, or pharmaceutically acceptable salt thereof, for use in a method of treating or preventing pain in a subject in need of treatment.

H. The compound for use of clause G, wherein the pain is acute pain, chronic pain, toxic pain, neuropathic pain, nociceptive pain, inflammatory pain, post-operative pain, visceral pain, chemotherapy-induced pain, peripheral neuropathy, fibromyalgia, or a combination thereof.

I. A compound of Formula (I) as hereinbefore described, or a prodrug, solvate, or pharmaceutically acceptable salt thereof, for use in a method of promoting an antihyperalgesic effect in a subject suffering from hyperalgesia.

J. A compound of Formula (I) as hereinbefore described, or a prodrug, solvate, or pharmaceutically acceptable salt thereof, for use in a method of reducing sensitivity to pain in a subject.

K. A compound of Formula (I) as hereinbefore described, or a prodrug, solvate, or pharmaceutically acceptable salt thereof, for use in a method of treating cancer in a subject in need thereof.

L. The compound for use of clause K, wherein the cancer is breast cancer, prostate cancer, colon cancer, rectal cancer, pancreatic cancer, liver cancer, bladder cancer, thyroid cancer, kidney cancer, skin cancer, non-Hodgkin lymphoma, or uterine cancer.

M. Use of a compound of Formula (I) as hereinbefore described, or a prodrug, solvate, or pharmaceutically acceptable salt thereof, in the manufacture of a medicament for treating or preventing a viral infection in a subject, or an illness resulting from the viral infection.

N. The use of clause M, wherein the viral infection is caused by a coronavirus, herpes simplex virus, human immunodeficiency virus, influenza, or human papillomavirus.

O. The use of clause N, wherein the coronavirus is SARS-CoV-2.

P. The use of any one of clauses M-O wherein the illness resulting from the viral infection is severe acute respiratory syndrome or COVID-19.

Q. Use of a compound of Formula (I) as hereinbefore described, or a prodrug, solvate, or pharmaceutically acceptable salt thereof, in the manufacture of a medicament for treating Alzheimer's disease.

R. Use of a compound of Formula (I) as hereinbefore described, or a prodrug, solvate, or pharmaceutically acceptable salt thereof, in the manufacture of a medicament for treating a disease, or symptom of a disease, wherein said disease or symptom of a disease is anxiety, depression, emotional abnormality, schizophrenia, narcotic intoxication, narcotic addiction, sharp pain, dyskinesia, cerebrovascular disease, epilepsy, dementia, Parkinson's syndrome, attention deficit disorder, irritable bowel syndrome, irritable colon, spastic colon, colitis mucosus, enterocolitis, diverticulitis, dysentery, hypertension, arrhythmia, or angina pectoris.

S. Use of a compound of Formula (I) as hereinbefore described, or a prodrug, solvate, or pharmaceutically acceptable salt thereof, in the manufacture of a medicament for treating or preventing pain in a subject in need of treatment.

T. The use of clause S, wherein the pain is acute pain, chronic pain, toxic pain, neuropathic pain, nociceptive pain, inflammatory pain, post-operative pain, visceral pain, chemotherapy-induced pain, peripheral neuropathy, fibromyalgia, or a combination thereof.

U. Use of a compound of Formula (I) as hereinbefore described, or a prodrug, solvate, or pharmaceutically acceptable salt thereof, in the manufacture of a medicament for promoting an antihyperalgesic effect in a subject suffering from hyperalgesia.

V. Use of a compound of Formula (I) as hereinbefore described, or a prodrug, solvate, or pharmaceutically acceptable salt thereof, in the manufacture of a medicament for reducing sensitivity to pain in a subject.

W. Use of a compound of Formula (I) as hereinbefore described, or a prodrug, solvate, or pharmaceutically acceptable salt thereof, in the manufacture of a medicament for treating cancer in a subject in need thereof.

X. The use of clause W, wherein the cancer is breast cancer, prostate cancer, colon cancer, rectal cancer, pancreatic cancer, liver cancer, bladder cancer, thyroid cancer, kidney cancer, skin cancer, non-Hodgkin lymphoma, or uterine cancer.

Y. Use of a compound of Formula (I) as hereinbefore described, or a prodrug, solvate, or pharmaceutically acceptable salt thereof, in a method of treating or preventing a viral infection in a subject, or an illness resulting from the viral infection.

Z. The use of clause Y, wherein the viral infection is caused by a coronavirus, herpes simplex virus, human immunodeficiency virus, influenza, or human papillomavirus.

AA. The use of clause Z, wherein the coronavirus is SARS-CoV-2.

BB. The use of any one of clauses Y-AA wherein the illness resulting from the viral infection is severe acute respiratory syndrome or COVID-19.

CC. Use of a compound of Formula (I) as hereinbefore described, or a prodrug, solvate, or pharmaceutically acceptable salt thereof, in a method of treating Alzheimer's disease.

DD. Use of a compound of Formula (I) as hereinbefore described, or a prodrug, solvate, or pharmaceutically acceptable salt thereof, in a method of treating a disease, or symptom of a disease, wherein said disease or symptom of a disease is anxiety, depression, emotional abnormality, schizophrenia, narcotic intoxication, narcotic addiction, sharp pain, dyskinesia, cerebrovascular disease, epilepsy, dementia, Parkinson's syndrome, attention deficit disorder, irritable bowel syndrome, irritable colon, spastic colon, colitis *mucosus*, enterocolitis, diverticulitis, dysentery, hypertension, arrhythmia, angina pectoris, amyotrophic lateral sclerosis (ALS), Huntington disease, stroke, retinal degeneration, or cognitive impairment in neuropsychiatric diseases.

EE. Use of a compound of Formula (I) as hereinbefore described, or a prodrug, solvate, or pharmaceutically acceptable salt thereof, in a method of treating or preventing pain in a subject in need of treatment.

FF. The use of clause EE, wherein the pain is acute pain, chronic pain, toxic pain, neuropathic pain, nociceptive pain, inflammatory pain, post-operative pain, visceral pain, chemotherapy-induced pain, peripheral neuropathy, fibromyalgia, or a combination thereof.

GG. Use of a compound of Formula (I) as hereinbefore described, or a prodrug, solvate, or pharmaceutically acceptable salt thereof, in a method of promoting an antihyperalgesic effect in a subject suffering from hyperalgesia.

HH. Use of a compound of Formula (I) as hereinbefore described, or a prodrug, solvate, or pharmaceutically acceptable salt thereof, in a method of reducing sensitivity to pain in a subject.

II. Use of a compound of Formula (I) as hereinbefore described, or a prodrug, solvate, or pharmaceutically acceptable salt thereof, in a method of treating cancer in a subject in need thereof.

JJ. The use of clause II, wherein the cancer is breast cancer, prostate cancer, colon cancer, rectal cancer, pancreatic cancer, liver cancer, bladder cancer, thyroid cancer, kidney cancer, skin cancer, non-Hodgkin lymphoma, or uterine cancer.

The invention claimed is:
1. A compound of Formula (I):

(I)

or a solvate or pharmaceutically acceptable salt thereof, wherein $X_1$ is absent, —$(CR_3R_4)_q$—, —O—, —$S(O)_2$—, —C(O)—, —C(S)—, —S(O)—, —$NR_3C(O)$—, —$C(O)NR_3$—, —C(O)O—, or —OC(O)—;

$X_2$ is absent, —$(CR_3R_4)_q$—, —O—, —$S(O)_2$—, —C(O)—, —C(S)—, —S(O)—, —$NR_3C(O)$—, —$C(O)NR_3$—, —C(O)O—, or —OC(O)—;

$R_1$ is H, OH, halogen, $NH_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, $C_6$-$C_{10}$ aryl, 5- to 12-membered heteroaryl comprising 1-6 heteroatoms selected from N, O, and S, 5- to 14-membered saturated or unsaturated heterocycloalkyl comprising 1-5 heteroatoms selected from N, O, and S; wherein the alkyl, alkenyl, alkynyl, haloalkyl, alkoxyl, haloalkoxyl, cycloalkyl, aryl, heteroaryl, or heterocycloalkyl of any of the foregoing is optionally substituted with one or more $R_5$;

$R_2$ is $C_6$-$C_{10}$ aryl, 5- to 12-membered heteroaryl comprising 1-6 heteroatoms selected from N, O, and S, or 5- to 14-membered saturated or unsaturated heterocycloalkyl comprising 1-5 heteroatoms selected from N, O, and S; wherein the aryl, heteroaryl, or heterocycloalkyl of any of the foregoing is optionally substituted with one or more $R_6$;

each $R_3$ independently is H, halogen, or $C_1$-$C_6$ alkyl;
each $R_4$ independently is H, halogen, or $C_1$-$C_6$ alkyl;

each $R_5$ independently is OH, halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, $C_6$-$C_{10}$ aryl, or 5- to 14-membered saturated or unsaturated heterocycloalkyl comprising 1-5 heteroatoms selected from N, O, and S; wherein the alkyl, alkenyl, alkynyl, cycloalkyl, or aryl of any of the foregoing is optionally substituted with one or more —C(O)$C_1$-$C_6$alkyl, —C(O)O$C_1$-$C_6$alkyl, —C(O)NH$_2$, —C(O)NH$C_1$-$C_6$alkyl, or —C(O)N($C_1$-$C_6$alkyl)$_2$;

each $R_6$ independently is OH, halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, $C_6$-$C_{10}$ aryl, or 5- to 14-membered saturated or unsaturated heterocycloalkyl comprising 1-5 heteroatoms selected from N, O, and S; wherein the alkyl, alkenyl, alkynyl, cycloalkyl, aryl, or heterocycloalkyl of any of the foregoing is optionally substituted with one or more —C(O)$C_1$-$C_6$ alkyl, —C(O)O$C_1$-$C_6$ alkyl, —C(O) NH$_2$, —C(O)NH$C_1$-$C_6$ alkyl, or —C(O)N ($C_1$-$C_6$alkyl)$_2$;

$R_7$ is $C_1$-$C_6$ alkyl optionally substituted with one or more OH, halogen, or $C_1$-$C_6$ alkoxyl;

$R_8$ is $C_1$-$C_6$ alkyl optionally substituted with one or more OH, halogen, or $C_1$-$C_6$ alkoxyl;

m is 1;

n is 2;

p is 1; and each q independently is 1, 2, 3, or 4.

2. The compound of claim 1, wherein the compound is a compound of Formula (Ia):

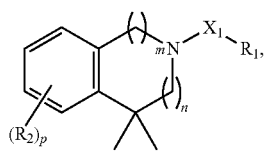

(Ia)

or a solvate or pharmaceutically acceptable salt thereof, wherein $X_1$ is absent, $(CR_3R_4)_q$, —C(O)—, —C(S)—, —S(O)—, —NR$_3$C(O)—, or —C(O)O—;

$R_1$ is H, OH, halogen, NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl, wherein the alkyl, alkenyl, alkynyl, haloalkyl, alkoxyl, haloalkoxyl, or cycloalkyl of any of the foregoing is optionally substituted with one or more $R_5$;

$R_2$ is $C_6$-$C_{10}$ aryl, 5- to 12-membered heteroaryl comprising 1-6 heteroatoms selected from N, O, and S, or 5- to 14-membered saturated or unsaturated heterocycloalkyl comprising 1-5 heteroatoms selected from N, O, and S; wherein the aryl, heteroaryl, or heterocycloalkyl of any of the foregoing is optionally substituted with one or more $R_6$;

each $R_3$ independently is H or halogen;

each $R_4$ independently is H or halogen;

each $R_5$ independently is OH, halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, or $C_6$-$C_{10}$ aryl, wherein the alkyl, alkenyl, alkynyl, cycloalkyl, or aryl of any of the foregoing is optionally substituted with one or more —C(O)$C_1$-$C_6$alkyl, —C(O)O$C_1$-$C_6$alkyl, —C(O)NH$_2$, —C(O)NH$C_1$-$C_6$alkyl, or —C(O)N($C_1$-$C_6$alkyl)$_2$; and each $R_6$ independently is OH, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, $C_6$-$C_{10}$ aryl, or 5- to 14-membered saturated or unsaturated heterocycloalkyl comprising 1-5 heteroatoms selected from N, O, and S; wherein the alkyl, alkenyl, alkynyl, cycloalkyl, or aryl of any of the foregoing is optionally substituted with one or more —C(O)$C_1$-$C_6$alkyl, —C(O)O$C_1$-$C_6$alkyl, —C(O)NH$_2$, —C(O)NH$C_1$-$C_6$alkyl, or —C(O)N($C_1$-$C_6$alkyl)$_2$.

3. The compound of claim 1, wherein $X_1$ is $(CR_3R_4)_q$, —C(O)—, —C(S)—, —S(O)—, —NR$_3$C(O)—, or —C(O) O—.

4. The compound of claim 1, wherein $X_1$ is absent.

5. The compound of claim 1, wherein $X_2$ is $(CR_3R_4)_q$, —C(O)—, —C(S)—, —S(O)—, —NR$_3$C(O)—, or —C(O) O—.

6. The compound of claim 1, wherein $X_2$ is absent.

7. The compound of claim 1, wherein $R_1$ is H or OH.

8. The compound of claim 1, wherein $R_1$ is halogen.

9. The compound of claim 1, wherein $R_1$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl, wherein the alkyl, alkenyl, alkynyl, haloalkyl, alkoxyl, haloalkoxyl, or cycloalkyl of any of the foregoing is optionally substituted with one or more $R_5$.

10. The compound of claim 1, wherein $R_1$ is $C_6$-$C_{10}$ aryl, 5- to 12-membered heteroaryl comprising 1-6 heteroatoms selected from N, O, and S, or 5- to 14-membered saturated or unsaturated heterocycloalkyl comprising 1-5 heteroatoms selected from N, O, and S; wherein the aryl, heteroaryl, or heterocycloalkyl of any of the foregoing is optionally substituted with one or more $R_5$.

11. The compound of claim 1, wherein $R_1$ is H, OH, methyl,

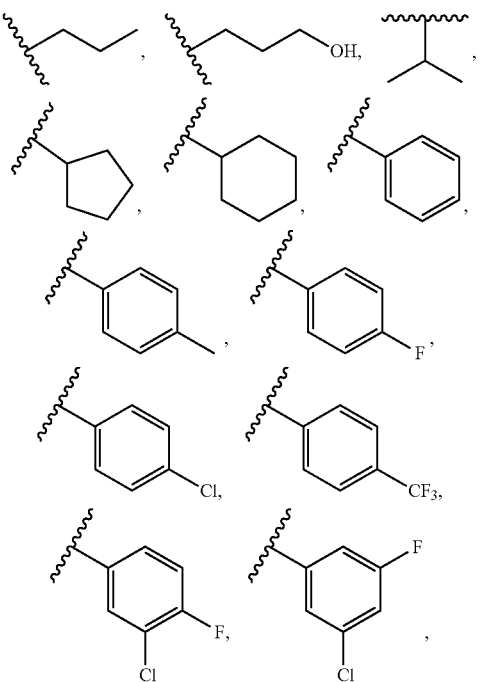

157
-continued

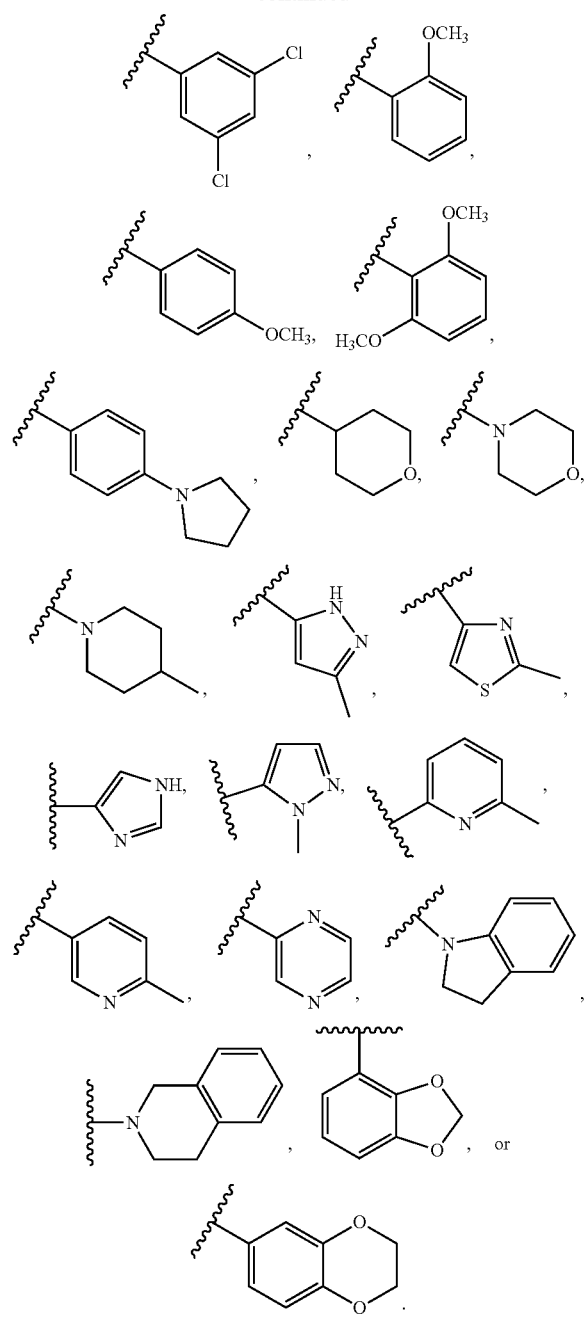

12. The compound of claim 1, wherein R$_2$ is

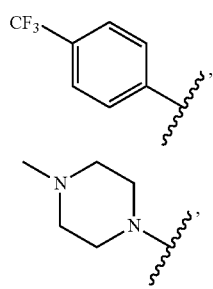

158
-continued

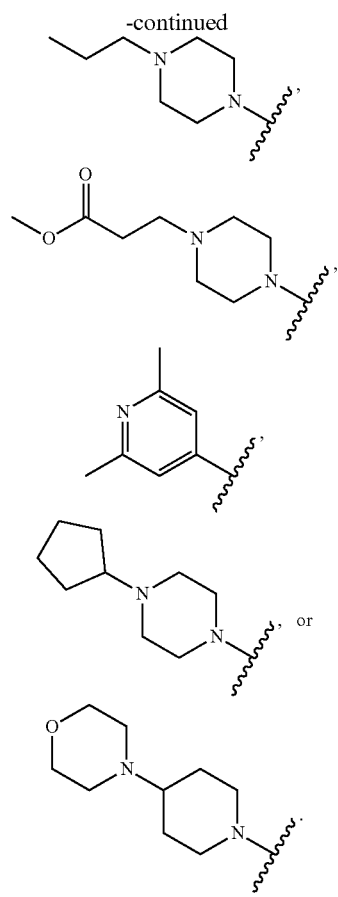

13. The compound of claim 1, wherein R$_5$ is OH or halogen.

14. The compound of claim 1, wherein R$_5$ is C$_1$-C$_6$ alkyl, C$_2$-C$_6$ alkenyl, or C$_2$-C$_6$ alkynyl.

15. The compound of claim 1, wherein R$_5$ is C$_1$-C$_6$ haloalkyl, C$_1$-C$_6$ alkoxyl, C$_1$-C$_6$ haloalkoxyl, or C$_3$-C$_6$ cycloalkyl.

16. The compound of claim 1, wherein R$_6$ is OH.

17. The compound of claim 1, wherein R$_6$ is C$_1$-C$_6$ alkyl, C$_2$-C$_6$ alkenyl, or C$_2$-C$_6$ alkynyl.

18. The compound of claim 1, wherein R$_6$ is C$_1$-C$_6$ haloalkyl, C$_1$-C$_6$ alkoxyl, C$_1$-C$_6$ haloalkoxyl, or C$_3$-C$_6$ cycloalkyl.

19. The compound of claim 1, wherein R$_6$ is a 5- to 14-membered saturated or unsaturated heterocycloalkyl comprising 1-5 heteroatoms selected from N, O, and S; wherein the heterocycloalkyl is optionally substituted with one or more —C(O)C$_1$-C$_6$alkyl, —C(O)OC$_1$-C$_6$alkyl, —C(O)NH$_2$, —C(O)NHC$_1$-C$_6$alkyl, or —C(O)N(C$_1$-C$_6$alkyl)$_2$.

20. The compound of claim 1, wherein R$_6$ is

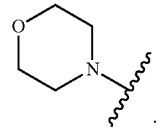

21. The compound of claim 1, wherein R$_7$ and R$_8$ are each methyl.

22. The compound of claim 1, wherein the compound is a compound of Formula (III):

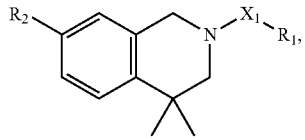
(II)

or a solvate or pharmaceutically acceptable salt thereof, wherein $X_1$, $R_1$, and $R_2$ are as described in claim 1.

23. The compound of claim 1, wherein the compound is

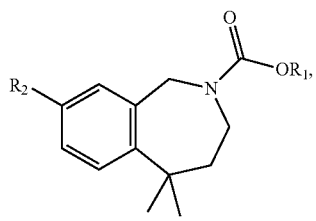
(IIIa)

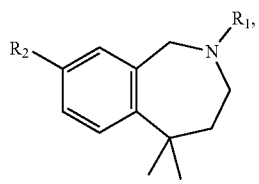
(IIIb)

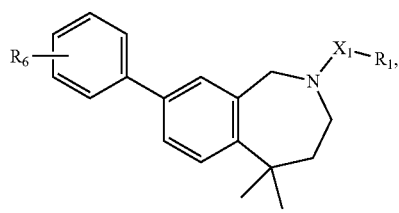
(IIIe)

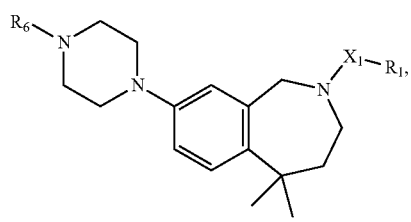
(IIIg)

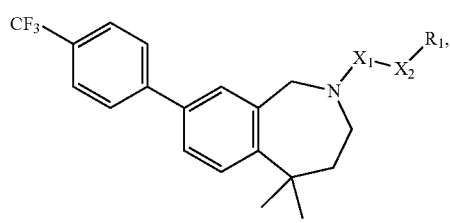
(IIIi)

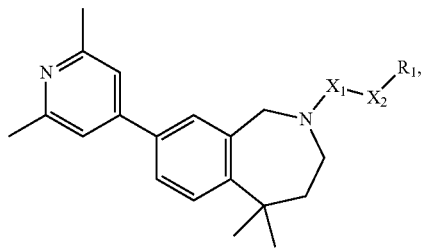
(IIIj)

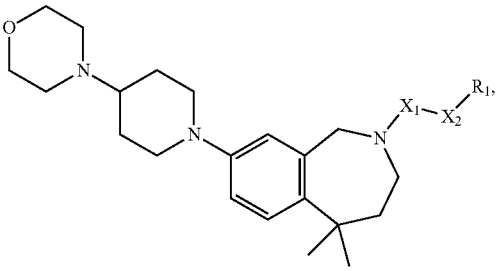
(IIIk)

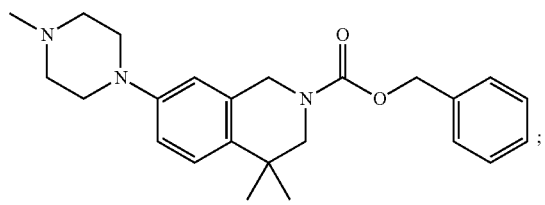
(IIIl)

or a solvate or pharmaceutically acceptable salt thereof, wherein $X_1$, $X_2$, $R_1$, $R_2$, and $R_6$ are as described in claim 1.

24. A compound that is:

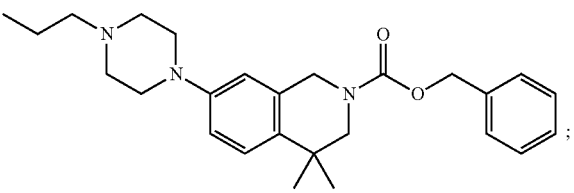

benzyl 4,4-dimethyl-7-(4-methylpiperazin-1-yl)-
3,4-dihydroisoquinoline-2(1H)-carboxylate benzyl 4,4-dimethyl-7-(4-methylpiperazin-1-yl)-
3,4-dihydroisoquinoline-2(1H)-carboxylate -continued

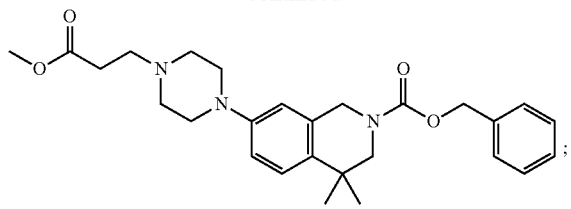

benzyl 7-(4-(3-methoxy-3-oxopropyl)piperazin-1-yl)-4,4-dimethyl-3,4-dihydroisoquinoline-2(1H)-carboxylate

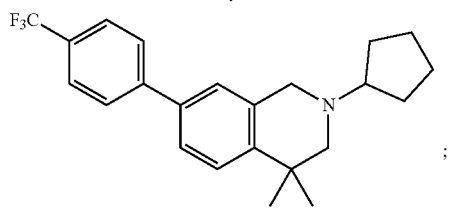

2-cyclopentyl-4,4-dimethyl-7-(4-(trifluoromethyl)phenyl)-1,2,3,4-tetrahydroisoquinoline

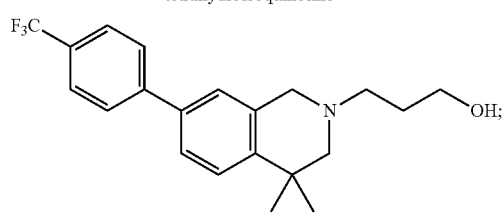

3-(4,4-dimethyl-7-(4-(trifluoromethyl)phenyl)-3,4-dihydroisoquinolin-2(1H)-yl)propan-1-ol

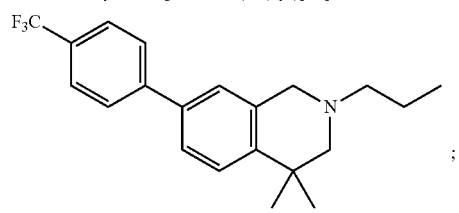

4,4-dimethyl-2-propyl-7-(4-(trifluoromethyl)phenyl)-1,2,3,4-tetrahydroisoquinoline

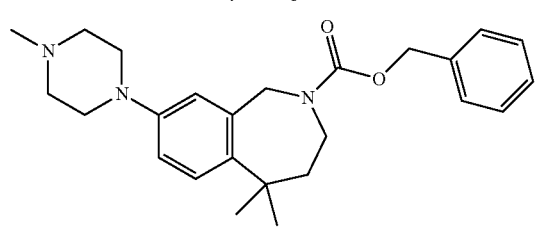

benzyl 5,5-dimethyl-8-(4-methylpiperazin-1-yl)-1,3,4,5-tetrahydro-2H-benzo[c]azepine-2-carboxylate

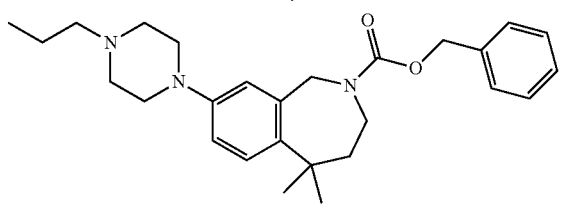

benzyl 5,5-dimethyl-8-(4-propylpiperazin-1-yl)-1,3,4,5-tetrahydro-2H-benzo[c]azepine-2-carboxylate -continued

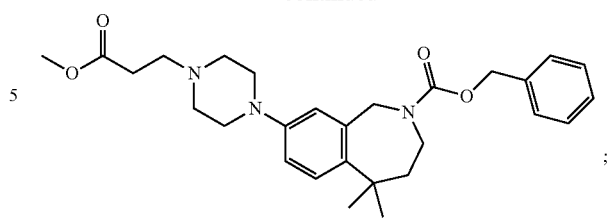

benzyl 8-(4-(3-methoxy-3-oxopropyl)piperazin-1-yl)-5,5-dimethyl-1,3,4,5-tetrahydro-2H-benzo[c]azepine-2-carboxylate

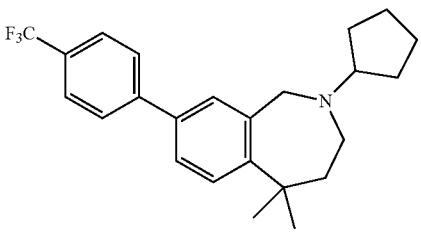

2-cyclopentyl-5,5-dimethyl-8-(4-(trifluoromethyl)phenyl)-2,3,4,5-tetrahydro-1H-benzo[c]azepine

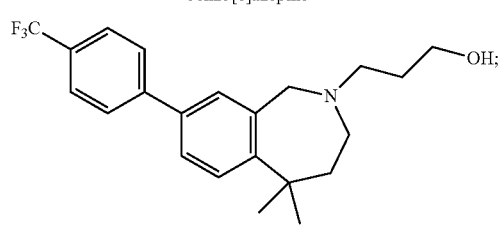

3-(5,5-dimethyl-8-(4-(trifluoromethyl)phenyl)-1,3,4,5-tetrahydro-2H-benzo[c]azepin-2-yl)propan-1-ol

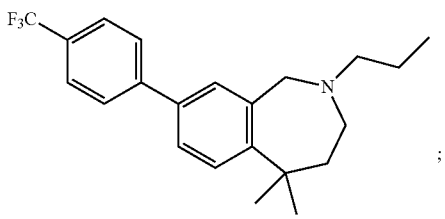

5,5-dimethyl-2-propyl-8-(4-(trifluoromethyl)phenyl)-2,3,4,5-tetrahydro-1H-benzo[c]azepine

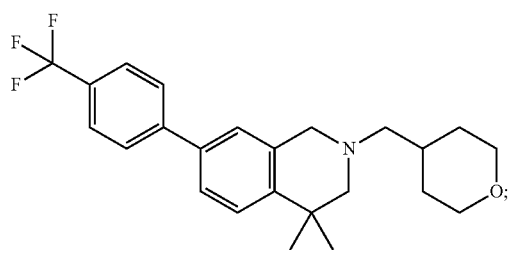

4,4-dimethyl-2-((tetrahydro-2-pyran-4-yl)methyl)-7-(4-(trifluoromethyl)phenyl-1,2,3,4-tetrahydroisoquinoline

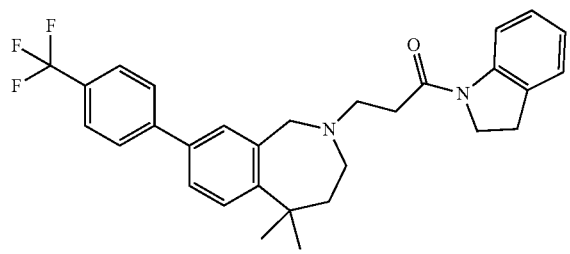

3-(5,5-dimethyl-8-(4-(trifluoromethyl)phenyl)-
1,3,4,5-tetrahydro-2H-benzo[c]azepin-2-yl)-1-
(indolin-1-yl)propan-1-one

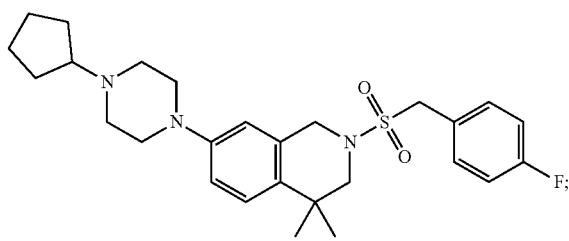

7-(4-cyclopentylpiperazin-1-yl)-2-((4-
fluorobenzyl)sulfonyl)-4,4-dimethyl-1,2,3,4-
tetrahydroisoquinoline

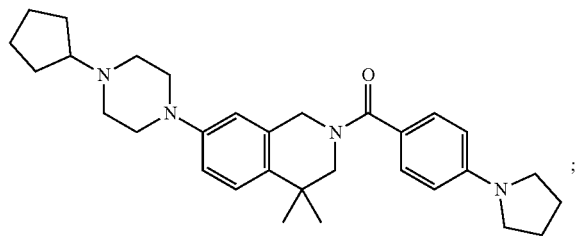

(7-(4-cyclopentylpiperazin-1-yl)-4,4-dimethyl-3,4-
dihydroisoquinolin-2(1H)-yl)(4-(pyrrolidin-1-
yl)phenyl)methanone

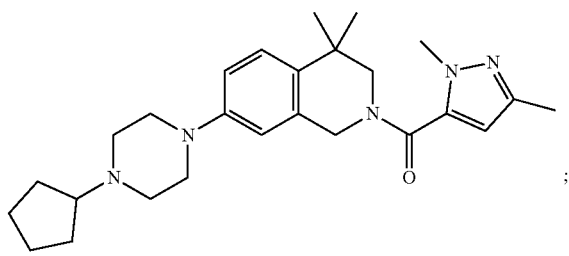

(7-(4-cyclopentylpiperazin-1-yl)-4,4-dimethyl-3,4-
dihydroisoquinolin-2(1H)-yl)(1,3-dimethyl-1H-
pyrazol-5-yl)methanone

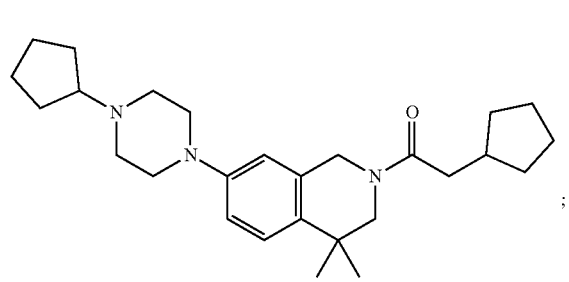

N-cyclopentyl-7-(4-cyclopentylpiperazin-1-yl)-4,4-
dimethyl-3,4-dihydroisoquinoline-2(1H)-
carboxamide;

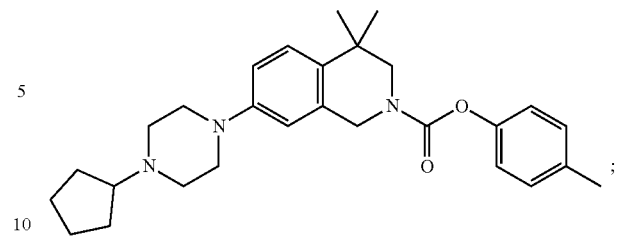

p-tolyl 7-(4-cyclopentylpiperazin-1-yl)-4,4-
dimethyl-3,4-dihydroisoquinoline-2(1H)-
carboxylate

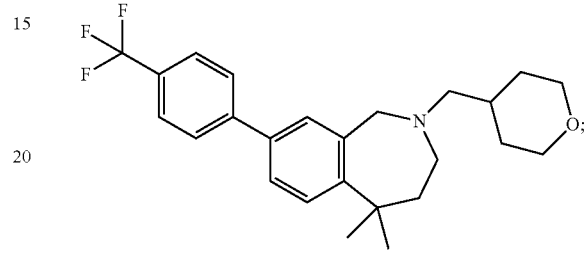

5,5-dimethyl-2-((tetrahydro-2H-pyran-4-
yl)methyl)-8-(4-(trifluoromethyl)phenyl)-2,3,4,5-
tetrahydro-1H-benzo[c]azepine;

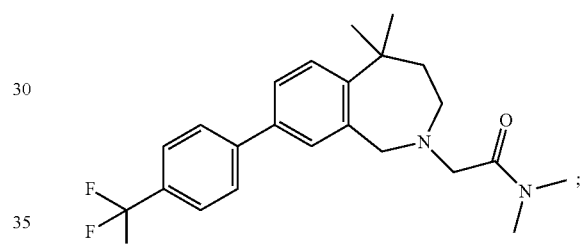

2-(5,5-dimethyl-8-(4-(trifluoromethyl)phenyl)-
1,3,4,5-tetrahydro-2H-benzo[c]azepin-2-yl)-N,N-
dimethylacetamide

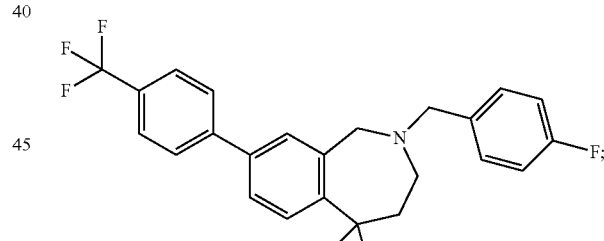

2-(4-fluorobenzyl)-5,5-dimethyl-8-(4-
(trifluoromethyl)phenyl)-2,3,4,5-tetrahydro-1H-
benzo[c]azepine

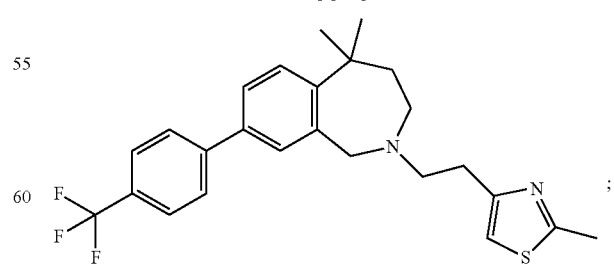

4-(2-(5,5-dimethyl-8-(4-(trifluoromethyl)phenyl)-
1,3,4,5-tetrahydro-2H-benzo[c]azepin-2-yl)ethyl)-
2-methylthiazole -continued

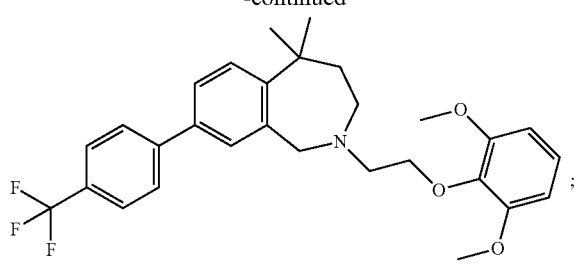

2-(2-(2,6-dimethoxyphenoxy)ethyl)-5,5-dimethyl-
8-(4-(trifluoromethyl)phenyl)-2,3,4,5-tetrahydro-
1H-benzo[c]azepine

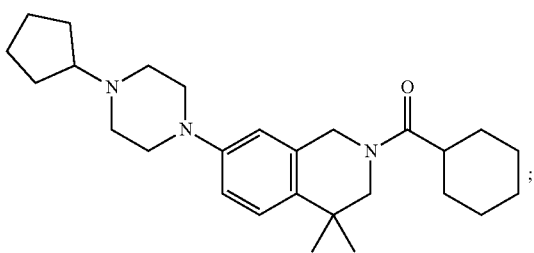

cyclohexyl(7-(4-cyclopentylpiperazin-1-yl)-4,4-
dimethyl-3,4-dihydroisoquinolin-2(1H)-
yl)methanone

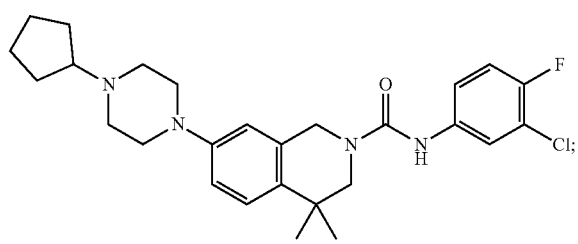

N-(3-chloro-4-fluorophenyl)-7-(4-
cyclopentylpiperazin-1-yl)-4,4-dimethyl-3,4-
dihydroisoquinoline-2(1H)-carboxamide

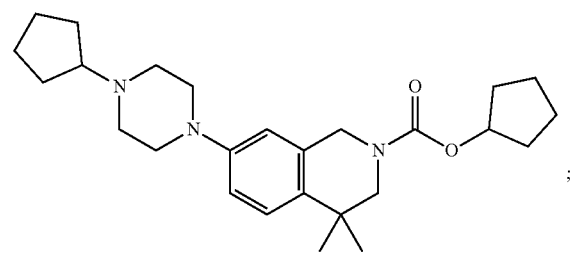

cyclopentyl 7-(4-cyclopentylpiperazin-1-yl)-4,4-
dimethyl-3,4-dihydroisoquinoline-2(1H)-
carboxylate

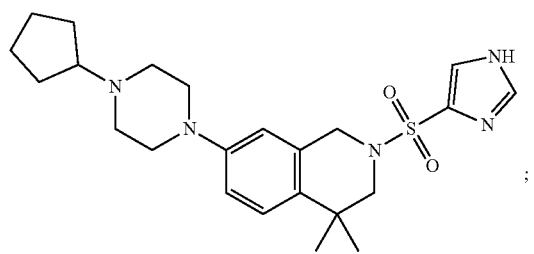

2-((1H-imidazol-4-yl)sulfonyl)-7-(4-
cyclopentylpiperazin-1-yl)-4,4-dimethyl-1,2,3,4-
tetrahydroisoquinoline -continued

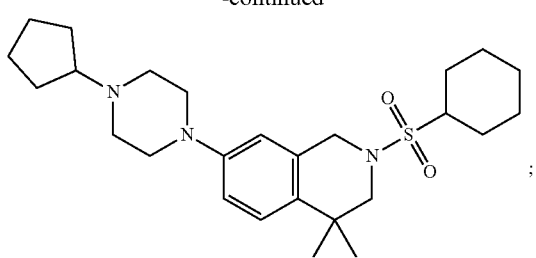

2-(cyclohexylsulfonyl)-7-(4-cyclopentylpiperazin-
1-yl)-4,4-dimethyl-1,2,3,4-tetrahydroisoquinoline;

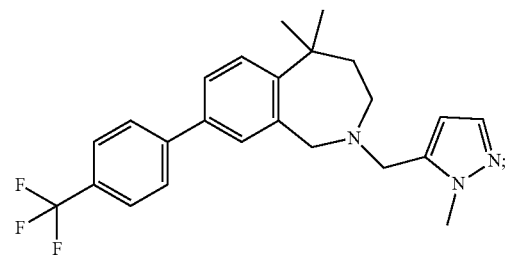

5,5-dimethyl-2-((1-methyl-1H-pyrazol-5-
yl)methyl)-8-(4-(trifluoromethyl)phenyl)-2,3,4,5-
tetrahydro-1H-benzo[c]azepine

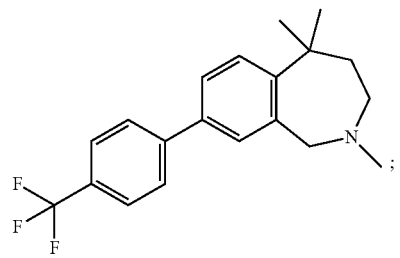

2,5,5-trimethyl-8-(4-(trifluoromethyl)phenyl)-
2,3,4,5-tetrahydro-1H-benzo[c]azepine

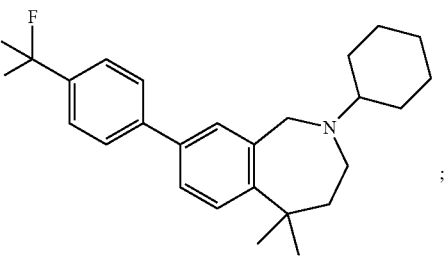

2-cyclohexyl-5,5-dimethyl-8-(4-
(trifluoromethyl)phenyl)-2,3,4,5-tetrahydro-1H-
benzo[c]azepine

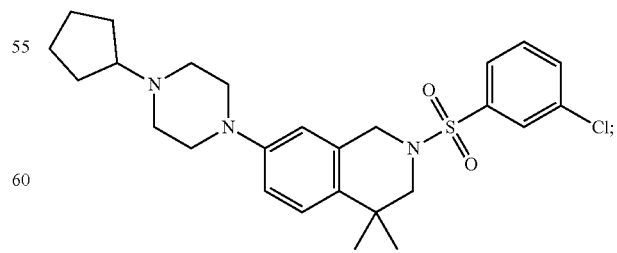

2-((3-chlorophenyl)sulfonyl)-7-(4-
cyclopentylpiperazin-1-yl)-4,4-dimethyl-1,2,3,4-
tetrahydroisoquinoline

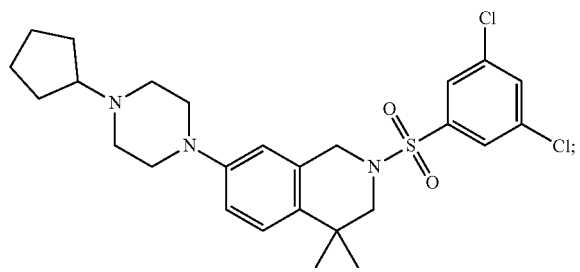

7-(4-cyclopentylpiperazin-1-yl)-2-((3,5-dichlorophenyl)sulfonyl)-4,4-dimethyl-1,2,3,4-tetrahydroisoquinoline

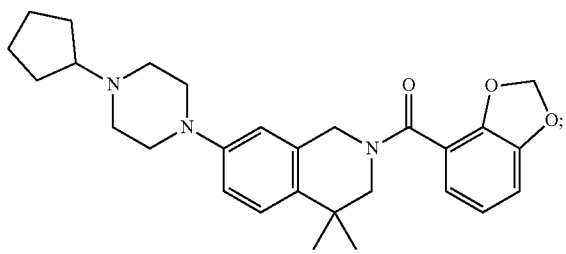

benzo[d][1,3]dioxol-4-yl(7-(4-cyclopentylpiperazin-1-yl)-4,4-dimethyl-3,4-dihydroisoquinolin-2(1H)-yl)methanone

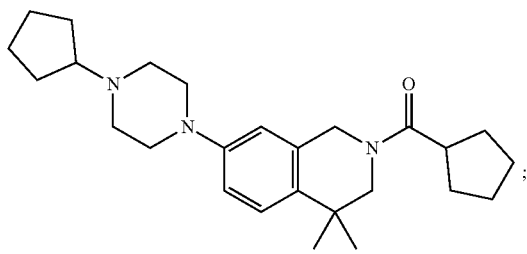

cyclopentyl(7-(4-cyclopentylpiperazin-1-yl)-4,4-dimethyl-3,4-dihydroisoquinolin-2(1H)-yl)methanone

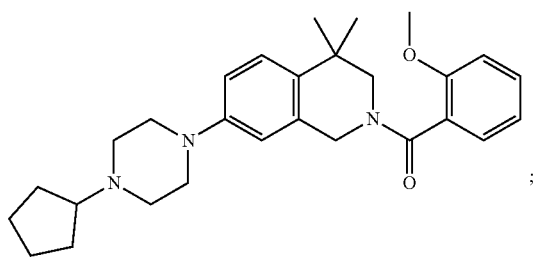

(7-(4-cyclopentylpiperazin-1-yl)-4,4-dimethyl-3,4-dihydroisoquinolin-2(1H)-yl)(2-methoxyphenyl)methanone

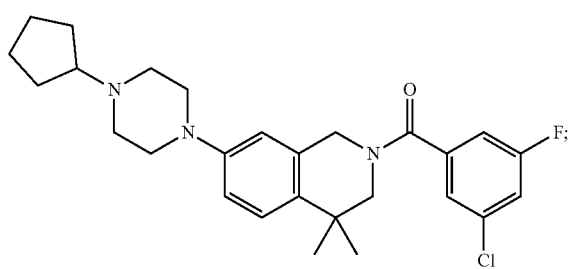

(3-chloro-5-fluorophenyl)(7-(4-cyclopentylpiperazin-1-yl)-4,4-dimethyl-3,4-dihydroisoquinolin-2(1H)-yl)methanone

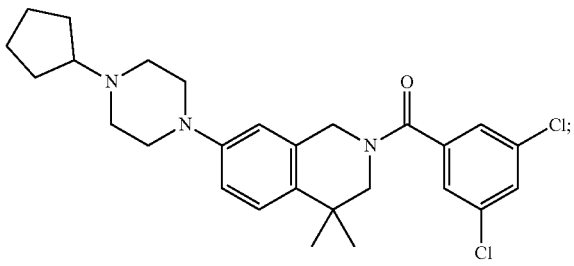

(7-(4-cyclopentylpiperazin-1-yl)-4,4-dimethyl-3,4-dihydroisoquinolin-2(1H)-yl)(3,5-dichlorophenyl)methanone

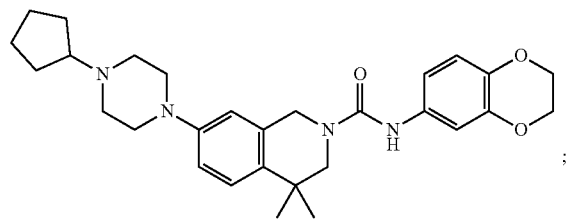

7-(4-cyclopentylpiperazin-1-yl)-N-(2,3-dihydrobenzo[b][1,4]dioxin-6-yl)-4,4-dimethyl-3,4-dihydroisoquinoline-2(1H)-carboxamide

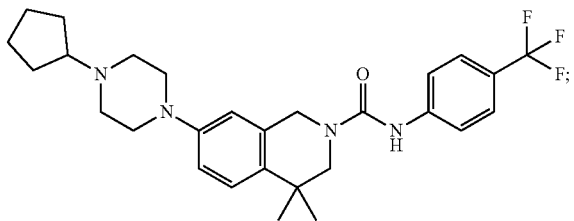

7-(4-cyclopentylpiperazin-1-yl)-4,4-dimethyl-N-(4-(trifluoromethyl)phenyl)-3,4-dihydroisoquinoline-2(1H)-carboxamide

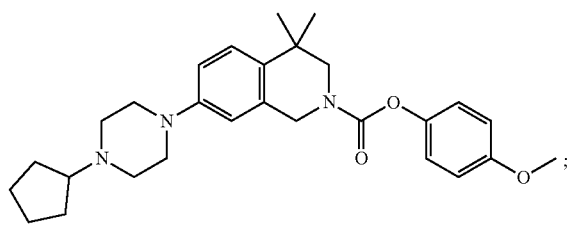

4-methoxyphenyl 7-(4-cyclopentylpiperazin-1-yl)-4,4-dimethyl-3,4-dihydroisoquinoline-2(1H)-carboxylate

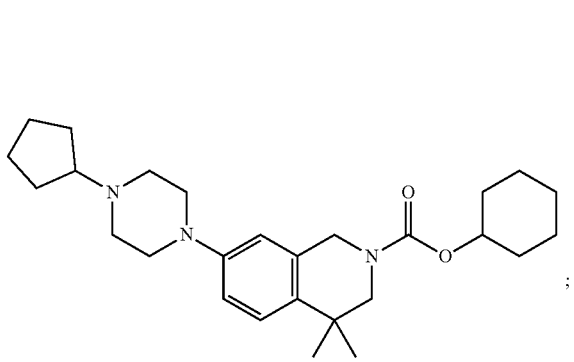

cyclohexyl 7-(4-cyclopentylpiperazin-1-yl)-4,4-dimethyl-3,4-dihydroisoquinoline-2(1H)-carboxylate

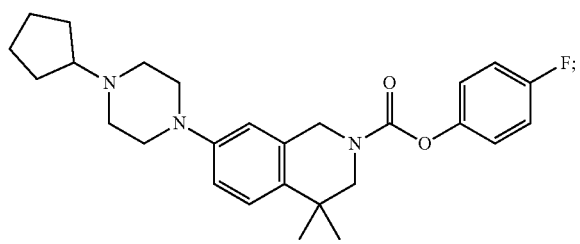

4-fluorophenyl 7-(4-cyclopentylpiperazin-1-yl)-
4,4-dimethyl-3,4-dihydroisoquinoline-2(1H)-
carboxylate

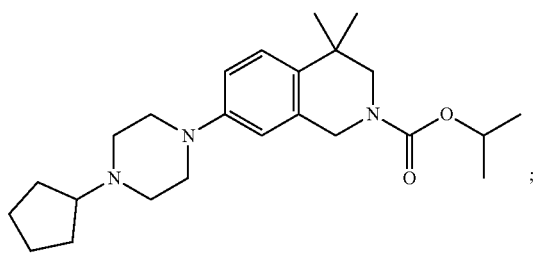

isopropyl 7-(4-cyclopentylpiperazin-1-yl)-4,4-
dimethyl-3,4-dihydroisoquinoline-2(1H)-
carboxylate

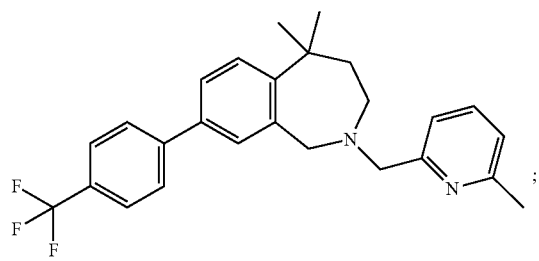

5,5-dimethyl-2-((6-methylpyridin-2-yl)methyl)-8-
(4-(trifluoromethyl)phenyl)-2,3,4,5-tetrahydro-1H-
benzo[c]azepine

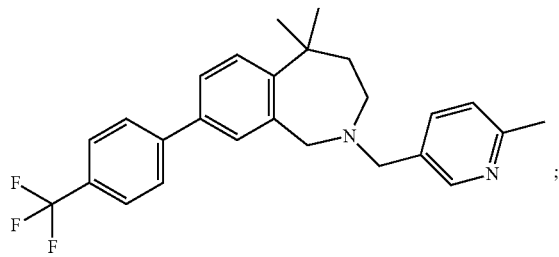

5,5-dimethyl-2-((6-methylpyridin-3-yl)methyl)-8-
(4-(trifluoromethyl)phenyl)-2,3,4,5-tetrahydro-1H-
benzo[c]azepine

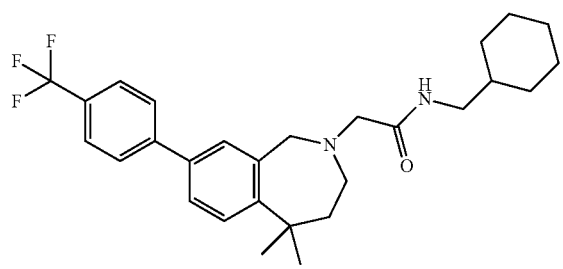

N-(cyclohexylmethyl)-2-(5,5-dimethyl-8-(4-
(trifluoromethyl)phenyl)-1,3,4,5-tetrahydro-2H-
benzo[c]azepin-2-yl)acetamide;

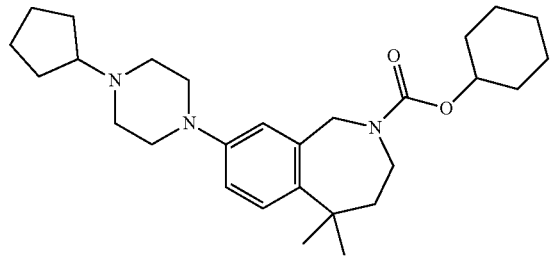

cyclohexyl 8-(4-cyclopentylpiperazine-1-yl)-5,5-
dimethyl-1,3,4,5-tetrahydro-2H-benzo[c]azepine-2-
carboxylate

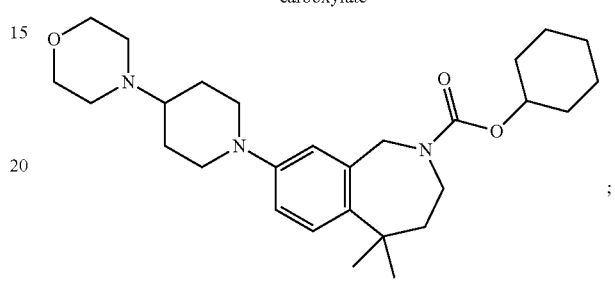

cyclohexyl 5,5-dimethyl-8-(4-morpholinopiperidin-
1-yl)-1,3,4,5-tetrahydro-2H-benzo[c]azepine-2-
carboxylate

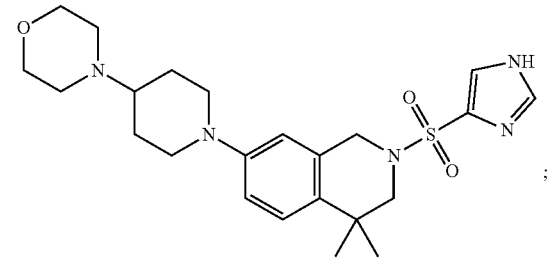

4-(1-(2-((1H-imidazol-4-yl)sulfonyl)-4,4-dimethyl-
1,2,3,4-tetrahydroisoquinolin-7-yl)piperidin-4-
yl)morpholine

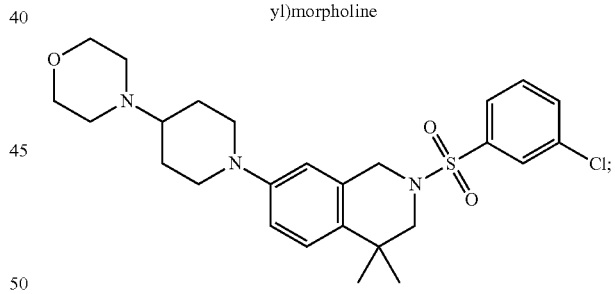

4-(1-(2-((3-chlorophenyl)sulfonyl)-4,4-dimethyl-
1,2,3,4-tetrahydroisoquinolin-7-yl)piperidin-4-
yl)morpholine

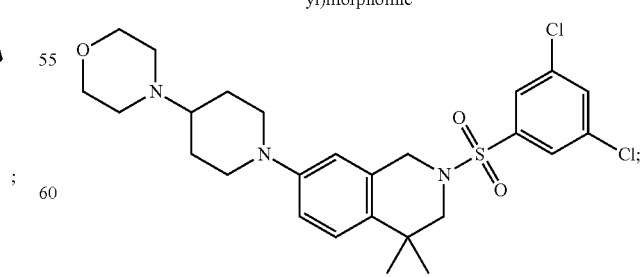

4-(1-(2-((3,5-dichlorophenyl)sulfonyl)-4,4-
dimethyl-1,2,3,4-tetrahydroisoquinolin-7-
yl)piperidin-4-yl)morpholine -continued

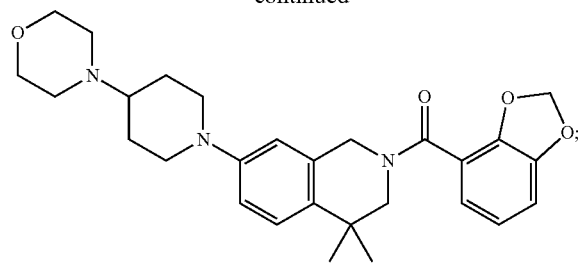

benzo[d][1,3]dioxol-4-yl(4,4-dimethyl-7-(4-morpholinopiperidin-1-yl)-3-4-dihydroisoquinolin-2(1H)-yl)methanone

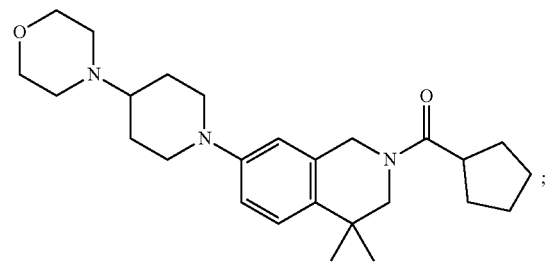

cyclopentyl(4,4-dimethyl-7-(4-morpholinopiperidin-1-yl)-3,4-dihydroisoquinolin-2(1H)-yl)methanone

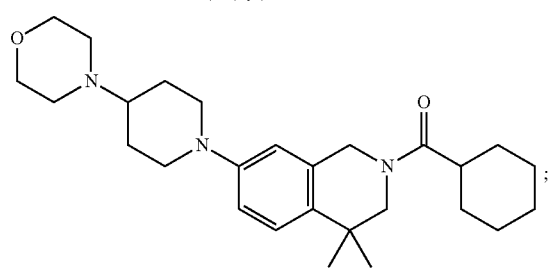

cyclohexyl(4,4-dimethyl-7-(4-morpholinopiperidin-1-yl)-3,4-dihydroisoquinolin-2(1H)-yl)methanone

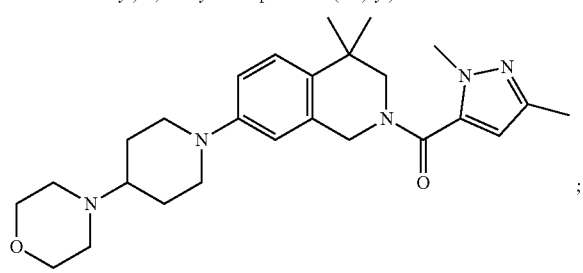

(1,3-dimethyl-1H-pyrazol-5-yl)(4,4-dimethyl-7-(4-morpholinopiperidin-1-yl)-3,4-dihydroisoquinolin-2(1H)-yl)methanone

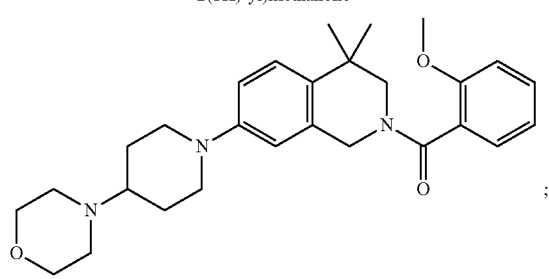

(4,4-dimethyl-7-(4-morpholinopiperidin-1-yl)-3,4-dihydroisoquinolin-2(1H)-yl)(2-methoxyphenyl)methanone

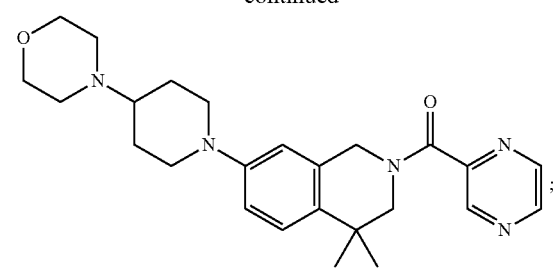

(4,4-dimethyl-7-(4-morpholinopiperidin-1-yl)-3,4-dihydroisoquinolin-2(1H)-yl)(pyrazin-2-yl)methanone

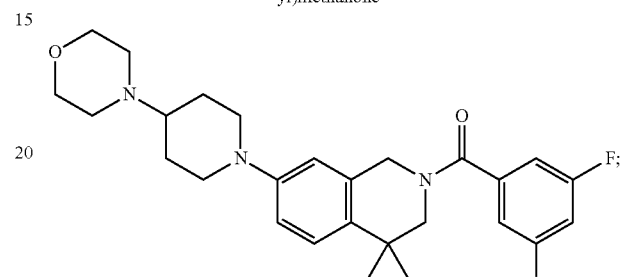

(3-chloro-5-fluorophenyl)(4,4-dimethyl-7-(4-morpholinopiperidin-1-yl)-3,4-dihydroisoquinolin-2(1H)-yl)methanone

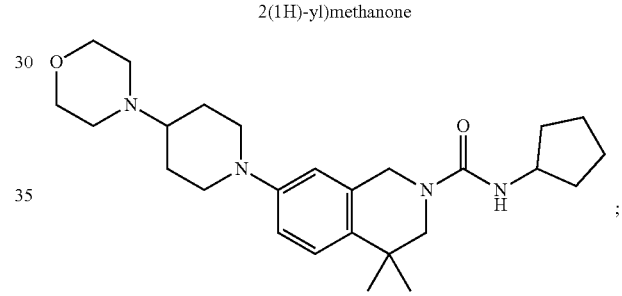

N-cyclopenyl-4,4-dimethyl-7-(4-morpholinopiperidin-1-yl)-3,4-dihydroisoquinoline-2(1H)-carboxamide

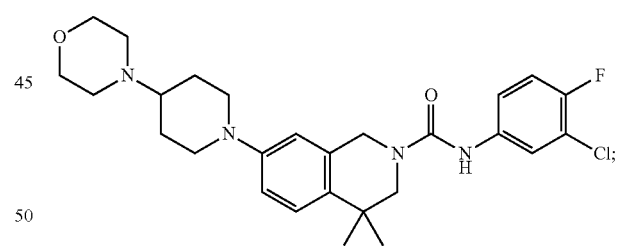

N-(3-chloro-4-fluorophenyl)-4,4-dimethyl-7-(4-morpholinopiperidin-1-yl)-3,4-dihydroisoquinoline-2(1H)-carboxamide

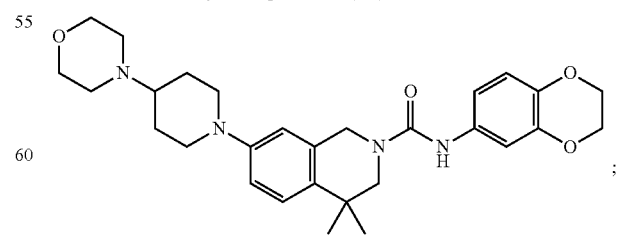

N-(2,3-dihydrobenzo[b][1,4]dioxin-6-yl)-4,4-dimethyl-7-(4-morpholinopiperidin-1-yl)-3,4-dihydroisoquinoline-2(1H)-carboxamide

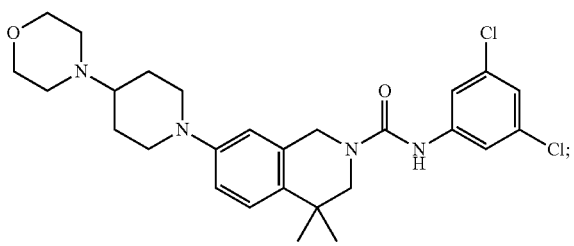

N-(3,5-dichlorophenyl)-4,4-dimethyl-7-(4-morpholinopiperidin-1-yl)-3,4-dihydroisoquinoline-2(1H)-carboxamide

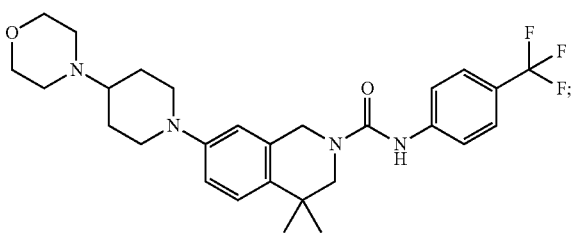

4,4-dimethyl-7-(4-morpholinopiperidin-1-yl)-N-(4-(trifluoromethyl)phenyl)-3,4-dihydroisoquinoline-2(1H)-carboxamide

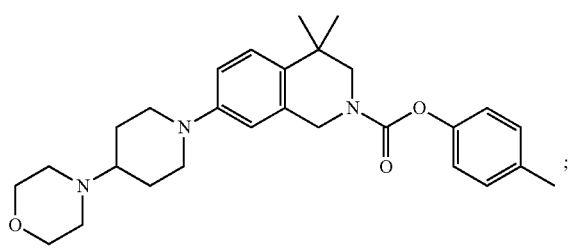

p-tolyl 4,4-dimethyl-7-(4-morpholinopiperidin-1-yl)-3,4-dihydroisoquinoline-2(1H)-carboxylate

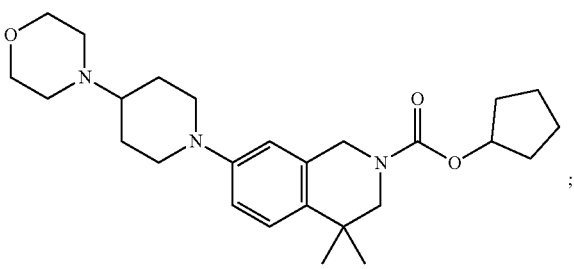

cyclopentyl 4,4-dimethyl-7-(4-morpholinopiperidin-1-yl)-3,4-dihydroisoquinoline-2(1H)-carboxylate

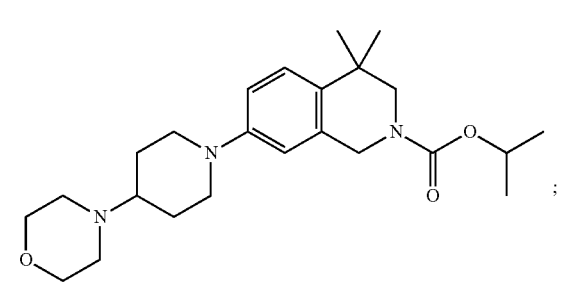

isopropyl 4,4-dimethyl-7-(4-morpholinopiperidin-1-yl)-3,4-dihydroisoquinoline-2(1H)-carboxylate

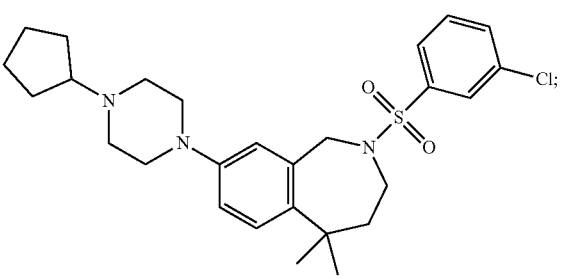

2-((3-chlorophenyl)sulfonyl)-8-(4-cyclopentylpiperazin-1-yl)-5,5-dimethyl-2,3,4,5-tetrahydro-1H-benzo[c]azepine

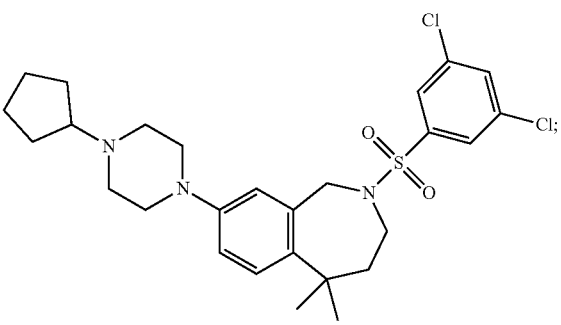

8-(4-cyclopentylpiperazin-1-yl)-2-((3,5-dichlorophenyl)sulfonyl)-5,5-dimethyl-2,3,4,5-tetrahydro-1H-benzo[c]azepine

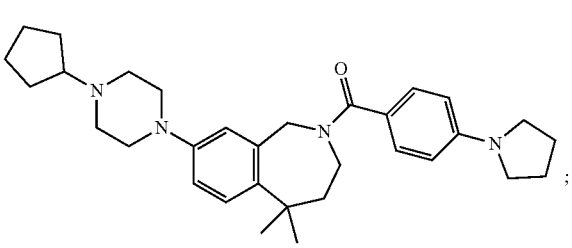

(8-(4-cyclopentylpiperazin-1-yl)-5,5-dimethyl-1,3,4,5-tetrahydro-2H-benzo[c]azepin-2-yl)(4-(pyrrolidin-1-yl)phenyl)methanone

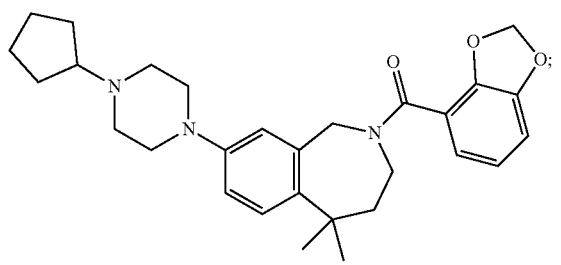

benzo[d][1,3]dioxol-4-yl(8-(4-cyclopentylpiperazin-1-yl)-5,5-dimethyl-1,3,4,5-tetrahydro-2H-benzo[c]azepin-2-yl)methanone -continued

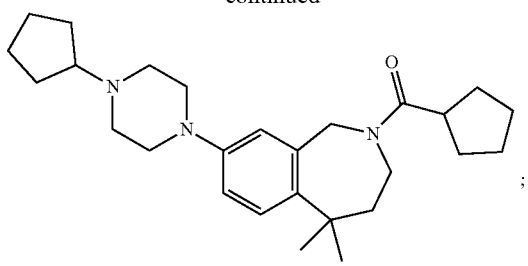

cyclopentyl(8-(4-cyclopentylpiperazin-1-yl)-5,5-
dimethyl-1,3,4,5-tetrahydro-2H-benzo[c]azepin-2-
yl)methanone

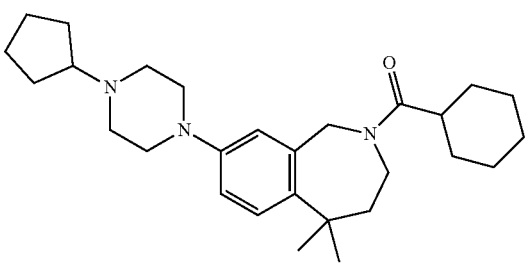

cyclohexyl(8-(4-cyclopentylpiperazin-1-yl)-5,5-
dimethyl-1,3,4,5-tetrahydro-2H-benzo[c]azepin-2-
yl)methanone

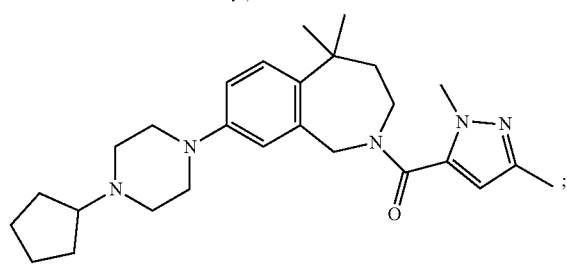

(8-(4-cyclopentylpiperazin-1-yl)-5,5-dimethyl-
1,3,4,5-tetrahydro-2H-benzo[c]azepin-2-yl)(1,3-
dimethyl-1H-pyrazol-5-yl)methanone

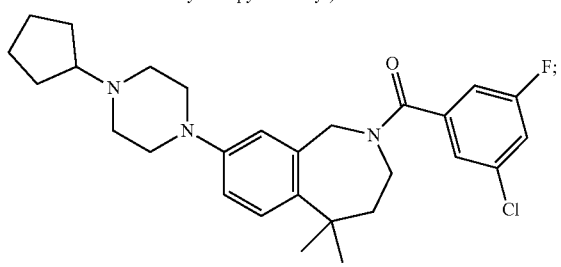

(3-chloro-5-fluorophenyl(8-(4-
cyclopentylpiperazin-1-yl)-5,5-dimethyl-1,3,4,5-
tetrahydro-2H-benzo[c]azepin-2-yl)methanone

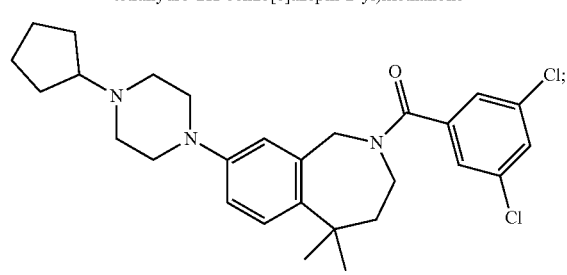

(8-(4-cyclopentylpiperazin-1-yl)-5,5-dimethyl-
1,3,4,5-tetrahydro-2H-benzo[c]azepin-2-yl)(3,5-
dichlorophenyl)methanone -continued

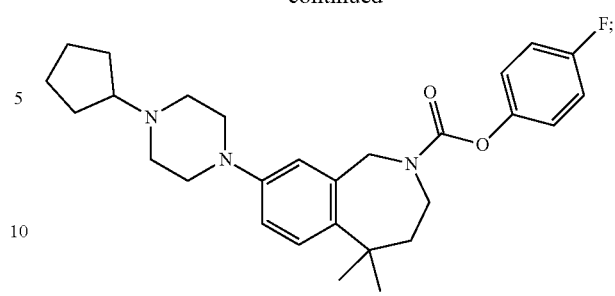

4-fluorophenyl (8-(4-cyclopentylpiperazin-1-yl)-
5,5-dimethyl-1,3,4,5-tetrahydro-2H-
benzo[c]azepine-2-carboxylate

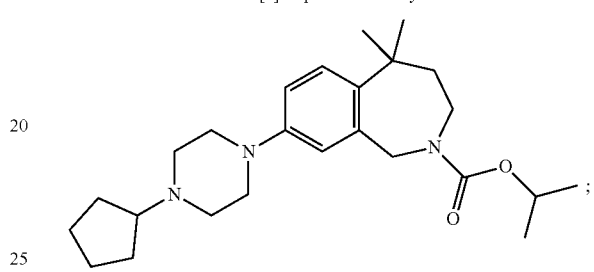

isopropyl 8-(4-cyclopentylpiperazin-1-yl)-5,5-
dimethyl-1,3,4,5-tetrahydro-2H-benzo[c]azepine-2-
carboxylate

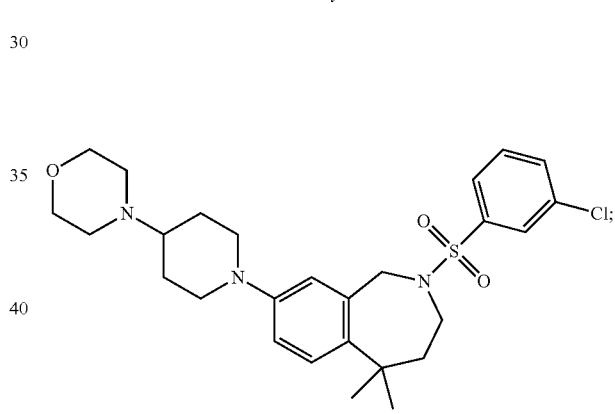

4-(1-(2-((3-chlorophenyl)sulfonyl)-5,5-dimethyl-
2,3,4,5-tetrahydro-1H-benzo[c]azepin-8-
yl)piperidin-4-yl)morpholine

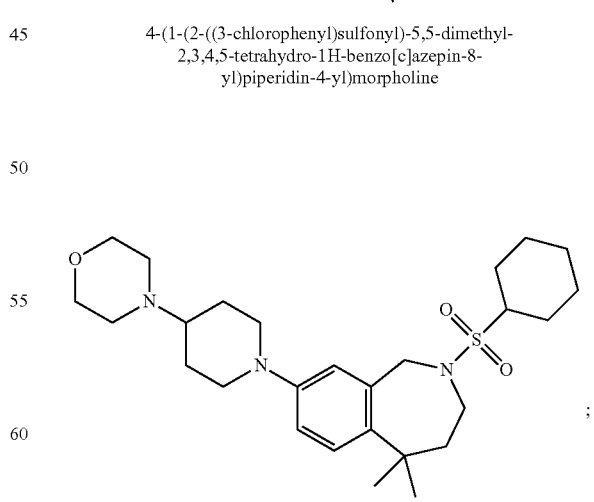

4-(1-(2-(cyclohexylsulfonyl)-5,5-dimethyl-2,3,4,5-
tetrahydro-1H-benzo[c]azepin-8-yl)piperidin-4-
yl)morpholine

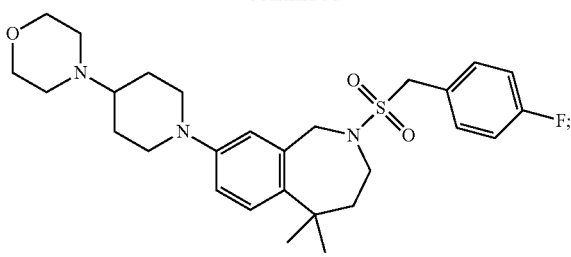

4-(1-(2-((4-fluorobenzyl)sulfonyl)-5,5-dimethyl-
2,3,4,5-tetrahydro-1H-benzo[c]azepin-8-
yl)piperidin-4-yl)morpholine

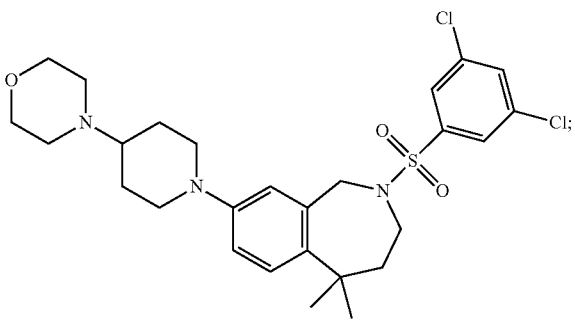

4-(1-(2-((3,5-dichlorophenyl)sulfonyl)-5,5-
dimethyl-2,3,4,5-tetrahydro-1H-benzo[c]azepin-8-
yl)piperidin-4-yl)morpholine

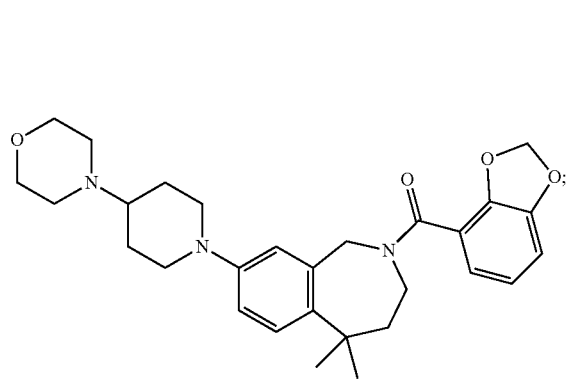

benzo[d][1,3]dioxol-4-yl(5,5-dimethyl-8-(4-
morpholinopiperidin-1-yl)-1,3,4,5-tetrahydro-2H-
benzo[c]azepin-2-yl)methanone

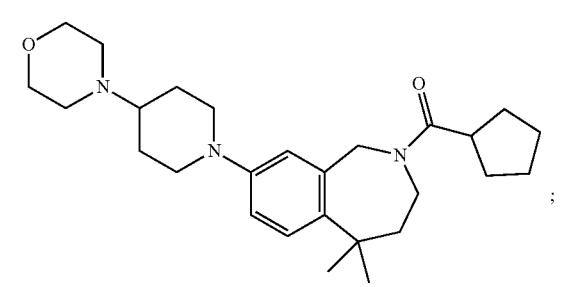

cyclopentyl(5,5-dimethyl-8-(4-
morpholinopiperidin-1-yl)-1,3,4,5-tetrahydro-2H-
benzo[c]azepin-2-yl)methanone

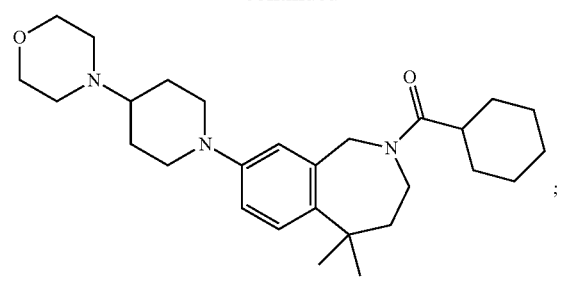

cyclohexyl(5,5-dimethyl-8-(4-morpholinopiperidin-
1-yl)-1,3,4,5-tetrahydro-2H-benzo[c]azepin-2-
yl)methanone

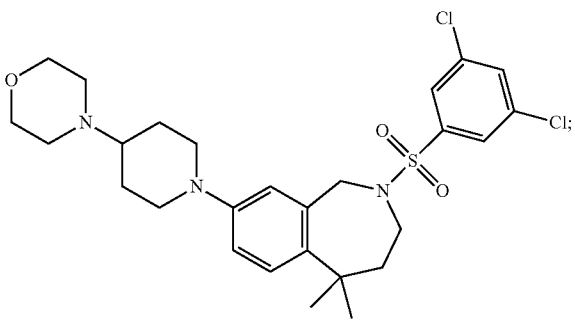

(1,3-dimethyl-1H-pyrazol-5-yl)(5,5-dimethyl-8-(4-
morpholinopiperidin-1-yl)-1,3,4,5-tetrahydro-2H-
benzo[c]azepin-2-yl)methanone

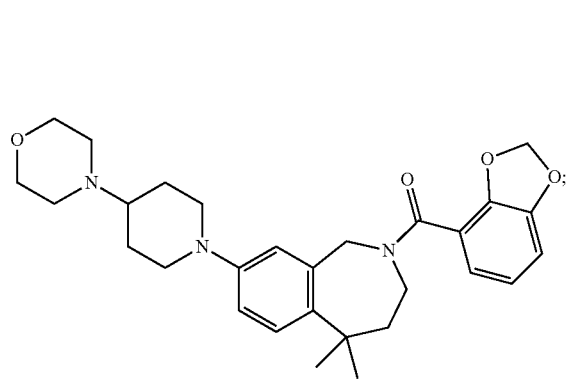

(3-chloro-5-fluorophenyl)(5,5-dimethyl-8-(4-
morpholinopiperidin-1-yl)-1,3,4,5-tetrahydro-2H-
benzo[c]azepin-2-yl)methanone

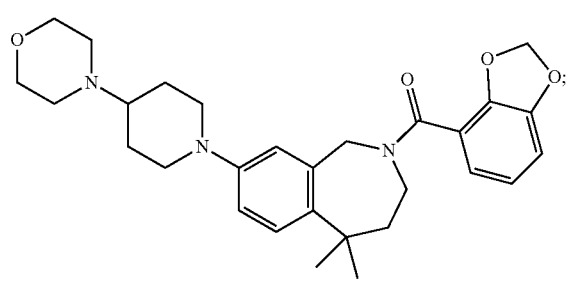

(3,5-dichlorophenyl)(5,5-dimethyl-8-(4-
morpholinopiperidin-1-yl)-1,3,4,5-tetrahydro-2H-
benzo[c]azepin-2-yl)methanone -continued

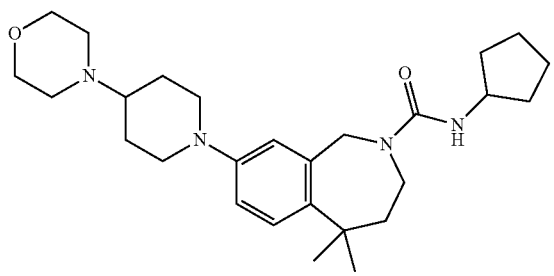

N-cyclopentyl-5,5-dimethyl-8-(4-
morpholinopiperidin-1-yl)-1,3,4,5-tetrahydro-2H-
benzo[c]azepine-2-carboxamide

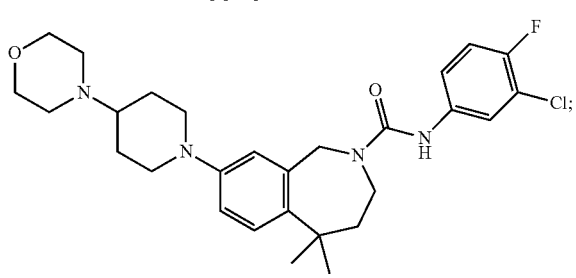

N-(3-chloro-4-fluorophenyl)-5,5-dimethyl-8-(4-
morpholinopiperidin-1-yl)-1,3,4,5-tetrahydro-2H-
benzo[c]azepine-2-carboxamide

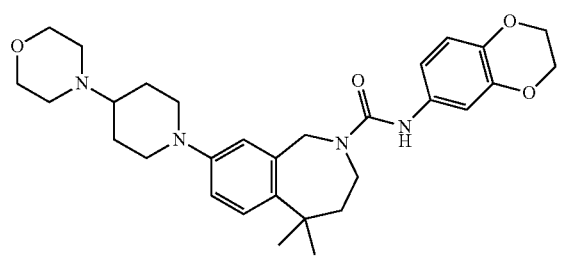

N-(2,3-dihydrobenzo[b][1,4]dioxin-6-yl)-5,5-
dimethyl-8-(4-morpholinopiperidin-1-yl)-1,3,4,5-
tetrahydro-2H-benzo[c]azepine-2-carboxamide

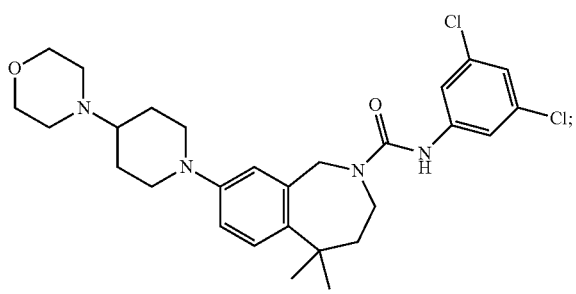

N-(3,5-dichlorophenyl)-5,5-dimethyl-8-(4-
morpholinopiperidin-1-yl)-1,3,4,5-tetrahydro-2H-
benzo[c]azepine-2-carboxamide -continued

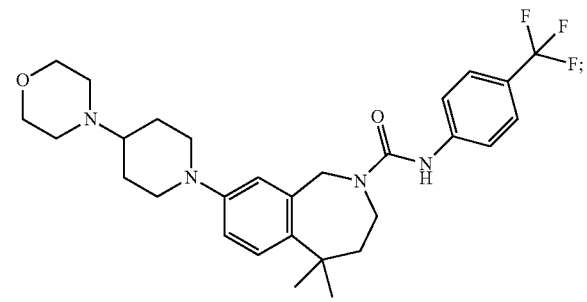

5,5-dimethyl-8-(4-morpholinopiperidin-1-yl)-N-(4-
(trifluoromethyl)phenyl)-1,3,4,5-tetrahydro-2H-
benzo[c]azepine-2-carboxamide

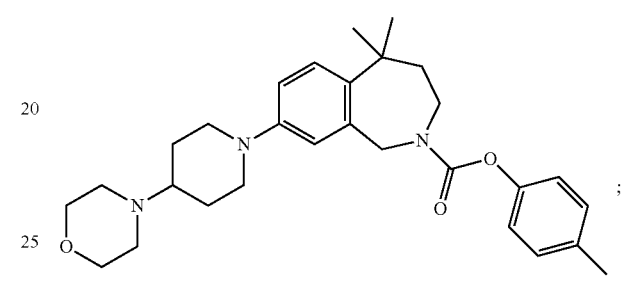

p-tolyl 5,5-dimethyl-8-(4-morpholinopiperidin-1-
yl)-1,3,4,5-tetrahydro-2H-benzo[c]azepine-2-
carboxylate

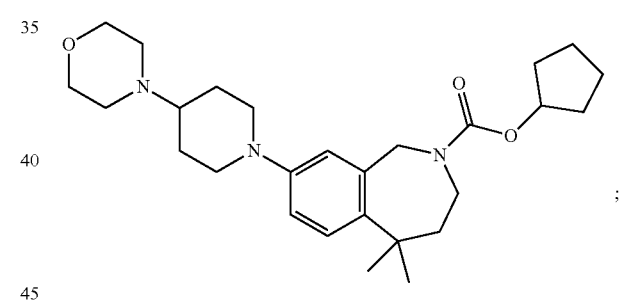

cyclopentyl 5,5-dimethyl-8-(4-
morpholinopiperidin-1-yl)-1,3,4,5-tetrahydro-2H-
benzo[c]azepine-2-carboxylate

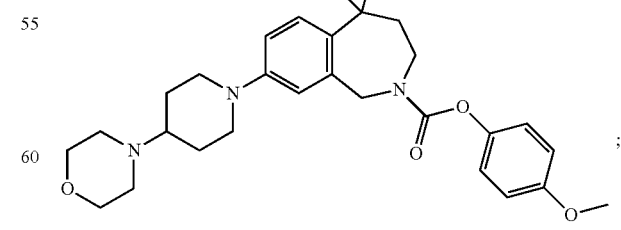

4-methoxyphenyl 5,5-dimethyl-8-(4-
morpholinopiperidin-1-yl)-1,3,4,5-tetrahydro-2H-
benzo[c]azepine-2-carboxylate

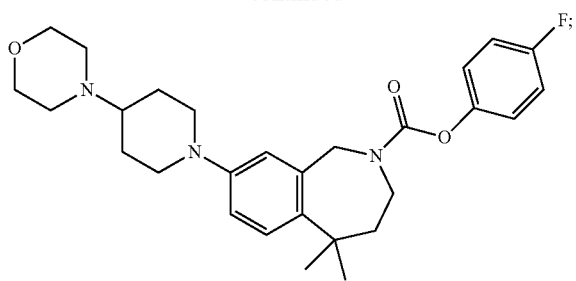

4-fluorophenyl 5,5-dimethyl-8-(4-morpholinopiperidin-1-yl)-1,3,4,5-tetrahydro-2H-benzo[c]azepine-2-carboxylate

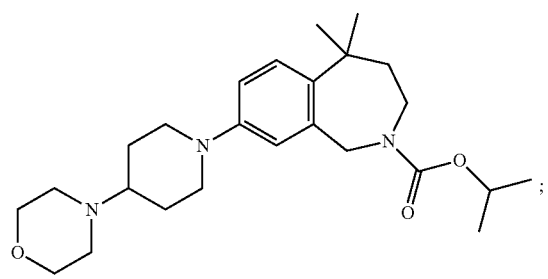

isopropyl 5,5-dimethyl-8-(4-morpholinopiperidin-1-yl)-1,3,4,5-tetrahydro-2H-benzo[c]azepine-2-carboxylate

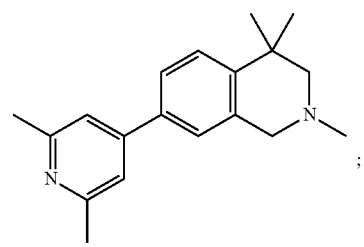

7-(2,6-dimethylpyridin-4-yl)-2,4,4-trimethyl-1,2,3,4-tetrahydroisoquinoline

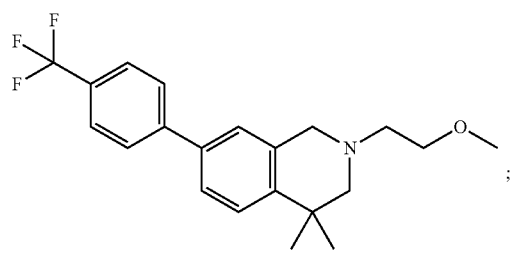

2-(2-methoxyethyl)-4,4-dimethyl-7-(4-(trifluoromethyl)phenyl)-1,2,3,4-tetrahydroisoquinoline

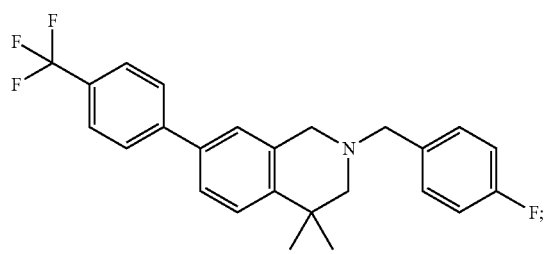

2-(4-fluorobenzyl)-4,4-dimethyl-7-(4-(trifluoromethyl)phenyl)-1,2,3,4-tetrahydroisoquinoline

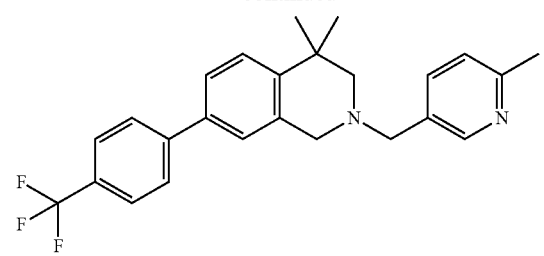

4,4-dimethyl-2-((6-methylpyridin-3-yl)methyl-7-(4-(trifluoromethyl)phenyl)-1,2,3,4-tetrahydroisoquinoline

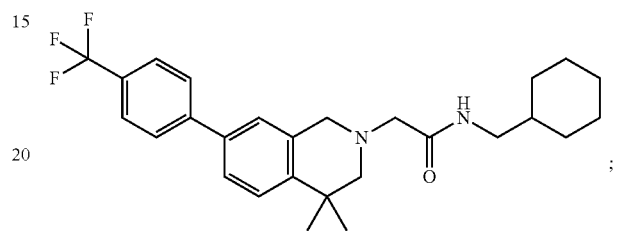

N-(cyclohexylmethyl)-2-(4,4-dimethyl-7-(4-(trifluoromethyl)phenyl)-3,4-dihydroisoquinolin-2(1H)-yl)acetamide

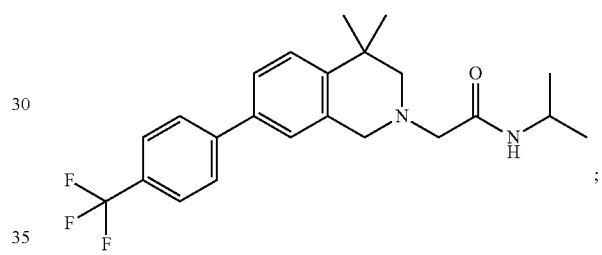

2-(4,4-dimethyl-7-(4-(trifluoromethyl)phenyl)-3,4-dihydroisoquinolin-2(1H)-yl)-N-isopropylacetamide

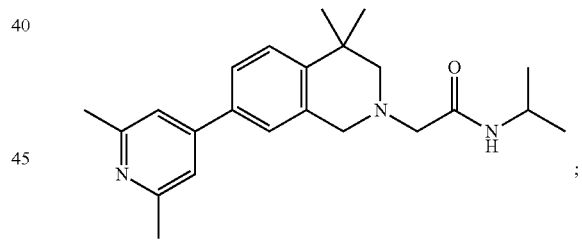

2-(7-(2,6-dimethylpyridin-4-yl)-4,4-dimethyl-3,4-dihydroisoquinolin-2(1H)-yl)-N-isopropylacetamide

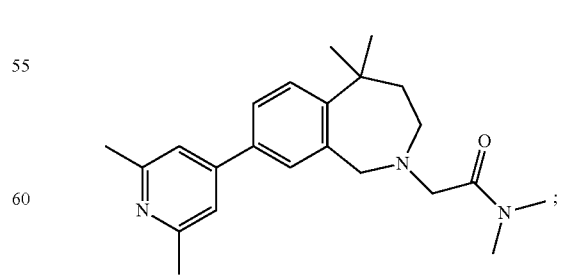

2-(8-(2,6-dimethylpyridin-4-yl)-5,5-dimethyl-1,3,4,5-tetrahydro-2H-benzo[c]azepin-2-yl)-N,N-dimethylacetamide

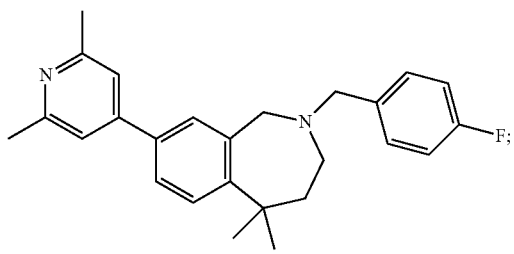

8-(2,6-dimethylpyridin-4-yl)-2-(4-fluorobenzyl)-
5,5-dimethyl-2,3,4,5-tetrahydro-1H-
benzo[c]azepine

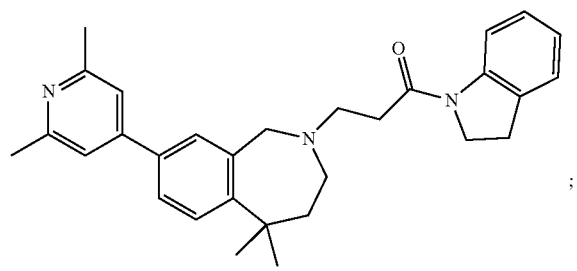

3-(8-(2,6-dimethylpyridin-4-yl)-5,5-dimethyl-
1,3,4,5-tetrahydro-2H-benzo[c]azepin-2-yl)-1-
(indolin-1-yl)propan-1-one

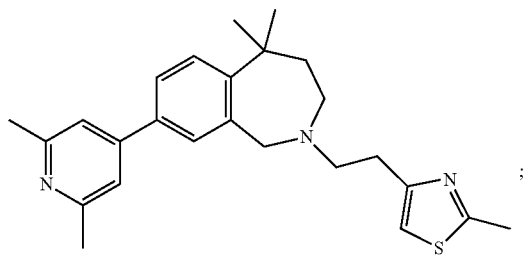

4-(2-(8-(2,6-dimethylpyridin-4-yl)-5,5-dimethyl-
1,3,4,5-tetrahydro-2H-benzo[c]azepin-2-yl)ethyl)-
2-methylthiazole

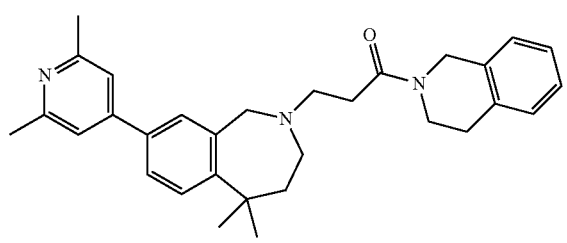

1-(3,4-dihydroisoquinolin-2(1H)-yl)-3-(8-(2,6-
dimethylpyridin-4-yl)-5,5-dimethyl-1,3,4,5-
tetrahydro-2H-benzo[c]azepin-2-yl)-1-propan-1-one

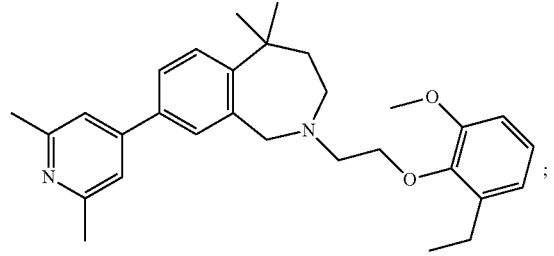

2-(2-(2,6-dimethoxyphenoxy)ethyl)-8-(2,6-
dimethylpyridin-4-yl)-5,5-dimethyl-2,3,4,5-
tetrahydro-1H-benzo[c]azepine

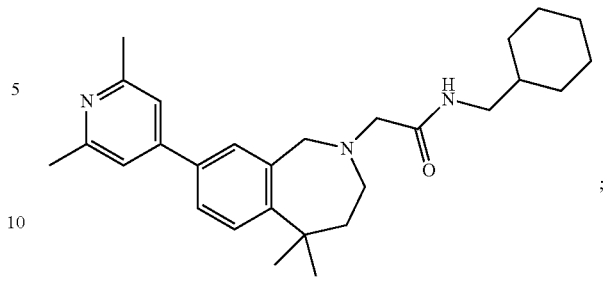

N-(cyclohexylmethyl)-2-(8-(2,6-dimethylpyridin-4
-yl)-5,5-dimethyl-1,3,4,5-tetrahydro-2H-
benzo[c]azepin-2-yl)acetamide

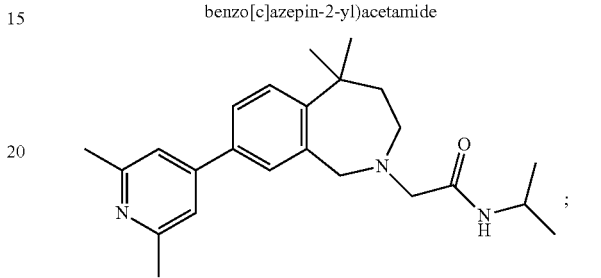

2-(8-(2,6-dimethylpyridin-4-yl)-5,5-dimethyl-
1,3,4,5-tetrahydro-2H-benzo[c]azepin-2-yl)-N-
isopropylacetamide

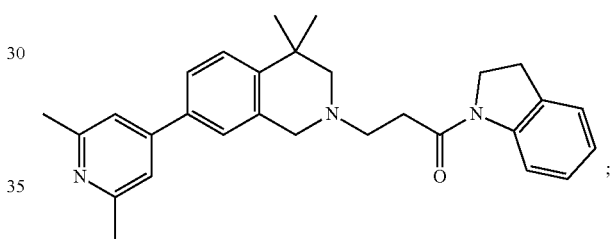

3-(7-(2,6-dimethylpyridin-4-yl)-4,4-dimethyl-3,4-
dihydroisoquinolin-2(1H)-yl)-1-(indolin-1-
yl)propan-1-one

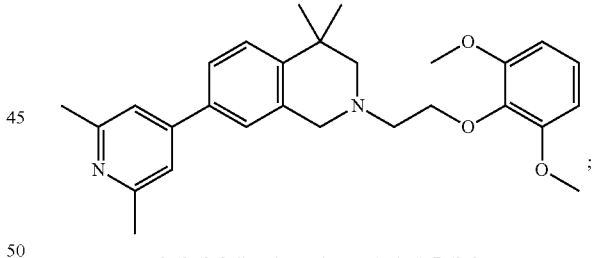

2-(2-(2,6-dimethoxyphenoxy)ethyl)-7-(2,6-
dimethylpyridin-4-yl)-4,4-dimethyl-1,2,3,4-
tetrahydroisoquinoline

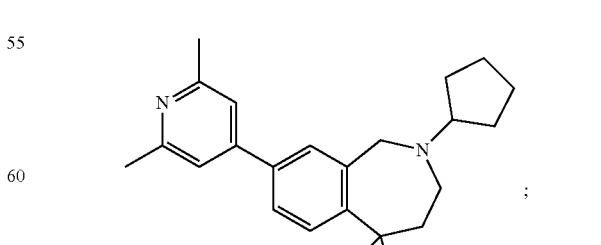

2-cyclopentyl-8-(2,6-dimethylpyridin-4-yl)-5,5-
dimethyl-2,3,4,5-tetrahydro-1H-benzo[c]azepine

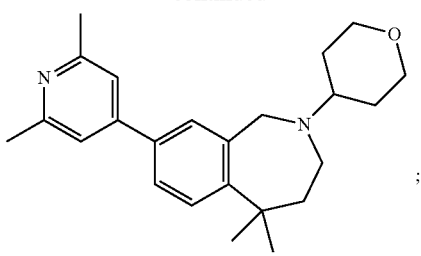

8-(2,6-dimethylpyridin-4-yl)-5,5-dimethyl-2-
(tetrahydro-2H-pyran-4-yl)-2,3,4,5-tetrahydro-1H-
benzo[c]azepine

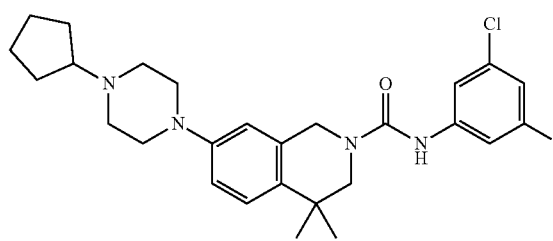

7-(4-cyclopentylpiperazin-1-yl)-N-(3,5-
dichlorophenyl)-4,4-dimethyl-3,4-
dihydroisoquinoline-2(1H)-carboxamide

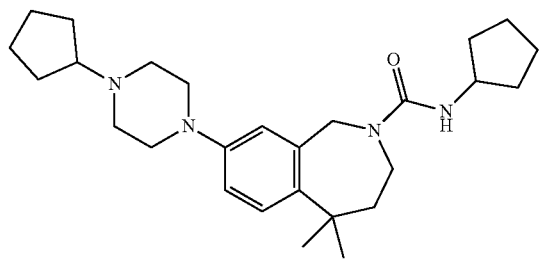

N-cyclopentyl-8-(4-cyclopentylpiperazin-1-yl)-5,5-
dimethyl-1,3,4,5-tetrahydro-2H-benzo[c]azepine-2-
carboxamide

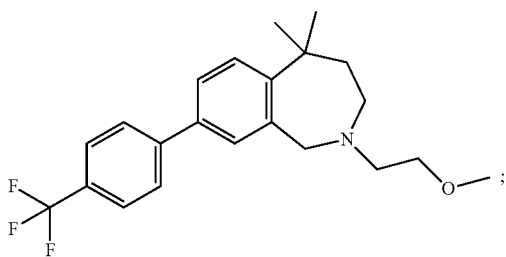

2-(2-methoxyethyl)-5,5-dimethyl-8-(4-
(trifluoromethyl)phenyl-2,3,4,5-tetrahydro-1H-
benzo[c]azepine

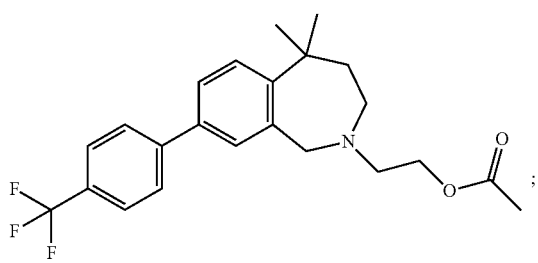

2-(5,5-dimethyl-8-(4-(trifluoromethyl)phenyl)-
1,3,4,5-tetrahydro-2H-benzo[c]azepin-2-yl)ethyl
acetate;

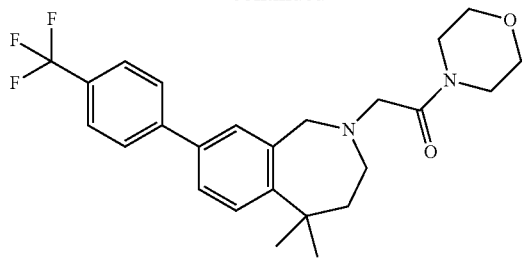

2-(5,5-dimethyl-8-(4-(trifluoromethyl)phenyl)-
1,3,4,5-tetrahydro-2H-benzo[c]azepin-2-yl)-1-
morpholinoethan-1-one

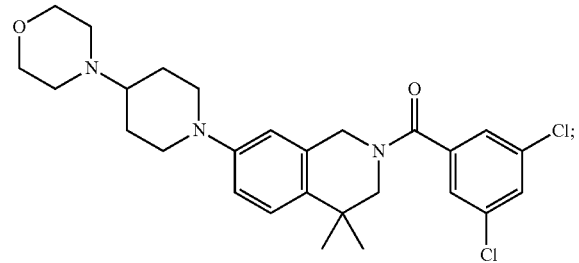

(3,5-dichlorophenyl)(4,4-dimethyl-7-(4-
morpholinopiperidin-1-yl)-3,4-dihydroisoquinolin-
2(1H)-yl)methanone

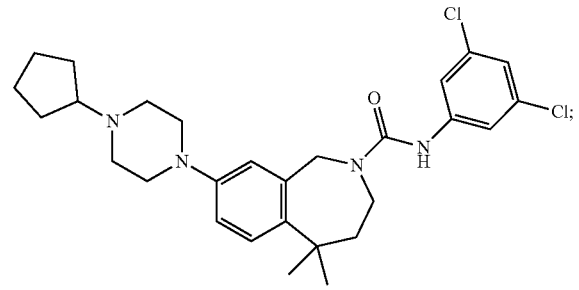

8-(4-cyclopentylpiperazin-1-yl)-N-(3,5-
dichlorophenyl)-5,5-dimethyl-1,3,4,5-tetrahydro-
2H-benzo[c]azepine-2-carboxamide

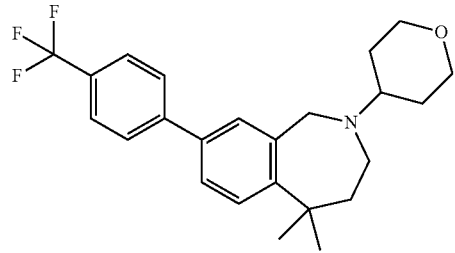

5,5-dimethyl-2-(tetrahydro-2H-pyran-4-yl)-8-(4-
(trifluoromethyl)phenyl)-2,3,4,5-tetrahydro-2H-
benzo[c]azepine

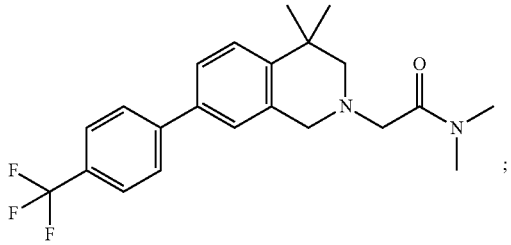

2-(4,4-dimethyl-7-(4-(trifluoromethyl)phenyl)-3,4-
dihydroisoquinolin-2(1H)-yl)-N,N-
dimethylacetamide -continued

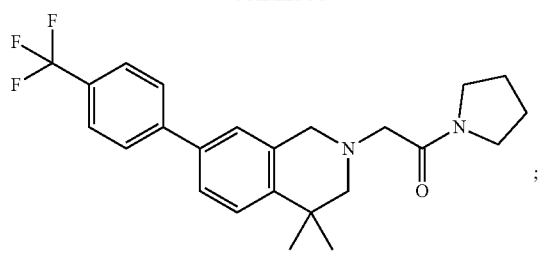

2-(4,4-dimethyl-7-(4-(trifluoromethyl)phenyl)-3,4-dihydroisoquinolin-2(1H)-yl)-1-(pyrrolidin-1-yl)ethan-1-one

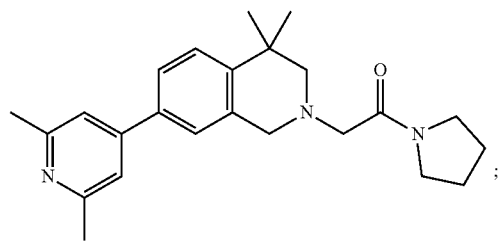

2-(7-(2,6-dimethylpyridin-4-yl)-4,4-dimethyl-3,4-dihydroisoquinolin-2(1H)-yl)-1-(pyrrolidin-1-yl)ethan-1-one

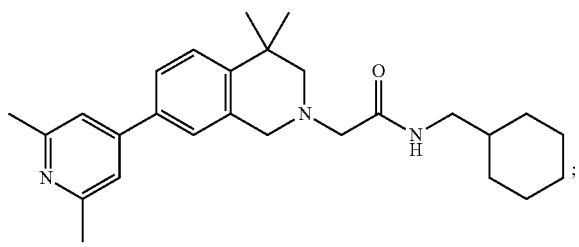

N-(cyclohexylmethyl)-2-(7-(2,6-dimethylpyridin-4-yl)-4,4-dimethyl-3,4-dihydroisoquinolin-2(1H)-yl)acetamide

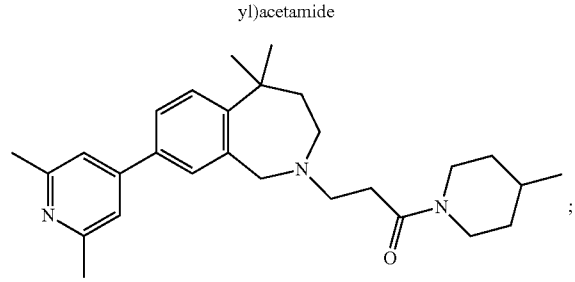

3-(8-(2,6-dimethylpyridin-4-yl)-5,5-dimethyl-1,3,4,5-tetrahydro-2H-benzo[c]azepin-2-yl)-1-(4-methylpiperidin-1-yl)propan-1-one

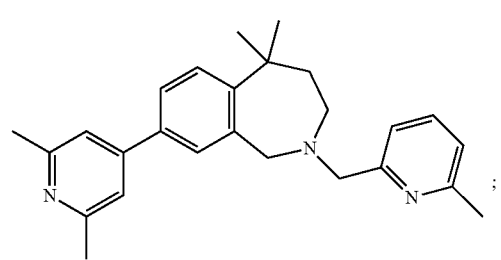

8-(2,6-dimethylpyridin-4-yl)-5,5-dimethyl-2-((6-methylpyridin-2-yl)methyl)-2,3,4,5-tetrahydro-1H-benzo[c]azepine -continued

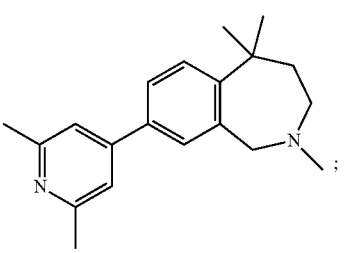

8-(2,6-dimethylpyridin-4-yl)-5,5-dimethyl-2-((tetrahydro-2-pyran-4-yl)methyl)-2,3,4,5-tetrahydro-1H-benzo[c]azepine

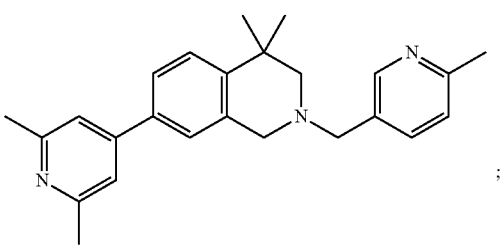

8-(2,6-dimethylpyridin-4-yl)-2,5,5-trimethyl-2,3,4,5-tetrahydro-1H-benzo[c]azepine

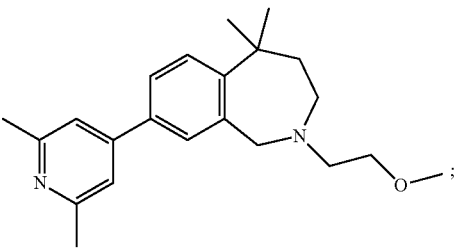

7-(2,6-dimethylpyridin-4-yl)-4,4-dimethyl-2-((6-methylpyridin-3-yl)methyl),1,2,3,4-tetrahydroisoquinoline

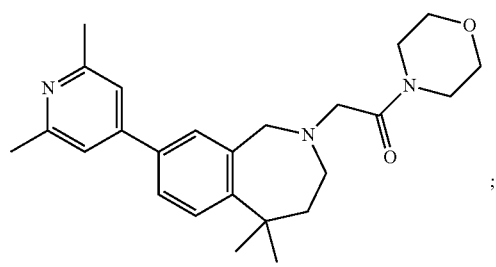

8-(2,6-dimethylpyridin-4-yl)-2-(2-methoxyethyl)-5,5-dimethyl-2,3,4,5-tetrahydro-1H-benzo[c]azepine 2-(8-(2,6-dimethylpyridin-4-yl)5,5-dimethyl-1,3,4,5-tetrahydro-2H-benzo[c]azepin-2-yl)-1-morpholinoethan-1-one or a solvate or pharmaceutically acceptable salt thereof.

25. A pharmaceutical composition comprising the compound of claim 1, or a pharmaceutically acceptable salt thereof, and a pharmaceutically acceptable diluent and/or carrier.

26. The compound of claim 1, wherein $R_2$ is or

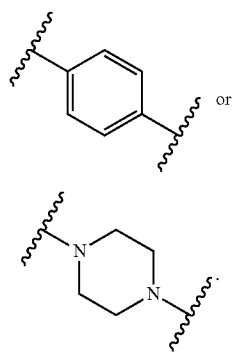

27. The compound of claim 1, wherein the compound is

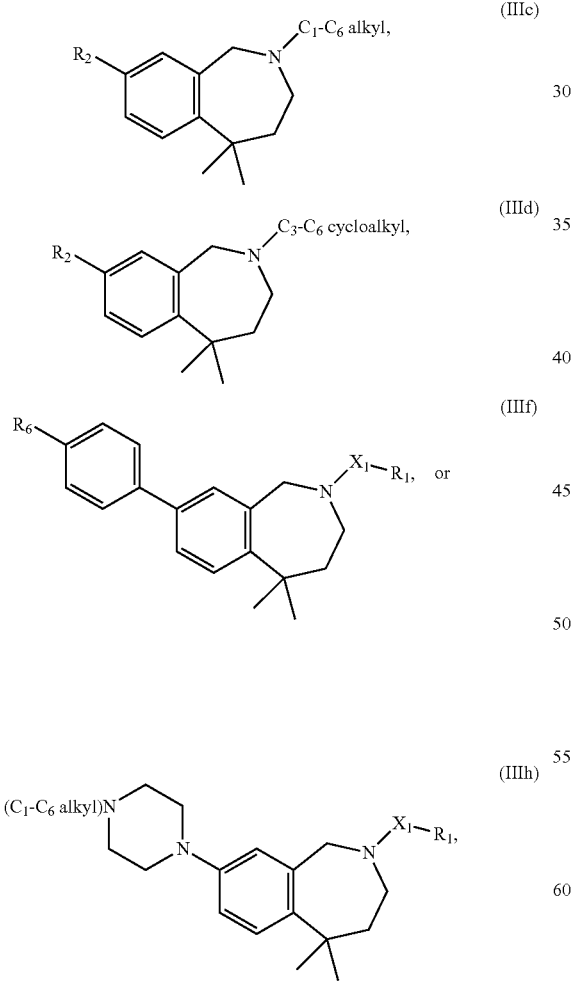

or a solvate or pharmaceutically acceptable salt thereof, wherein $X_1$, $R_1$, $R_2$, and $R_6$ are as described in claim 1.

28. A compound of Formula (I):

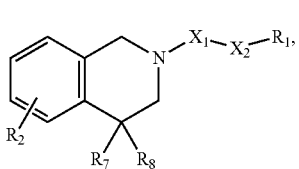

or a solvate or pharmaceutically acceptable salt thereof, wherein $X_1$ is absent, —$(CR_3R_4)_q$—, —O—, —S(O)$_2$—, —C(O)—, —C(S)—, —S(O)—, —NR$_3$C(O)—, —C(O)NR$_3$—, —C(O)O—, or —OC(O)—;

$X_2$ is absent, —$(CR_3R_4)_q$—, —O—, —S(O$_2$)—, —C(O)—, —C(S)—, —S(O)—, —NR$_3$C(O)—, —C(O)NR$_3$—, —C(O)O—, or —OC(O)—;

$R_1$ is H, OH, halogen, NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, $C_6$-$C_{10}$ aryl, 5- to 12-membered heteroaryl comprising 1-6 heteroatoms selected from N, O, and S, 5- to 14-membered saturated or unsaturated heterocycloalkyl comprising 1-5 heteroatoms selected from N, O, and S; wherein the alkyl, alkenyl, alkynyl, haloalkyl, alkoxyl, haloalkoxyl, cycloalkyl, aryl, heteroaryl, or heterocycloalkyl of any of the foregoing is optionally substituted with one or more $R_5$;

$R_2$ is

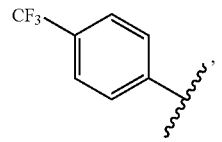

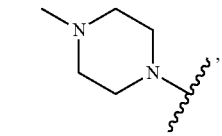

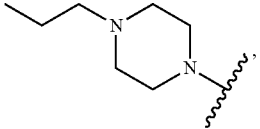

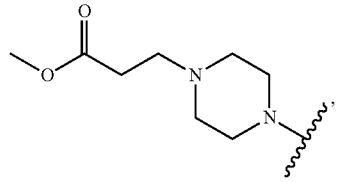

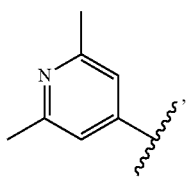

-continued

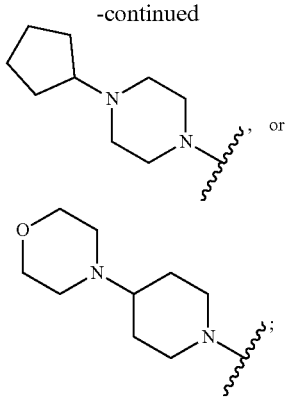

each R₃ independently is H, halogen, or $C_1$-$C_6$ alkyl;
each R₄ independently is H, halogen, or $C_1$-$C_6$ alkyl;
each R₅ independently is OH, halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, $C_3$-$C_6$ cycloalkyl, $C_6$-$C_{10}$ aryl, or 5- to 14-membered saturated or unsaturated heterocycloalkyl comprising 1-5 heteroatoms selected from N, O, and S; wherein the alkyl, alkenyl, alkynyl, cycloalkyl, or aryl of any of the foregoing is optionally substituted with one or more —C(O)$C_1$-$C_6$alkyl, —C(O)O$C_1$-$C_6$alkyl, —C(O)NH₂, —C(O)NH$C_1$-$C_6$alkyl, or —C(O)N($C_1$-$C_6$alkyl)₂;

R₇ is $C_1$-$C_6$ alkyl optionally substituted with one or more OH, halogen, or $C_1$-$C_6$ alkoxyl;

R₈ is $C_1$-$C_6$ alkyl optionally substituted with one or more OH, halogen, or $C_1$-$C_6$ alkoxyl; and each q independently is 1, 2, 3, or 4.

29. The compound of claim 28, wherein R₅ is OH or halogen.

30. The compound of claim 28, wherein X₁ is (CR₃R₄)$_q$, —C(O)—, —C(S)—, —S(O)—, —S(O)₂—, —NR₃C(O)—, or —C(O)O—.

31. The compound of claim 28, wherein X₁ is absent.

32. The compound of claim 28, wherein X₂ is (CR₃R₄)$_q$, —C(O)—, —C(S)—, —S(O)—, —NR₃C(O)—, or —C(O)O—.

33. The compound of claim 28, wherein X₂ is absent.

34. The compound of 28, wherein R₁ is H, OH, or halogen.

35. The compound of claim 28, wherein R₁ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl, wherein the alkyl, alkenyl, alkynyl, haloalkyl, alkoxyl, haloalkoxyl, or cycloalkyl of any of the foregoing is optionally substituted with one or more R₅.

36. The compound of claim 28, wherein R₁ is $C_6$-$C_{10}$ aryl, 5- to 12-membered heteroaryl comprising 1-6 heteroatoms selected from N, O, and S, or 5- to 14-membered saturated or unsaturated heterocycloalkyl comprising 1-5 heteroatoms selected from N, O, and S; wherein the aryl, heteroaryl, or heterocycloalkyl of any of the foregoing is optionally substituted with one or more R₅.

37. The compound of claim 28, wherein R₇ and R₈ are each methyl.

38. The compound of claim 28, wherein the compound is a compound of Formula (II):

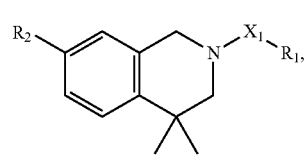

or a solvate or pharmaceutically acceptable salt thereof, wherein X₁, R₁, and R₂ are as described in claim 28.

39. The compound of claim 28, wherein the compound is

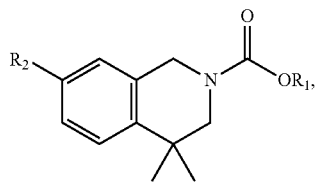

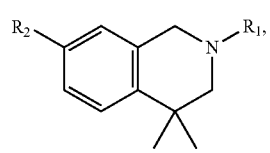

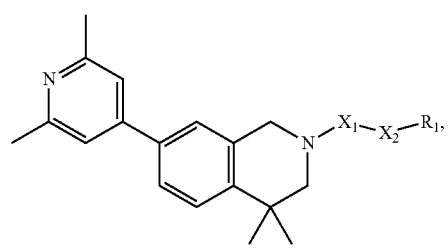

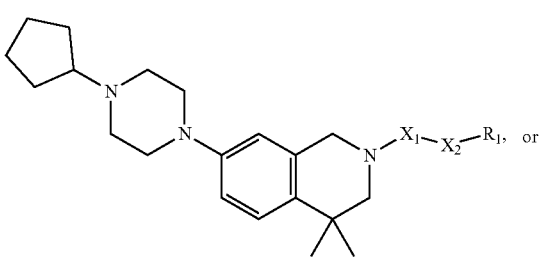

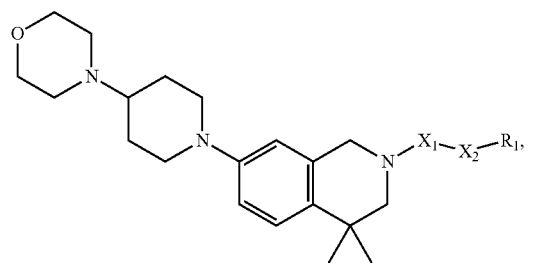

or a solvate or pharmaceutically acceptable salt thereof, wherein X₁, X₂, R₁, and R₂ are as described in claim 28.

40. The compound of claim 28, wherein the compound is
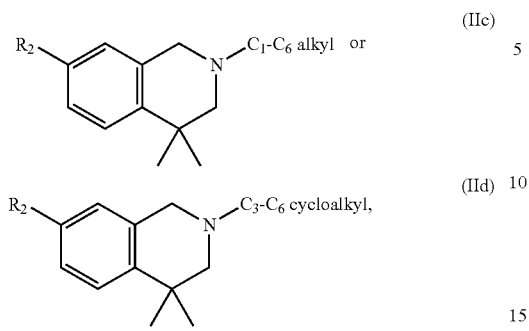
or a solvate or pharmaceutically acceptable salt thereof, wherein $R_2$ is as described in claim 28.
41. A pharmaceutical composition comprising the compound of claim 28, or a pharmaceutically acceptable salt thereof, and a pharmaceutically acceptable diluent and/or carrier.
* * * * *

UNITED STATES PATENT AND TRADEMARK OFFICE
CERTIFICATE OF CORRECTION

PATENT NO. : 12,006,300 B2
APPLICATION NO. : 17/400207
DATED : June 11, 2024
INVENTOR(S) : Remy Luthringer et al.

It is certified that error appears in the above-identified patent and that said Letters Patent is hereby corrected as shown below:

In the Claims

At Column 159, Claim number 22, Line number 5:

"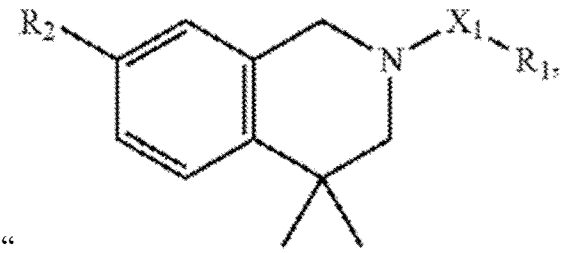"

Should read:

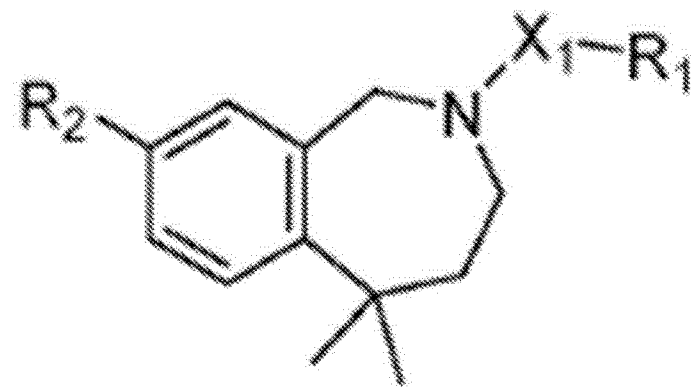
--

At Column 160, Claim number 24, Line number 65:
"benzyl 4,4-dimethyl-7-(4-methylpiperazin-1-yl)-"
Should read:
--benzyl 4,4-dimethyl-7-(4-propylpiperazin-1-yl)- --

Signed and Sealed this
Twenty-ninth Day of October, 2024

*Katherine Kelly Vidal*
Katherine Kelly Vidal
*Director of the United States Patent and Trademark Office*

CERTIFICATE OF CORRECTION (continued)
U.S. Pat. No. 12,006,300 B2

At Column 162, Claim number 24, Line number 63:
"4,4-dimethyl-2-((tetrahydro-2-pyran-4-"
Should read:
--4,4-dimethyl-2-((tetrahydro-2H-pyran-4- --

At Column 163, Claim number 24, Line number 60:

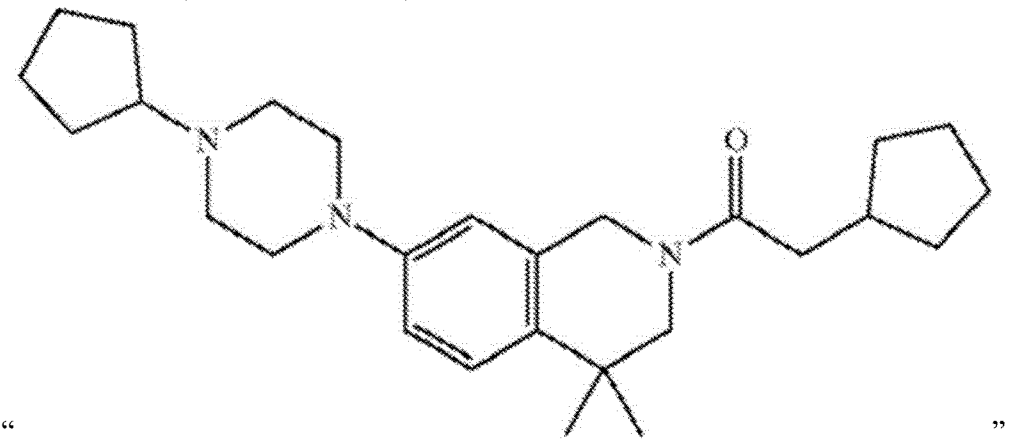

"

Should read:

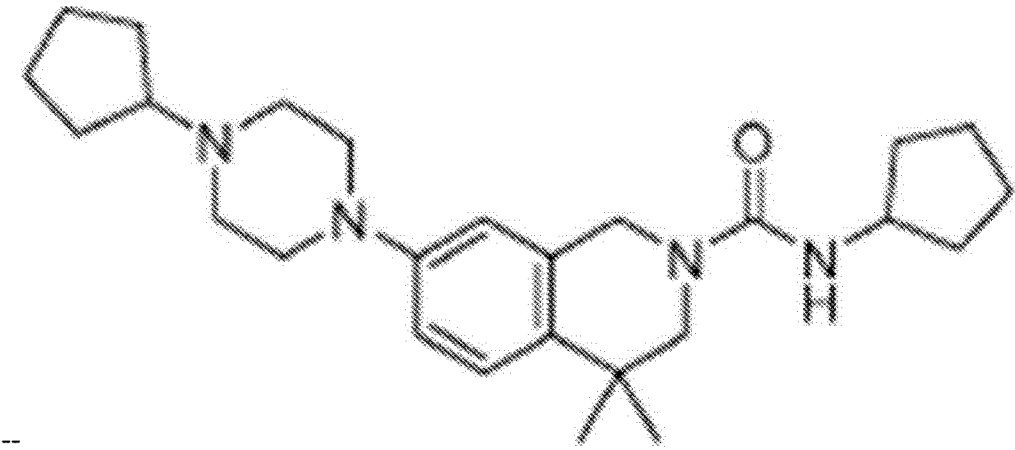

"

--

At Column 183, Claim number 24, Line number 51:
"1-(3,4-dihydroisoquinolin-2(1H)-yl-3-(8-(2,6-"
Should read:
--1-(3,4-dihydroisoquinolin-2(1H)-yl)-3-(8-(2,6- --

CERTIFICATE OF CORRECTION (continued)
U.S. Pat. No. 12,006,300 B2

At Column 183, Claim number 24, Line number 60:

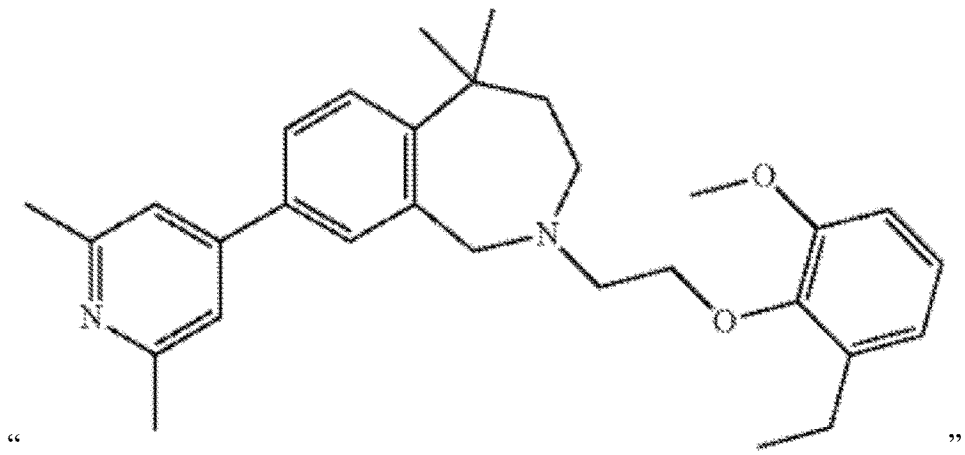

"

Should read:

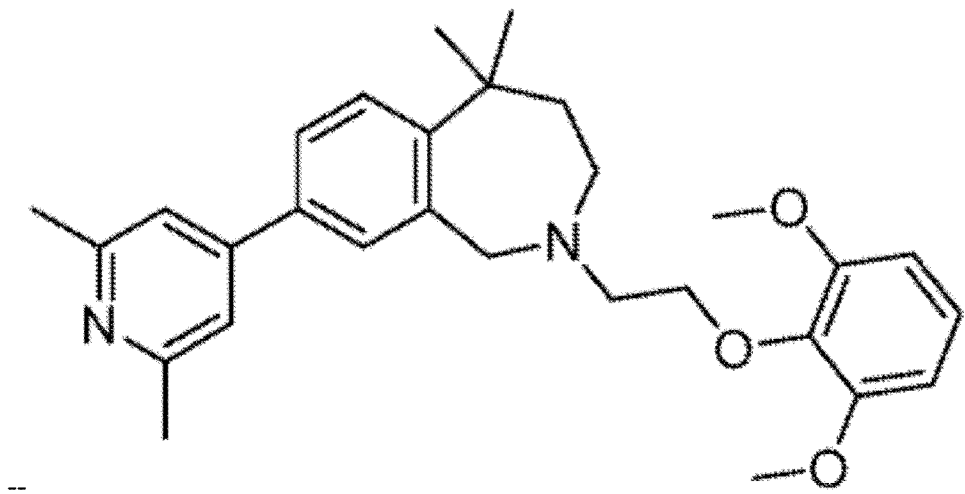

--

At Column 186, Claim number 24, Line number 53:
"(trifluoromethyl)phenyl)-2,3,4,5-tetrahydro-2H-"
Should read:
--(trifluoromethyl)phenyl)-2,3,4,5-tetrahydro-1H- --

At Column 188, Claim number 24, Line number 13:
"((tetrahydro-2-pyran-4-yl)methyl)-2,3,4,5-"
Should read:
--((tetrahydro-2H-pyran-4-yl)methyl)-2,3,4,5- --